(12) United States Patent
Davis et al.

(10) Patent No.: US 11,505,525 B2
(45) Date of Patent: *Nov. 22, 2022

(54) BRANCHED DISCRETE PEG CONSTRUCTS

(71) Applicants: Quanta BioDesign, Ltd., Plain City, OH (US); University of Washington, Seattle, WA (US)

(72) Inventors: Paul D. Davis, Dublin, OH (US); D. Scott Wilbur, Seattle, WA (US)

(73) Assignees: Quanta BioDesign, Ltd., Powell, OH (US); University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,986

(22) Filed: Jun. 23, 2017

(65) Prior Publication Data

US 2017/0313656 A1 Nov. 2, 2017

Related U.S. Application Data

(62) Division of application No. 13/600,188, filed on Aug. 30, 2012, now abandoned.

(Continued)

(51) Int. Cl.
*A61K 9/00* (2006.01)
*C07D 209/60* (2006.01)
(Continued)

(52) U.S. Cl.
CPC .......... *C07D 209/60* (2013.01); *A61K 51/106* (2013.01); *C07C 235/08* (2013.01); *C07C 235/48* (2013.01); *C07C 271/16* (2013.01); *C07C 279/24* (2013.01); *C07C 317/44* (2013.01); *C07C 331/28* (2013.01); *C07D 207/404* (2013.01); *C07D 209/48* (2013.01); *C07D 257/02* (2013.01); *C07D 403/14* (2013.01); *C07K 14/605* (2013.01); *C07K 16/3069* (2013.01); *C07K 16/40* (2013.01); *C07C 2603/18* (2017.05)

(58) Field of Classification Search
CPC .................................................. C07D 209/60
See application file for complete search history.

(56) References Cited

U.S. PATENT DOCUMENTS

| | | | | |
|---|---|---|---|---|
| 5,932,462 A * | 8/1999 | Harris | .................. | C08G 65/329 424/94.3 |
| 2008/0020043 A1 * | 1/2008 | Gingras | ................. | A61K 47/60 424/486 |

* cited by examiner

*Primary Examiner* — Paul W Dickinson
(74) *Attorney, Agent, or Firm* — Cooley LLP

(57) ABSTRACT

Disclosed are general and "substantially pure" branched discrete polyethylene glycol constructs useful in attaching to a variety of biologically active groups, for example, preferential locators, as well as biologics like enzymes, for use in diagnostics, e.g. imaging, therapeutics, theranostics, and moieties specific for other applications. In its simplest intermediate state, a branched discrete polyethylene glycol construct is terminated at one end by a chemically reactive moiety, "A", a group that is reactive with a biologic material that creates "A", which is a biologically reactive group, connected through ⁓⁓⁓ to a branched core (BC) which has attached at least two dPEG-containing chains, indicated by the solid line, ⸺ , having terminal groups, which can be charged, non-reactive or reactable moieties and containing between about 2 and 64 dPEG residues.

12 Claims, 13 Drawing Sheets

Related U.S. Application Data

(60) Provisional application No. 61/528,915, filed on Aug. 30, 2011.

(51) Int. Cl.
*C07C 271/16* (2006.01)
*C07C 279/24* (2006.01)
*C07D 403/14* (2006.01)
*C07C 317/44* (2006.01)
*C07C 331/28* (2006.01)
*C07K 14/605* (2006.01)
*C07D 257/02* (2006.01)
*C07C 235/08* (2006.01)
*C07C 235/48* (2006.01)
*C07D 207/404* (2006.01)
*C07D 209/48* (2006.01)
*C07K 16/30* (2006.01)
*C07K 16/40* (2006.01)
*A61K 51/10* (2006.01)

BRANCHED DISCRETE PEG CONSTRUCTS

CROSS-REFERENCE TO RELATED APPLICATIONS

This application is a continuation of U.S. Ser. No. 13/600,188, filed on Aug. 30, 2012, which itself claims benefit of application Ser. No. 61/528,915 filed on Aug. 30, 2011, the disclosures of which are expressly incorporated herein by reference.

STATEMENT REGARDING FEDERALLY SPONSORED RESEARCH

Not applicable.

FIELD OF DISCLOSURE

The present disclosure sets forth substantially pure branched discrete polyethylene glycol construct compositions (dPEG® reagents, a registered trademark of Quanta BioDesign, Ltd., Powell, Ohio) that can be attached to a large range of useful compounds, primarily of therapeutic or diagnostic significance, in order to significantly effect and control the biodistribution and pharmacokinetics of the useful compounds. Such branched dPEG reagents can be used alone or in combination with linear discrete polyethylene glycols (dPEGs). These compositions can also be made to attach "A" (biologically active groups) in multiples or in combinations in order to control the total avidity of "A." These compositions can be made as part of dPEG containing templates to enhance the functionality and overall utility of the compositions, e.g., by incorporating both diagnostic and therapeutic functionality. Disclosed also are methods for preparation of the branched construct intermediates that can be used to attach other compounds, like toxins or other drugs, to effect a certain action in the body, as well as the compositions themselves.

As used herein, "dPEG" (and discrete PEG or discrete poly(ethylene) glycol) means a specific and single defined number of ethylene oxide units in a linear construct, e.g., a $dPEG_8$ is an ethylene oxide chain that contains precisely and only 8 ethylene oxide units, in a purity of at least about 90% or can be readily purified to yield such purity. As use herein, "single compound (single molecule compound)" means a compound that is not a mixture, one that is made from chemical procedures (as defined in U.S. Pat. No. 7,888,536 which are patented to make the single product the procedure targets to make. This term is used in contrast to "a polymeric or polydisperse mixture," which is the result of a polymer reaction, and is the case in all of the conventional polymeric PEGylation technology (PEGs) referenced herein. The absolute purity of the dPEG compound is defined further in terms of the particular processes used to produce or purity said compositions to the necessary state as defined by the application.

BACKGROUND—THE CONVENTIONAL PEGYLATION ART

The use of conventional polymeric PEGylation reagents have become the standard methodology for modifying biological compounds with the primary intent and result of extending the serum half-life of the biologically active agent, particularly for biological compounds of therapeutic significance. These are generally compounds that due to their small "size" and MW have to be dosed at a high frequency that is too high to be tolerated toxicologically or immunologically by the patient. Generally these small and lower MW biological compounds without the PEGs are being excreted through the filtration system in the kidney, generally very quickly excreting compounds of MW less than about 60-65 kD in minutes rather than hours or days that are optimal for many therapeutic applications.

The existing paradigm by those skilled in the art is that the primary use and application of these conventional polymer PEGylation reagents in therapy or for in vivo imaging/diagnostics is to increase the blood serum half-life of the protein or peptide or other biologically active agent of interest. As one viewing the art, this seems to be the sole purpose of PEGylation, the additional properties of protection from proteolysis, reduced toxicity and water solubility, are inherent with the PEG construct, polymeric or not, and welcome benefits when observed. Also, the minimum sizes of the polymeric PEGylation reagents that have a benefit on the serum half-life are generally at least 20,000 D (20 kD), or preferably at least 40,000 D (40 kD). Potential customers often will not even consider purchasing PEGylation reagents that do not offer a linear 20 kD or branched 40 kD PEG construct. The current paradigm in the art seems to be to use no PEGylation reagent with a MW less than 40 kD.

However, with the benefit of the increased blood half-life, there are serious drawbacks with these polymers. This disclosure addresses improvements to these drawbacks as well as those benefits unique to the branched dPEG constructs.

Additionally, there is no clear (or generally accepted) model as to the structure of the polymeric PEGs in solution, much less the conformational options that exist in solution. The general embodiment of this disclosure is to form a branched dPEG construct that may form a more "rigid" structure in solution and in vivo. The optimal "rigid" construct will be a combination of the length of the component linear dPEG components, as well as extent of the branching and the nature of the terminal charge(s). A branched configuration with shorter linear dPEGs as the component parts could also have additional contrasting features within the biological context due to the branched and smaller nature of the PEG, specifically the composition of the dPEG chains in the wavy and solid lines of the branched dPEG construct. As important is the fact that the branched dPEG constructs are essentially a single component with a single set of properties, while even the extant linear polymeric PEGs are mixtures of tens to hundreds of components and hence produce a range of properties.

In this disclosure we demonstrate that significant and unexpected effects on the PK (serum half-life) of a Fab' can be easily observed with attached branched dPEG constructs of this disclosure with molecular weights beginning as low as 2,500 (2.5 kD) and with increasing serum half-lives as the size and MW increase. This disclosure also demonstrates completely novel and unexpected functional features of the branched dPEG constructs that impact the PK and the biodistribution (BD) of A, the biologically active group, especially when the terminal group on the branched chains is negatively charged. These have not been incorporated into any of the existing conventional polymeric PEG art.

The high molecular weight polymeric PEGs are, first of all, extraordinarily complex mixtures, containing up to hundreds of individual and inseparable components, making characterization of the products virtually impossible and as is known in the art of polymer chemistry, the key challenge is in the reproducibility of the polymer's mixture by careful process control. The term purity is not used in this scenario (Ref.: H. Mark, "Purity and Identity of Polymers," Anal. Chem., 20(2), 104-110(1948)). Also, these large sizes most often significantly block the site of action on the compound it is modifying and the activity is commonly decreased significantly, often by as much as 10 to 100-fold. See e.g., FIG. 1 in the recent review by S. Jevsˇevar (Ref.: S. Jevsˇevar, M. Kunstelj and V. Gaberc Porekar "PEGylation of therapeutic proteins," Biotechnol. J., 5, 113-128 (2010) (FIG. 1 in this reference. Influence of the molecular weight (Mw) of N-terminally PEGylated IFN-α2b conjugates (bearing linear 10-, 20-, 30- and branched 45-kDa PEGs) on their in vitro potency determined by reporter gene assay (Molineux, G., The design and development of pegfilgrastim (PEG-rmetHuG-CSF, Neulasta). *Curr. Pharm. Des.,* 10, 1235-1244(2004)) and elimination half-life in rats after i.v. administration.

Additionally, due to the size and flexibility, and other features of these large polymers, which are not generally fully understood, the polymeric PEGs tend to control the PK (pharmacokinetics) and the biodistribution of the modified biological. In the current state of the art for the design and production of biologics, often as single homogenous species, this power of the design control is largely lost to the properties of the polymeric PEG when they as modification reagents. An example of this using a small targeting peptide to a tumor with both small linear dPEGs, contrasted to some longer polymeric PEGs can be seen in this reference (Ref.: L. Zhu, et al., "Real-Time Video Imaging of Protease Expression in Vivo," Theranostics, 1, 18-27(2011)). It is clear that there is a transition from the peptide controlling the PK to the attached PEG reagent controlling the PK.

This disclosure addresses these issues through the design of general branched dPEG constructs.

In spite of these significant and serious drawbacks with conventional polymeric PEGylation reagents, there are a number of PEGylated biologics that have been approved by the FDA for therapy. (Ref.: Steevens N. S. Alconcel, Arnold S. Baas and Heather D. Maynard, "FDA-approved poly (ethylene glycol)-protein conjugate drugs", Polym. Chem., 2, 1442-1448 (2011). However, it would be exceedingly valuable if there were PEGylation constructs that were essentially single compounds, built from linear and pure single component dPEG compounds (U.S. Pat. No. 7,888, 536 B2) and that also had properties that could be used to modify the biologically active compounds, the resulting compounds would potentially be ones that are (a) essentially single compounds and, therefore, completely and uniquely characterizable; (b) have the ability to control and significantly increase the serum half-life or enhance the targeting properties of the same; (c) and do so without affecting the activity of the biological; d) stabilize against proteases, (e) decrease immunogenicity, and other significant enhancements, this breakthrough would provide a powerful tool and set of tools for and add dramatically to the growing biologic design arsenal of the drug and in vivo diagnostic and theranostic designers. In addition these tools could be applied to other broad sets of unexplored applications, currently inaccessible due to a lack of proper tools for modification with control. Regardless, of the many other drawbacks of conventional polymeric PEGs being used to modify biologics, their sheer size overwhelms the precision that should be apparent from the constructs set forth herein. It should be added that with the other parameters the dPEGs maintain their very hydrophilic character, and therefore provide an ideal infrastructure for the more complex constructs disclosed herein.

This is the intended but not limiting impact of the current disclosure.

Some additional drawbacks of the current art which are directly and intentionally impacted by the current invention include the following:

The formation of intractable mixtures is further exacerbated when the conventional polymeric PEGs are formed into branched constructs, making their reproducible preparation impractical and exacerbates the issues already stated for a single polymer chain.

The very large minimum size of the polymers currently in use, i.e., 40 kDa, to effect serum half-life also most often has seriously deleterious effects on the activity of the biological With the "one size fits all" solution of the conventional PEGylation, there are few options for a fine-tuning the pharmacokinetics of biologics, as there will be with using a range of branched dPEG constructs in the context of the growing art of engineered protein and other biological scaffolds.

Hence, the art of PEGylation is in need of significant improvement and advancement. Ones that will not only give the drug and diagnostic developers the ability to control the apparent size of their "A" (biologic) to the body, primarily PK, but also the biodistribution, through a safe and biocompatible construct that has, multiple and precise design parameters, both in chemical functionality (based on the various chemically reactive or reactable moiety options), charge, and architecture of design for putting in various therapeutic and/or diagnostic groups. Additionally, the branched and attachment dPEG cores taught in this disclosure give options for creating novel compositions of "A" (biologically active group).

BRIEF SUMMARY

Broadly disclosed are general and "substantially pure" branched dPEG constructs useful in attaching to a variety of biologically active groups, for example, preferential locators, as well as biologics like enzymes, for use in diagnostics, e.g. imaging, therapeutics, theranostics, and moieties specific for other applications. In its simplest intermediate state, a branched dPEG construct is terminated at one end by a chemically reactive moiety, "A", a group that is reactive with a biologic material that creates "A", which is a biologically reactive group, connected through ∼∼∼∼ to a branched core (BC) which has attached at least two dPEG-containing chains, indicated by the solid line, ▬▬▬▬▬ , having terminal groups, which can be charged, non-reactive or reactable moieties and containing between about 2 and 64 dPEG residues. Any chemically reactive or reactable group on the ends may or may not be the same; generally they are different. There is the case where two of the solid lines can be different, and in these cases generally two different branched dPEG constructs would be utilized. Connecting these two terminal elements is, ∿∿∿∿∿ a hydrocarbon chain (aliphatic/alkyl, aromatic/aryl, or aliphatic-aromatic alkyl-aryl) containing a dPEG residue and optionally substituted with O, N, S, Si, Se or P, and optionally having side chains, which may or may not also contain dPEG residues. Optionally the chain can be cleavable. These side chains are incorporated through specific attachment cores, that can be the same or different.

In one final product form, the chemically reactive moiety has been directly or indirectly attached to a biologically active group—that is, a group that performs a desired function/interaction in vivo, whether as a preferential locator (e.g., an antibody or antibody fragment), a nanoparticle, an enzyme, or other substance. More than one kind of biologically active group could be carried by the disclosed branched dPEG constructs as part of "A" giving multimeric "A" or bis- or higher heterospecificity. Optionally more than one branched dPEG construct is attachable to one biologically active group, and this can occur randomly, yet characterizable or site specifically through design of the biologic.

Such disclosed branched dPEG constructs generally can be represented by the following:

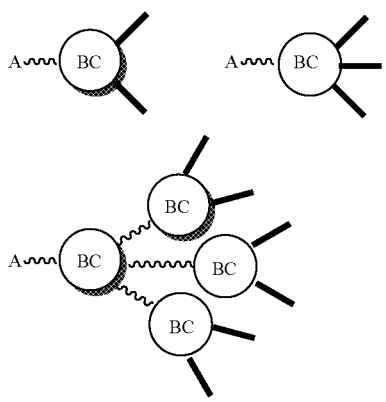

where, A is a chemically reactable group (a group that is reactive or can be made reactive, such as a chemically reactive moiety or a chemically reactive moiety with a protective group); the wavy line, ~~~~~, as a hydrocarbon chain containing a dPEG residue and optionally substituted with O, N, S, Si, Se or P, and optionally having branching side chains, which may or may not also contain dPEG residues; and

as part of

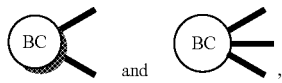

are dPEG-containing chains having terminal reactive or non-reactive groups or functionality and may contain additional branching.

One product formed from such intermediate can also be represented by

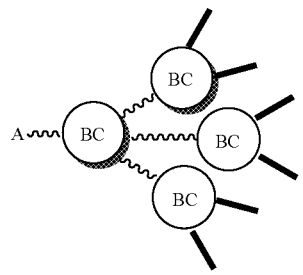

wherein, "A" is now a biologically active group—that is, a group that performs a desired function/interaction in vivo, whether as a preferential locator (e.g., an antibody, fragment, peptide, aptamer, etc.), a nanoparticle, an enzyme, lectin, or other substance of diagnostic or therapeutic significance, e.g., where "A" can also be randomly labeled with a detectable probe, e.g., a radionuclide on the preferential locator.

Disclosed, then are substantially pure compounds represented by:

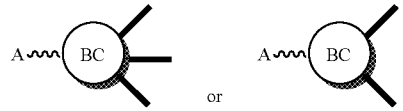

In such structures, A is a biologically active group or a chemically reactive or reactable moiety; the wavy line, ~~~~~, is a linear discrete polyethylene glycol chain containing between about 4 and 48 discrete ethylene oxide residues optionally substituted with N, S, Si, Se, or P, aryl groups, or alkyl groups; and having chemically reactive or reactable end groups that are independently reactable; and optionally having branching side chains which can contain diagnostic or therapeutic groups; BC is a branching core containing a carbon core with 3 or 4 reactable sites, one of said carbon reactable sites being unique, for attachment of ~~~~~ and the other 2 or 3 carbon reactable sites being independently reactive or reactable moieties, for attachment of ■■■■■, respectively; and

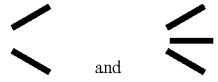

are part of

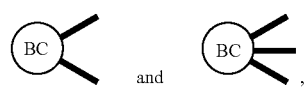

respectively, where the solid lines, ■■■■■, are discrete polyethylene glycol containing chains that have between about 2 and 64 ethylene oxide residues and have a terminal moiety, wherein the terminal moiety can be neutral, charged, or independently reactable.

Such substantially pure compound also can be represented by:

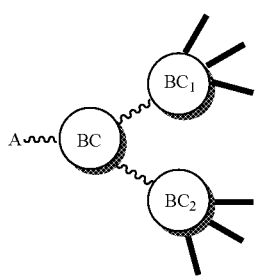

wherein, BC is a trifunctional core and may be the same as $BC_1$, or $BC_2$; where $BC_1$ and $BC_2$ are not the same; and $BC_1$ and $BC_2$ independently may have attached either

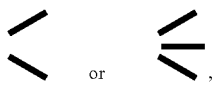

where each is different for attachment to $BC_1$ and $BC_2$, respectively, but can be either

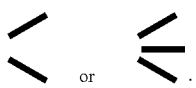

Preferred BC is tryrosine.

This latter compound is useful in externally imaging an antibody, antibody fragment, or a peptide attached to an externally imagable radiolabel, where an imagable radiolabel is attached to and the antibody, antibody fragment, or a peptide, wherein RG is the radiolabel and A is the antibody, antibody fragment, or a peptide.

The basic premise of this disclosure is, then:

Conjugation of a branched dPEG construct modulates the in vivo pharmacokinetics (absorption, distribution, metabolism, excretion) of the biologically active molecule; and By designing the chemical connections through A (chemically reactable moiety) and within ⁓⁓⁓⁓ and their attachment within the various branched cores versatile multifunctional constructs one can control the architecture and functional multiplicity of the general branched dPEG construct, thereby allowing a variety of in vivo parameters to be designed into the final conjugate, along with the ability to detect or probe with it, and deliver a therapeutic.

And optionally these branched dPEG constructs can be used in combination to further define the functionality and the stealth properties of the surfaces of various nano and microparticles for similar applications.

BRIEF DESCRIPTION OF THE DRAWINGS

For a fuller understanding of the nature and advantages of the present media and process, reference should be had to the following detailed description taken in connection with the accompanying drawings, in which.

Figure 1:
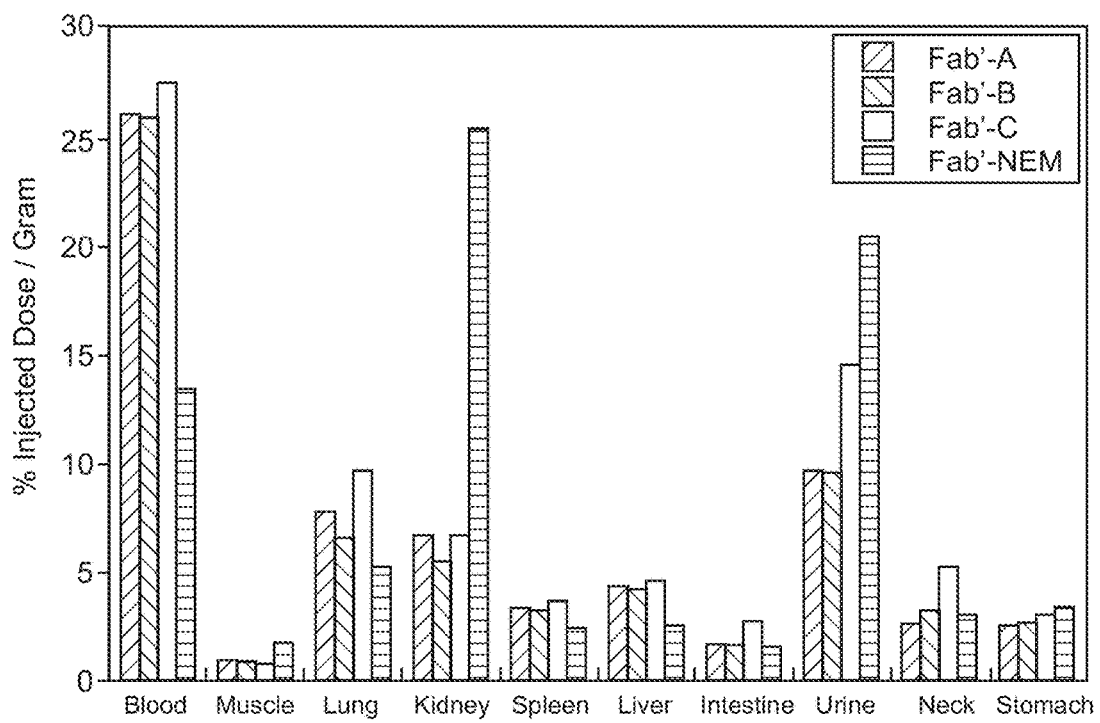
FIG. 1 is a bar graph showing the results of the untargeted biodistribution studies of Fab'-A, Fab' with MAL-dPEG$_4$-Tris(m-dPEG$_{24}$)$_3$, Fab'-B Fab' with MAL-dPEG$_4$-Tris(-dPEG$_{24}$ CO$_2$H)$_3$, Fab'-C Fab' with MAL-dPEG$_4$-Tris(-dPEG$_4$-Tris(m-dPEG$_{12}$)$_3$)$_3$, and, Fab'-NEM=Fab' with N-ethylmaleimide (NEM), as reported in Examples.

The drawings will be described in greater detail below.

DETAILED DESCRIPTION

Definitions (General)

The following definitions of terms as used herein are listed below:

Unless defined otherwise, all technical and scientific terms used herein generally have the same meaning as commonly understood by one of ordinary skill in the art to which this disclosure belongs. Generally, the nomenclature used herein and the laboratory procedures in cell culture, protein engineering, molecular genetics, organic chemistry and nucleic acid chemistry, and hybridization described below are those well known and commonly employed in the art. Standard techniques are used for nucleic acid and peptide synthesis. Generally, enzymatic reactions, protein and related modification and crosslinking chemistry and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Substantially pure"—This purity is like that of traditional chemical synthesis where the components, which create the branched discrete polyethylene glycol (dPEG)

construct, are each single compounds. The branched dPEG constructs are built from combinations of the individually pure components,   and , in a like manner. The 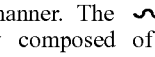 and 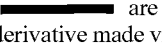 are primarily composed of a dPEG and derivative made via the processes developed in U.S. Pat. No. 7,888,536 B2. Additional purification to remove non-dPEG impurities can be carried out using conventional purification methodologies where necessary and optimized. Thus, the disclosed branched dPEG compounds typically are synthesized in a purity of greater than 60% for those with more complex molecular architecture and often greater than 80% or 90% or above for those with less complicated molecular architecture. Methods can generally be developed to make the branched dPEG construct of purities exceeding 97% or 98%. Even 60% purity is exceedingly higher than the simplest linear monodisperse mixture, where "purity" of the average component is much less than a few % in the best case (PDI=1.01).

"Wavy line", "". The wavy line, 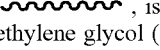, is a linear chain containing a discrete polyethylene glycol (dPEG) residue optionally substituted with N, S, Si, Se, or P, and optionally having branching side chains. Such wavy line may contain aryl groups, alkyl groups, amino acids, and the like. The end components of  have independently chemically reactable or reactive moieties at each end. These are incorporated such that each end can be reacted independently during its incorporation to any branched dPEG construct or intermediates in the process of building the same. When the ends of the wavy line are chemically reactive groups, they can be reactive on their own, or can be masked groups, e.g., an azide as an amine, or protected reactable groups that must be converted to chemically reactive groups. The chemical construction of these compositions can have multiple wavy lines, the same or different. When they are different, the end groups, "A" must not react at the same time, and can be biorthogonal, or other combinations of masked or protected reactable groups known in the art. (Ref.: E. M. Sletten and C. R. Bertozzi, "Biorthogonal Chemistry: Fishing for Selectivity in a Sea of Functionality," Angew. Chem. Int. Ed., 48, 6974-6998(2009); G. Hermanson, Bioconjugate Techniques, $2^{nd}$ Edition, Academic Press, 2008.; T. Greene and Wutz . . . ) The use is the same as that disclosed in our U.S. Pat. No. 7,888,536. Some of the more preferred options are shown in Tables 1 and 2. The chemically reactable or chemically reactive moieties as end groups on the wavy line also can be converted to biologically active groups. Generally this will be a final step or series of steps in the building of the compositions in this disclosure.

Furthermore, the wavy line , which in the art also is termed a linker or spacer or spacer arm, means a chemical moiety comprising a covalent bond or a chain of atoms that covalently attaches a "preferential locator", like an antibody, or to a diagnostic or therapeutic group, like a drug moiety. Exemplary linker abbreviations include: MC=6-maleimidocaproyl, MPS=maleimidopropanoyl, val-cit=valine-citrulline, dipeptide site in protease-cleavable linker, ala-phe=alanine-phenylalanine, dipeptide site in protease-cleavable linker, PAB=paminobenzyloxycarbonyl, SPP=N-Succinimidyl 4-(2-pyridylthio) pentanoate, SMCC=N-Succinimidyl 4-(Nmaleimidomethyl) cyclohexane-I carboxylate, SIAB=NSuccinimidyl (4-iodo-acetyl) aminobenzoate, and these and others known in the art can be and preferred to be used in the disclose composition containing a linear dPEG, as well as those containing dPEG constructs described and defined below.

The wavy line 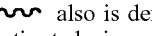 also is defined such that it contributes important properties to be incorporated into or as part of the composition, as part of controlling and including the length and size of the dPEG. These also have practical considerations as they variably control the accessibility for reaction and also the dynamics and size on the final construct, as well as other design functions desirable to the application, e.g., cleavable/releasable, multifunctional. And the optimal lengths of the wavy line are preferred in this disclosure, where for $dPEG_x$, x is preferred from 2 to 72, more preferred from 8-24. The inherent properties of the dPEG as a type of PEG are well known in the art.

The wavy line is defined to optionally incorporate a bond or chemical construct known in the art that will result in a cleavable bond or construct. Also see Tables 1 and 2 below for the preferred chemistries to use in this disclosure as part of the definition for the wavy line, .

"Solid line,"  " solid lines, 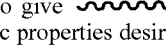, are dPEG-containing chains that have between about 2 and 64 ethylene oxide residues and have a terminal moiety that is not an ethylene oxide. Optionally containing non-dPEGs, but a chain having only dPEGs is preferred. The terminal group generally will be a methyl group or methoxy group, or a charged group. The composition of the end groups on the solid line can be different. Both ends, independently, also could be chemically reactable group(s) or chemically reactive moiety(s), such that they can be incorporated into the branched composition during a synthetic process, or are as defined above. The solid line can contain aryl, alkyl, etc. groups, but it is preferred that it be a "simple" linear dPEG. On occasion, the solid line could incorporate a wavy line or be incorporated into a wavy line.

"A" can be a "biologically active group" or a "chemically reactive moiety" or a "chemically reactable moiety."

"A" as a "Chemically reactive moiety"—a "chemically reactive moiety" is one that will react as it is presented to and allowed to react in the chemical process. This is to be distinguished from a "chemically reactable group" can be used interchangeably, but is a chemical reactive group that is masked, like an azide, reducible to an amine, or a protected "chemically reactive group."

As used herein, or A—chemically reactive moiety—when two chemically reactive moieties are present in a construct, they are optimally designed to have complimentary reactivity. Hence the A's as "chemically reactive moieties" are a pair of reactive chemical moieties that will by the nature of atoms (well known in the art) react with one another, and designed to only react with each other under the predetermined process conditions in building the branched dPEG construct. They are selected from various chemistries known in the art in such a way to give 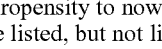 the desired chemical, physical or steric properties desired for a particular application as it is built into the branched dPEG architecture. Including and optionally giving the ends or a position in 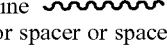 the propensity to now be a releasable. Some preferred options are listed, but not limited to, Tables 1 and 2.

When the wavy line is being incorporated initially to a branched core and both ends are "A", the same is true as the intermolecular reactability above.

Other A's include other sulfhydryl/thiol specific like iodo(halo)acetamides, vinyl sulfone, ETAC (that can react to two thiols, that can be the same or two different in a bispecific application, or bridge a disulfide); Aminooxy derivatives to react with carbonyls like ketones and aldehydes; Acetylides that can react with azides via a copper catalyzed or copper free click reactions.

"Chemically reactive moiety" also is a reactive functional group, and as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989). The reactive functional groups may be protected or unprotected (see, for example, Greene's Protective Groups in Organic Synthesis, Peter G. M. Wuts and Theodora W. Greene, John Wiley and Sons, 2007.

The term "Chemically reactable group" as "A" and as used herein is a masked or protected "chemically reactive group" and used such that where more than one "A" is in a method for making the branched dPEG constructs, these do not interfere in the successful outcome of the syntheses. These options for having "chemically reactable groups" in the presence of "chemically reactive groups" are well known in the art. Many of these are shown below in Tables 1 and 2.

Most of the chemically reactive moieties most preferred in this disclosure can be found in application in the representative references by Hermanson and Bertozzi, but not limited to these, and many are well known to those skilled in the art. (Ref.: Bioconjugate Techniques, Greg T. Hermanson, Elsevier, 2008; ISBN 978-0-12-370501-3; b) "Biorthogonal Chemistry: Fishing for Selectivity in a Sea of Functionality," Ellen. M. Sletten and Carolyn R. Bertozzi, *Angewandte Chemie Int. Ed.,* 2009, 48, 6974-6998.)

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl, benzyl, benzoyl, tetrahydropyranyl, and trialkylsilyl. A "carboxy-protecting group" refers to a substituent of the carboxy group that blocks or protects the carboxy functionality. Common carboxy-protecting groups include $-CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitro ethyl and the like. For a general description of d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process (Ref.: Greene's Protective Groups in Organic Synthesis, Peter G. M. Wuts and Theodora W. Greene, John Wiley and Sons, 2007.

"A" as a "Biologically active group"—This is a biologically active group that is either able to target (preferential locator) a particular compound that is matched to A with a specific non-covalent affinity, e.g., or one that can interact with a target in specific and complementary ways, e.g., enzyme inhibitor peptide (A) to an enzyme released at a disease sight. Any of these biologically active groups inhibitor can be delivered with a radiolabel or a toxic drug that would kill the target, or can deliver a detectable probe as a diagnostic agent, or both.

"A" as a biologically active group is introduced into the branched dPEG construct by the many chemistries known in the art, e.g. references: E. M. Sletten and C. R. Bertozzi, "Biorthogonal Chemistry: Fishing for Selectivity in a Sea of Functionality," Angew. Chem. Int. Ed., 48, 6974-6998 (2009); G. Hermanson, Bioconjugate Techniques, $2^{nd}$ Edition, Academic Press, 2008. In addition the option for incorporating a cleavable chemistry into the linkage formed also is a preferred option. This could include but not limited to a cleavable peptide, a disulfide, or a hydrazone.

As used herein, "A" can be a targeting agent, or carrier with targeting agent (e.g., a nanoparticle that has the targeting agents attached to the particle with various linear and branched dPEG constructs), the targeting agent matched to a particular target. A can be e.g., a MMP (matrix metalloprotease) inhibitor substrate, an RGD peptide, antibody, antibody fragment, engineered scaffold, liposome, a PLGA, silica or a metal nanoparticle, such as gold or silver, all well known in the art or targeting for diagnostics and therapeutics.

When there is more than one "A" as a "biologically active group", the term used is a multivalent group. The "A" independently can be the same or different depending on the intent and need of the particular application of "A". E.g., Two different "A's" give a bispecific interaction, or where "A" is the same, a single interaction can be enhanced, but in both cases there can be a very large advantage over having just one "A" and the design of the ～～～～～ can control that synergy of having more than one "A."

The term, Terminal moiety, as used herein in this disclosure, is defined in terms of the group at the end of the solid line, ▬▬▬▬▬, in a branched dPEG construct. Preferred groups are the methyl or methoxy, and the carboxyl/carboxylate, optionally other negatively charged groups, like a sulfonate. In certain cases, the terminal group can be a positively charged group, like guanidine, amine and the like. These groups may control cell penetration either positively or to prevent it, as well as the orientation and geometry of the branched dPEG constructs. Having multiple charged terminal groups, especially the carboxyl, is preferred in controlling the biodistribution, to unexpectedly increasing the apparent size of the branched dPEG construct and thereby give "small" constructs that will not go out the kidney and stay out of other organs, as well and thereby control much of the biodistribution of a branched dPEG construct having "A" with a biologically active group attached and thereby direct the biologically active group to a preferred location very specifically without diversion while carrying a diagnostic or therapeutic or both groups, and also control the PK of the final branched dPEG construct.

Charged group: A charged group or groups are functional groups that have a net positive or negative charge. The presence and nature of the charge is generally dictated by the pH of the environment in which the group is found. E.g., at physiological pH of just above 7 the amine group is positive and the carboxylate is negative, as are the phosphate and sulfonate groups. Other positively charged groups may include guanidine. The preferred function is the same as for the terminal group, where the preferred terminal group is negatively charged, more preferred the carboxyl group, but optionally having a positive charge. Some branched dPEG constructs may be designed having both negative and positive charges in them by design.

BC or

is a branching core (branching moiety), as used herein, BC=is a "core" chemical moiety which is multi-functional, and can be tri or tetra functional, wherein at least one functional group is always unique and the other at least two functionalities are independently identical to each other and attached to the same carbon core; thus, creating a branched structure. Each functional group also is independently reactable whether they are the same or are different, provided that at least one functional group is always unique. Optionally, N, Si, P, Se cores can be used; carbon is preferred. Examples of cores include Tris (TBE), various amino acids with functional side chains, both natural and unnatural (Ref.: e.g., FIG. 1 in C. Liu and P. Schultz, "Adding New Chemistries to the Genetic Code," Annu. Rev. Biochem., 79, 413-444(2010)) as well as many dendron cores as described by Newkome. (Ref.: G. R. Newkome, and C. Shreiner, "Dendrimers Derived from 1→3 Branching Motifs," Chemical Reviews, 110, 6338-6442(2010)). Tri-substituted aromatic compounds, like the 5-aminoisophthalic acid, also can be used and are included by example, but are not limited to this compound.

AC or

is an attachment core: The attachment core is a group, generally with a carbon core, but the core could also be N, Si, Se, or P, that has the potential of being incorporated into a linear template, where there is more than one

, which independently can be the same or different, and can be separated by a dPEG and 〰〰〰 . The

has an additional functional group that can be reactive or is reactable with another group to incorporate the

into the template construct as part of a more useful and versatile branched dPEG construct composition.

can be incorporated before the template is constructed, as part of

or can be added after the template is built. The latter would be preferred when the

, s and

, s are the same, and the former when the

, s and

, s are different.

G or (DG and TG) is a group that is attached to

via ～～～ and can be a chemically reactable or reactive moiety to which is attached a diagnostic or therapeutic group or a basic branched dPEG construct,

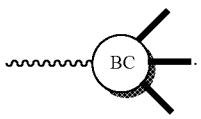

The templates can look like the following,

to which

s are added, and in this case the

s will be the same, or they can be built from the individual pieces,

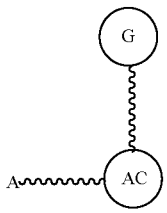

to give an

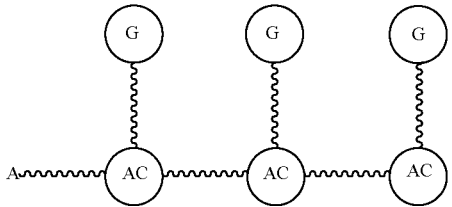

or an

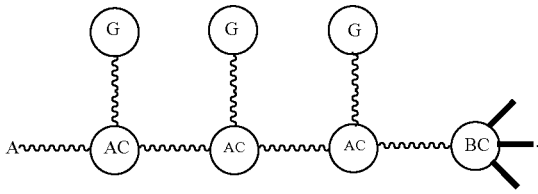

When the

s are the same, the disclosure herein uses the term, homotemplate or homomer or homomeric template; and when the

s are different, we herein use the terms heterotemplate or heteromer or heteromeric template.

can be any side functional amino acid, natural or unnatural, preferred are the lysine, tyrosine, or aspartic acid, but not limited to. Disclosed herein is the versatility of the tyrosine as a multifunctional core, especially to include dPEGs on the phenolic OH, and especially for creating novel and versatile

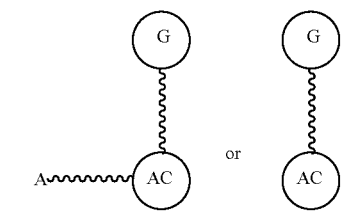

constructs.

As used herein, "G" means a protected or masked reactive chemical moiety; "reactive chemical moiety"=group of atoms that will react with another group of atoms to form the desired chemical bond or bonds based on the electronic and/or steric nature of the reacting group of atoms. "G" has the same options at "A" (chemically reactive group above), but have defined it separately to distinguish it as reactive functionality coming off of template AC's wavy lines. (Refs.: a) March's Advanced Organic Chemistry: Reactions, Mechanism and Structure, Michael B. Smith and Jerry March, John Wiley & Sons, 2001; b) Greene's Protective Groups in Organic Synthesis, Peter G. M. Wuts and Theodora Greene, John Wiley & Sons, 2007.) "G" is convertible to a "G" that can be a "DG", diagnostic group, or a "TG", a therapeutic group, but is not limited to groups with just these functionality and applicability.

Diagnostic Group

The term "diagnostic group", abbreviated "DG," which is used interchangeably with "detectable label" is intended to mean a moiety having a detectable physical, chemical, or magnetic property. This includes such labels as biotin and its derivatives, which are matched with the entire range of streptavidin conjugates, dyes, fluorescent and chromogenic, radioisotopes as labels, including chelating groups such as DOTA and NOTA derivative. In all of these cases the use of the linear dPEG in the attachment chemistry is preferred. (Ref.: a. D. Scott Wilbur, "Chemical and Radiochemical Considerations in Radiolabeling with alpha-Emitting Radio-nuclides," Current Radiopharmaceuticals, 4, 214-247 (2011); M. Famulok, et al., "Functional Aptamers and Aptazymes in Biotechnology, Diagnostics, and Therapy," Chem. Rev., 107(9), 3715-3743(2007); S. S. Kelkar and T. M. Reineke, "Theranostics: Combining. Imaging and Therapy," Bioconjugate Chemistry, 22, 1879-1903); "Molecular Probes Handbook, A Guide to Fluorescent Probes and Labeling Technologies," 11$^{th}$ Edition, Iain Johnson and M. Spence, Ed., ISBN-10: 0982927916.

A novel DOTA derivative that can be used to make a wide range of useful chelating reagents to create a diagnostic group as an imaging agent, especially incorporating various dPEG constructs as wavy lines, to control where it is place in the diagnostic or imaging system and can be used as effective parts of branched dPEG constructs.

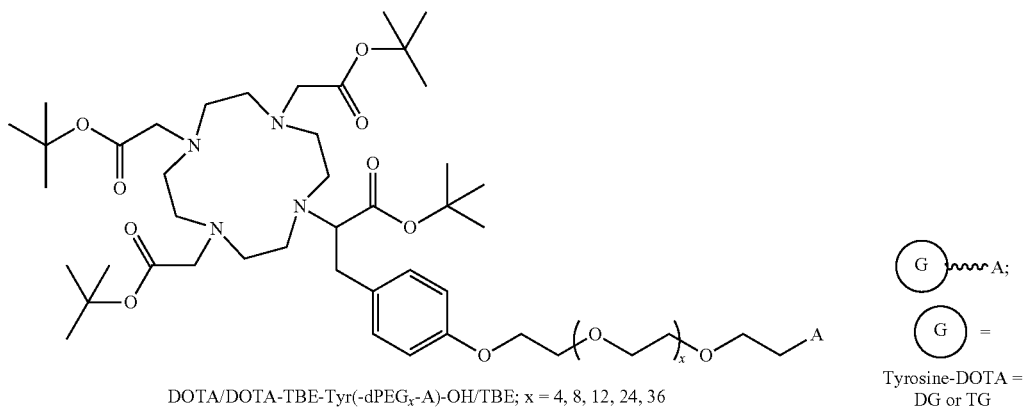

DOTA/DOTA-TBE-Tyr(-dPEG$_x$-A)-OH/TBE; x = 4, 8, 12, 24, 36

Tyrosine-DOTA = DG or TG

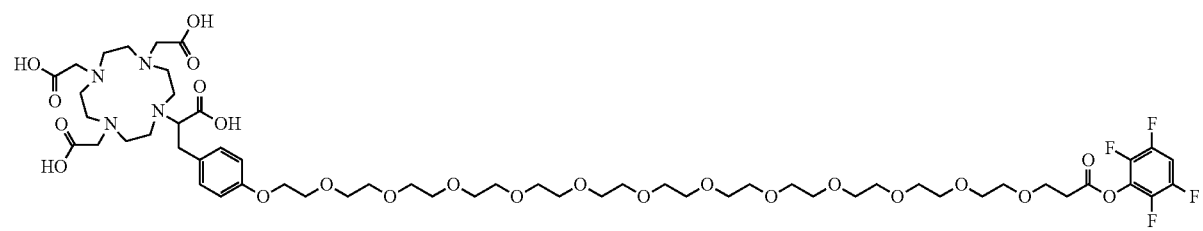

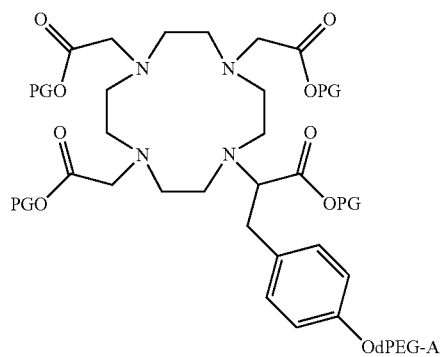

OdPEG-A 19                                    20
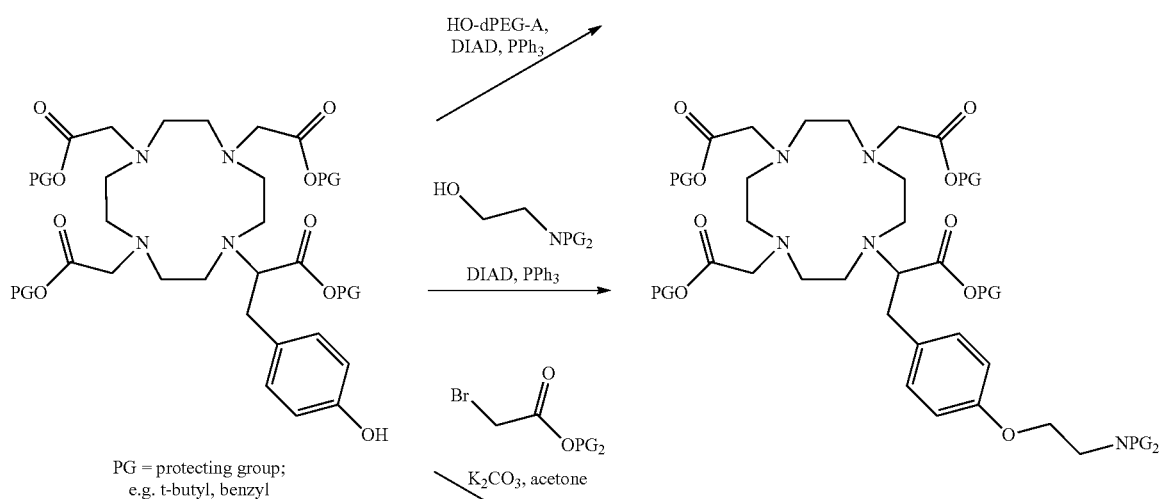
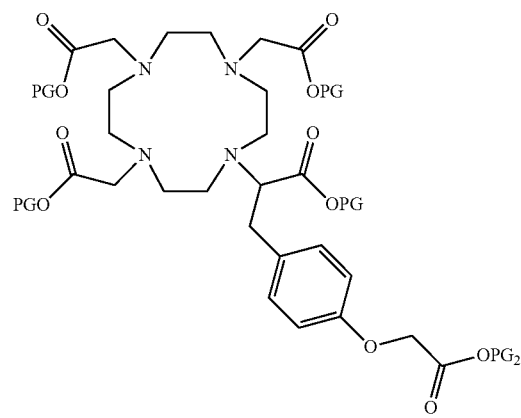
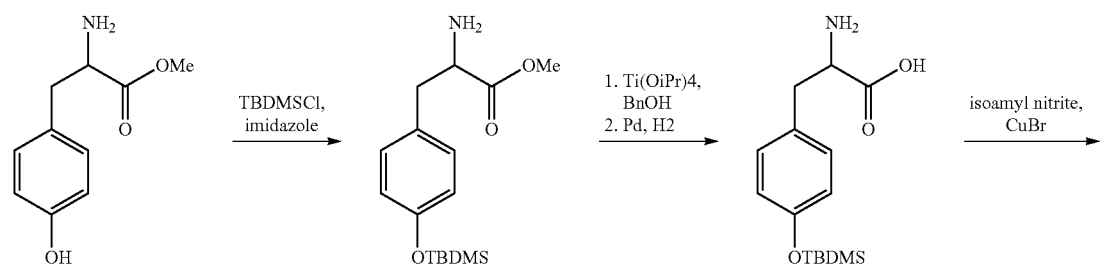

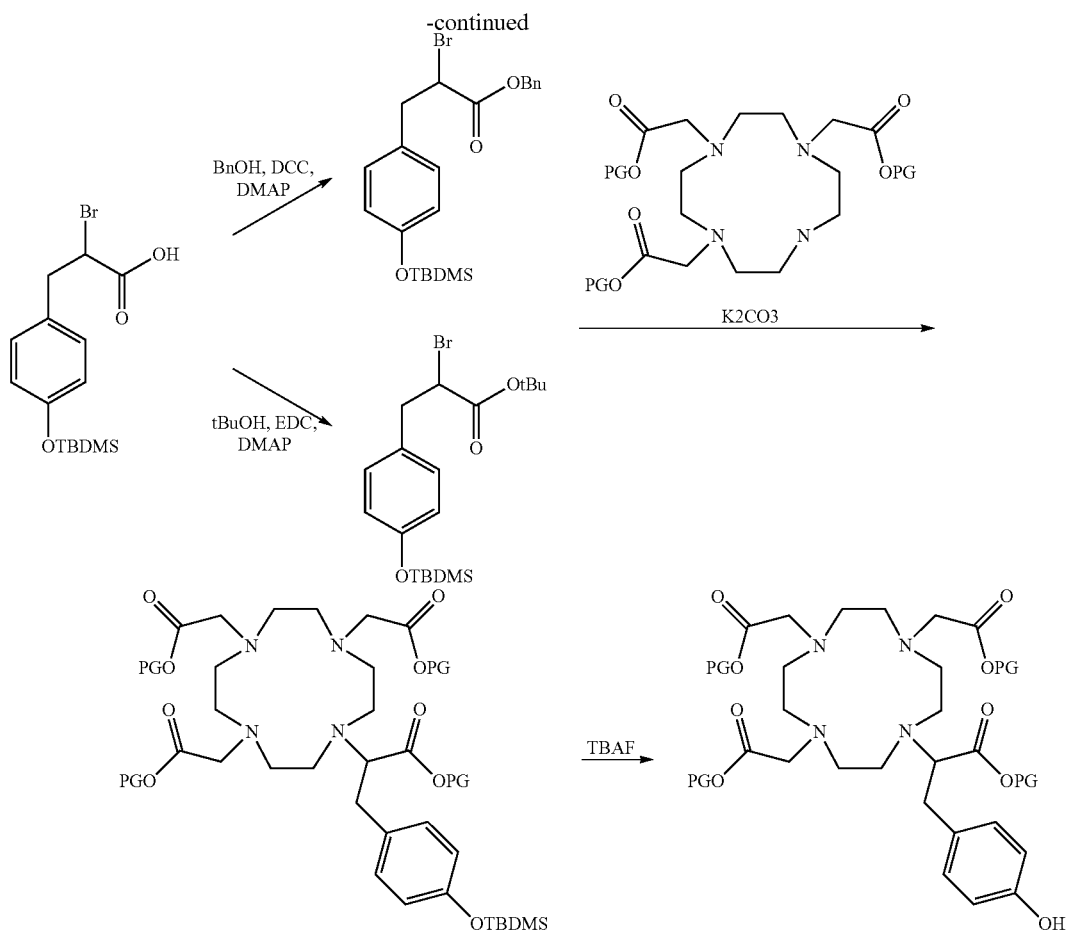

TG (Therapeutic Group)

The term "therapeutic (group)" abbreviated "TG," is intended to mean a compound that, when present in a therapeutically effective amount, produces a desired therapeutic effect on a mammal. For treating carcinomas, it is desirable that the therapeutic agent also be capable of entering the target cell. A therapeutic group can be from among the cytotoxins. Herein, the term "cytotoxin" is intended to mean a therapeutic agent having the desired effect of being cytotoxic to cancer cells. Cytotoxic means that the agent arrests the growth of or kills the cells. Exemplary cytotoxins include, by way of example and not limitation, combretastatins, duocarmycins, the CC-1065 anti-tumor antibiotics, anthracyclines, and related compounds. Other cytotoxins include mycotoxins, ricin and its analogues, calicheamycins, doxirubicin and maytansinoids. A good recent review reference on natural products and their potential impact on new anti-cancer drugs is referenced here. ("Impact of Natural Products on Developing New Anti-Cancer Agents," David J. Newman, et al., *Chemical Reviews*, 2009, 109, 3012-3043,)

As used herein, the term "therapeutic group" is any compound that is a "drug", "anticancer agent", "chemotherapeutic agent", "antineoplastic", and "antitumor agent" are used interchangeably and refer to agent(s) (unless further qualified) that have the property of inhibiting or reducing aberrant cell growth, e.g., a cancer. The foregoing terms also are intended to include cytotoxic, cytocidal, or cytostatic agents. The term "agent" includes small molecules, macromolecules (e.g., peptides, proteins, antibodies, or antibody fragments), and nucleic acids (e.g., gene therapy constructs), recombinant viruses, nucleic acid fragments (including, e.g., synthetic nucleic acid fragments). (Ref.: M. Famulok, "Functional Aptamers and Atazymes in Biotechnology, Diagnostics, and Therapy," Chem. Rev., 107(9), 3715 (2007)

Therapeutic groups also can be radionuclides (Ref. a. D. Scott Wilbur, "Chemical and Radiochemical Considerations in Radiolabeling with Emitting Radionuclides," Current Radiopharmaceuticals, 4, 214-247(2011); b. Monoclonal antibody and peptide-targeted radiotherapy of cancer, R. M. Reilly, ed., J. Wiley and Sons, 2010, ISBN 978-0-470-24372-5.; c. Targeted Radionuclide Therapy, Tod W. Speer, ed., Lippincott, 2011, ISBN 978-0-7817-9693-4.)

Nanoparticle

As used herein, the term "nanoparticles" refers to particles of about 0.1 nm to about 1 μm, 1 nm to about 1 μm, about 10 nm to about 1 μm, about 50 nm to about 1 μm, about 100 nm to about 1 μm, about 250-900 nm in size, or, advantageously, about 600-800 nm. The nanoparticles may comprise macromolecules, gene therapy constructs, or chemotherapeutic agents, for example.

As used herein, the term "microparticles" refers to particles of about 0.1 μm to about 100 μm, about 0.5 μm to about 50 μm, 0.5 μm to about 20 μm in size, advantageously, particles of about 1 μm to about 10 μm in size, about 5 μm in size, or mixtures thereof. The microparticles may comprise macromolecules, gene therapy constructs, or chemotherapeutic agents, for example.

The term "cleavable group" is intended to mean a moiety that can be unstable in vivo. Preferably the "cleavable group" allows for activation of the marker or therapeutic agent by cleaving the marker or agent from the rest of the conjugate. Operatively defined, the linker is preferably cleaved in vivo by the biological environment. The cleavage may come from any process without limitation, e.g., enzymatic, reductive, pH, etc. Preferably, the cleavable group is selected so that activation occurs at the desired site of action, which can be a site in or near the target cells (e.g., carcinoma cells) or tissues such as at the site of therapeutic action or marker activity. Such cleavage may be enzymatic and exemplary enzymatically cleavable groups include natural amino acids or peptide sequences that end with a natural amino acid, and are attached at their carboxyl terminus to the linker. While the degree of cleavage rate enhancement is not critical to the disclosure, preferred examples of cleavable linkers are those in which at least about 10% of the cleavable groups are cleaved in the blood stream within 24 hours of administration, most preferably at, least about 35%. Included in this term is the option of having a "self immolative spacer". The term "self-immolative spacer" refers to a bifunctional chemical moiety that is capable of covalently linking two chemical moieties into a normally stable tripartite molecule. The self-immolative spacer is capable of spontaneously separating from the second moiety if the bond to the first moiety is cleaved. Listed are references representing the range of cleavable chemistries potentially applicable in this disclosure, which can be utilized with the benefit by incorporation into the wavy or solid lines, especially containing dPEGs, as part, of the branched core or the attachment core.

a. "Releasable PEGylation of proteins with customized linkers," David Filpula and Hong Zhao, Advances in Drug Delivery Reviews, 2008, 60, 29-49.

b. "A Mild Chemically Cleavable Linker System for Functional Proteomic Applications," Steven H. L. Verhelst, Marko Fonovic, and Matthew Bogyo, Angew. Chem. Int. Ed. 2007, 46, 1-4 c. "Enzyme-Catalyzed Activation of Anticancer Prodrugs," MARTIJN ROOSEBOOM, JAN N. M. COMMANDEUR, AND NICO P. E. VERMEULEN, Pharmacol Rev 56:53-102, 2004.

d. "Elongated Multiple Electronic Cascade and Cyclization Spacer Systems in Activatible Anticancer Prodrugs for Enhanced Drug Release," Hans W. Scheeren, et al., *J. Org. Chem.* 2001, 66, 8815-8830 e. "Controlled Release of Proteins from Their Poly(Ethylene Glycol) Conjugates: Drug Delivery Systems Employing 1,6-Elimination," Richard B. Greenwald, et al., *Bioconjugate Chem.* 2003, 14, 395-403.

The term "pro drug" and the term "cleavable moiety" often can be used herein interchangeably. Both refer to a compound that is relatively innocuous to cells while still in the conjugated form, but which is selectively degraded to a pharmacologically active form by conditions, e.g., enzymes, located within or in the proximity of target cells. (Ref.: P. J. Sinko, et al., "Recent Trends in Targeted Anticancer Prodrug and Conjugate Design," Curr. Med. Chem., 15(18), 1802-1826(2008); S. S. Banerjee, et al., Poly(ethylene glycol)-Prodrug Conjugates: Concept, Design, and Applications," J. of Drug Delivery, Article ID 103973 (2012); J. Rautio, et al., "Prodrugs: design and clinical applications," Nature Review, Drug Discovery, 7, 255-270 (2008).)

Preferential locator often can be used largely interchangeably with ligand or "targeting group" and can be either a "diagnostic group" or a "therapeutic group" or the like. Broadly, preferential locators are molecularly targeted agent defined as drugs that target growth factor receptors and signal transduction pathways. NPOA molecule is used for targeting molecular entities, cells, tissues or organs in a biological system. With respect to neoplastic tissue (cancer cells), a "preferential locator" (or "locator") specifically binds a marker produced by or associated with, for example, neoplastic tissue, antibodies and somatostatin congeners being representative such locators. Broader, however, a "locator" includes a substance that preferentially concentrates at the tumor sites by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No. 4,946,778, incorporated herein by reference) and like substances have been developed and may similarly prove efficacious. For example, genetic engineering has been used to generate a variety of modified antibody molecules with distinctive properties. These include various antibody fragments and various antibody formats. An antibody fragment is intended to mean any portion of a complete antibody molecule. These include terminal deletions and protease digestion-derived molecules, as well as immunoglobulin molecules with internal deletions, such as deletions in the IgG constant region that alter Fc mediated antibody effector functions. Thus, an IgG heavy chain with a deletion of the Fc CH2 domain is an example of an antibody fragment. It is also useful to engineer antibody molecules to provide various antibody formats. In addition to single chain antibodies, useful antibody formats include divalent antibodies, tetrabodies, triabodies, diabodies, minibodies, camelid derived antibodies, shark derived antibodies, and other antibody formats. Aptomers form yet a further class of preferential locators. All of these antibody-derived molecules are example of preferential locators.

Various suitable antibodies (including fragments, single chains, domain deletions, humanized, etc.) include, for example, 872.3, CC49, V59, and 3E8 (see U.S. Pat. No. 8,119,132), all directed against adenocarcinomas.

In addition to antibodies, biochemistry and genetic engineering have been used to produce protein molecules that mimic the function of antibodies. Avimers are an example of such molecules. See, generally, Jeong, et al., "Avimers hold their own", *Nature Biotechnology* Vol. 23 No. 12 (December 2005). Avimers are useful because they have low immunogenicity in vivo and can be engineered to preferentially locate to a wide range of target molecules such as cell specific cell surface molecules. Although such substances may not be subsumed within the traditional definition of "antibody", avimer molecules that selectively concentrate at the sites of neoplastic tissue are intended to be included within the definition of preferential locator. Thus, the terms "locator" was chosen, to include present-day antibodies and equivalents thereof, such as avimers, as well as other engineered proteins and substances, either already demonstrated or yet to be discovered, which mimic the specific binding properties of antibodies in the inventive method disclosed therein. (Refs.: "Engineered protein scaffolds as next-generation antibody therapeutics," Michaela Gebauer and Arne Skerra, *Current Opinion in Chemical Biology,* 2009, 13, 245-255; "Adnectins: engineered target-binding protein therapeutics," D Lipovsek, *Protein Engineering, Design & Selection,* 2010, 1-7.)

For other disease types or states, other compounds will serve as preferential locators.

The term "preferential locator" also can include terms like "targeting group" and "targeting agent" and are intended to mean a moiety that is (1) able to direct the entity to which it is attached (e.g., therapeutic agent or marker) to a target cell, for example to a specific type of tumor cell or (2) is preferentially activated at a target tissue, for example a tumor. The targeting group or targeting agent can be a small molecule, which is intended to include both nonpeptides and peptides. The targeting group also can be a macromolecule, which includes saccharides, lectins, receptors, ligands for receptors, proteins such as BSA, antibodies, and so forth. (Refs.: a) "Peptides and Peptide Hormones for Molecular Imaging and Disease Diagnosis," Xiaoyuan Chen, et al., *Chemical Reviews*, 2010, 110, 3087-3111; b), "Integrin Targeted Therapeutics," N. Neamati, et al., *Theranostics*, 2011, 1, 154-188; c) "Integrin Targeting for Tumor Optical Imaging," Yunpeng Ye, et al., *Theranostics*, 2011, 1, 102-126.)

The term "marker" is intended to mean a compound useful in the characterization of tumors or other medical condition, and is therefore a target for the "preferential locator". E.g., in the cases of the, diagnosis, progression of a tumor, and assay of the factors secreted by tumor cells. Markers are considered a subset of "diagnostic agents." (Ref.: "Antibody-Drug Conjugate Targets," B. A. Teicher, *Current Cancer Drug Targets*, 2009, 9, 982-1004.) Marker is one target, a major target of a preferential locator. The term "ligand" means any molecule that specifically binds or reactively associates or complexes with a receptor, substrate, antigenic determinant, or other binding site on a target cell or tissue. Examples of ligands include antibodies and fragments thereof (e.g., a monoclonal antibody or fragment thereof), enzymes (e.g., fibrinolytic enzymes), biologic response modifiers (e.g., interleukins, interferons, erythropoietin, or colony stimulating factors), peptide hormones, and antigen-binding fragments thereof. (Ref.: U.S. Pat. No. 7,553,816 B2)

The terms "polypeptide," "peptide" and "protein" are used interchangeably herein to refer to a defined polymer of amino acid residues, optionally incorporating a dPEG spacer or side chain. The terms apply to defined amino acid polymers in which one or more amino acid residue is an artificial chemical mimetic of a corresponding naturally occurring amino acid, as well as to naturally occurring defined amino acid polymers and non-naturally occurring amino acid sequences.

The term "amino acid" refers to naturally occurring and synthetic amino acids, either of L- or D-stereochemical configurations. (Ref.: U.S. Pat. No. 7,553,816 B2; Chang C. Liu and Peter G. Schultz, "Adding New Chemistries to the Genetic Code," Annu. Rev. Biochem., 79, 413-444(2010)).

Chemical Nomenclature Shorthand Specifically for this Disclosure and the Branched dPEG Constructs In the following shorthand nomenclature for the branched dPEG constructs, the following abbreviations are used:

a. dPEGx, where x refers to the exact and single number of oxygens in the ethylene oxide linker chain to which is it assigned, e.g., a dPEG$_4$ has exactly and only 4 ethylene oxide units, and a dPEG$_{24}$ has exactly and only 24 ethylene oxide units.

b. MAL=Malimidopropionic acid c. Tris (generally)

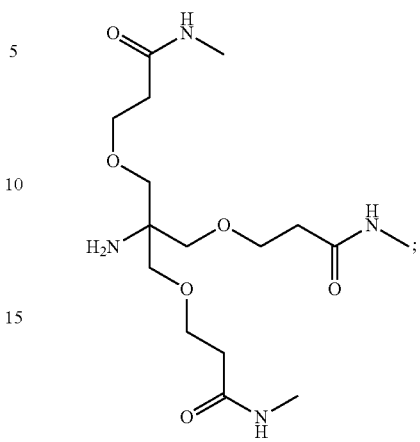

optionally other bonds, like an ester could be incorporated.

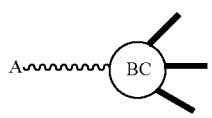

MAL-dPEG$_{12}$-Tris(-dPEG$_{12}$-CO$_2$H)$_3$;

=MAL-dPEG$_{12}$;

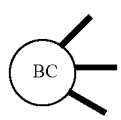

=-Tris(-dPEG$_{24}$-CO$_2$H)$_3$; Terminal group is —CO$_2$H or CO$_2^-$

Optionally, a further simplification is where MAL-dPEG$_{12}$-Tris(-dPEG$_{12}$-CO$_2$H)$_3$ is simply:
MAL-12-Tris(12-CO$_2$H)$_3$ or even MAL-12-(12-acid)$_3$, where the dPEG is dropped and only the x subscript is included.

There simple branched dPEG constructs like,

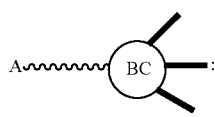

MAL-dPEG$_{12}$-Tris(-dPEG$_{24}$-CO$_2$H)$_3$
MAL-dPEG$_{12}$-Tris(m-dPEG$_{24}$)$_3$
MAL-dPEG$_{12}$-Tris(-dPEG$_{12}$-Tris(m-dPEG$_{11}$)$_3$)$_3$
CC49 Fab'-S-MAL-dPEG$_{12}$-Tris(-dPEG$_{12}$-CO$_2$H)$_3$

27

=CC49 Fab'-S-MAL-dPEG$_{12}$;

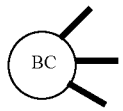

28

=-Tris(-dPEG$_{24}$-CO$_2$H)$_3$

CC49 Fab'-S-MAL-dPEG$_{12}$-Tris(-dPEG$_{24}$-CO$_2$H)$_3$

CC49 Fab'-S-MAL-dPEG$_{12}$-Tris(m-dPEG$_{24}$)$_3$

CC49 Fab'-S-MAL-dPEG$_{12}$-Tris(-dPEG$_{12}$-Tris(m-dPEG$_{11}$)$_3$)$_3$

CC49 Fab'-S-NEM

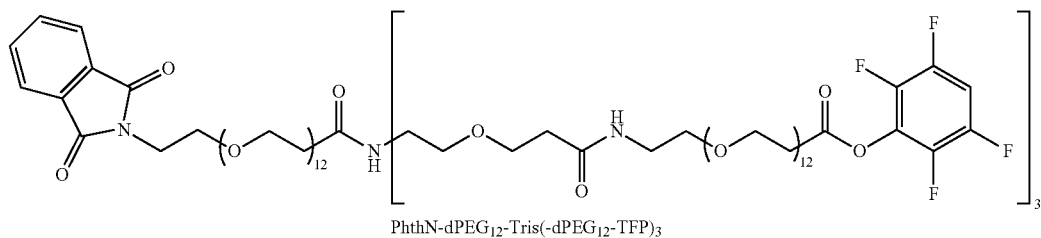

PhthN-dPEG$_{12}$-Tris(-dPEG$_{12}$-TFP)$_3$

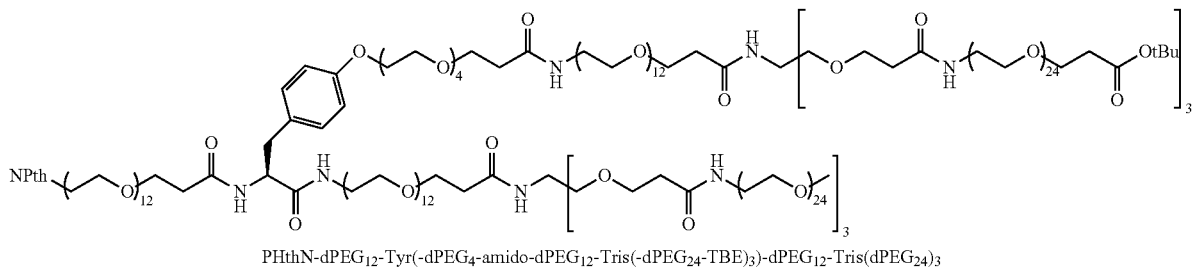

PHthN-dPEG$_{12}$-Tyr(-dPEG$_4$-amido-dPEG$_{12}$-Tris(-dPEG$_{24}$-TBE)$_3$)-dPEG$_{12}$-Tris(dPEG$_{24}$)$_3$ Template Examples

Example of a heteromer template, with a protected lysine, tryrosine and protected glutaric acid:

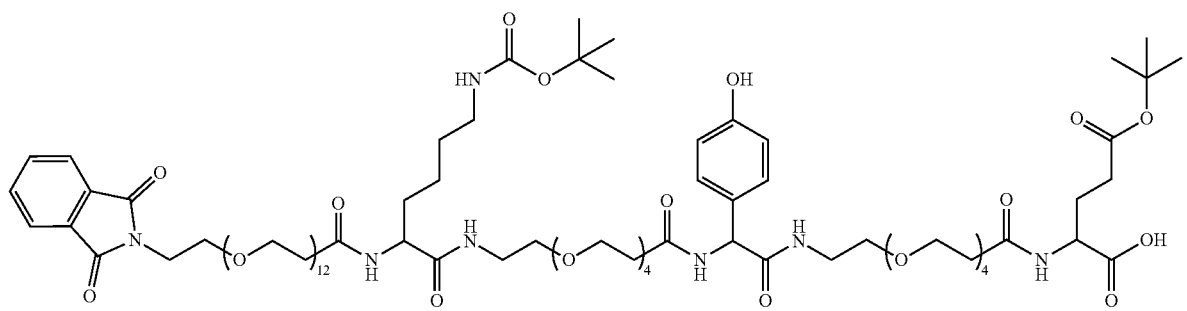

Chemical Formula: C$_{85}$H$_{141}$N$_7$O$_{34}$
Molecular Weight: 1805.06
PhthN-dPEG®$_{12}$-Lys(t-boc)-dPEG®$_4$-Tyr-dPEG®$_4$-Glu(t-butyl)-OH Structure (X) shows a simple example of a homomer template, with 4× lysine each with a dPEG₄ spacer between,
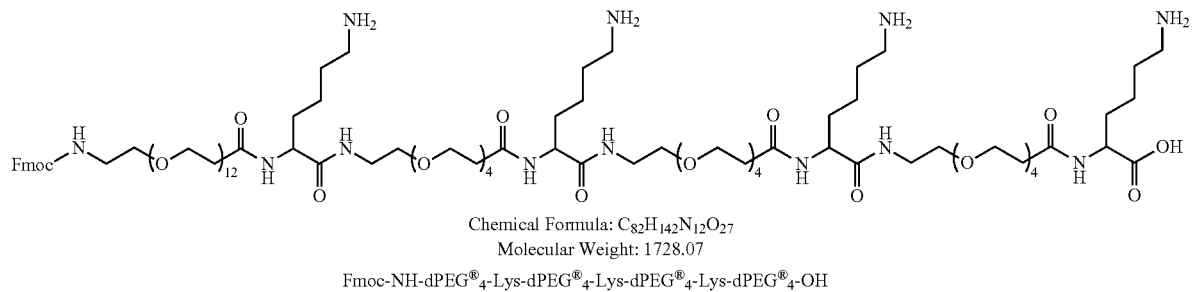
Chemical Formula: $C_{82}H_{142}N_{12}O_{27}$
Molecular Weight: 1728.07
Fmoc-NH-dPEG®₄-Lys-dPEG®₄-Lys-dPEG®₄-Lys-dPEG®₄-OH
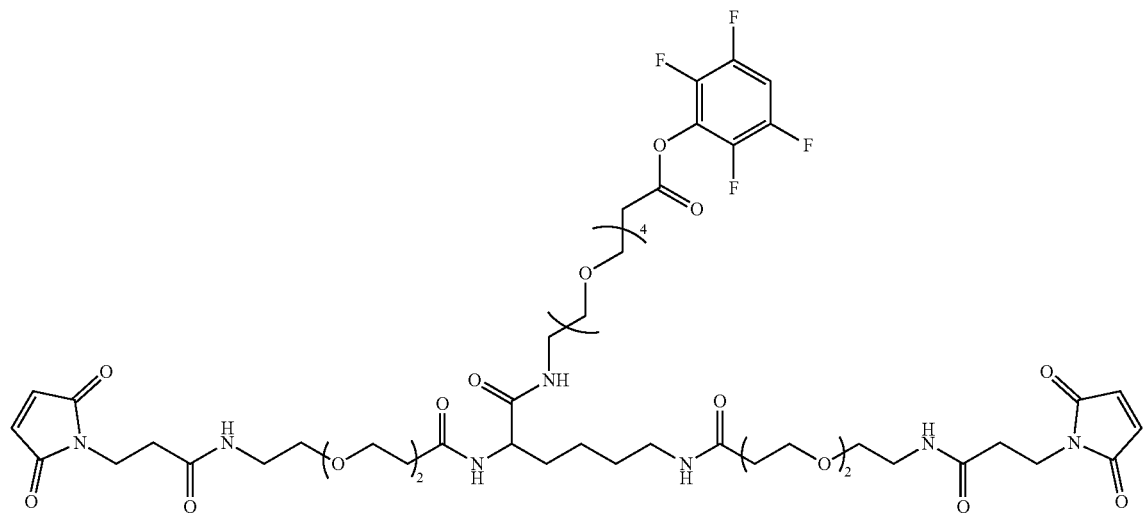
Chemical Formula: $C_{51}H_{71}F_4N_7O_{19}$
Molecular Weight: 1162.14
MAL-dPEG®₁₂-Lys(-dPEG®₂-MAL)-dPEG®₄-CO-TFP or
Bis(MAL-dPEG®₂)-Lys-dPEG®₄-CO-TFP

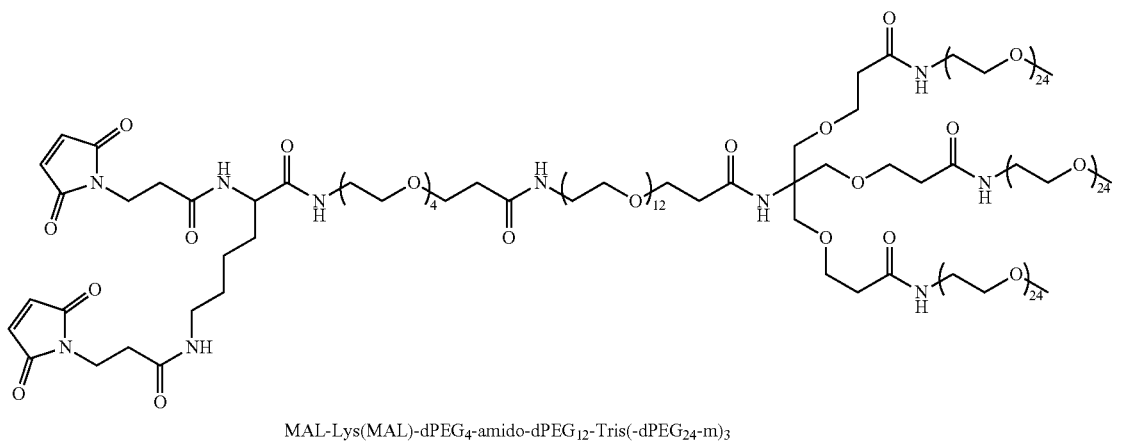

MAL-Lys(MAL)-dPEG$_4$-amido-dPEG$_{12}$-Tris(-dPEG$_{24}$-m)$_3$

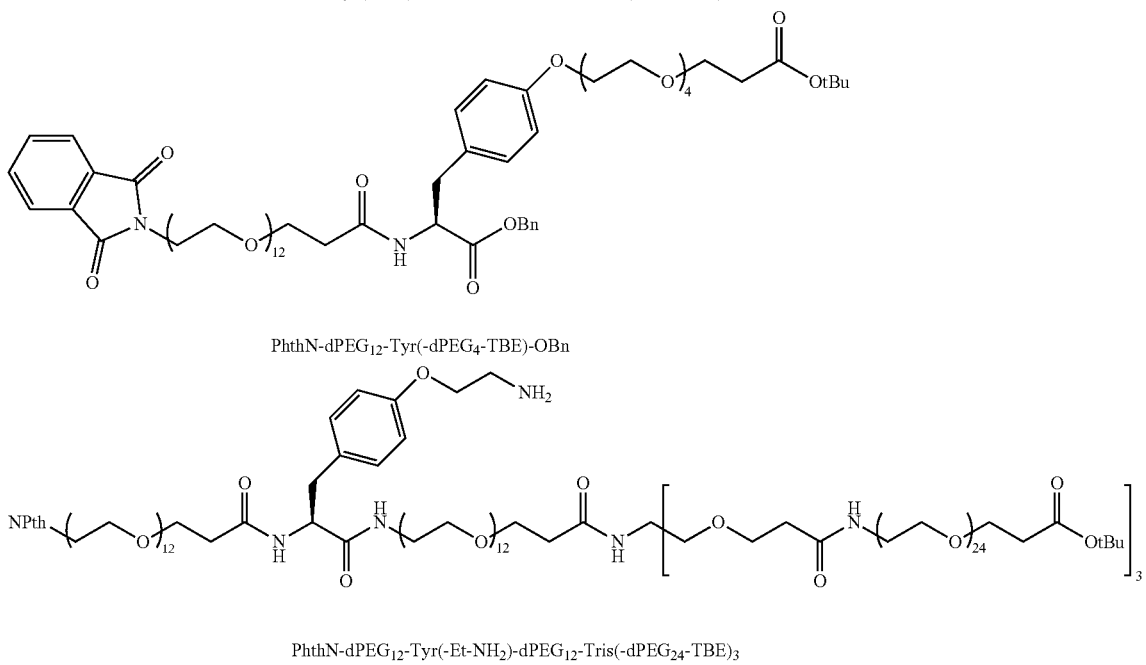

PhthN-dPEG$_{12}$-Tyr(-dPEG$_4$-TBE)-OBn

PhthN-dPEG$_{12}$-Tyr(-Et-NH$_2$)-dPEG$_{12}$-Tris(-dPEG$_{24}$-TBE)$_3$

TABLE 1

Various Representative A's as Chemically Reactive Moieties. Examples are shown where the A's are different. However, each entry or pair of entries can also be used along as an "A" as a chemically reactive moiety.

| A (chemically reactive moiety with protecting group) | A (chemically reactive moiety) | A (compatible chemically reactive moiety) | A (compatible chemically reactive moiety with protecting group) |
|---|---|---|---|
| acetal | aldehyde | hydrazide | t-boc |
| acetal/ketal | Aldehyde/ketone | hydrazide | Fmoc, EDG-trityl, t-boc, etc. |
| Acetal or ketal | Benzaldehyde, alkyl aldeyhye (serine) | aminooxy | Fmoc-, EDG-trityl, t-boc, etc. |
| Acid, ester | Active ester (NHS, etc.) | amine | Protected amine |
| PG-thiol | Thiol | Maleimide | |
| Phthalimide | Amine | NHS ester, TFP ester, Acid, NCS, amine reactive | Acid, PG-acid, amine, |
| | azide | Acetylide (copper catalyzed Click) | |
| | azide | Aryl phosphine | |
| | Thioene chemistry thiol | tosylate | |
| PG—OH | | isocyanate | amine |
| PG-amine | amine | isothiocyanate | amine |
| PG—OH | | acid | ester |
| PG—OH | Active carbonate | amine | amine |

TABLE 1-continued

Various Representative A's as Chemically Reactive Moieties.
Examples are shown where the A's are different.
However, each entry or pair of entries can also be used along as
an "A" as a chemically reactive moiety.

| A (chemically reactive moiety with protecting group) | A (chemically reactive moiety) | A (compatible chemically reactive moiety) | A (compatible chemically reactive moiety with protecting group) |
|---|---|---|---|
| Thiolacetyl, EDG-Trityl-S-, PDP | Thiol, ETAC, Trans-cyclooctene, Azide | Maleimide, Vinyl sulfone disulfide thiol triazine, Cyclooctyne derivatives (copper free click) | PG—S— |

EDG = Electron donating group as aromatic substituent;
PG = protective group

EDG=Electron donating group as aromatic substituent; PG=protective group Reference: a) This a key general reference to these and other chemistry options for conjugation. Bioconjugate Techniques, Greg T. Hermanson, Elsevier, 2008; ISBN 978-0-12-370501-3; b) also an leading reference on the recent advances in biorthogonal chemistry is, "Biorthogonal Chemistry: Fishing for Selectivity in a Sea of Functionality," Ellen M. Sletten and Carolyn R. Bertozzi, *Angewandte Chemie Int. Ed.,* 2009, 48, 6974-6998.

As used herein, "multifunctional chemical moiety" is a chemical moiety using it in the context of conjugation and building molecules will typically have at least two functionalities, either the same or different, homo- and hetero-bifunctional, respectively. A multifunctional is defined as a chemical moiety having at least three or more functionalities, with all being different, or, e.g., in the case of a tri-functional, one could be the same, the other two different, or each or the three be different.

TABLE 2

Representative "A"'s as Chemically Reactive
Moieties and conversions to the most preferred reactive groups for
the conversion to "A" to react with a Biologically
Active group, or a diagnostic group or a therapeutic group

| A (chemically reactive moiety) | React with A → | A (chemically reactive moiety) | Reacts with | Bond formed in A (biologically active group) |
|---|---|---|---|---|
| Amine | MPS | Maleimide | Sulfhydryl | thioether |
| Amine | Alpha haloacid | Iodoacetamide | Sulfhydryl | Thioether (no new stereoisomers) |
| Alcohol | Vinyl sulfone | Vinyl sulfone | Sulfhydryl | thioether |
| Amine | Vinyl sulfone equivalent | Vinyl sulfone | Sulfhydryl | thioether |
| Amine | Aminooxy eq. | Aminooxy | Carbonyl | oxime |
| Amine | Lipoic acid dimmers, etc. | Lipoamide | Metal surfaces | M—S—S— |
| Amine | Lipoic acid | | | |
| Amine | ETAC-acid | ETAC | Disulfide or two sulfhydryls, same or different | Various |

TABLE 2-continued

Representative "A"'s as Chemically Reactive
Moieties and conversions to the most preferred reactive groups for
the conversion to "A" to react with a Biologically
Active group, or a diagnostic group or a therapeutic group

| A (chemically reactive moiety) | React with A → | A (chemically reactive moiety) | Reacts with | Bond formed in A (biologically active group) |
|---|---|---|---|---|
| Aryl amine | DCTI | Aryl-ITC | Amine | amide |
| Alcohol | DSC | Active carbonate | amine | carbamate |
| Carboxylic acid | NHS, TFP, etc. | NHS ester, TFP ester, etc | amine | amide |
| Carboxylic acid | Hydrazine, PG-hydrazide | Hydrazide | Carbonyl (aromatic, control EDG's and control the cleavability of product | Hydrazone |
| Various | Acetylide | acetylide | Azide, e.g., in unnatural aa in protein | Triazole |

Reference: This a key general reference to these and other chemistry options for conjugation. Bioconjugate Techniques, Greg T. Hermanson, Elsevier, 2008; ISBN 978-0-12-370501-3. Also, "Biorthogonal Chemistry: Fishing for Selectivity in a Sea of Functionality, Ellen M. Sletten and Carolyn R. Bertozzi, *Angewandte Chemie Int. Ed.,* 2009, 48, 6974-6998.

Building Branched Constructs

Branched constructs can be synthesized from any molecular core, especially that have a 1:3, 1:2, or 1:1:1 arrangement of reactive functional groups as part of the chemically reactive groups on BC. The Tris core, amino-Tris(TBE)$_3$, shown below, is an example of a 1:3 arrangement, while aspartic acid (Asp), glutamic acid (Glu), tyrosine (Tyr) and lysine (Lys) have 1:2 arrangement. Tyrosine (Tyr) cores can be 1:1:1, but can be converted to 1:2 and in this invention provides a novel core for making an AC. There are other amino acids, natural and unnatural that can be used in this disclosure as well. (Ref.: A. J. de Graaf, et al., "Nonnatural Amino Acids for Site-Specific Protein Conjugation," Bioconjugate Chemistry, 20(7), 1281-1295 (2009). Thus, amino acids also are useful as a molecular core for synthesizing the branched dPEGs disclosed herein. Peptide templates provide further elaboration of functionality in the cores. Thus, the novel branched dPEGs constructs disclosed herein will be built from the following cores: tris, amino acids, and peptide dPEG templates, where the amino acid or other AC's can be the same or different, are optionally separated by a ∿∿∿∿ that is a dPEG.

The disclosed branched dPEG constructs can have the following uses, inter alia:
  Functional modifiers for conjugation to biologics to effect and control biodistribution and general pharmokinetic ("PK") properties of the biologics;
  Multifunctional branched dPEGs (i.e., carrying combinations of modifiers, and drug and therapeutic agents to control imaging, assay and drug delivery options
  Have the optional effects of reducing protease activity, toxicity and immunogenicity. The discrete and singular nature of the constructs and the chemistry incorporable has the ability to match the growing control in protein engineering, e.g., in controlling this properties site specifically.

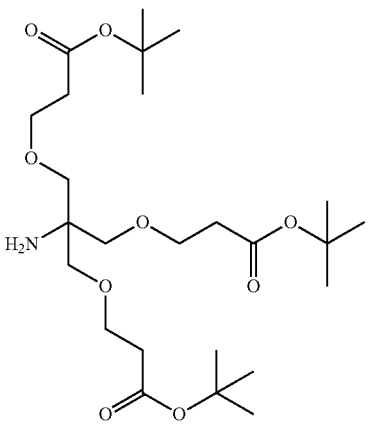

Tris BC; Amino-Tris(TBE)₃ as example of a 1:3 Core

1:3: Reference: G. R. Newkome, and C. Shreiner, "Dendrimers Derived from 1→3 Branching Motifs," Chemical Reviews, 110, 6338-6442(2010).

dPEG Branched Constructs: The Story

The very long and large MW linear polymeric PEGs are highly flexible and can take on many conformational forms all in the same application, depending on its local physical environment and this could lead to a range of changing influences on an application, limiting or eliminating design control of these polymeric constructs. This is a limitation stacked on to the others already described above.

Therefore, the disclosure includes a construct that is not only discrete in MW, but also branched and, therefore, more stable/rigid, and creating a larger apparent size with lower MW materials, and with numerous other design variables, such as terminal charge, would be a very significant contribution to the art of biological modification technologies. In addition, having a more rigid conformation should limit the dynamics of many conformations within an application. That is what we have done, as well as having the ability to incorporate other important components via the

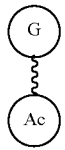

and dPEG spacers for enhancing or enabling a wide range of diagnostic and therapeutic or combined applications!

Additionally the rigidity of the construct should not allow it to wrap onto or around the biologically reactive group, as is often the case with the long polymeric PEGs, and most often lowering or eliminating the biological activity of the same. As well the branched dPEG constructs can actually cover a predictable part of the biologic with the branched dPEG construct, e.g., a protein, and thereby control better the coverage where issues such as immunogenicity are important to minimize.

And as one can see from the simple models, the potential rigid size of the branched dPEG constructs can appear to be very, very large, with a 50 kD Fab' as "A" and size reference. The serum half-life of a biologic is often controlled by the radius in the kidney and a MW in the range of 60-70 kD. Obviously the shape and flexibility of the construct are critical variables.

Figure 45:
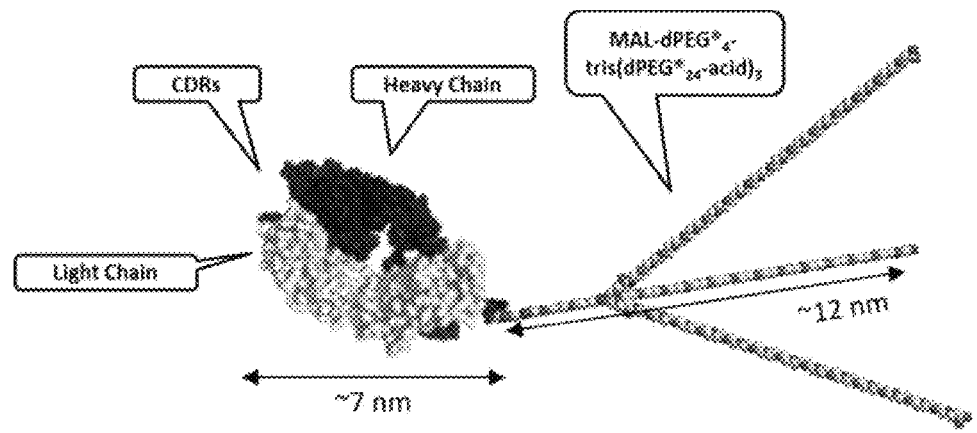
FIG. 45 is a 3D Structural model of Fab'HIV 4E10-MAL-dPEG$_4$-Tris(-dPEG$_4$-CO$_2$H)$_3$.
Figure 46:
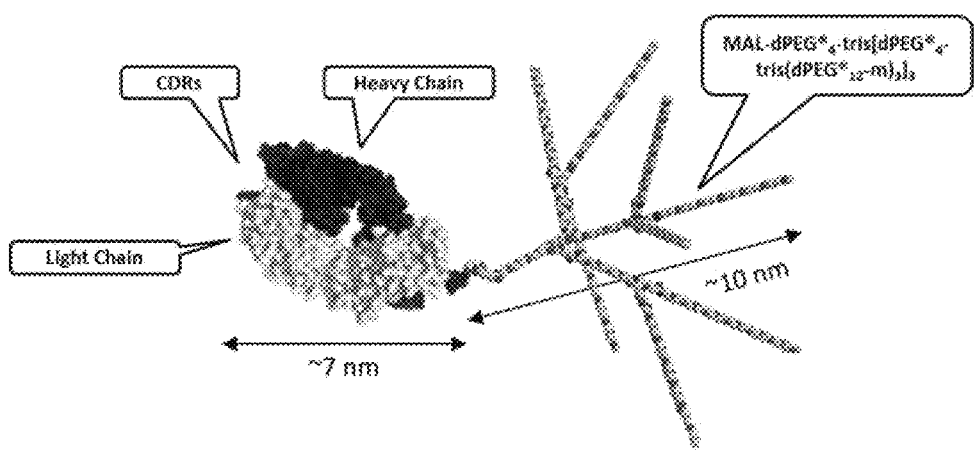
FIG. 46 is a 3D Structural model of Fab'HIV 4E10-MAL-dPEG$_4$-Tris(-dPEG$_4$-Tris(-dPEG$_{12}$-m)$_3$)$_3$.

A 3D Structural Model of Fab'HIV 4E10-MAL-dPEG₄-Tris (-dPEG₂₄-CO₂H)₃ is seen in FIG. 45. A 3D Structural model of Fab'HIV 4E10-MAL-dPEG₄-Tris(-dPEG₄-Tris(-dPEG₁₂-m)₃)₃ is seen in FIG. 46. One can see, how the size of this "rigid" construct can be controlled through the length of the ∿∿∿∿ and ▬▬▬, and the nature of its terminal group. Optimally, the length of ∿∿∿∿ in the general

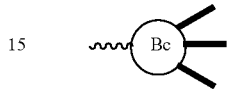

is larger than dPEG₄, up to about dPEG₂₄, but can be as high as dPEG₄₈, optionally with other groups in the ∿∿∿∿ including a cleavable group as well as a type of

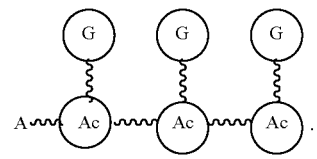

The solid line ▬▬▬ is optimally primarily or only a dPEG$_x$ with a terminal group, neutral or charged, and where x is greater than at least 7 or 8, and up to x of about 72.

By contrast to the polymeric PEGs, where the standard PEG is 40 kD, for modification when incorporated site specifically, whereas in the data we show below shows that we can see the impact of a MW less than 3000 (3 kD) on the serum half-life as low as, trending much longer by changing both the size and the terminal charge, up to about 8000 (8 kD), with unexpected effects shown by the terminal charge on apparent size and biodistribution. Anticipating that this can be controlled at larger sizes or with multiple site specifically, optionally different constructs, branched dPEG constructs.

All of the commercial products that have been approved by the FDA have a large linear PEG of at least 10 or 20 kD, but currently and most typically is the use of a 2 branched, off of a lysine core, of 20 kD polymer PEG each, for the 40 kD polymeric construct. This is essentially a bis-20 kD linear construct, though there are some subtle differences. The paradigm seems well entrenched that this is what MW and "size" it requires to give adequate serum half-life in general application to proteins of about 50 kD or less.

Some key conventional PEGylation references include:
1. Francesco M. Veronese, Ed., *PEGylated Protein Drugs: Basic Science and Clinical Applications*, 2009, Birkhauser.
2. David Filpula and Hong Zhao, "Releasable PEGylation of proteins with customized linkers", *Advanced Drug Delivery Reviews* 60 (2008) 29-49.
3. Francesco M. Veronese and Gianfranco Pasut, "PEGylation, successful approach to drug delivery", *Drug Discovery Today*, 10 (21), 1451-1458 (2005).
4. Jung Seok Kang, Patrick P DeLuca and Kang Choon Lee, "Emerging PEGylated drugs," *Expert Opin. Emerging Drugs* (2009) 14(2):363-380.

5. Yanling, L., et al., "Effect of PEGylation on the Solution Conformation of Antibody Fragments," *Journal of Pharmaceutical Sciences*, 97(6), 2062-2079(2008).
6. C. S. Fishburn, "The Pharmacology of PEGylation: Balancing PD with PK to Generate Novel Therapeutics," *Journal of Pharmaceutical Sciences*, 97(10), 4167-4183 (2008).

Experimental Design Concept:

Therefore, the concept of a branched dPEG construct is to incorporate shorter linear dPEGs onto a branched core, from about $dPEG_7$ to about $dPEG_{48}$, but not limited in some cases, in a moderately branched construct, with the number of branches in the ranges of, for example, 2, 3, 6, 9, 12 or 27, 54. The branched dPEG constructs are chemically attached to a biologically active group, in this case a Fab', thereby testing the idea that having more compact and more rigid structures, potentially due to the steric restraints of the dPEGs to fold onto themselves, and the high degree of hydrogen-bonded water, making this interaction potentially more thermodynamically favorable and more stable, would create its own more rigid and definable environment as is possible with the long linear polymeric PEGs. The latter are highly flexible and will change and adapt to a much greater extent. And as well, these branched dPEG constructs would NOT have the capability to wrap onto themselves or around the biologically active groups to which it or they are attached, as do the linear polymeric PEGs, but rather retain their rigidity as a consistently sized construct on the surface, while protecting, and not impeding the activity of the protein.

Additionally, with the ability to build discrete single molecule constructs, there was and is the option of, and in the place of the methoxy, to place a charged terminal group, or a group with properties that on the termini of the branches to modify its properties to aid the protein or other biological in optimally performing its function. E.g., in these data, a negative charge in the form of a carboxyl group was placed on the termini of one of the 3-branched constructs with the idea of specifically causing this construct to stay out of the kidney, which itself is negatively charged. The negative charges may also repel each other and thereby create a larger size or further give the branched dPEG construct its rigidity. There are many God created compounds that stay in the body that were designed with the negative charge to remain in the blood and not be released quickly from the body! This powerful effect of the negative charge has been shown for the protein streptavidin in the reference listed (Ref.: D. S. Wilbur, et al., "Streptavidin in Antibody Pretargeting. 3. Comparison of Biotin Binding and Tissue Localization of 1,2-Cyclohexanedione and Succinic Anhydride Modified Recombinant Streptavidin," Bioconjugate Chemistry, 13, 611-620(2002)).

An added feature of this model, is that with that with the highly unexpected results and as referenced above for a diabody developed by Avipep (below), the single molecule nature of the branched dPEG constructs make the incipient biological and other constructs completely characterizable, even if a random substitution chemistry is chosen. There may be cases of molecular biology or economics that dictate a random substitution, but with the branched dPEG constructs giving dramatic results at smaller MWs compared to the conventional polymeric PEGs, this could provide a very viable option to a completely controllable process and characterizable product.

For our first experiments we chose to look at Fab' conjugates with the branched dPEG constructs with which to gather in vivo data. The Fab' fragment were chosen because they are known to have very short serum half-lives due to their approximately 50 kD size, usually less than 30 minutes. The first experiments were for a Mab 107-1A4 directed to the prostate specific antigen, and our imaging detailed PK studies are with the Fab' conjugates of CC49 which is specific for TAG-72.

In Vivo Experiments with 107-1A4 Mab Fab'-Branched dPEG Construct Conjugates.

Fab' conjugates of Branched compounds: The Fab' fragment, in this case of the monoclonal antibody 107-1A4, an IgG1 mAb, was conjugated to three branched dPEG constructs; a) $MAL-dPEG_4-Tris(-dPEG_{12}-m)_3$; to give: Fab'-A, b) $MAL-dPEG_4-Tris(-dPEG_{24}$ acid$)_3$ to give Fab'-B and c) $MAL-dPEG_4-Tris(-dPEG_4-Tris(dPEG_{12}-m)_3)_3$ to give Fab'-C (see Examples for details) and these were, a) compared via SEC (size exclusion chromatography), to compare their "sizes." This is at least one of many ways to compare and estimate sizes of proteins and protein conjugates. And the method chosen to compare these conjugates in this application. In this case the Fab'-X conjugates were also made from the Fab' of the commercial monoclonal antibody Erbitux.

b) And the biodistributions of Fab'-A-C were compared a single time point in mice (see details below in the Examples) that had not been treated with tumor (non-targeted), but labeled with $^{125}I$ and $^{131}I$ so the BD and PK of this were not looked at with a target as with the NIH and Avipep examples presented herein. These experiments will be performed and with expectations to surpass those of the linear dPEG constructs in a targeted model.

Rationale for choice of Fab': The Fab' fragments are generated from two different whole antibodies from a standard process shown in the figure below, shown for the fragmentation of the whole CC49 murine antibody. The choice of the Fab' was twofold, a) to use a protein that, was significantly smaller in size (Fab' fragments are generally about 50 kD) lower than the 65-70 kD glomerular cutoff and given the size of the branched constructs (2.3 kD to 7.8 kD) (the range of the 4 branched dPEG constructs used), these conjugates are ALL well below what is considered minimal for using a PEG for increasing serum half-life, typically at least 20 kD even for Fab', but typically the 2λbranched polymer PEG of 40 kD is chosen. The F(ab')$_2$ is used as a "high" MW/size standard for the SEC data b) Taking advantage of the single site of attachment for the Fab', at the hinge —SH (sulfhydryl), hence putting on, just ONE branched dPEG construct per antibody so as to have a MW to assign to the construct. And which for future targeting experiments is also away from the active site of the antibody. It can also establish a control of experiments looking at the impact of binding and targeting in a potentially simpler random conjugation options.

Structures of the branched dPEG construct used are shown here.
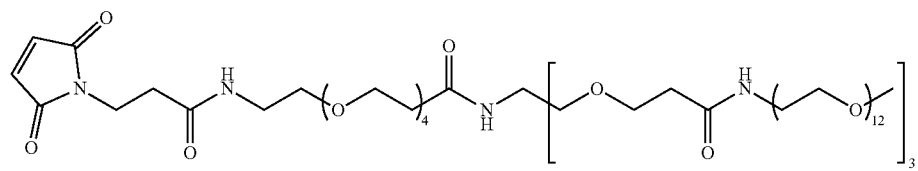
Molecular Weight: 2360.75; single compound
MAL-dPEG$_4$-Tris(-dPEG$_{12}$-m)
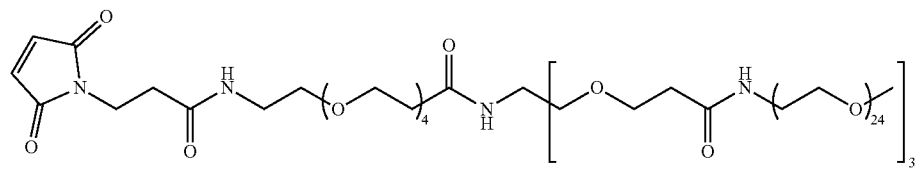
Chemical Formula: $C_{178}H_{346}N_6O_{86}$
Molecular Weight: 3946.64
MAL-dPEG$_4$-Tris(-dPEG$_{24}$-m)
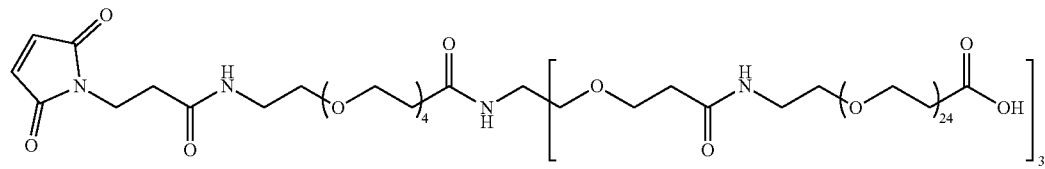
Chemical Formula: $C_{184}H_{352}N_6O_{92}$
Molecular Weight: 4120.75
MAL-dPEG$_4$-Tris(-dPEG$_{24}$-CO$_2$H)
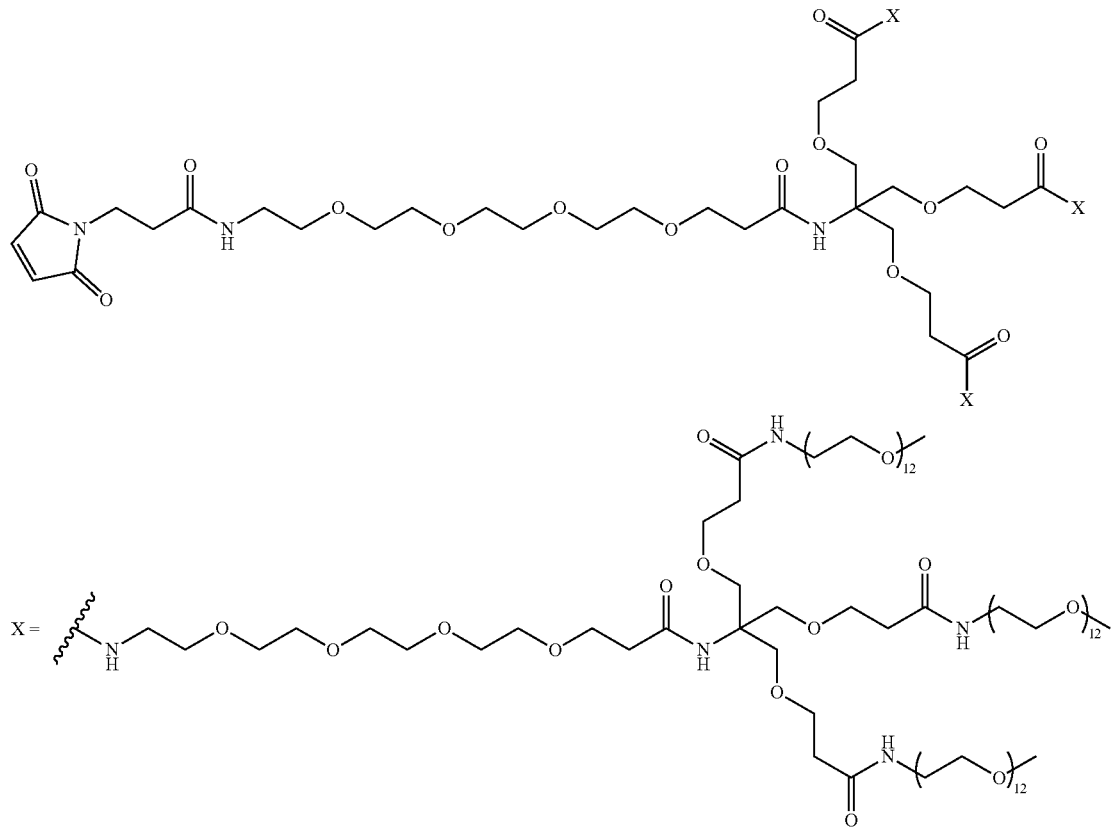
$C_{328}H_{634}N_{18}O_{155}$
Mol. Wt.: 7310.57
MAL-dPEG$_4$-Tris(-dPEG$_4$-Tris(-dPEG$_{12}$-m)

The first three are three-branched dPEG constructs and the fourth, is a 9-branched dPEG construct. The single point attachment on all is a $dPEG_4$ (probably too short for the practical applications and made the synthesis more difficult than necessary).

The branches for compounds 1-4 are:

$MAL\text{-}dPEG_4\text{-}Tris(\text{-}dPEG_{12}\text{-}m)$: 3×m-$dPEG_{12}$ (termini neutral) MW=2,360.75

$MAL\text{-}dPEG_4\text{-}Tris(\text{-}dPEG_{24}\text{-}m)$: 3×m-$dPEG_{24}$ (termini neutral) MW=3,946.64

$MAL\text{-}dPEG_4\text{-}Tris(\text{-}dPEG_{24}\text{-}CO_2H)$:3×-$dPEG_{24}$-carboxyl (termini negative charge) MW=4,120.75

$MAL\text{-}dPEG_4\text{-}Tris(\text{-}dPEG_4\text{-}Tris(\text{-}dPEG_{12}\text{-}m)$: 9×m-$dPEG_{12}$ (termini neutral) MW=7,310.57

The Size Exclusion Data in shown in the following table.

SEC Results: The Fab' conjugates were obtained in high yields (81-99%). Comparison of SE-HPLC retention times for the Fab' conjugates [Rt=9.6 min (Fab'-1); 9.4 min (Fab'-2); 8.5 min (Fab'-3); 8.8 min (Fab'-4)] relative to Fab' and F(ab')2 [$R_t$=10.0 min & 8.6 min, resp.] provided data that indicated all of the effective Fab' sizes were increased, and that the carboxyl-terminated conjugate Fab'-3 had an apparent effective molecular size larger than $F(ab')_2$.

TABLE 3

| Compound | Retention time SE-HPLC | Molecular Weight |
|---|---|---|
| Fab' | 10.0 min | 50,000 (endron.) |
| Fab'-1 | 9.6 | +2,360.75 |
| Fab'-2 | 9.4 | +3,946.64 |
| Fab'-3 | 8.5 | +4,120.75 |
| Fab'-4 | 8.8 | +7,832.90 |
| F(ab')$_2$ | 8.6 | 100,000 (endron) |

It is clear that the result for $MAL\text{-}dPEG_4\text{-}Tris(\text{-}dPEG_{24}\text{-}CO_2H)_3$ is astonishing, given its low apparent MW, and as well it does not fall in line with the other conjugates, and with ONLY a MW of just over 4.1 kD to appear to be about 60 kD or more!! Hence, there is also something unique about the carboxyl terminated branched dPEG construct. We attempted to find a similar correlation of plotting chromatographic parameters as it done with the conventional PEGs, but there is something unique about having the charged terminal group, different from the discussion in the exiting art. In the case of the branched dPEG constructs there are additional considerations, one being the charge on the terminus of the modifying dPEG branched chain. This could also be applied in other embodiments using linear dPEG constructs as well into various parts of a biologically active group, as a way to control the apparent and large size of the final branched dPEG constructs.

The dramatic difference in the SEC properties between the various branched dPEG constructs with a neutral (methyl-/methoxy-) vs. the terminal charge is important in designing an apparently larger MW construct. This may be due to charge repulsion that locks in the rigidity of the construct, in addition to that inherent in the branched construct itself.

Below the charge also gives the clear option of IEC to purity the Fab' branched dPEG constructs when a size discriminating option is impractical or inefficient.

Further evidence of the unexpected increase in size is shown in the preparation of the CC49 Fab' conjugate the $MAL\text{-}dPEG_{12}\text{-}Tris(\text{-}dPEG_{12}\text{-}Tris(m\text{-}dPEG11)_3)_3$. In attempting to separate this conjugate, it co-eluted with the F(ab')2, and it was necessary to use ion exchange chromatography to separate these compounds!

As well, below in the PET/CT in vivo studies with the CC49 Fab' branched dPEG constructs, the CC49 Fab-MAL-$dPEG_{12}\text{-}Tris(\text{-}dPEG_{24}\text{ carboxyl})_3$ MW 46endron . . . 55 kDa) actually cleared more slowly than did a $CH_2$ domain deleted whole antibody, of 3E8, MW 46endron. 120 kDa).

Representative references to the issues of apparent size imparted by the conventional linear and two-branched PEGs and the inconsistencies in the art are shown here:

1. Mateja Kusterle, et al., "Size of Pegylated Protein Conjugates Studied by Various Methods," Acta Chimica Slovenia, 55, 594-601 (2008.).
2. R. D. Tilton, et al., "The Conformation of the Poly (ethylene glycol) Chain in Mono-PEGylated Lysozyme and Mono-PEGylated Human Growth Hormone," Bioconjugate Chemistry, 22(11), 2317-2323(2011).
3. David Filpula, et al., "Prolonged Circulating Lives of Single-Chain Fv Proteins Conjugated with Polyethylene Glycol: A comparison of Conjugation Chemistries and Compounds." Bioconjugate Chemistry, 1999, 10, 973-981.
4. Conan J. Fee, "Size Comparison Between Proteins PEGylated with Branched and Linear Poly(Ethylene Glycol) Molecules," Biotechnology and Bioengineering, 98(4), 725-731 (2007).
5. Conan J. Fee and James M. Van Alstine, "Prediction of the Viscosity Radius and the size Exclusion Chromatography Behavior of PEGylated Proteins," Bioconjugate Chemistry, 15, 1304-1313 (2004)
6. Mateja Kusterle, et al., "Correlations between in vitro potency of poly(ethylene glycol-protein conjugates and their chromatographic behavior," Analytical Biochemistry, 389, 27-31 (2009).
7. Mateja Kusterle, et al., "The Characterization and Potential Use of G-CSF Dimers and their Pegylated Conjugates," Acta Chimica Slovenia, 58, 1-8 (2011).
8. Pascal Bailon, et al., "Rational Design of a Potent, Long-Lasting. Form of interferon: A 40 kDa Branched Polyethylene Glycol-Conjugated Interferon alpha-2a for the Treatment of Hepatitis C," Bioconjugate Chemistry, 12, 195-202 (2001).
9. Mary S. Rosendahl, "A Long-Acting, Highly Potent Interferon alpha-2 Conjugate Created Using Site-Specific PEGylation," Bioconjugate Chemistry, 16, 200-207 (2005.). Site-specific with a variety of PEGs.
10. Hans Senn, et al., "Structural and Biophysical Characterization of the 40 kDa PEG-Interferon-alpha-2a and Its Individual Positional Isomers," Bioconjugate Chemistry, 16, 504 (2005).
11. Hans Senn, et al., "Structural, Kinetic, and Thermodynamic Analysis of the Binding of the 40 kDa PEG-Interferon-alpha-2a and Its Individual Positional isomers to, the Extracellular Domain of the Receptor IFNAR2," Bioconjugate Chemistry, 16, 518-527 (2005).

Biodistribution Results:

In the biodistribution study without a tumor target for this preferential locator, it was shown that the blood concentrations for Fab'-A, Fab'-B and Fab'-C were significantly higher (24.0-25.5% ID/g) than the Fab'-NEM blood concentrations (endron. 13% ID/g) at the 1-hour time point. Conversely, the results showed that kidney concentrations of the FaV-PEG conjugates (5-6% ID/g) were dramatically lower than the Fab'-NEM kidney concentrations (~24% ID/g).

Although it has been known for some time that Fab' conjugates of polyethylene glycol (PEG) have increased effective sizes and have longer blood half-lives than the non-conjugated Fab', conjugation of linear PEG molecules (5-6 kDa) can reduce the antigen binding (ref 1)]. Conjugation of a smaller linear conventional polymeric PEG-3400 to an anti-CEA diabody resulted in a "significant" improvement in kidney concentration over the non-conjugated diabody, but a concentration of 50% ID/g in kidney was still obtained (ref. b of a. Delgado et al. (1996) *British J. Cancer* 73, 175-182; b. "Improved Biodistribution and Radioimmunoimaging with Poly(ethylene glycol)-DOTA-Conjugated Anti-CEA Diabody," Lin Li, et al., Bioconjugate Chemistry, 17, 68-76 (2006)).

In the bar graph in FIG. 1 is shown the results of the untargeted biodistribution studies.

Fab'-A Fab' with MAL-dPEG$_4$-Tris(m-dPEG$_{24}$)$_3$
Fab'-B Fab' with MAL-dPEG$_4$-Tris(-dPEG$_{24}$CO$_2$H)$_3$
Fab'-C Fab' with MAL-dPEG$_4$-Tris(-dPEG$_4$-Tris(m-dPEG$_{12}$)$_3$)$_3$
Fab'-NEM=Fab' with N-ethylmaleimide (NEM)

What stands out initially is the kidney data and is totally unexpected given the small sizes of the branched dPEG constructs and contrasted to published data reported above for the anti-CEA diabody (of about the same size, maybe slightly bigger, than the Fab'-NEM control.

This kidney data more closely parallels a second example reported with Avipep's AVP04 diabody using 4× m-dPEG$_{24}$ on 4 separate dPEGylation sites designed as two disulfides in positions away from the diabody's epitopes. Also the size of the diabody and the Fab' are nearly the same (references below)! Whereas, we are looking at a non-targeted situation- and ONLY a SINGLE site of a branched dPEG construct. This 6-7% in the kidney reflects the normal blood flow in the kidney and not material going out and being trapped in the kidney. This again is contrasted to the example above with a linear 3.4 kDa linear polymeric PEG on the anti-CEA antibody that have very high kidney uptake. The branched dPEG constructs appear to have a unique design that counter and contrasts the limitations and complicated issues with even the short linear polymeric PEGs. This may be the rigidity making the branched dPEG construct look like water rather than PEG, a very "rigid" water due to the branched construct. There is data suggesting these single linear PEGs compete in the biology. (Ref.: L. Zhu, et al., "Real-Time Video Imaging of Protease Expression in Vivo," Theranostics, 1, 18-27(2011)).

The other data contrasting the Fab'-dPEG branched construct vs. the control Fab'-NEM are apparent, with high kidney, and much less in the blood especially. The differences within the biodistribution data for the three different dPEG branched constructs is within the error bars in all cases, so the next experiments need to look at a smaller protein onto which to conjugate the dPEG branched constructs in order to ascertain the full impact and contrast of the 3×m-dPEG$_x$ vs. a 3× carboxyl-dPEG$_x$ vs. a 9×m-dPEG$_x$ vs 9× carboxyl-dPEG$_x$ (and higher branched) terminated constructs, and how the details of the dPEG branched construct can be tuned to maximize the BD and PK needs of the targeting compound (antibody, protein, or other biological or nanoparticle with a targeting payload). This can be done as well with more than one branched dPEG construct as disclosed herein.

The biodistribution data for the other organs is typical of the presence of compound in the blood in those organs. E.g., with the lungs, which have large blood capacity, the blood levels are higher than in say the intestine.

Hence these data are unexpected with the branched dPEG constructs, and are consistent with further tumor targeting studies shown below with a different preferential locator. The small absolute size in MW of the branched dPEG construct giving these data makes these results highly unexpected. As we will show below, the binding activity of ALL the conjugates studied were identical to those of the Fab'-NEM control.

Avipep diabody, AVP04, references:
a. L. Li, et al., "Site-Specific Conjugation. of Monodispersed DOTA-PEGn to a Thiolated Diabody Reveals the Effect of Increasing PEG Size on Kidney Clearance and Tumor Uptake with Improved 64-Copper PET Imaging," Bioconjugate Chemistry, 22(4), 709-716 (2011);
b. Peter Hudson, "Engineered Diabodies for the Diagnosis and Therapy of Prostate and Ovarian Cancer, PEGS (Protein Engineering Summit), Boston, 2011, May 3, 2011;
c. Hudson, et al., "Immuno-conjugates and Methods for Producing Them." U.S. Patent Publication No. US 2012/0164068 A1, Jun. 28, 2012.

In related biodistribution studies using a metallo-peptide modified with either a linear dPEG or one of the disclosed branched discrete PEG constructs, (private communication), the linear discrete PEG dramatically increased liver uptake while the branched discrete PEG constructs lowered liver uptake while dramatically increasing plasma concentration. Thus, discrete PEG molecules can be used to direct drugs to and away from organs. Having terminal positive or negative groups is expected to aid in such efforts, based on data to date.

In Vivo Experiments Using CC49 Fab'-Branched dPEG Construct Conjugates:

CC49 Fab'-Branched dPEG Construct Conjugates:

The branched dPEG constructs with the maleimide, as the chemically reactive moiety, A:

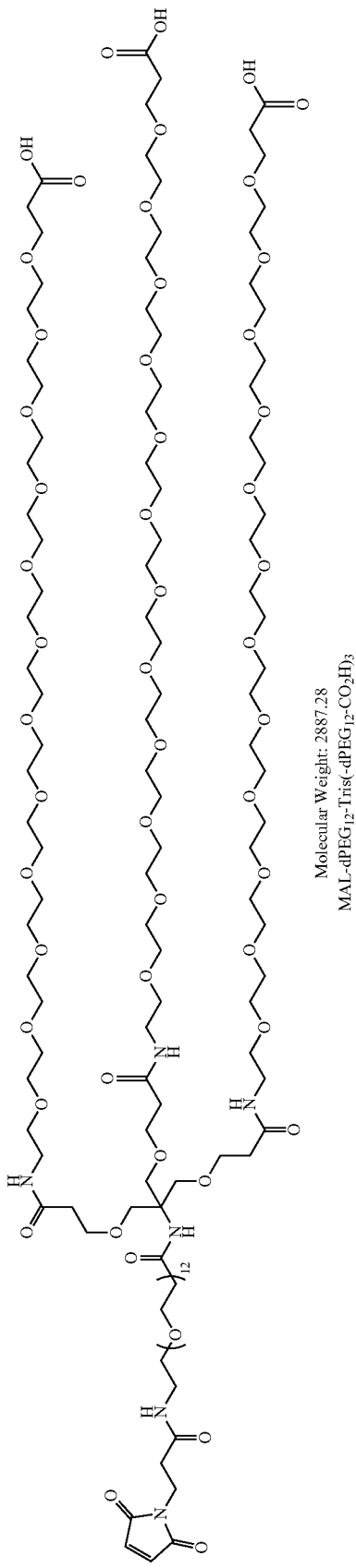
Molecular Weight: 2887.28
MAL-dPEG₁₂-Tris(-dPEG₁₂-CO₂H)₃
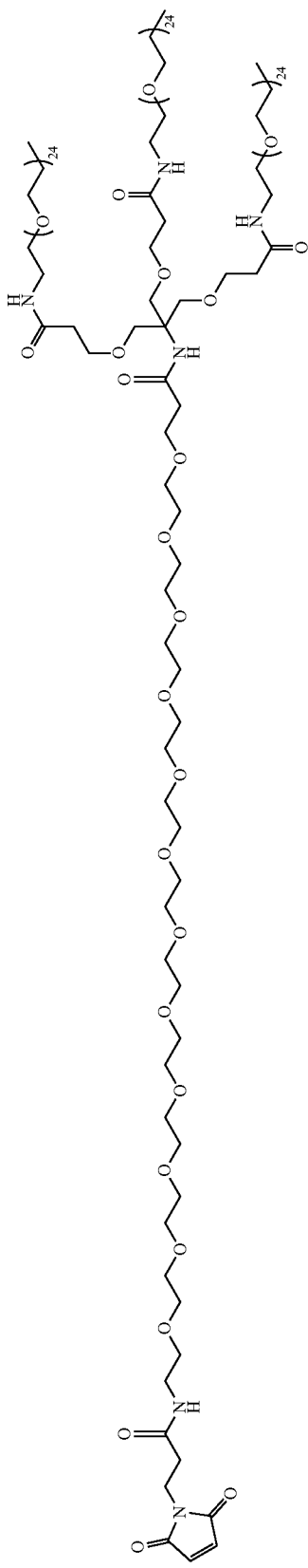
Molecular Weight: 4299.06
MAL-dPEG₁₂-Tris(m-dPEG₂₄)₃

-continued
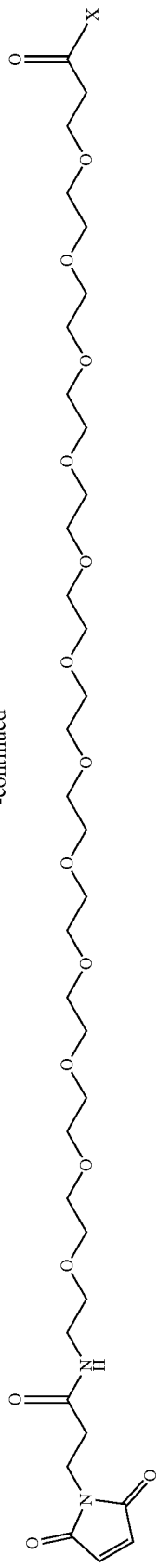
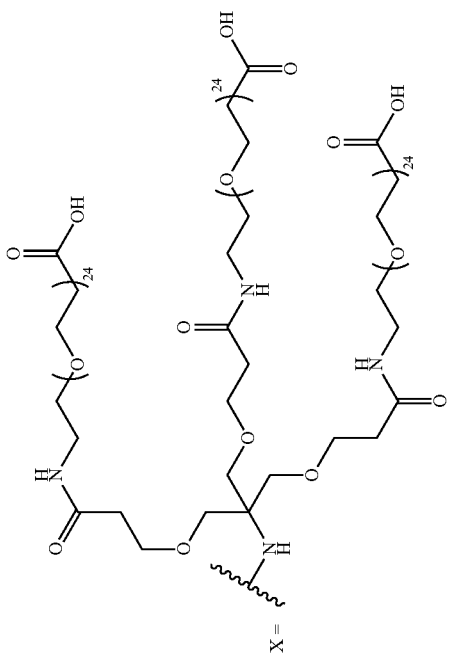
Molecular Weight: 4473.17
MAL-dPEG$_{12}$-Tris(-dPEG$_{24}$-CO$_2$H)$_3$ -continued
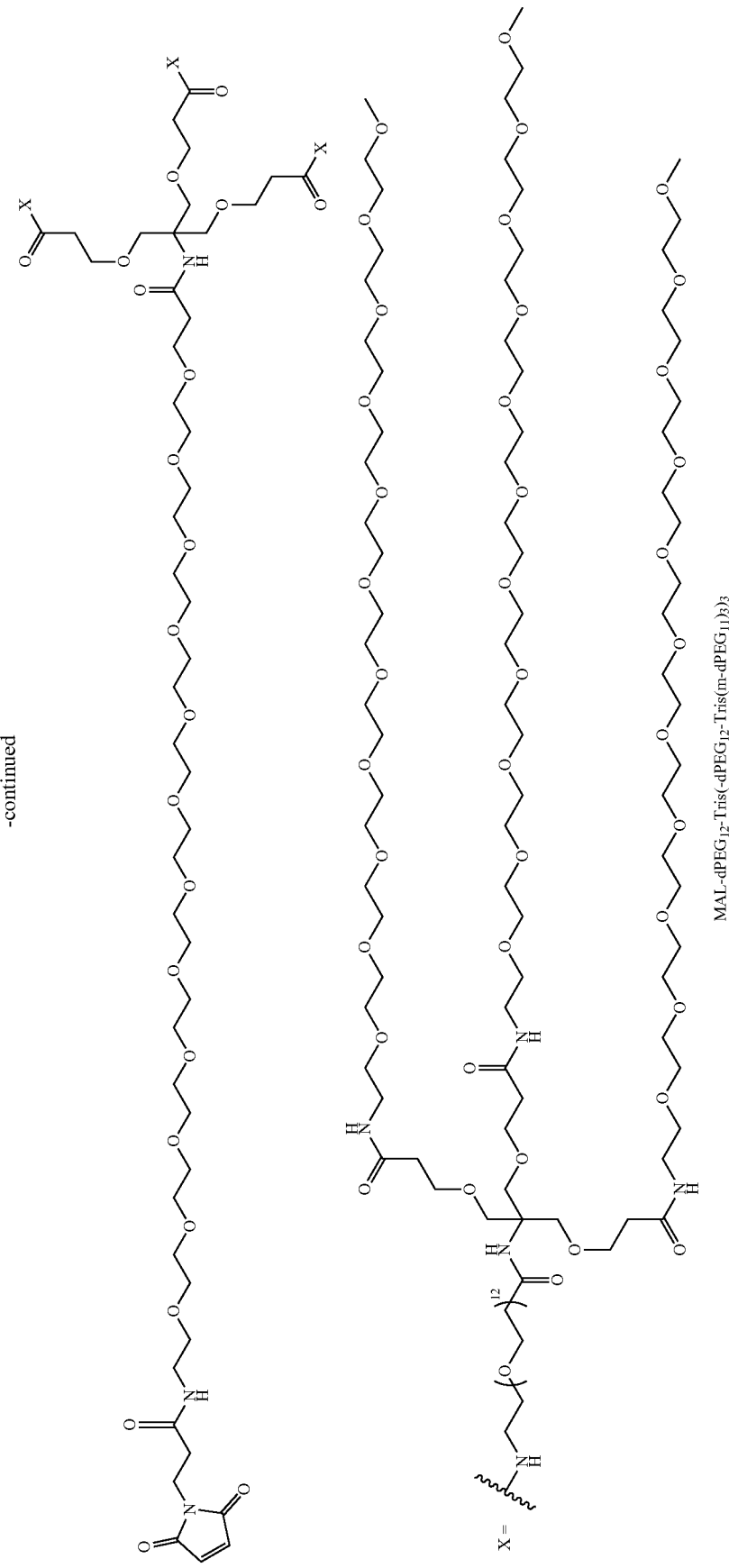
MAL-dPEG$_{12}$-Tris(-dPEG$_{12}$-Tris(m-dPEG$_{11}$)$_3$)$_3$ The process for making the CC49 Fab'-SH:
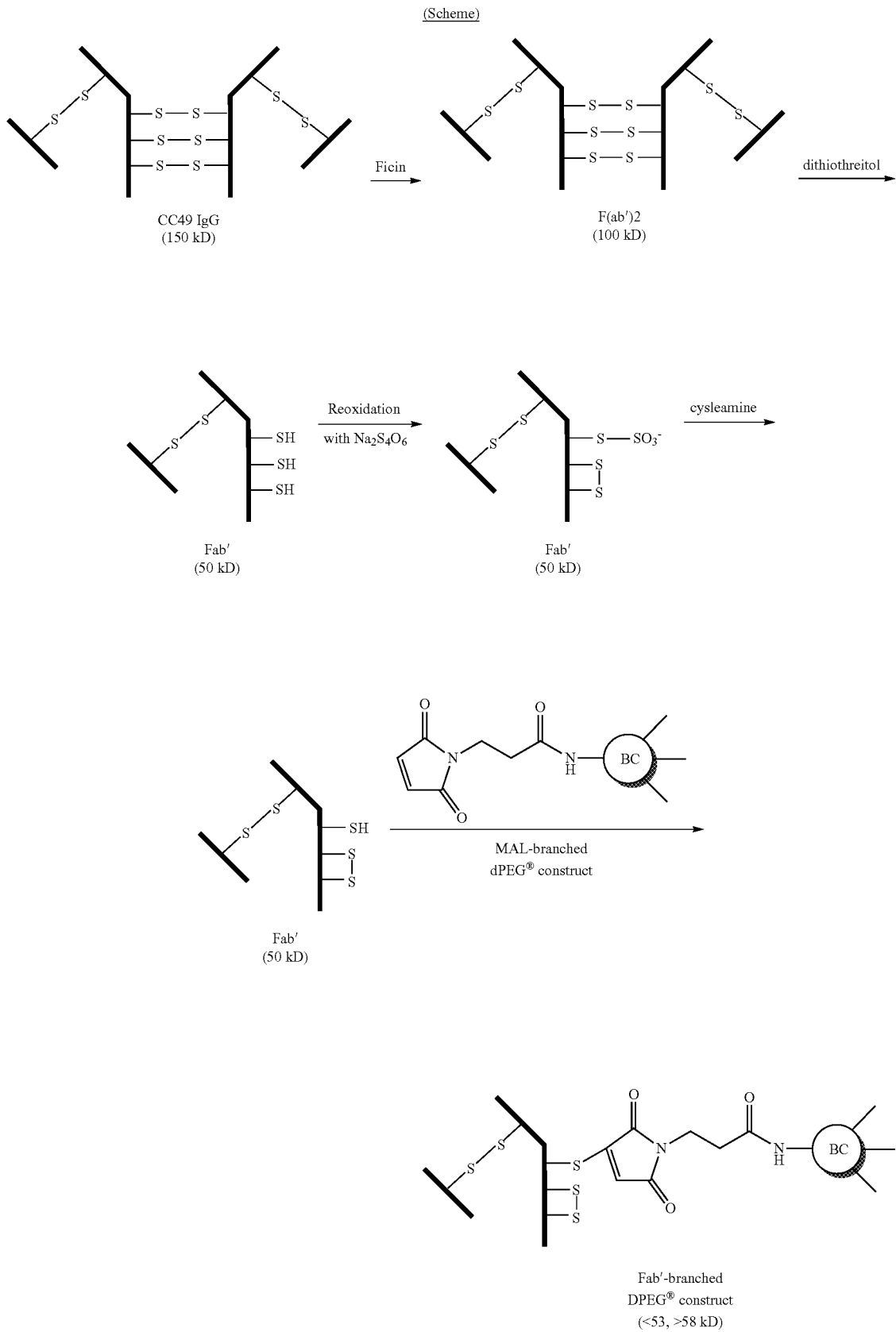

The CC49 Fab'-S-Branched dPEG Constructs:
CC49 Fab'-S-MAL-dPEG$_{12}$-Tris(-dPEG$_{12}$-CO$_2$H)$_3$
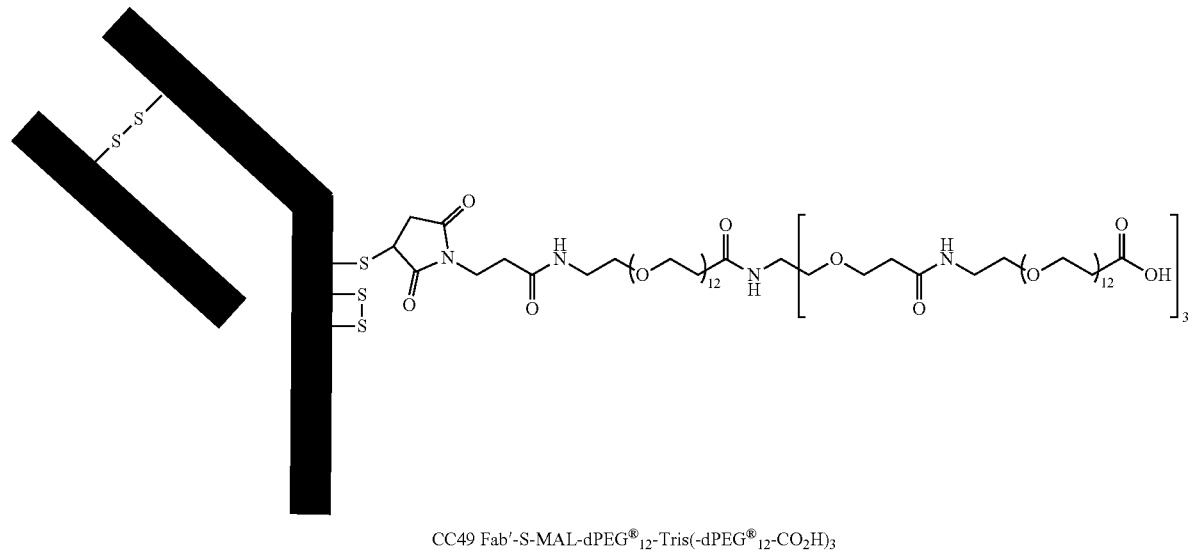
CC49 Fab'-S-MAL-dPEG®$_{12}$-Tris(-dPEG®$_{12}$-CO$_2$H)$_3$
CC49 Fab'-S-dPEG$_{12}$-Tris(-dPEG$_{24}$ CO$_2$H)$_3$
CC49 Fab'-S-MAL-dPEG$_{12}$-Tris(-dPEG$_{24}$-CO$_2$H)$_3$
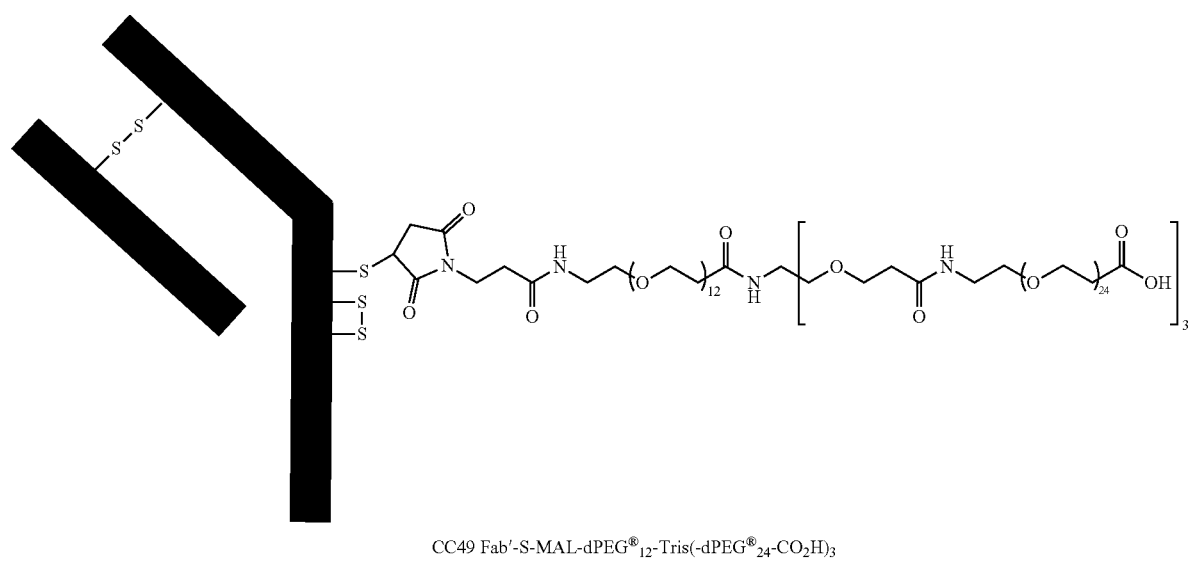
CC49 Fab'-S-MAL-dPEG®$_{12}$-Tris(-dPEG®$_{24}$-CO$_2$H)$_3$ CC49 Fab'-S-MAL-dPEG$_{12}$-Tris(m-dPEG$_{24}$)$_3$
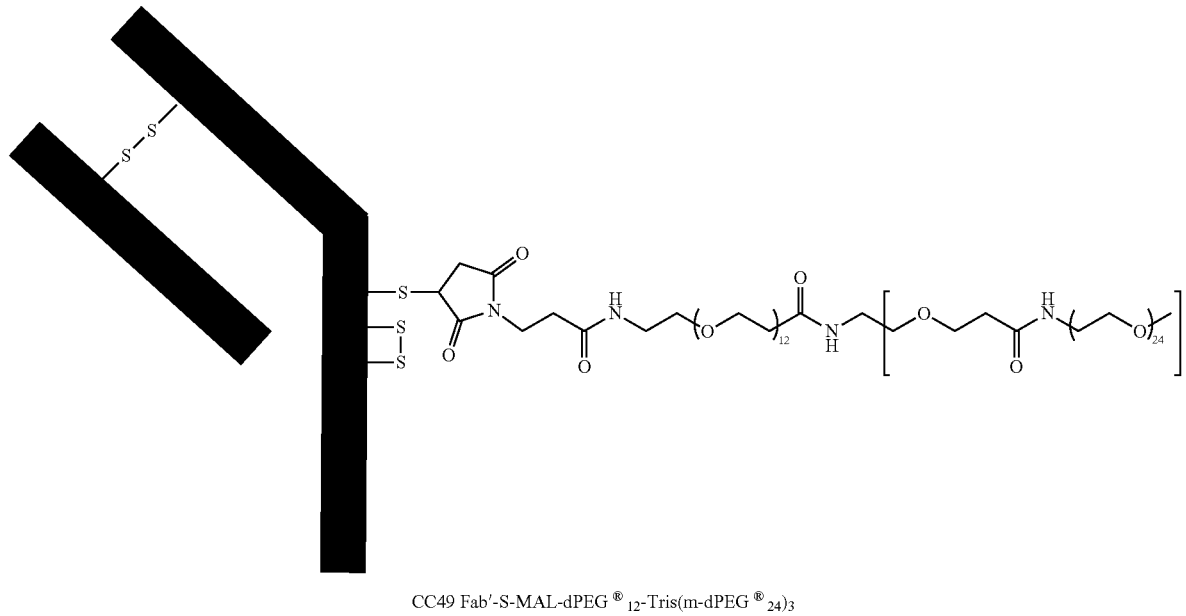
CC49 Fab'-S-MAL-dPEG$_{12}$-Tris(m-dPEG$_{24}$)$_3$
CC49 Fab'-S-MAL-dPEG$_{12}$-Tris(-dPEG$_{12}$-Tris(m-dPEG$_{11}$)$_3$)$_3$
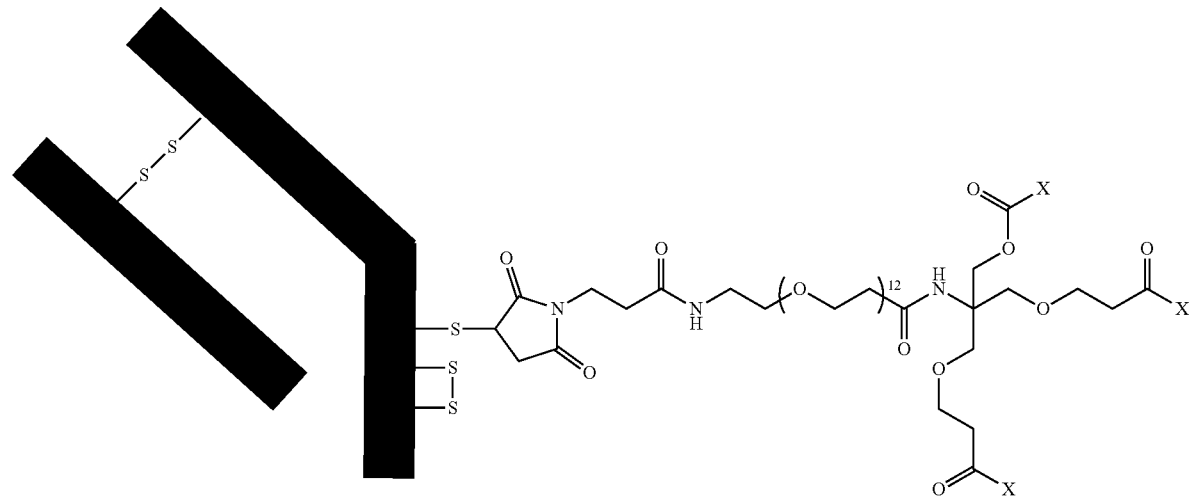
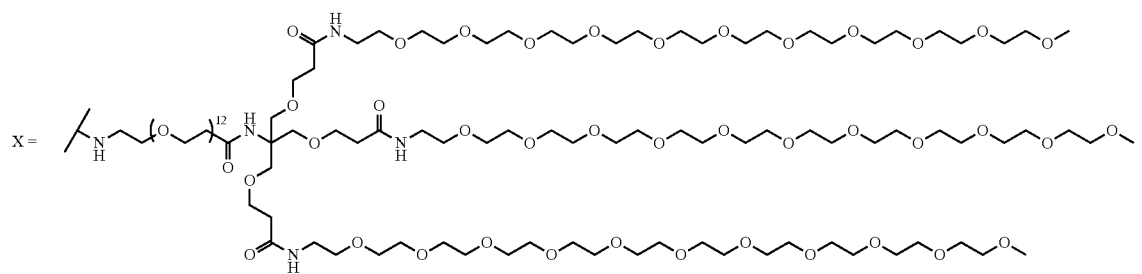

CC49 Fab'-S-NEM

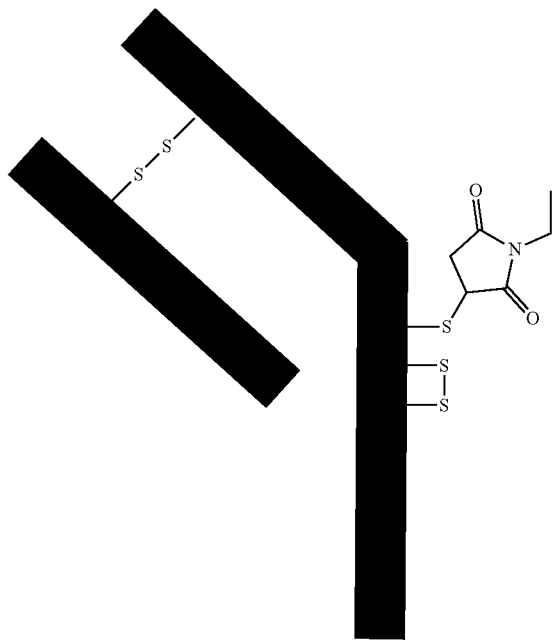

Fused PET/CT images of mice were taken of different antibody conjugates to determine their ability to localize implanted tumors (see Examples below). In particular, CC49 Fab'-S-NEM control was compared to CC49 Fab'-dPEG$_{12}$-Tris(dPEG$_{24}$ carboxyl)$_3$, the CC49 Fab' MoAb modified with one of the disclosed branched dPEGs containing terminal carboxyl groups. At 24 hours post injection, the NEM conjugate mice evidenced a lot of background (see FIGS. 37-40), whereas the Acid branched dPEG MoAb localized the tumors well with very little background showing up. At 48 hours post injection, only tumors were seen in the Acid branched dPEG MoAb mice.

In a different study, PK data was taken on normal athymic mice injected with: mCC49 Fab'-dPEG12-Tris(dPEG12-Tris(m-dPEG11)$_3$)$_3$, mCC49 Fab'-dPEG12-Tris(dPEG24-acid)$_3$, mCC49 Fab'-dPEG12-Tris(m-dPEG24)$_3$, and mCC49 Fab'-dPEG12-Tris(dPEG12-acid)$_3$. The Fab-dPEG-D: mCC49 Fab'-dPEG12-Tris(dPEG12-Tris(m-dPEG11)$_3$)$_3$ showed the least rapid clearance. The mCC49 Fab'-dPEG12-Tris(dPEG24-acid)$_3$ and the mCC49 Fab'-dPEG 12-Tris(m-dPEG24)$_3$ were very similar in their clearance over time. The mCC49 Fab'-dPEG12-Tris(dPEG12-acid)$_3$ had early higher percent injected dose that dropped off rapidly to about 4 hours (see FIG. 42).

From FIG. 1 and other similar data, the conventional polymeric PEGylation reagents do not show a trending towards an increase in PK until at least a MW of 10 kD. It is clear from Table 3 that there is a trend towards increasing serum half-life at a MW of just over 2 kD and increasing dramatically, even at a MW of just 8 kD, well below the point where the conventional PEGylation begins to show an effect. Generally, the practice is to use these polymeric constructs at MW of 40 kD.

A competition assay was run with a series of CC49-Fab'-dPEGs. In this run, single aliquots of each compound were assayed. The affinity constant of Fab'-NEM is defined as 1.0. From the data, it is that clear that the Relative Affinity Constant, which is a measure of how well the Fab' binds to its molecular target, is minimally impacted by conjugation to branched dPEG products. Table 14 displays the results for Fab'-dPEG12-Tris(dPEG12-acid)$_3$, Fab'-dPEG12-Tris(m-dPEG24)$_3$, and Fab'-dPEG12-Tris(dPEG12-Tris(m-dPEG11)$_3$)$_3$.

Branched dPEG Constructs as Substantially Pure SINGLE Compounds (and the Process Optimization to Get there) Vs. The Mixtures of the Conventional Polymeric PEGs!

Keys in this disclosure are the methods for making branched dPEG constructs that are substantially pure compositions. These are built from and comprised of the single compounds components of the linear dPEG components that are synthetically reacted together in combinations currently disclosed or using chemistries known in the art to make these substantially pure branched dPEG constructs. (Ref. U.S. Pat. No. 7,888,536). The single component nature of the component linear and branched core dPEGs species or moieties allows for the building of increasingly complex branched dPEG constructs as disclosed in this application as the substantially pure constructs. These constructs depending on the total number of component branches can range for a purity of about 60% to 99% or higher.

In making the branched dPEG constructs the goal is to begin with essentially pure components with respect to the oligomer purity. The processes for making these can be controlled to where it can be up to greater than 99%. When it is at this level of purity, than the branched dPEG constructs and their ultimate oligomeric purity is controlled by the efficiency and effectiveness of each step and the purification as is known in the art of organic chemistry. However when the oligomeric purity is less then 99%, then the purity of the final construct will be controlled largely by that purity, though no all construct will be necessarily from the same oligomeric pure batch. But for instance, if for a 4-branched dPEG construct built from component parts that are 98% pure alone, the oligomeric purity of the final construct would still be 92%. As compared to the conventional polymeric PEGs, the discussion of purity is nearly meaningless, but it is noted briefly below as contrast to the novel nature of the branched dPEG constructs disclosed herein and the methods for their preparation.

Figure 2:
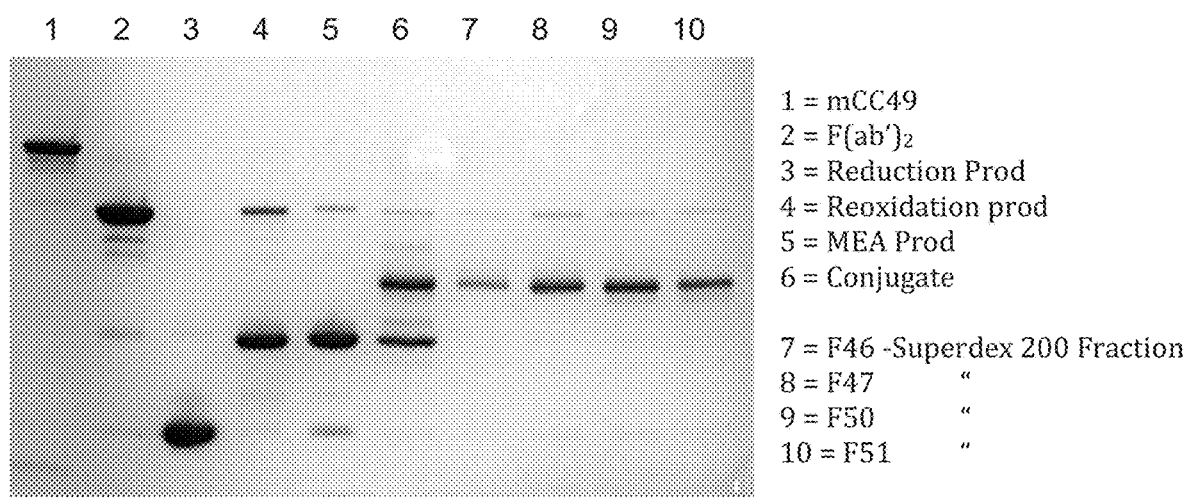
FIGS. 2 and 3 display SDS-PAGE gels for Reaction Intermediates, Conjugate, and Superdex 200 Fractions for CC49 Fab'-dPEG$_{12}$-Tris(dPEG$_{24}$ acid)$_3$, CC49 Fab'-dPEG$_{12}$-Tris(dPEG$_{12}$ acid)$_3$ Acid, and the mCC49Fab-NEM control.

It is important to briefly contrast this to the conventional polymeric PEGS. To make a simple point, let us look as some highly hypothetical mixtures, very "pure" by polymer standards. Also, in the art, the term "monodispersed" is used to indicate a single component; however, these are still HIGHLY complex mixtures of approximately 20-25 and 30-40 for linear 1000 and 3400 MW polymers. Hence, this term is highly misleading when used in the art. (Ref. Example of a monodisperse polymeric PEG, PDI (polydispersity index)=1.01, FIG. 2 in reference, Y. Li, et al., "MALDI-TOF Mas Spectral Characterization of Polymers Containing an Azide Group: Evidence of Metastable Ions," Macromolecules, 43(14), 6225-6228(2010)).

The following, again, are very simple and completely hypothetical examples of the complexity imparted by just a linear polymer, and exacerbated by building these into branches! Remembering that with a single component linear dPEG component, the final branched dPEG construct is substantially pure and through the use of the taught methods can be essentially a single component.

For a simple mixture of just 3 components in a 3 branched. The most prominent component would have a "purity" of less than 50%, the other two making up the balance. To take a three-component mixture to a 3-branched, the final mixture would now have 7 components. For a more realistic monodisperse with a linear component of about 1000, with "only" 20 components, the final 3 branched would have at least 60 components! And this is for a so-called "monodisperse" system.

Another simple example of having just 5 components and converting this into a more typical 4 branched construct, which is preferred in this disclosure in some cases, would in this highly hypothetical polymer give a combined mixture in the 4 branched of 17 components. Hence the purity of a single component would likely be less than 6%.

From this simple analysis of the "purity" of the polymeric PEGs, it is apparent that there are hugely difficult characterization issues, but additionally the insoluble issue of reconciling the range of MW leading to a large range of PK and BD properties imparted by this huge mass of different biologically active agents all built in by the range of components in the polymer mixture. This does not address the primary issue on polymerization, which is the challenge of mixture process reproducibility.

Figure 14:
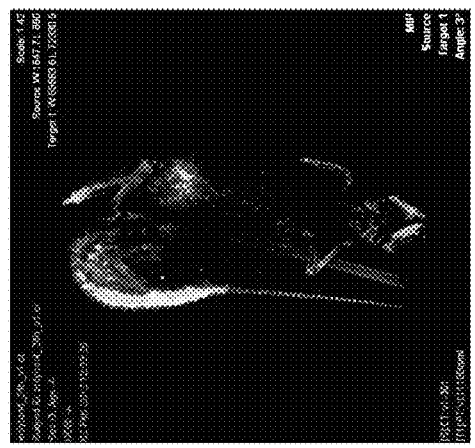
Figure 15:
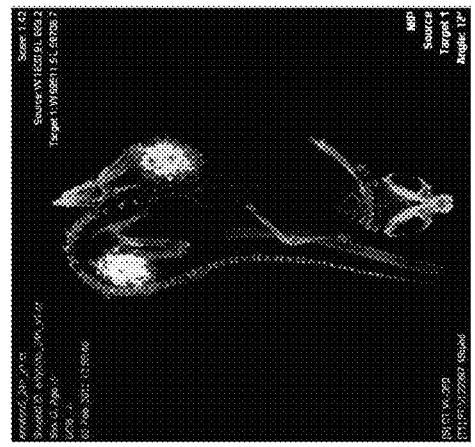
Figure 16:
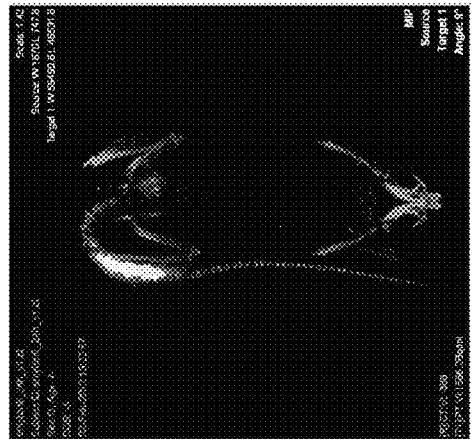
Figure 17:
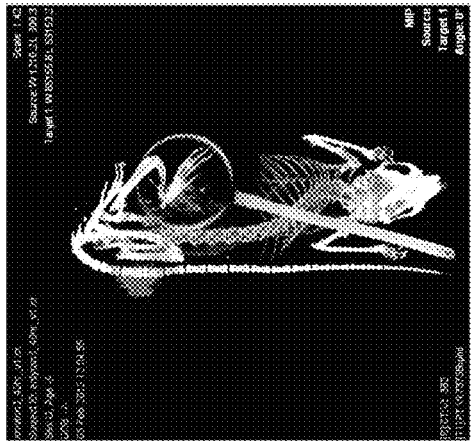
Figure 18:
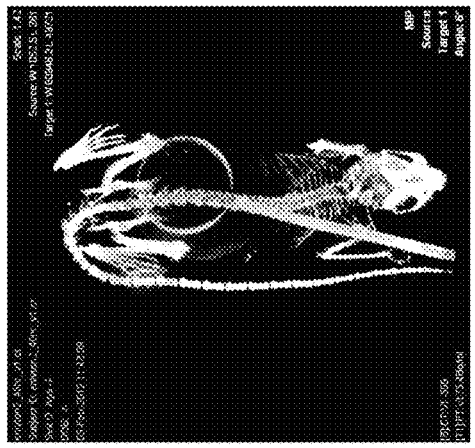
Figure 19:
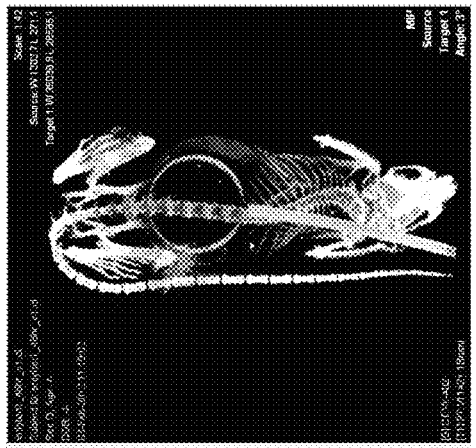
Figure 20:
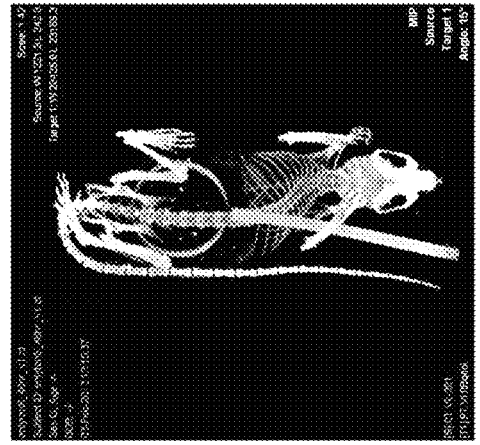
Figure 21:
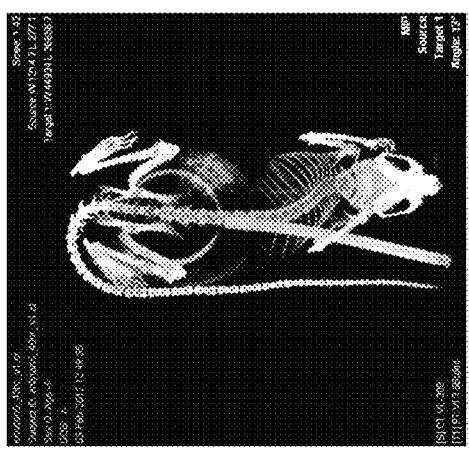
Figure 22:
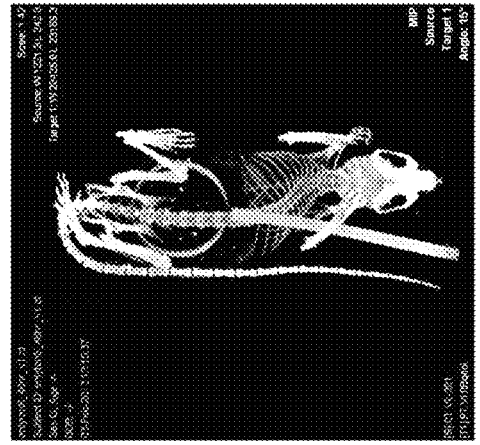
Figure 23:
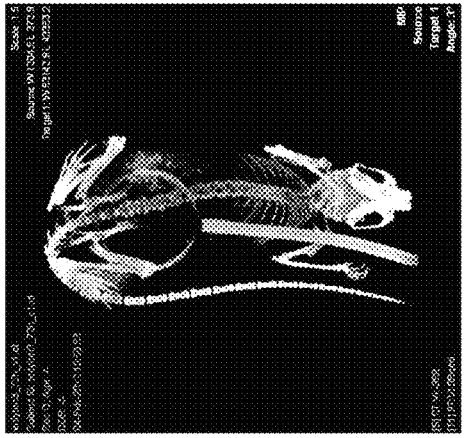
Figure 26:
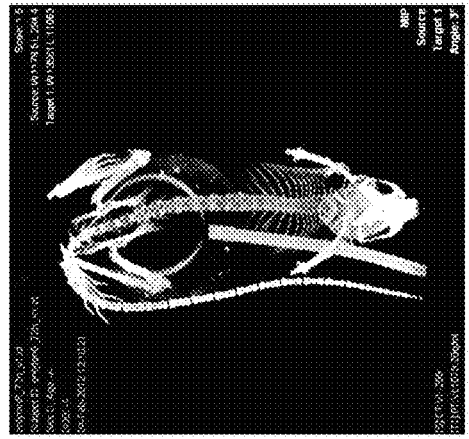
Figure 24:
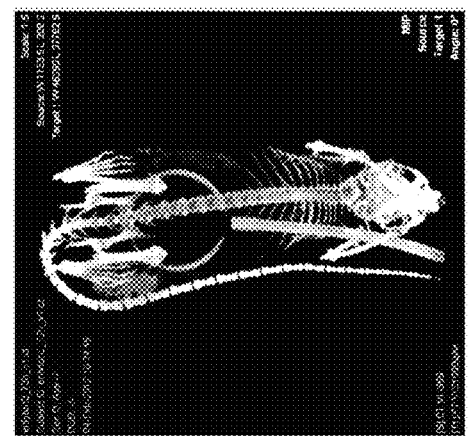
Figure 27:
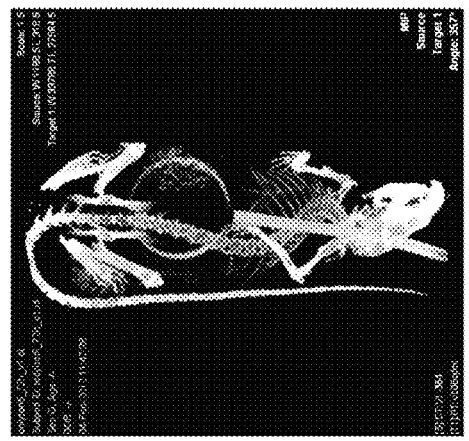
Figure 25:
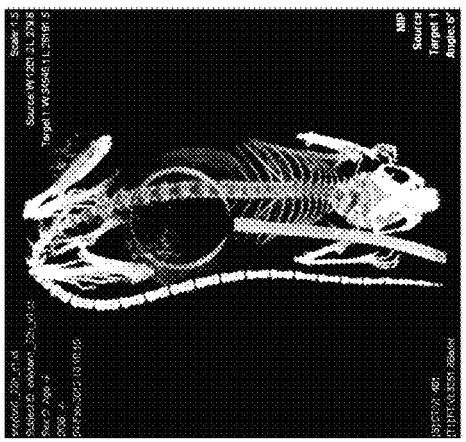
Figure 28:
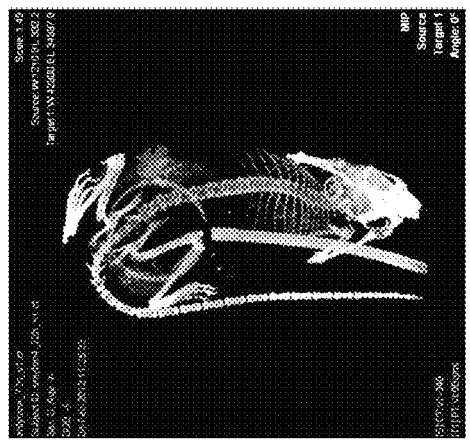
Figure 29:
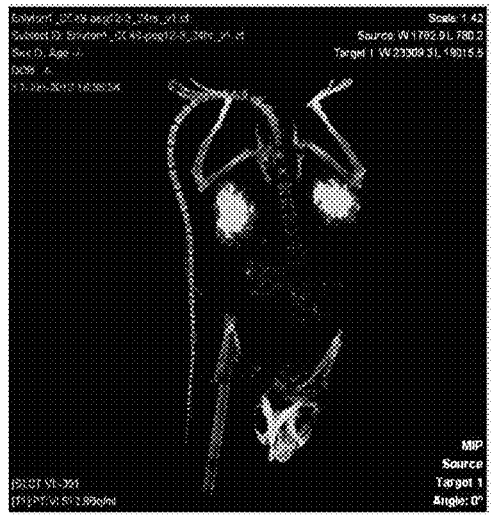
Figure 30:
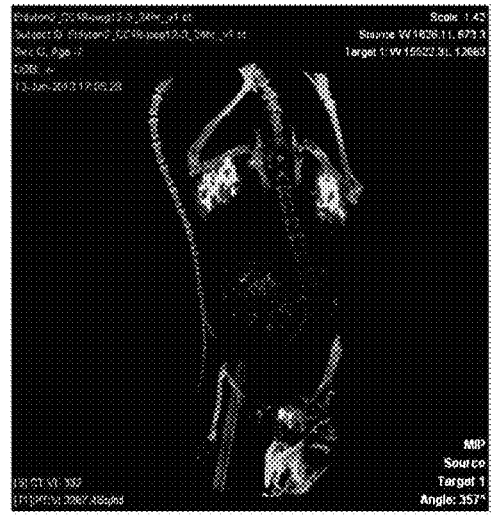
Figure 31:
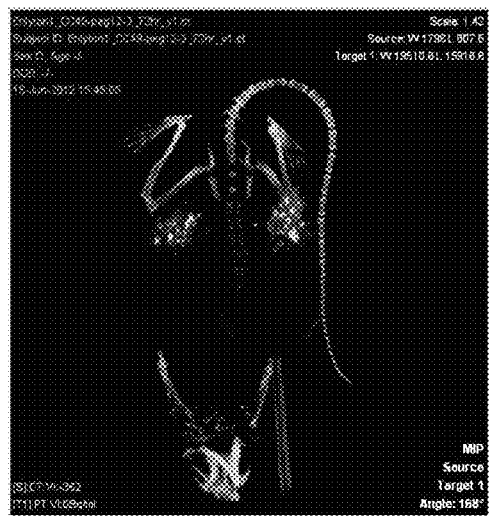
Figure 32:
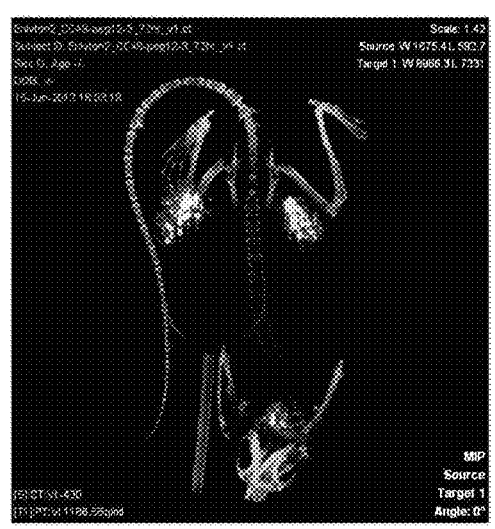
Figure 33:
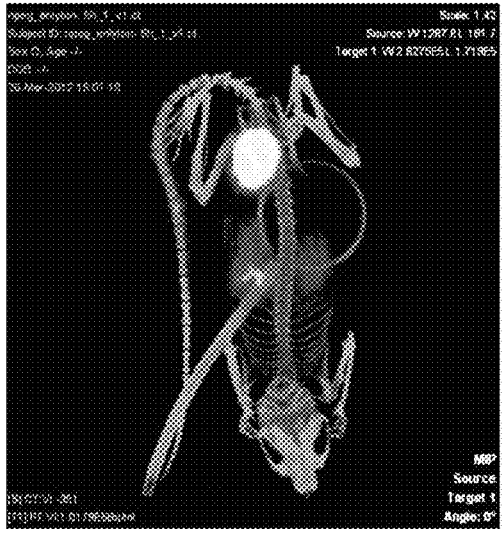
Figure 34:
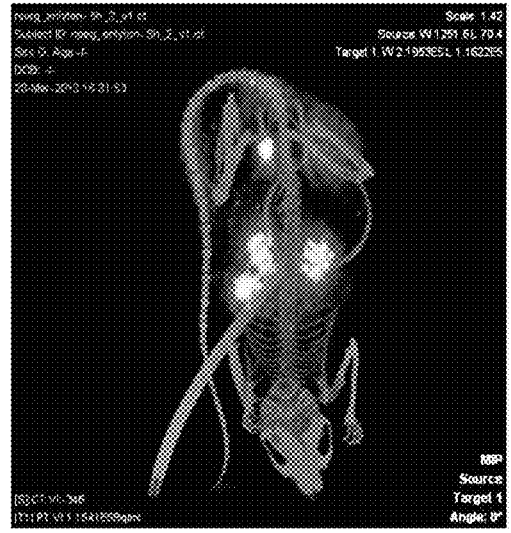
Figure 35:
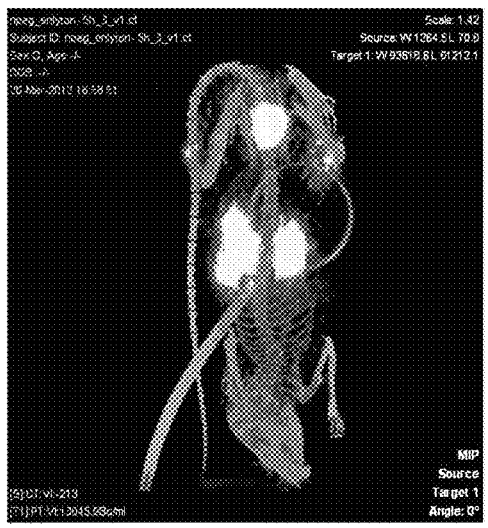
Figure 36:
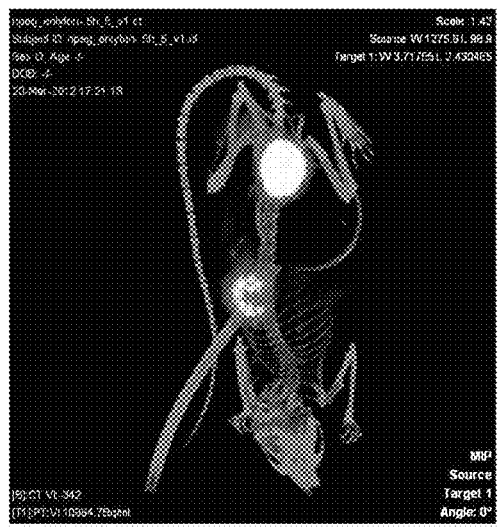
Figure 37:
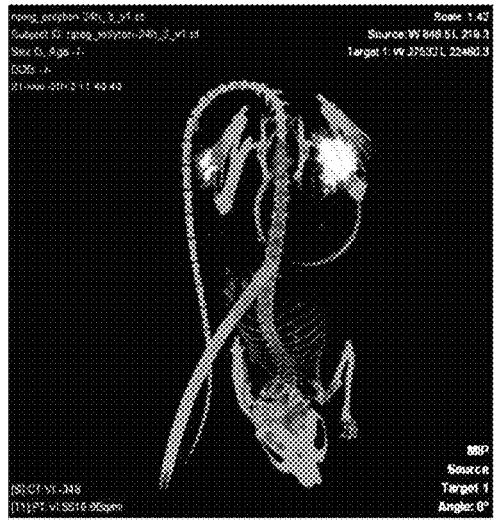
Figure 38:
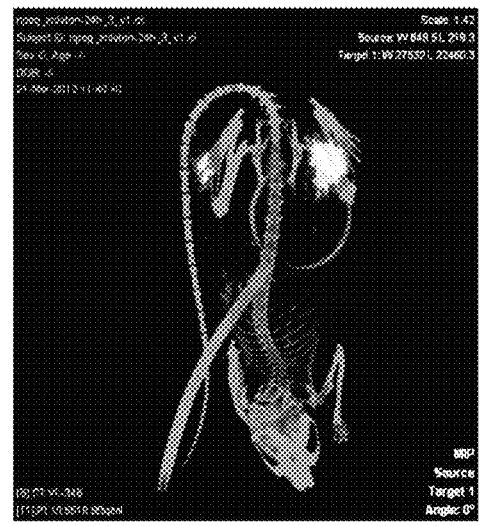
Figure 39:
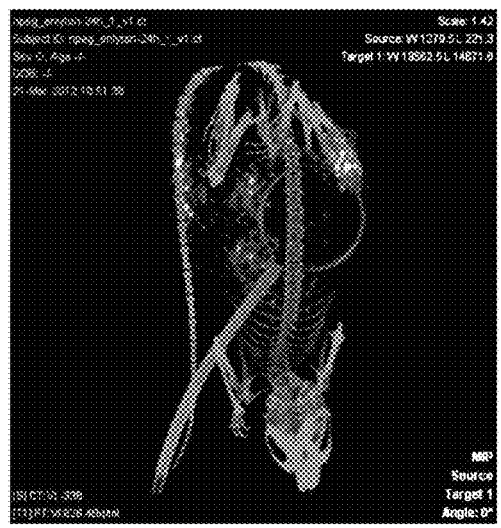
Figure 40:
Figure 41:
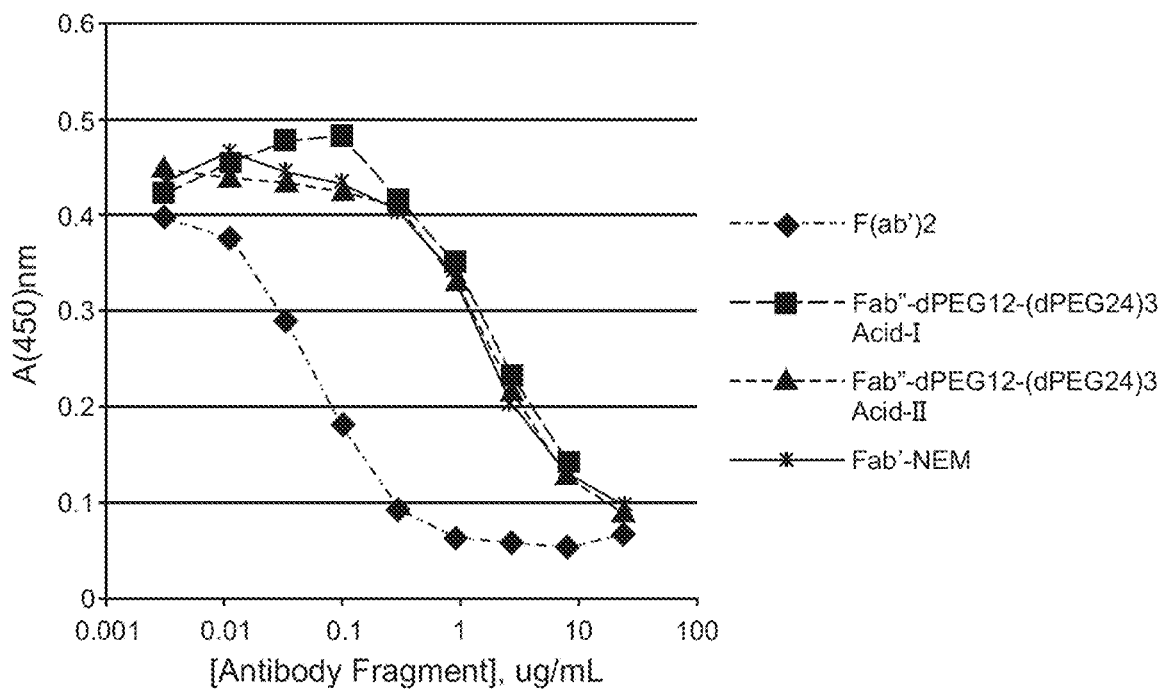
FIG. 41 graphically plots mCC49 competition ELISA results reported in Example 7.

In contrast, it can be seen with Avipep's dPEGylated diabody in vivo diagnostic product with of 4×m-dPEG$_{24}$ (four single chain linear dPEGs), where they see just ONE peak in the mass spec. (Ref. FIG. 14 in Hudson, et al., "Immuno-conjugates and Methods for Producing them," US 2010/0164068 A1 Jun. 28, 2012. This specifically is something that the FDA is very intrigued with in this instance in particular. The single peak in dramatic contrast to what one sees when a conventional polymeric PEG is attached. In fact, in a perusal of the published literature one will not see published images of these data, as they are highly complex. One can anticipate this by an example where just the MALDI mass spectra of a 5 kDa polydisperse polymer raw material in the m-PEG (5 kDa) amine, is contrasted to a linear dPEG. In the former one can see peaks going below 2 kDa and above 7 kDa, representing over 100 components, which the dPEG is a single peak. (See FIG. 2 in Anna Mero, Barbara Spolaore, Francesco M. Veronese and Angelo Fontana, "Transglutaminase-Mediated PEGylation of Proteins: Direct Identification of the Sites of Protein Modification by Mass Spectrometry using a Novel Monodisperse PEG," Bioconjugate Chem., 2009, 20 (2), pp 384-389.)

In our own experience with the conjugation of the branched dPEG constructs to the CC49. Fab' at the single sulfhydryl, the MALDI-TOF MS show a single peak for a 1:1 ratio of the CC49 Fab':branched dPEG construct.

Above, we have presented compelling and unexpected data about the properties of both linear and branched dPEG constructs. Below is summarized a list of individual and general branched dPEG constructs of show their range of design.

Description of the Branched dPEG Constructs

The scheme shown in equations below are general methods to build key branched dPEG constructs

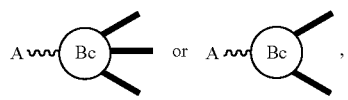

where the single branched point represented by the wavy line is added to the BC first, followed by the addition of the solid lines. The end groups are each matched so that the chemistry is specific for making the desired two or three branched construct. This can be used to build higher branched or added to a template, AC or series of AC's, and part of a group attached to the template, G.

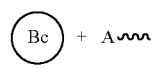

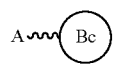

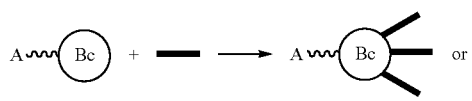

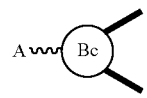

Alternatively,

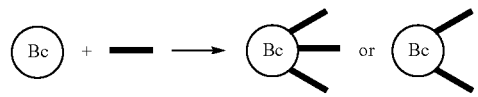

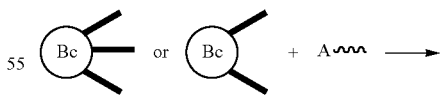

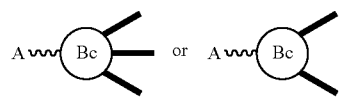

Preparation of PhthN-12-Tris(CO$_2$H)$_3$

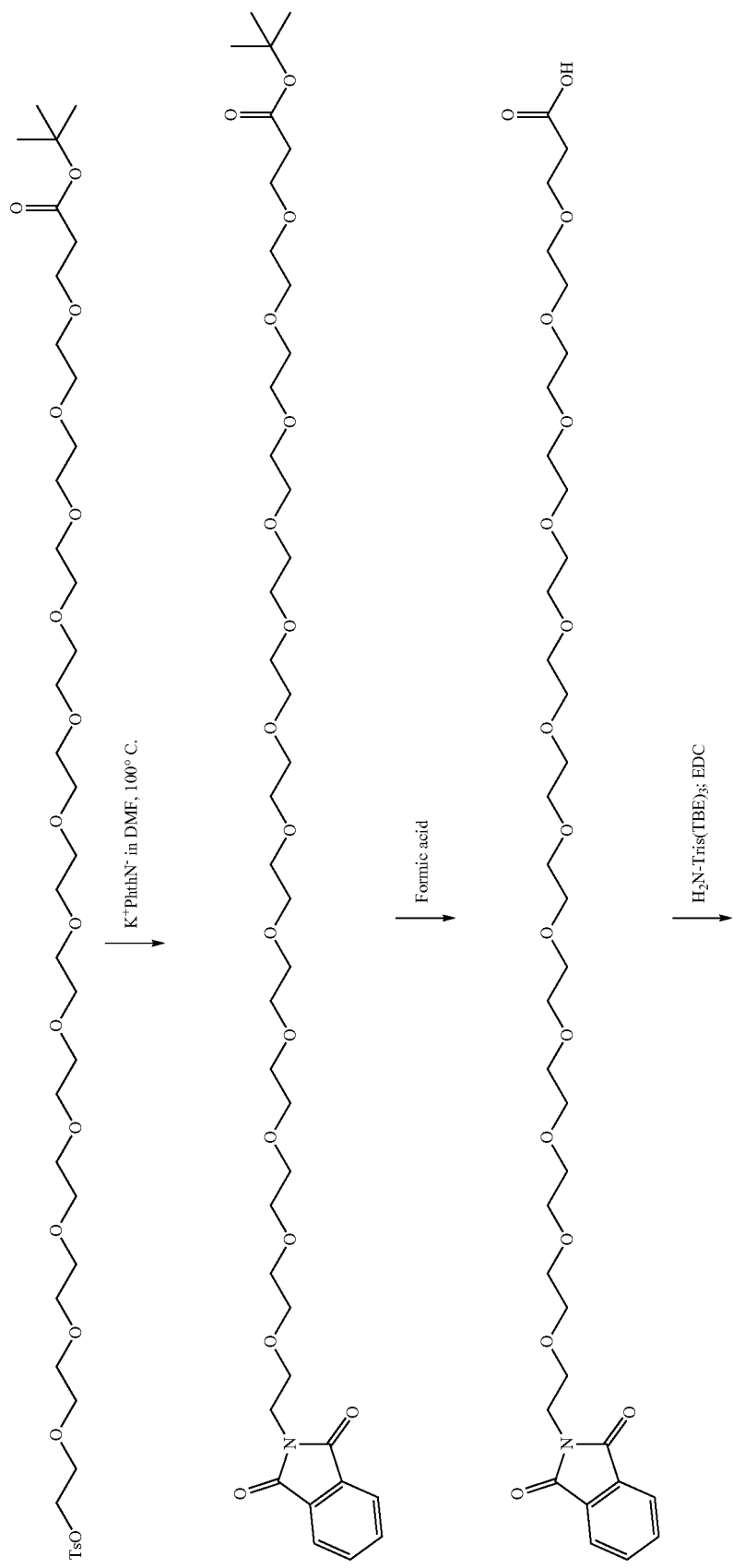

-continued
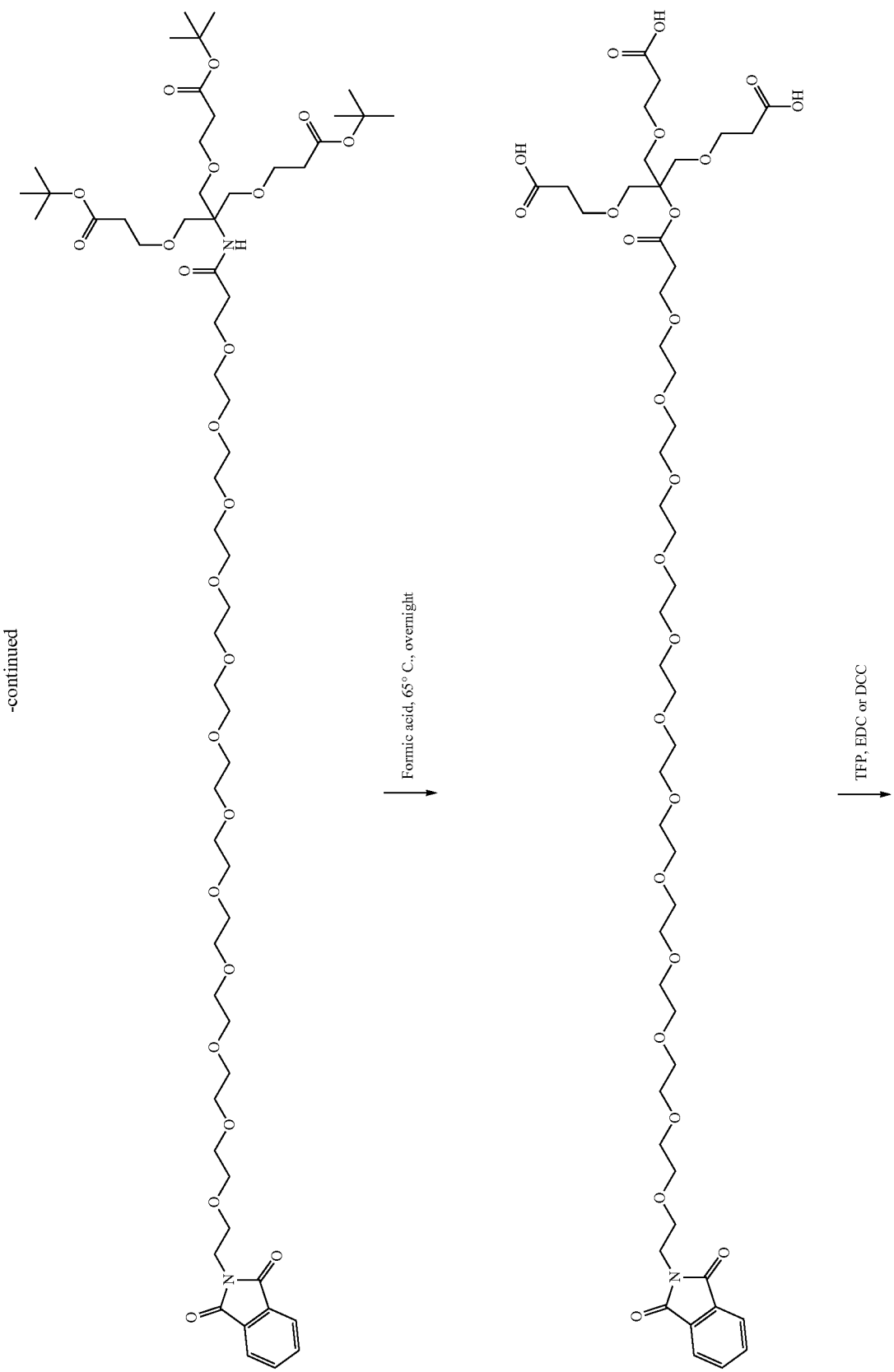

-continued
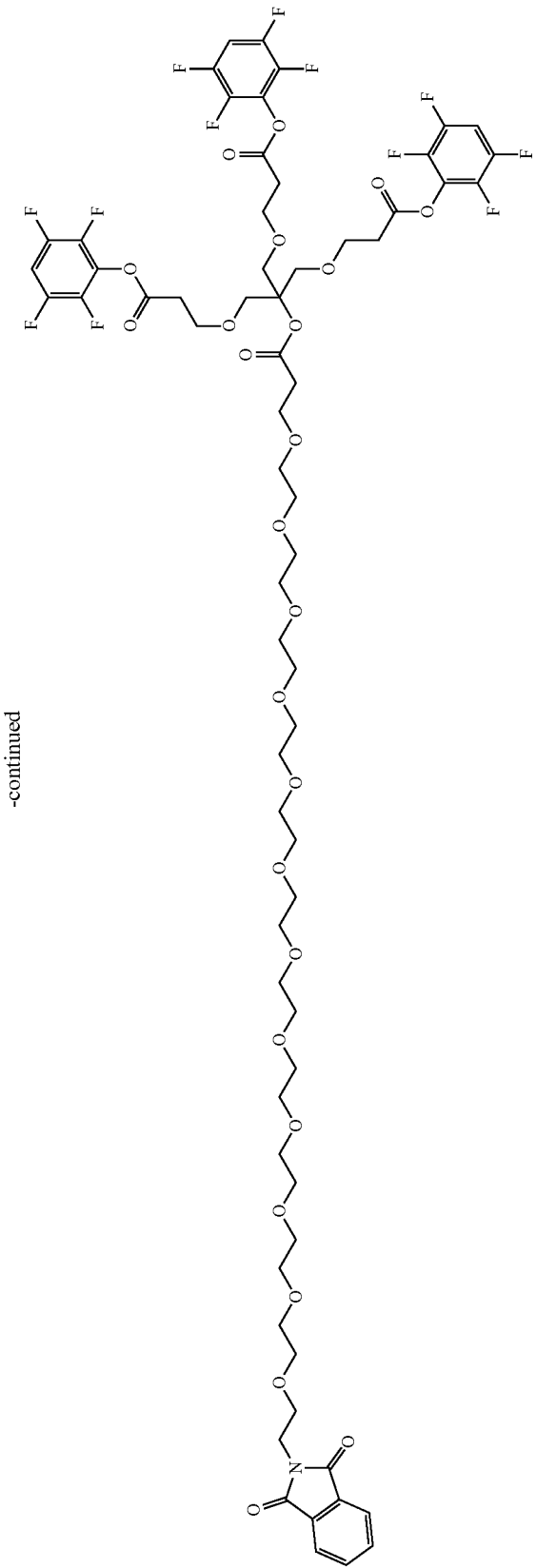

Preparation of MAL-12-Tris(-12-Tris (m-11)₃)₃
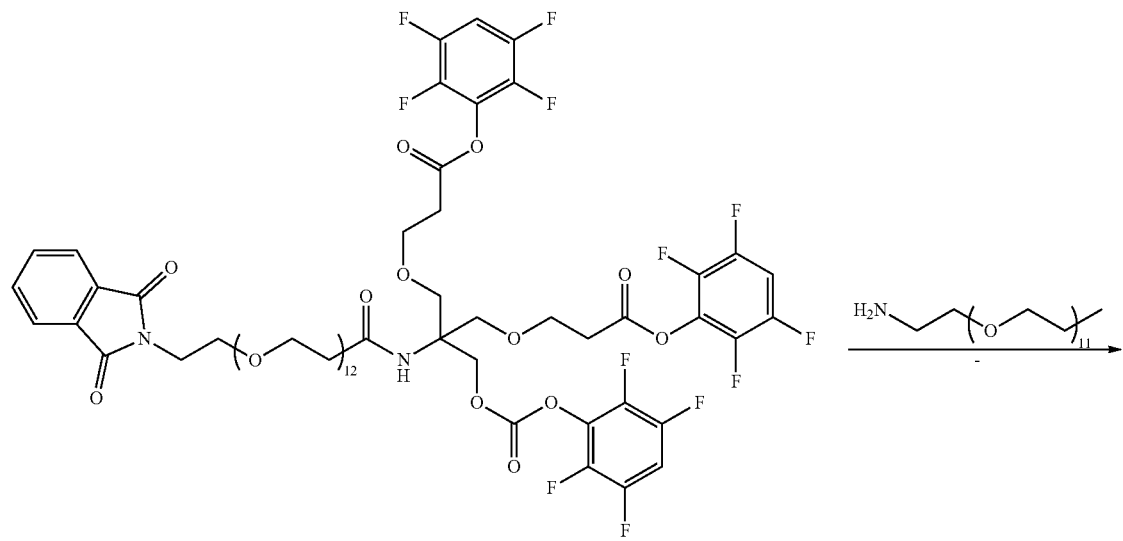
Intermediate 1
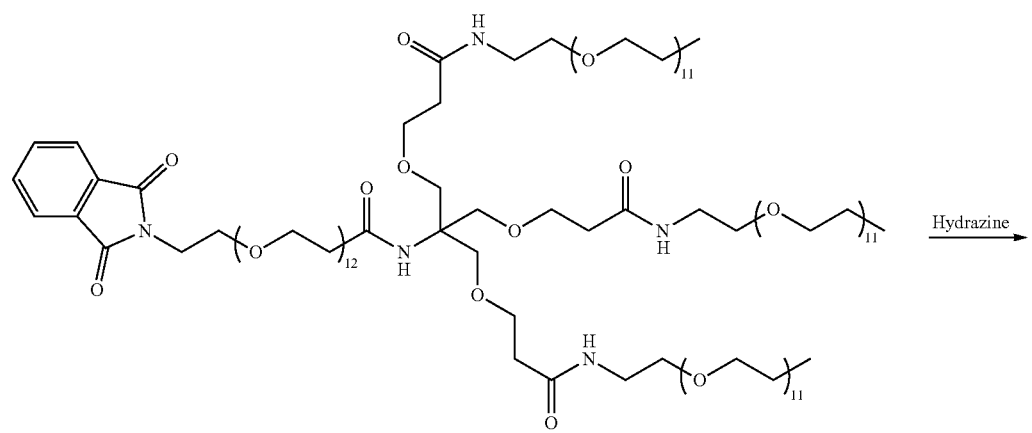
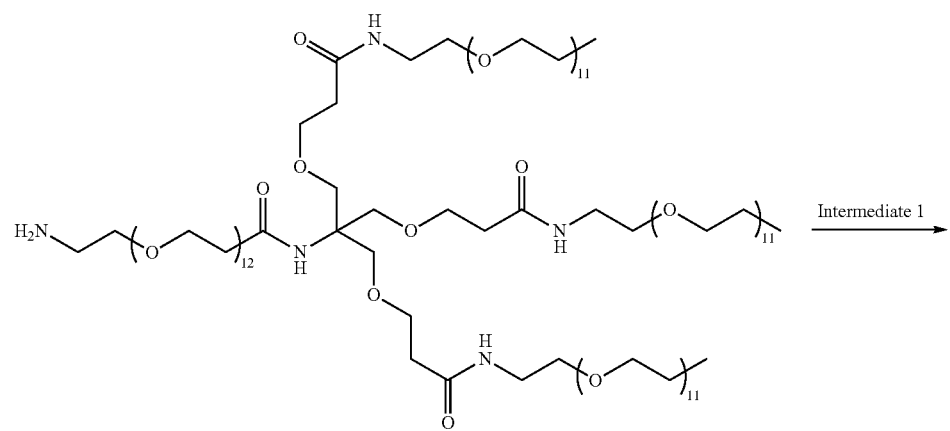

-continued

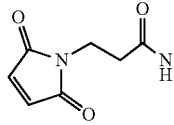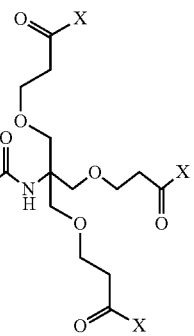

Molecular Weight: 8323.78

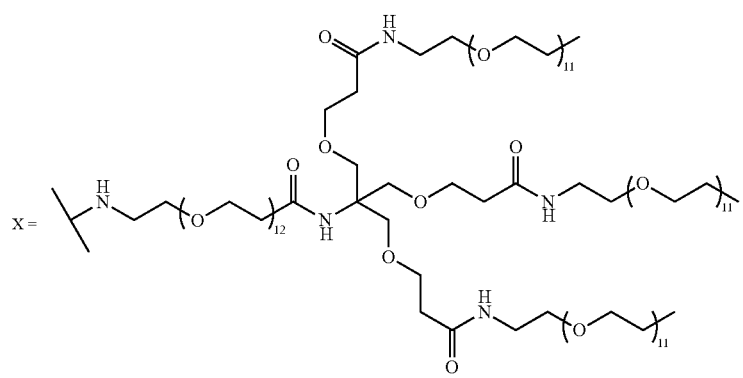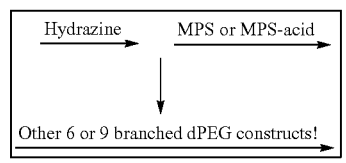

Optionally, the branch points can be extended and then a terminal functional group or a chemically reactive or reactable group could be added per the simple dendron examples of Newkome, et al., in the references listed presently. This could be best when ▬▬▬ is shorter, and ∿∿∿ is an optimal length such that the resulting higher branched and more compact construct can bet reacted with A and when A is a, biologically active group.

REFERENCES a. "Convenient Synthesis of 1→3 C-Branched Dendrons," George R. Newkome, Kishore K: Kotta, and Charles N. Moorefield *J. Org. Chem.* 2005, 70, 4893-4896.

b. "Dendrimers Derived from 1→3 Branching Motifs," George R. Newkome and Carol Shreiner, *Chem. Rev.* 2010, 110, 6338-6442.

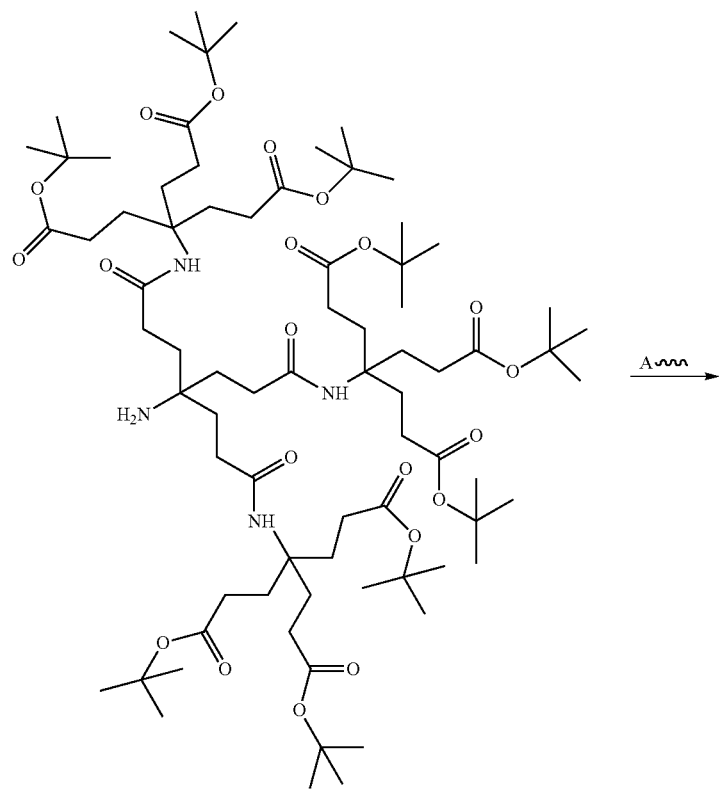
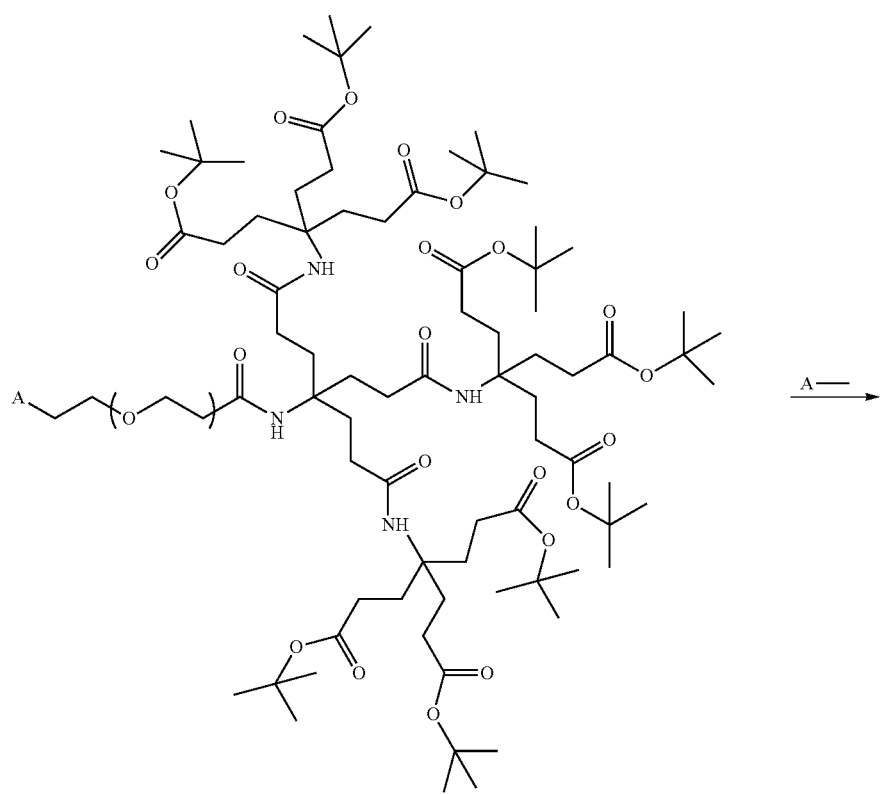

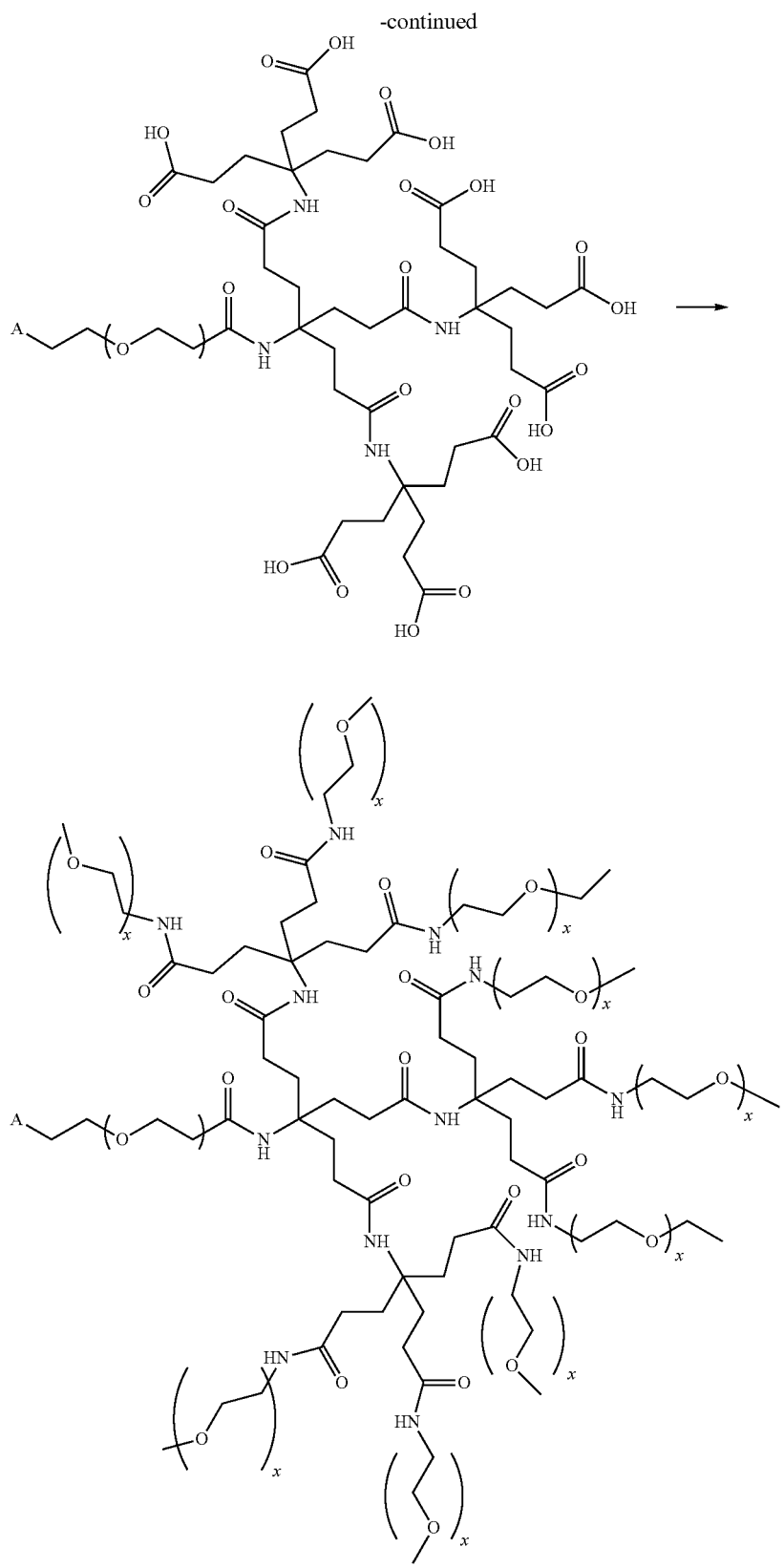
preferred x > 6;
terminal group
could be 'A'

To those skilled in the art, implementing a chemical process using chemistry in a convergent mode is likely to be the most efficient, in the cases of the cores shown, this would optimally utilize a 2:1 or 3:1 optimized stoichiometry. And in this disclosure is the preferred method for making the range of most useful basic branched dPEG constructs,

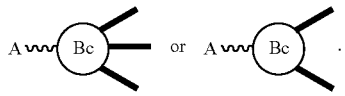

However as shown above in the example core drawn from Dr. George Newkome's work, optionally extrapolated to a Tris core, it may be optimal, depending on the physical properties of the intermediates and the ability to isolate and purify, to actually use a higher stoichiometric ratio of 9:1 optimized. This is also preferred. The final design of a particular branched dPEG construct and the optimal chemical methodology to achieve that best final outcome will determine what stoichiometry is preferred in various cases. This is all part of optimizing the chemistry in the context of many options of structure, physical properties and chemistry according to the requirements of the application into which the branched dPEG construct is to be utilized. These options are considered in this disclosure as providing the broadest possible useful set of constructs, as well as chemistry options to achieve an optimal solution to the wide range of biologically active groups or sets of groups, template design acid function, and the nanoparticles to which these constructs can be applied. Experience also will dictate the most efficient chemistry to get the most substantially pure composition.

Another embodiment of a convergent approach that overcomes potential reactivity constraints and increases process optimization variables, the chemically reactive moiety at the terminus of the solid line can be a reactable group and react with a wavy line BC multiple solid line. This can be useful both in controlling the geometry of the final construct as well as overcoming potential steric problems for certain lengths of ▬▬▬ or the compactness of the branched core, BC, without an additional ∿∿∿ with a terminal chemically reactive moiety to give the core a greater reactivity through steric accessibility. Ones skilled in the art can see the tremendous range of options that these few general convergent options provide for making a very broad range of final branched dPEG constructs.

Higher Branched dPEG Constructs and Methods for Making the Compositions:

In the equation below, it can be seen that a simpler branched dPEG construct with the proper choice of A,

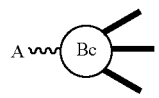

can be used as invaluable intermediates for building higher branched constructs.

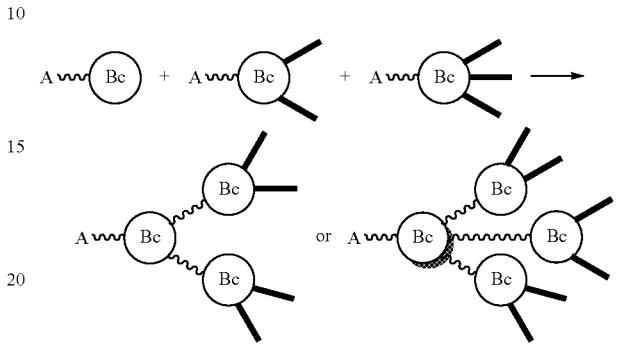

Shown below are some valuable simple branched dPEG constructs that can be used in this embodiment. But it can be seen by the disclosure the wide range of intermediates that can be designed while optimizing the length and nature of ∿∿∿∿ , with a dPEGx length in the range greater than about x=4, preferably between about x=8 to 24, optionally up to x=48. Much of this will depend on the size of the

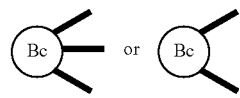

and the length of and terminal group in the ▬▬▬ . The length of the ∿∿∿∿ can be shorter when the ▬▬▬ is shorter, but as the ▬▬▬ gets longer the nature of

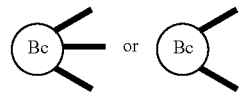

will often require that the ∿∿∿∿ be longer as defined in the preferences for x in the dPEG.

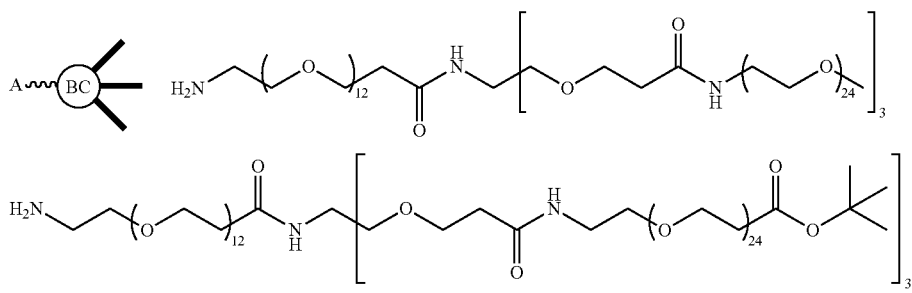

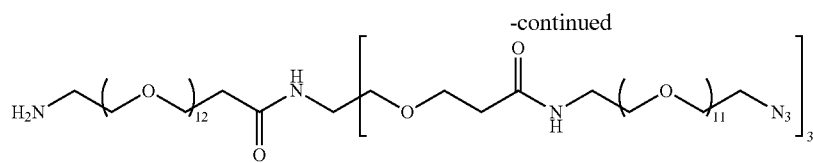
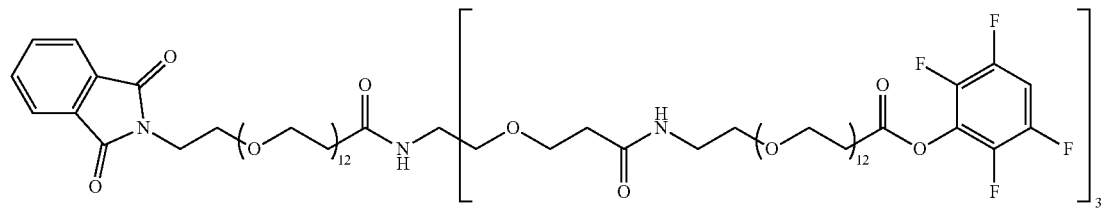
Preparation of MAL-12-Tris(-12-Tris (m-11)₃)₃
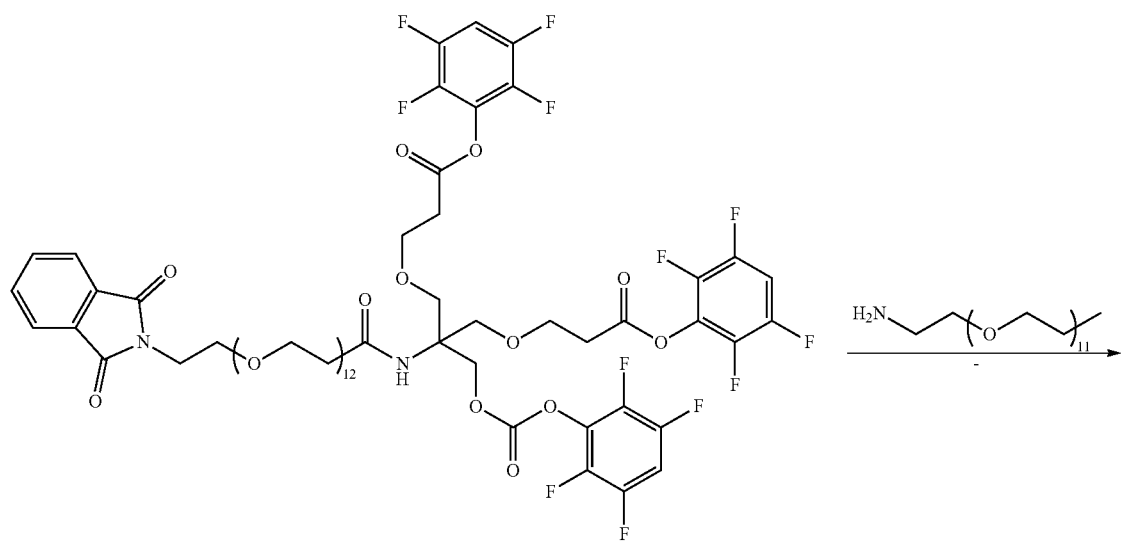
Intermediate 1
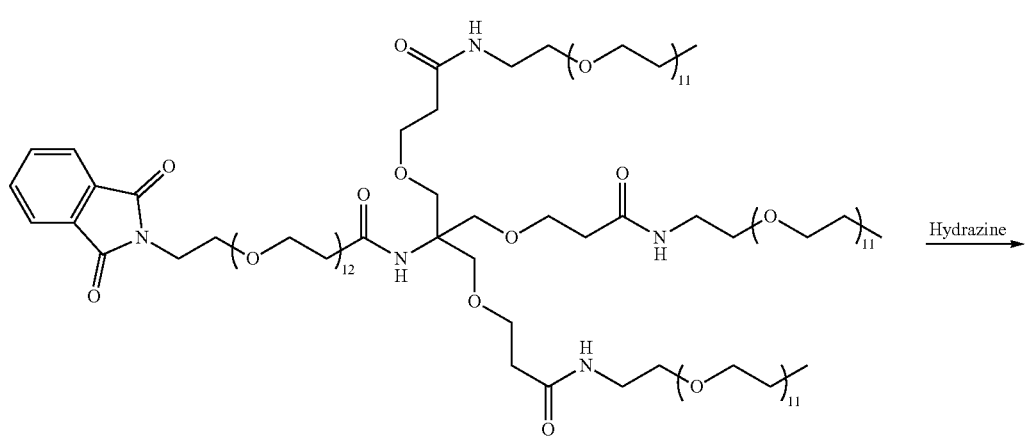

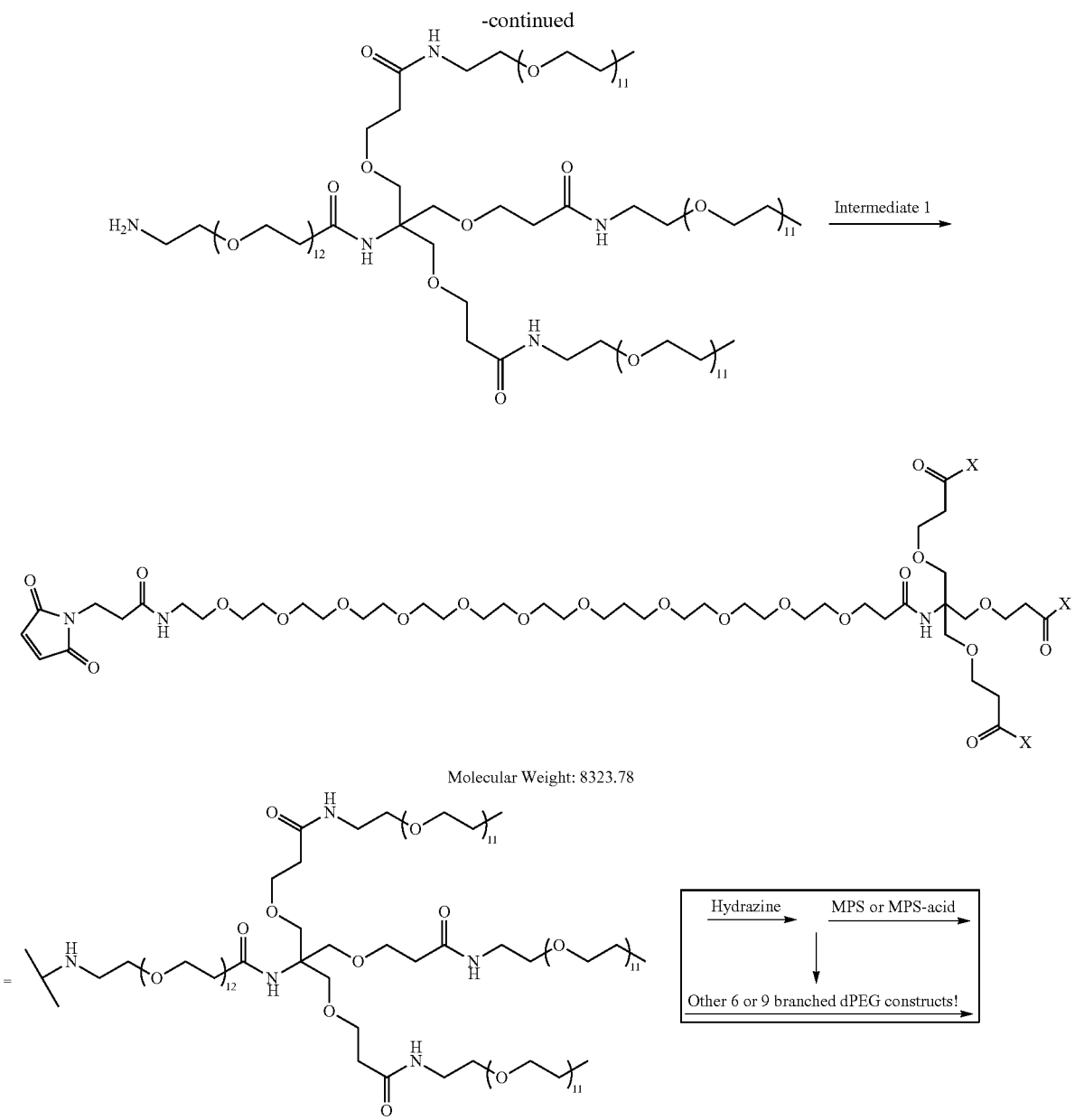
This is just shown by example, but it can be see that there are numerous other convergent options that would be within the capability the skilled artisan. This can be expanded to even higher branches as can be seen in the general equation shown below.
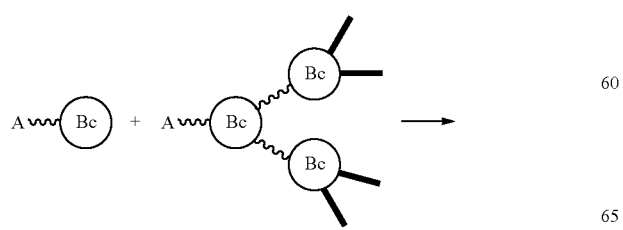
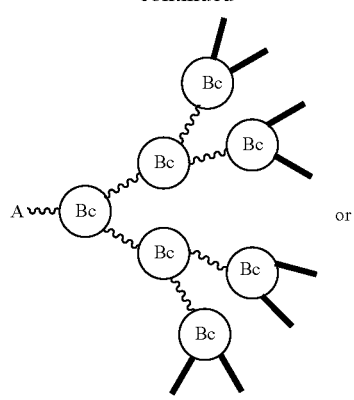

-continued

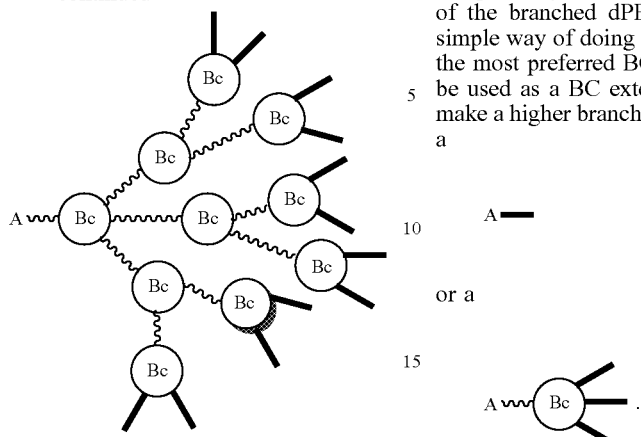

In extending the branching, the length and nature of ⁓⁓⁓⁓ is important so as to control the flexibility and the volume created by the resulting branched dPEG construct, as is ▬▬▬ and has been discussed above!

Optionally, to add a higher charge density to the "surface" of the branched dPEG construct, the following shows a simple way of doing that using the same core used to make the most preferred BC (Tris core). Optionally this can also be used as a BC extended away from the primary core to make a higher branched with a 9:1 stoichiometry with either a

A▬ or a

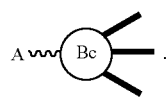

For the example below it is shown for the latter case to make a 27-branched compound from the nona-activated ester, preferably as the TFP or similar ester.

MAL-dPEG$_{12}$-Tris(-dPEG$_{12}$-(Tris(-CO$_2$H)

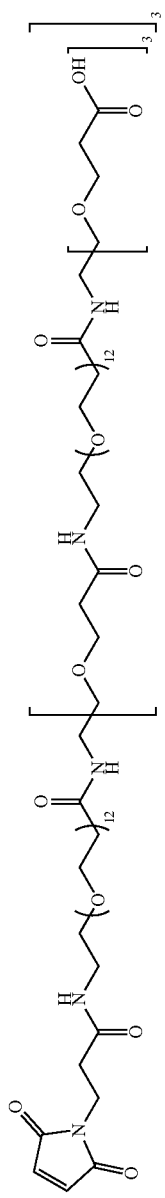
Chemical Formula: $C_{167}H_{303}N_9O_{88}$
Molecular Weight: 3845.20
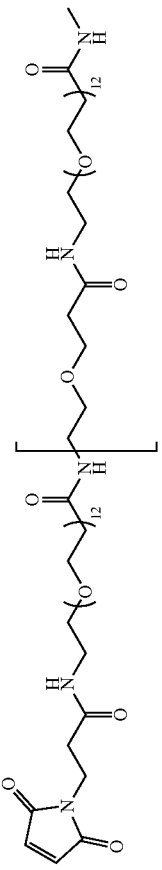
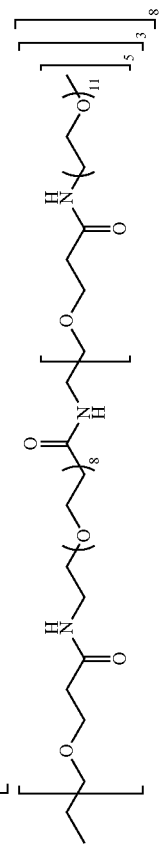
Chemical Formula: $C_{1978}H_{2094}N_{64}O_{511}$
Molecular Weight: 23966.19
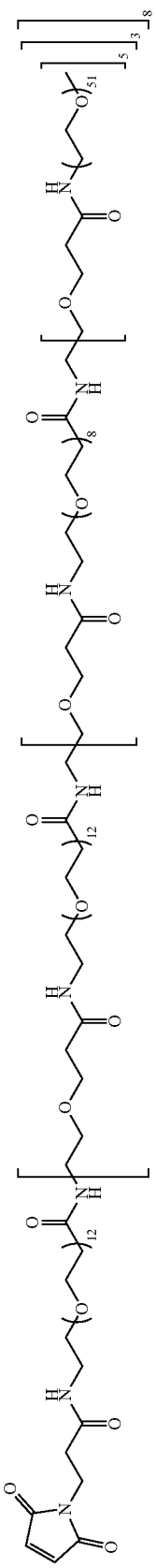
Chemical Formula: $C_{1978}H_{2094}N_{64}O_{511}$
Molecular Weight: 23966.19

MAL-dPEG$_{12}$-Tris(-dPEG$_{12}$-Tris(dPEG$_8$-Tris(-dPEG$_{11}$-m)$_3$)$_3$)$_3$, or optionally preferred as MAL-dPEG$_{24}$-Tris(-dPEG$_{12}$-Tris(dPEG$_8$-Tris(-dPEG$_{11}$-m)$_3$)$_3$)$_3$, or the simplest short hand or MAL-24-Tris(-12-Tris(-8-Tris(m-11)$_3$)$_3$)$_3$ Another embodiment is to have different branched dPEG branches on a core, e.g., having a branched were one of the solid lines is terminated with an inert, e.g., methoxy, and a second solid line with a charged or reactable group attached. This is preferred to come off of the preferred AC's like the lysine or aspartic or glutaric acid, but as disclosed herein is the most preferred and flexible use of the tyrosine core.

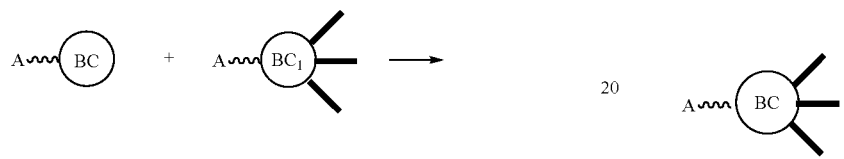

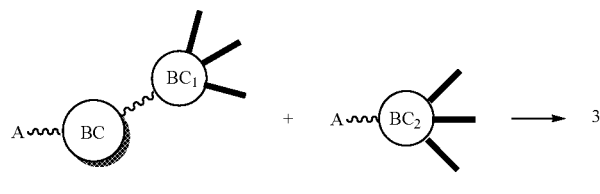

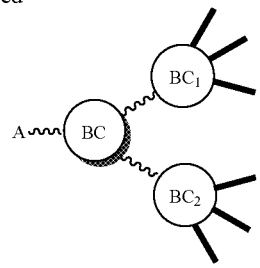

Shown below is a novel use of the tyrosine, where it can be used to incorporate a variety of orthogonal functionality as a chemically reactable group, which can have a linear dPEG and wavy line, ∿∿∿∿∿ or a where A is a hydroxyl, can directly incorporate the branched, with the optional terminal groups being charged or neutral. In this case of making this interesting six branched dPEG construct, the protected tyrosine is first converted to the protected acid via a Mitsunobu reaction with a HO-dPEG$_4$-COO-t-butyl, then deprotected and the first 3-branched dPEG construct with the protected carboxyl is added, followed by the incorporation of a different second 3-branched dPEG construct. This is one simple example of many options and shows the novel use of the tyrosine.

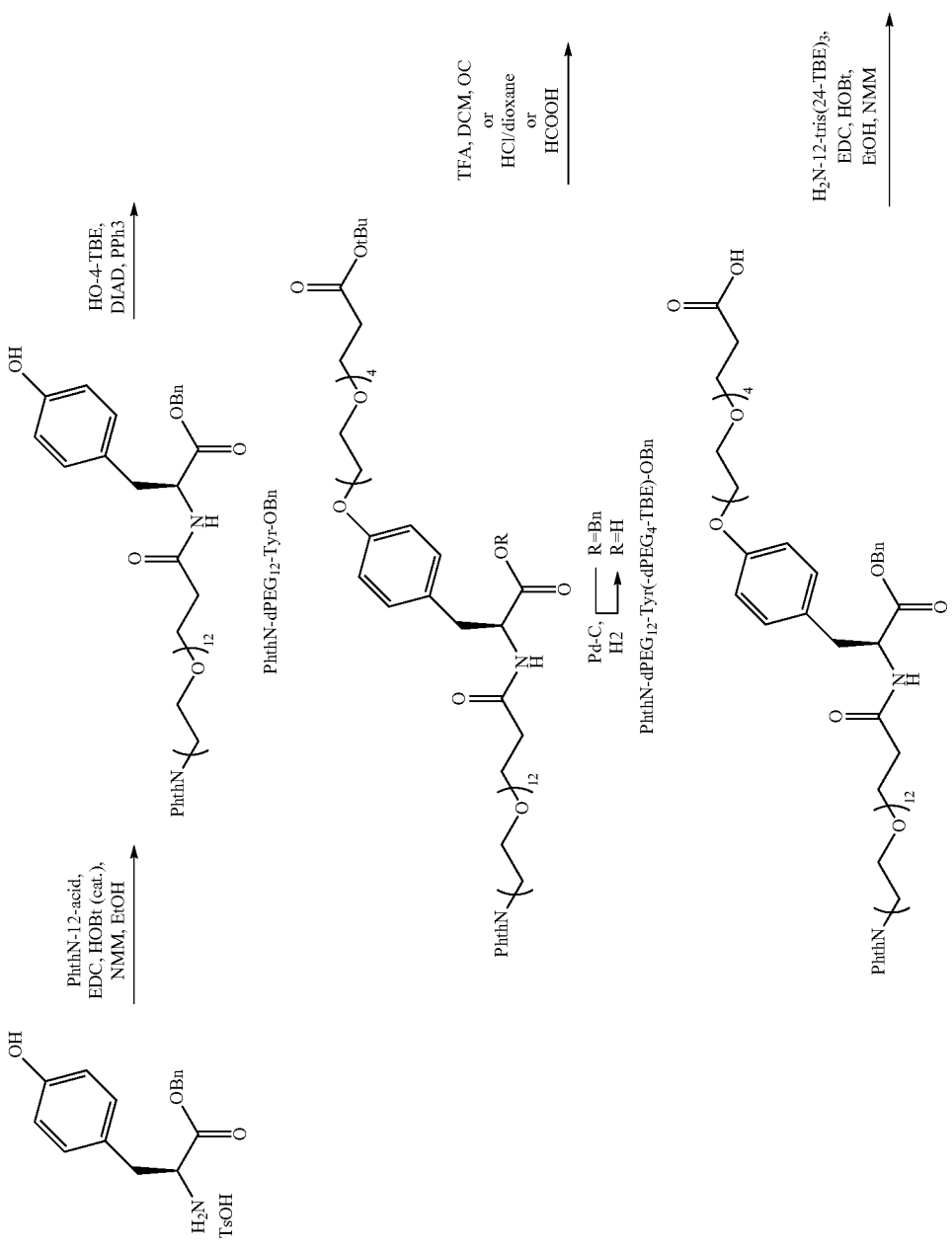

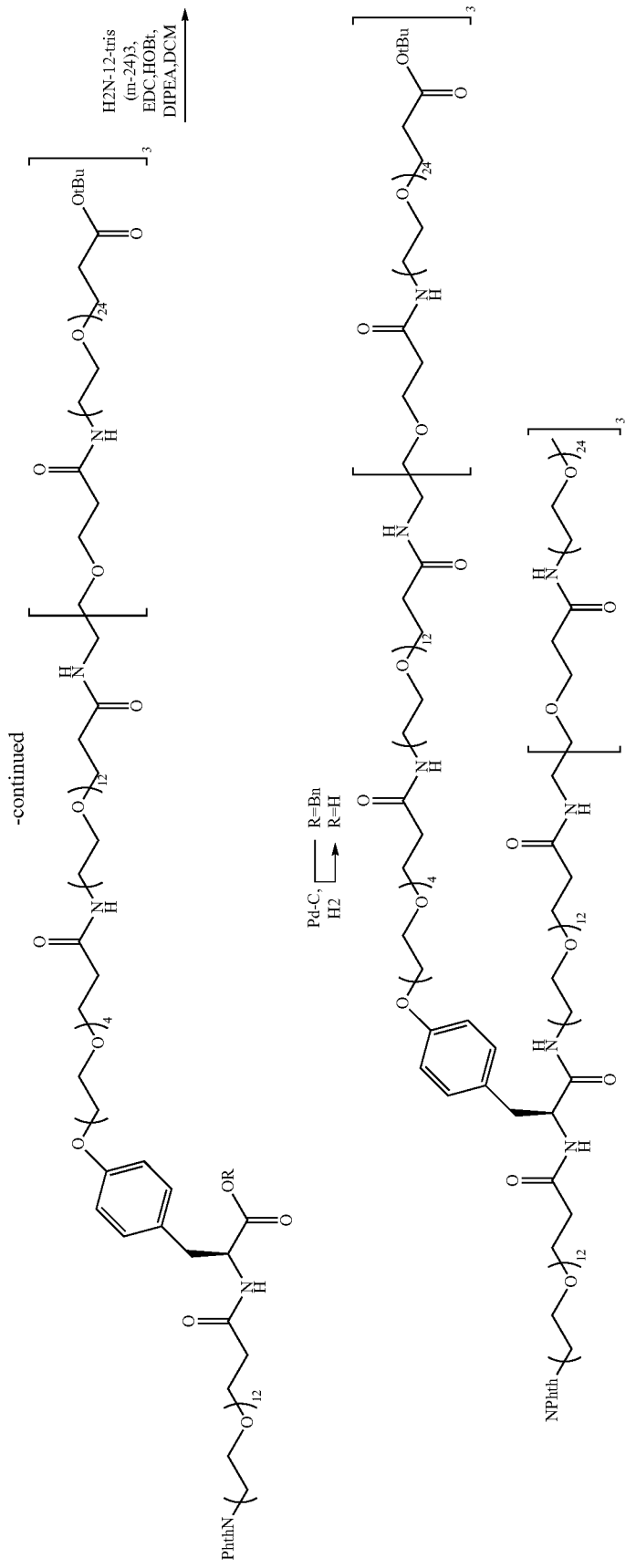

Where,
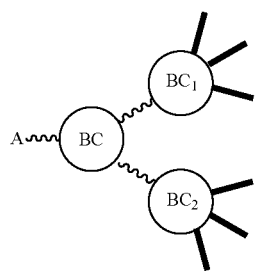
is
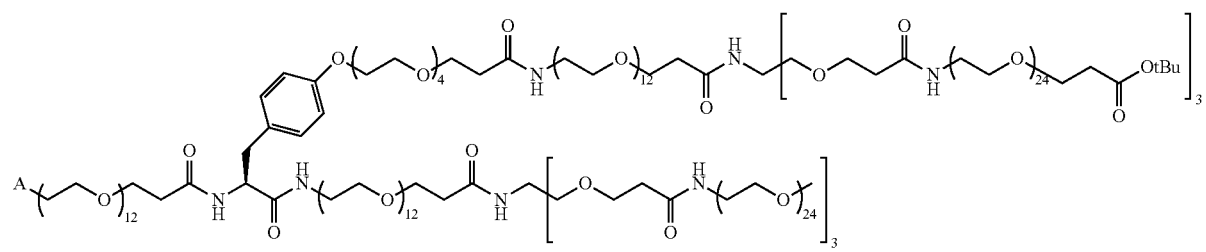
And in the example in the scheme above is the protected amine as the PhthN- for "A" in PhthN-dPEG$_{12}$-Tyr(-dPEG$_4$-amido-dPEG$_{12}$-Tris(-dPEG$_{24}$TBE)$_3$-dPEG$_{12}$-Tris(-dPEG$_{24}$-m)$_3$.
The scheme below begins to show the versatility of the tyrosine BC core for this purpose and is disclosed exclusively herein.
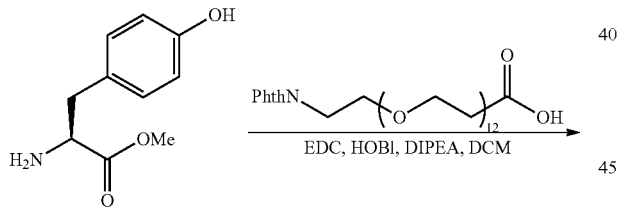
-continued
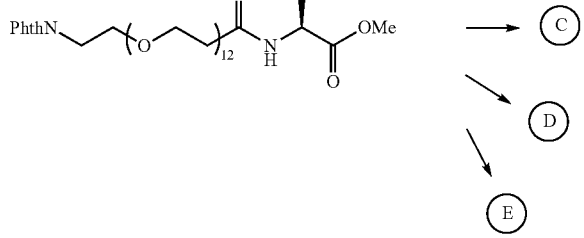

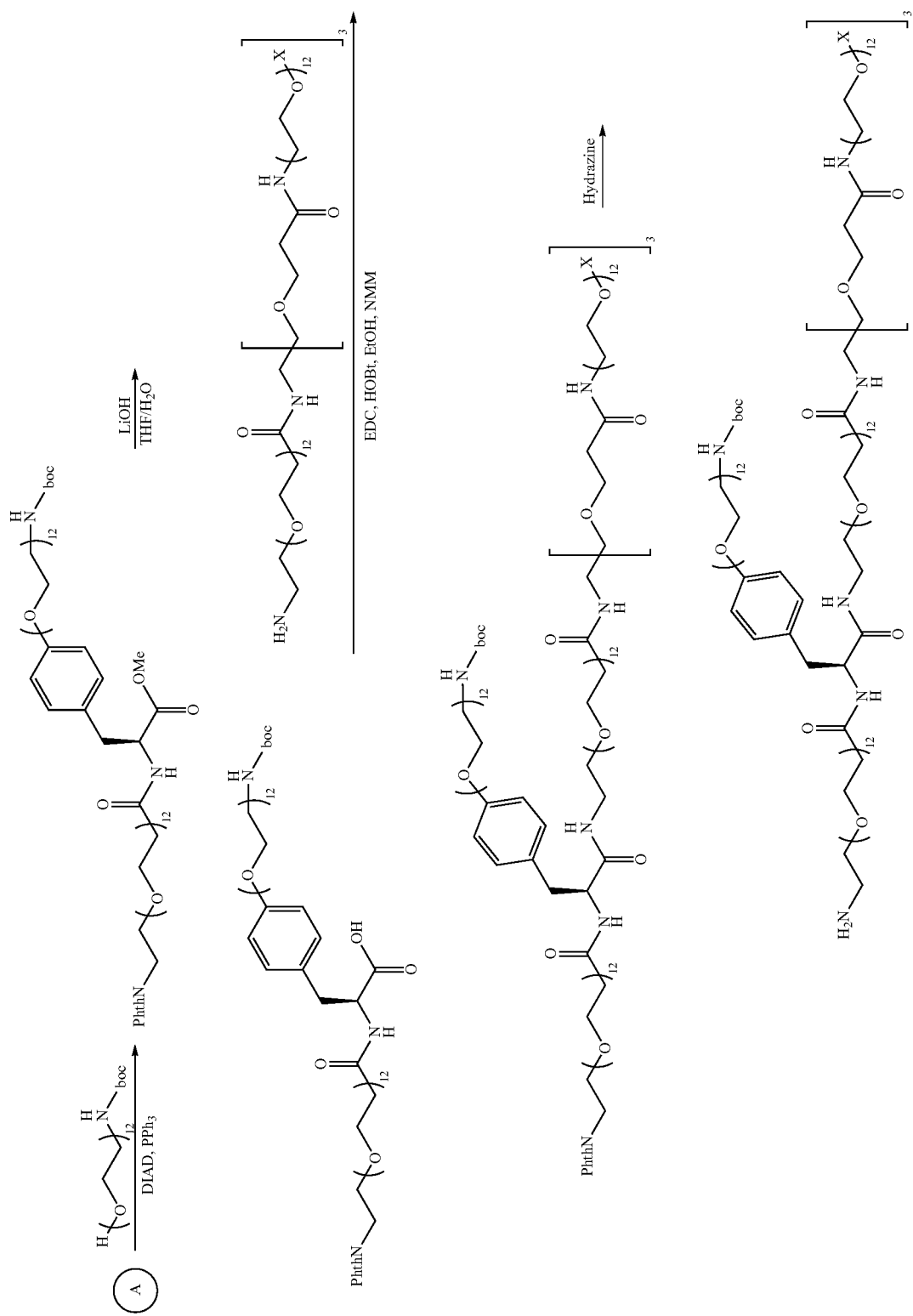

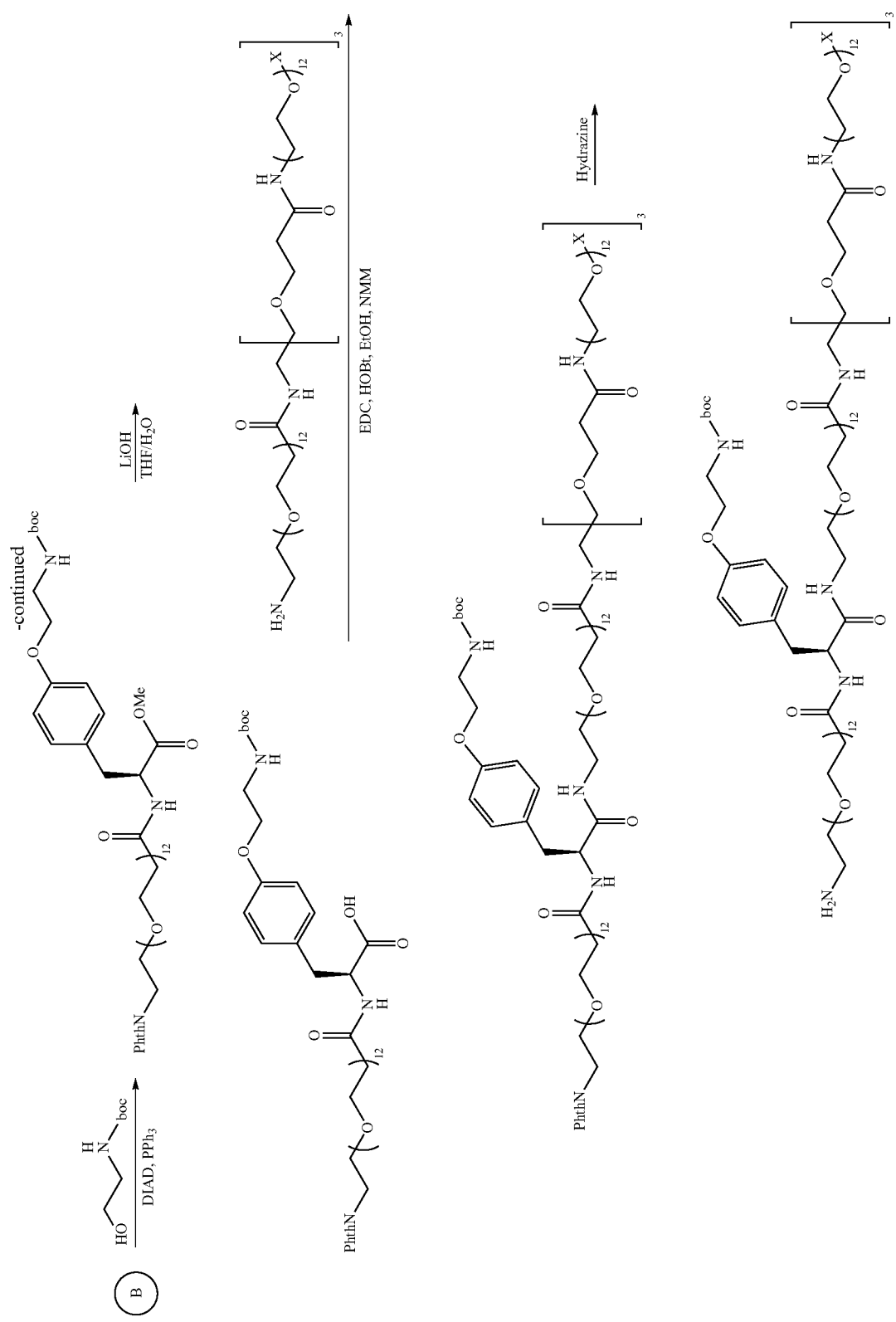

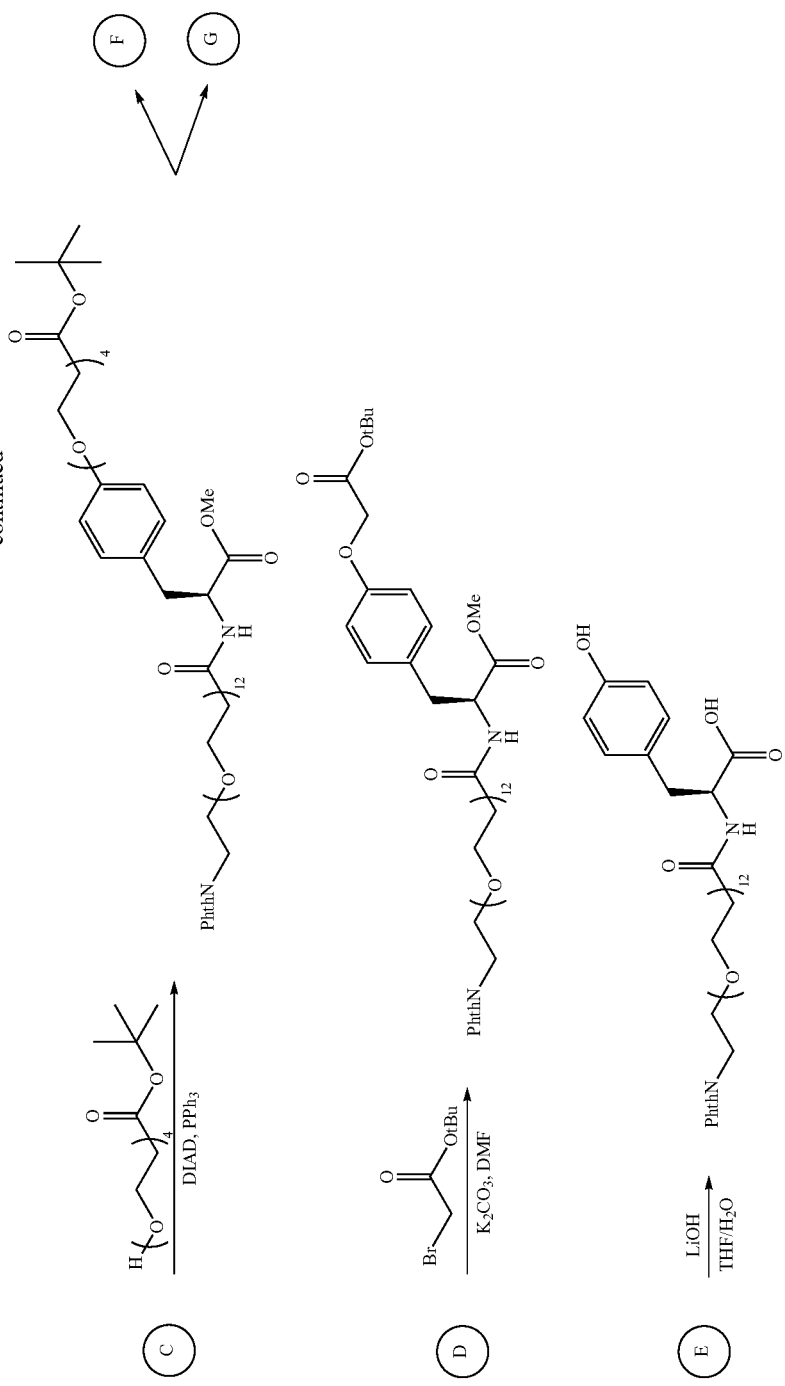

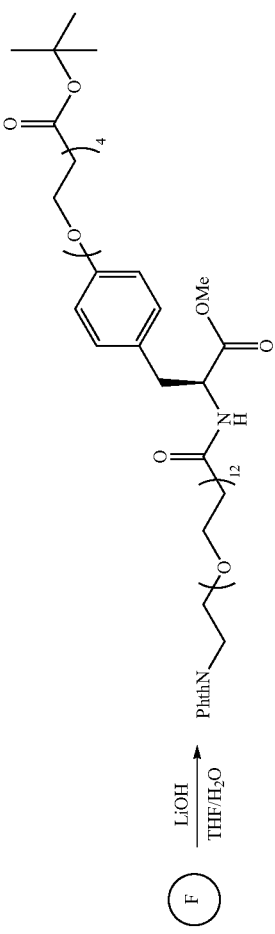
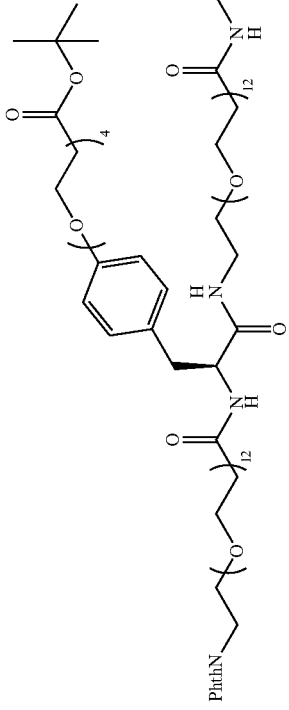
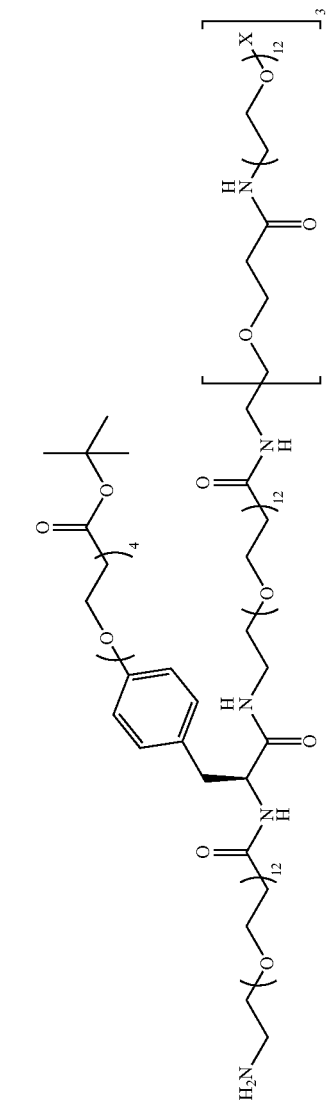
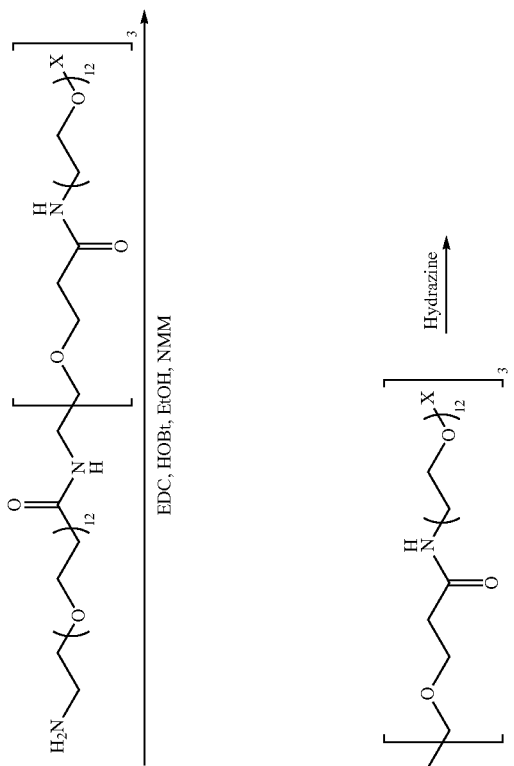

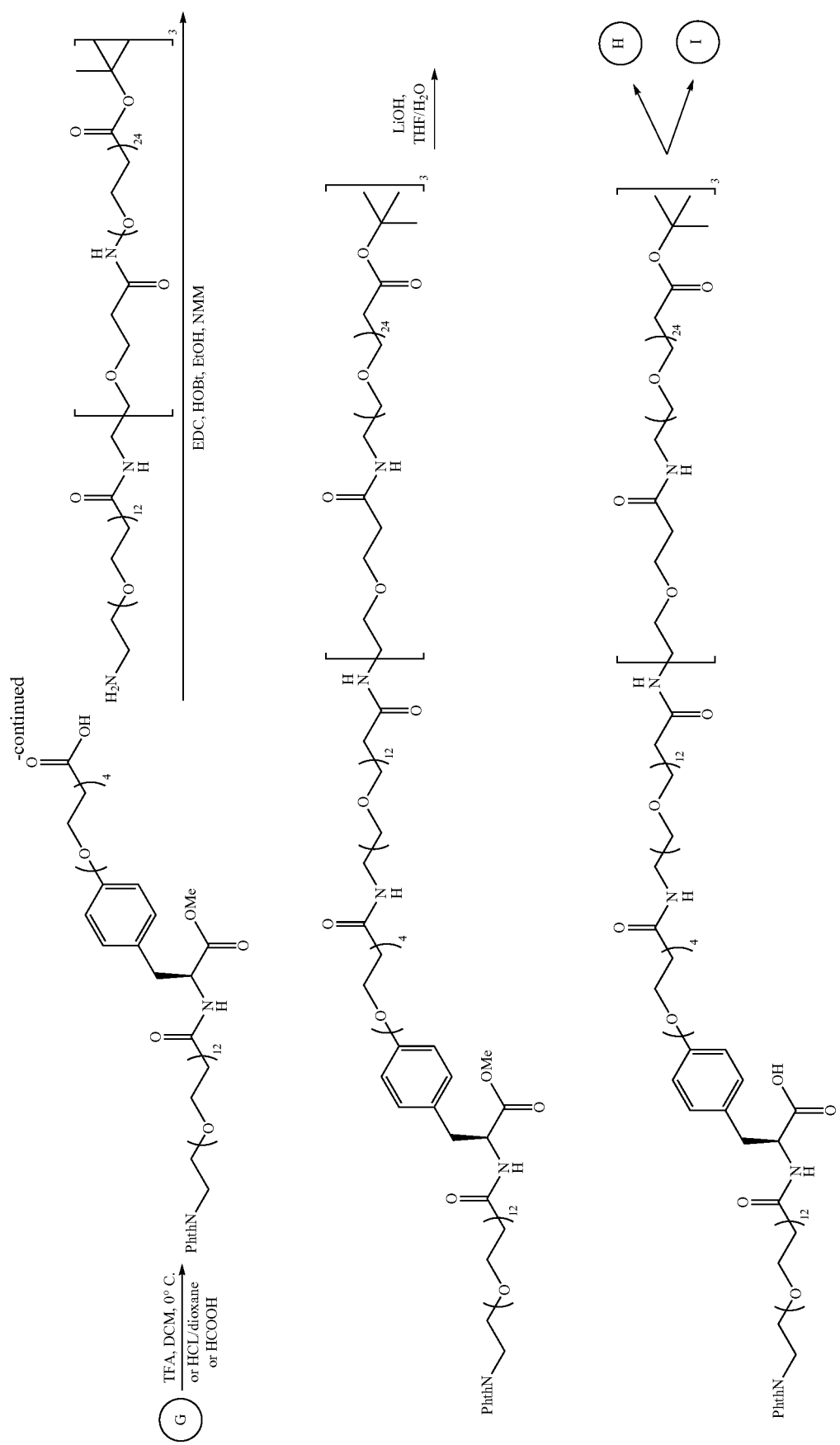

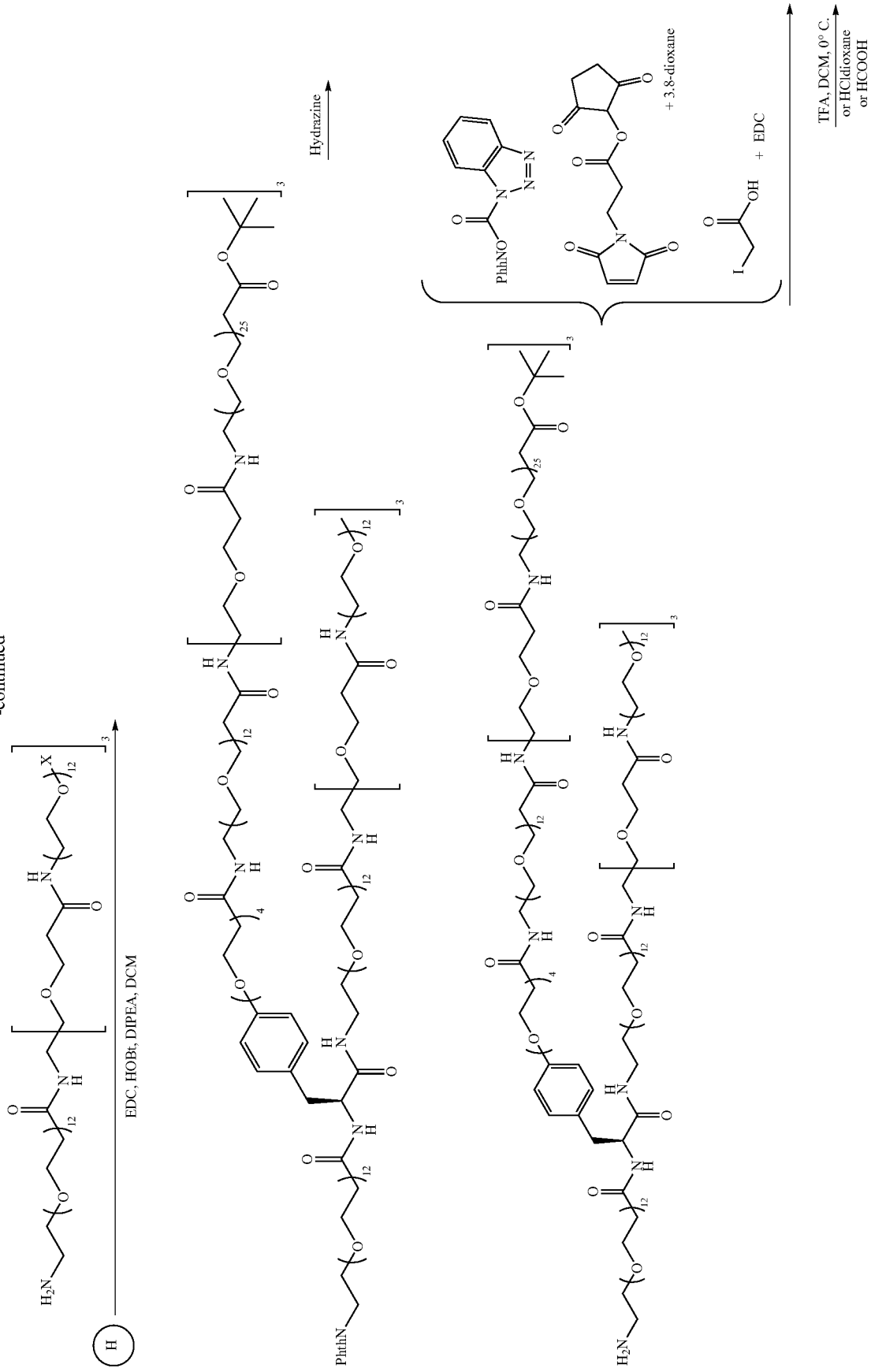

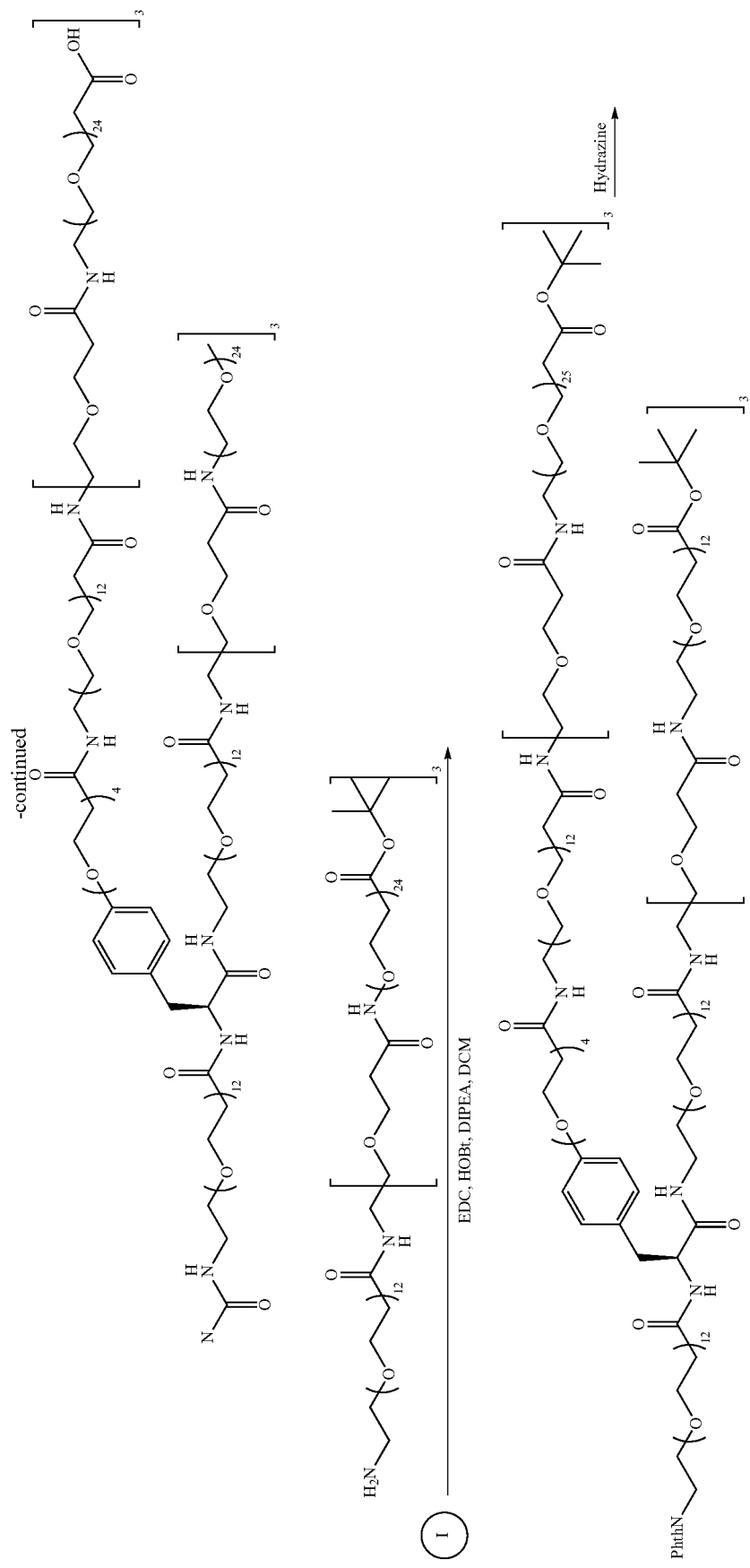

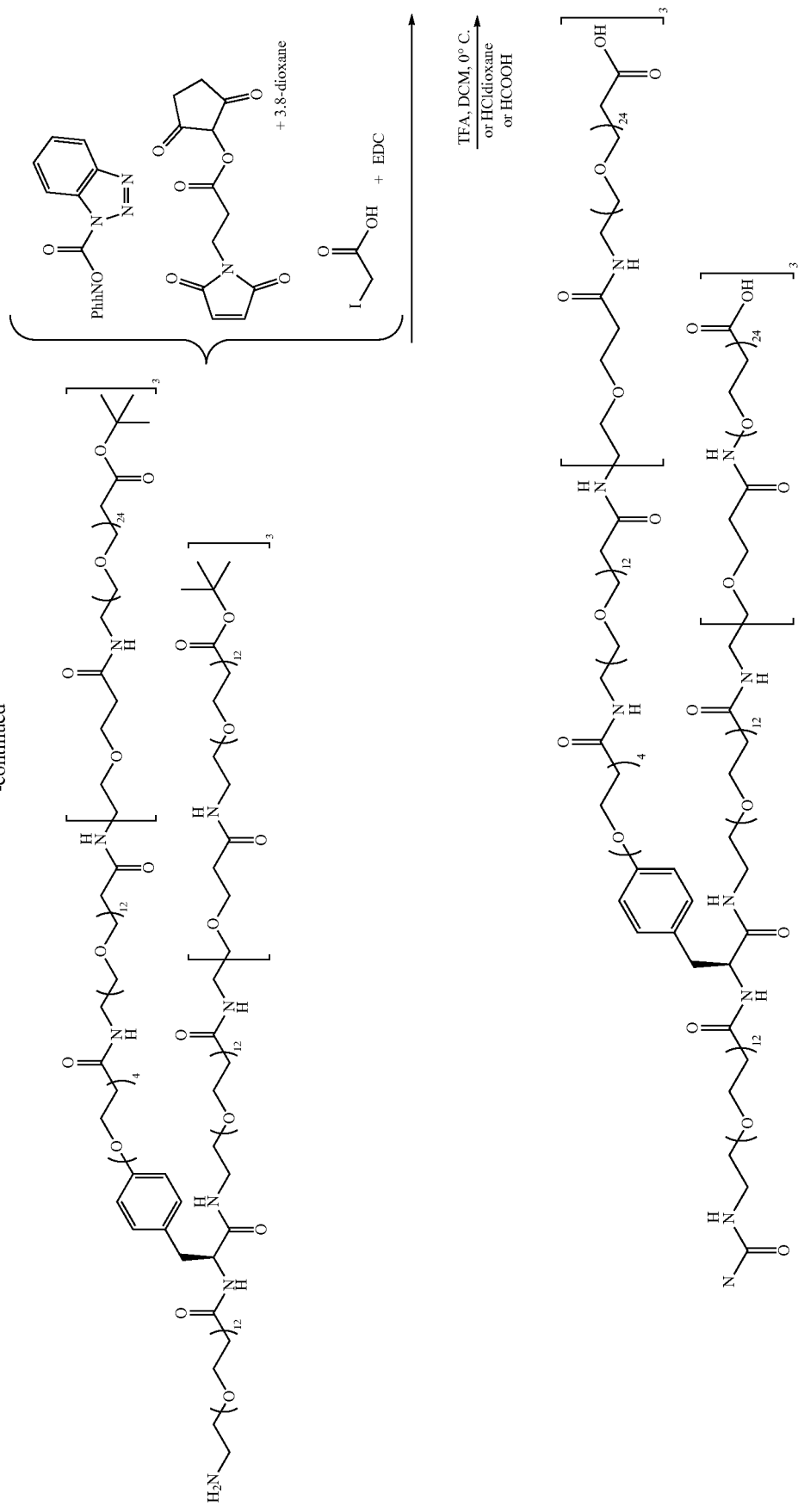

Shown here is another example based on a glutaric acid core.

While we have shown here an example where the dPEG in the ~~~~ is dPEG$_{12}$, and the linear dPEG in ▬▬ is a dPEG$_{24}$, one with a neutral terminal group methyl and in the other, the preferred charged group, carboxyl, these could easily be made shorter or longer, and can be adapted to the application in the context of the dominating effects of which terminal group. As in the example above, MAL-dPEG$_{12}$-Tris(-dPEG$_{12}$-(Tris(-CO$_2$H)$_3$)$_3$, this higher density of charge could be added, with the dPEG shortened, or the neutral charged could be shortened or lengthened to the need of the application.

that can be reacted with AC, as well as converting A, as a chemically reactive group, OH, on a branched dPEG construct to a different A, one with alternate utility.

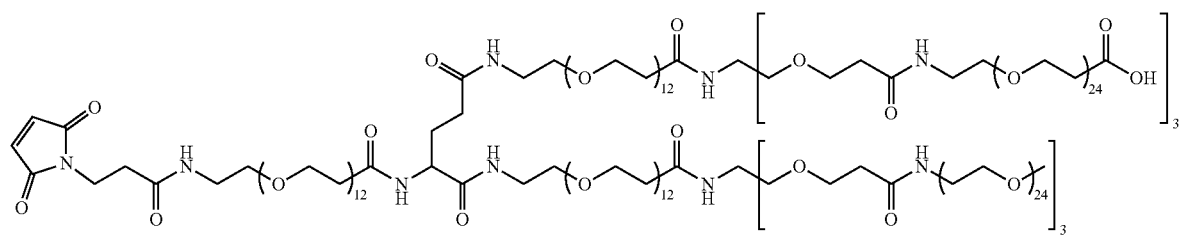

Chemical Formula: C$_{419}$H$_{815}$N$_{13}$O$_{204}$
Molecular Weight: 9299.92

We disclose that the substituted phenol moiety is a very useful chemical moiety to use with the various dPEG constructs and intermediates to make others that can be uniquely incorporated into the general branched dPEG construct compositions. The aryl ring of the general phenol can be substituted with any known substituent to which a functionalized linear dPEG can be reacted, which could include, but not limited to the formyl, amine, carboxyl, a second hydroxyl (with one protected with an appropriate and optional protecting groups). The hydroxyl of the phenol can be reacted with alpha-halo-keto or acetyl moieties to make ketones or carboxyl derivatives, in the former case it can make a very useful precursor to a stable and unique set of conjugation reagents to react with an aminooxy compound or a hydrazine derivative. The former forming a very stable linkage and the latter a potentially cleavable one. Uniquely, the phenol can be used with hydroxyl terminate dPEG constructs including branched dPEG constructs using the Mitsunobu reactions and variations of the same (Ref.: K. C. Kumara Swamy, et al., "Mitsunobu and Related Reactions: Advances and Applications," Chem. Rev., 109, 2551-2651 (2009)). In particular, the phenol as tyrosine derivatives can be used in and are preferred in this disclosure as an AC and its derivatives, derivatives as Some of the embodiments are shown below.

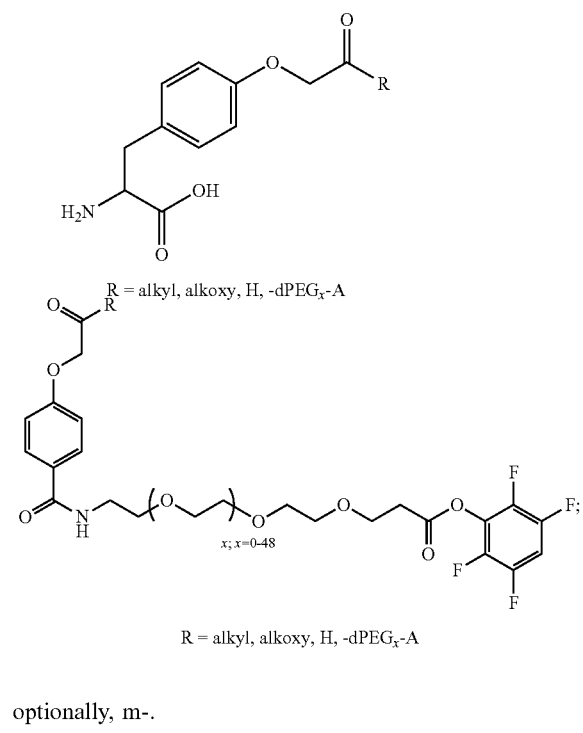

R = alkyl, alkoxy, H, -dPEG$_x$-A

R = alkyl, alkoxy, H, -dPEG$_x$-A optionally, m-.

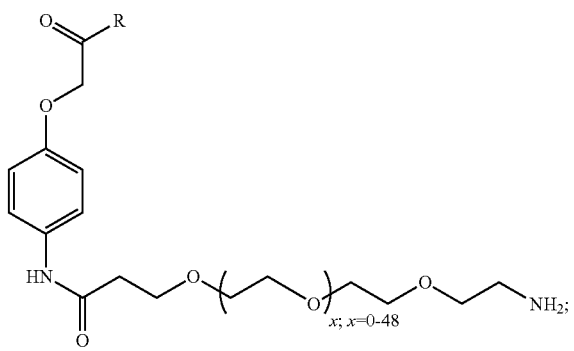

R = alkyl, alkoxy, H, -dPEG$_x$-A optionally, m- and amine convertible to a wide variety of A's, see Tables 1 and 2.

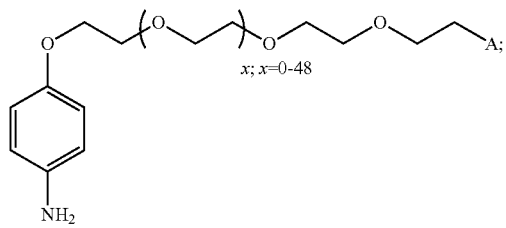

optionally m- and amine can be converted to other A's and optionally including dPEG constructs.

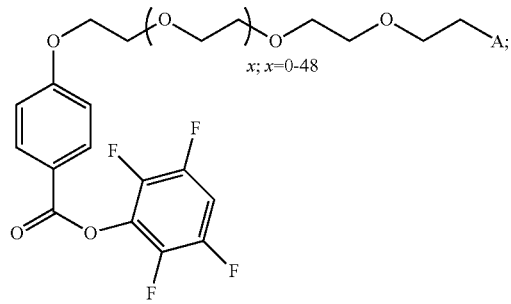

optionally m- and the active ester, or the carboxylic acid can be converted to other A's and optionally including dPEG constructs.

The following is a preferred general construct for incorporating into a branched dPEG template construct as part of or as

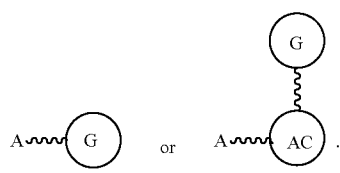

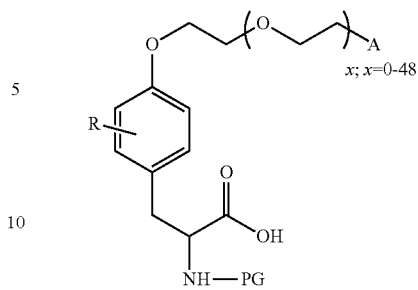

Another embodiment and using this same strategy, instead of reacting a second branched dPEG construct onto the hetero reactive position of the BC, a TG or DG can be incorporated within this branched environment, either attaching it as a

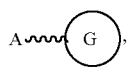

where G is the DG or TG, or it can be reacted with G where it is a chemically reactable group converted to a chemically reactive group. A potential objective might be to "hide" the inherent natural hydrophobic character from the environment, which is very common for many TG and DG's. Also in the case of the TG, the wavy line could optionally be a cleavable group, like a disulfide or a hydrazone, optionally a peptide sequence that can be cleaved specifically in the cell. The equation below shows just one approach to the final structures. In this case AC can be an amino acid with a functional side group, e.g., lysine, tyrosine, aspartic and glutaric acids, serine, as well as a number of non-natural amino acids, including those with carbonyl, propargyl and azido functionality in them (see A. J. DeGraaf, et al., "Non-natural Amino Acids for Site-Specific Protein Conjugation," Bioconjugate Chemistry, 20(7), 1281-1295; Peter G. Schultz and Lei Wang, "Expanding the Genetic Code," Angew. Chem. Int. Ed., 44, 34-66(2005)). And BC can be from those described above and taught throughout the disclosure.

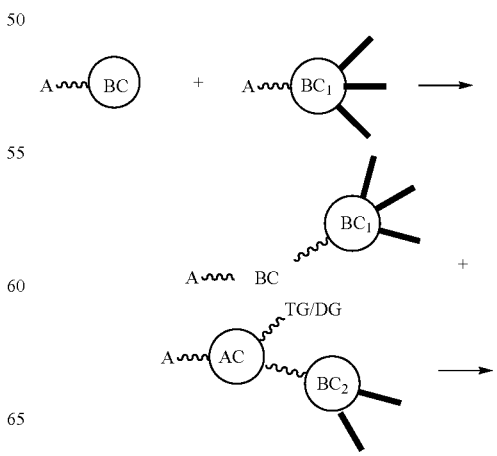

-continued

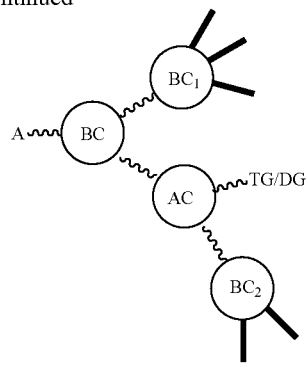

Or optionally the following general equation will make unique branched dPEG construct that is potentially smaller than in the above example.

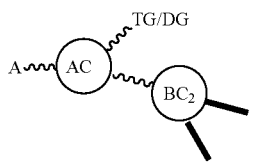

Also and optionally,

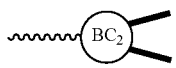

can also be just a linear solid line,  .

Examples of this embodiment include the options of delivering specifically a diagnostic or therapeutic group using a corresponding biologically active group, preferred is a preferential locator. Where the preferential locator is a TG (therapeutic group) the wavy line can contain a cleavable group. The attached branched group can be for controlling the PK and increase the biocompatibility of the TG (therapeutic group).

Another preferred embodiment of this disclosure is where "A" in the branched dPEG constructs occurs in multiples, where "A" is the same, or where "A" is different. The key advantage is to use the technology disclosed herein to control the design of

and especially the properties of the ∼∼∼∼∼ as disclosed herein to give additional design options in constructs with multivalent interactions add benefit and can be controlled in biological systems. Heretofore, the ability to control the final properties has been limited by unavailability of constructs that give the control that the disclosed dPEG constructs have the potential to do, and with the level of design variability available in the wavy line with the dPEG, as well as into the various other attached branched dPEG constructs.

Some of the options of this disclosure are shown in equations below. Initially disclosed is the embodiment with Multiples of the same A, indicated her just as $A_1$. Two simple options are shown here in the following equations for incorporating

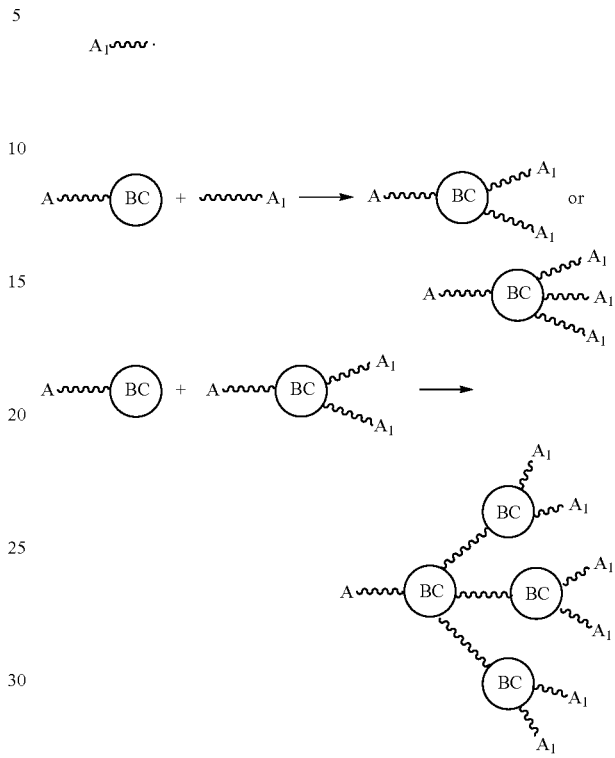

Polyvalent interactions in biological systems are well known and has been reviewed (Ref.: M. Mammen, et al., "Polyvalent Interactions in Biological sSystems: Implications for Design and Use of Multivalent Ligands and Inhibitors," Angew. Chem. Int. Ed., 37, 2754-2794(1998). Some of the more recent emphases have been on the polyvalency of peptides, often for enhancing immunogenicity (Refs.: a. D. Andreu, et al., "Strategies and Limitations in Dendrimeric Immunogen Synthesis: The Influenza Virus M2e Epitope as a Case Study," Bioconjugate Chemistry, 21, 102-110 (2010); b. P. M. H. Heegaard, et al., "Dendrimers for Vaccine and Immunostimulatory Uses. A Review," Bioconjugate Chemistry, 21, 405-418(2010)) but also to increase the binding avidity. For the larger engineered scaffolds, these have been crosslinked to increase binding efficiency, or more likely to add multiple binding specificities, as in the construction of bispecific antibodies and other bispecific engineered scaffolds. This is generally done as part of the molecular biologic designs, and so the options for bringing in the powerful design tools disclosed herein are not optional (Ref.: M. Gebauer and A. Skerra, "Engineered protein scaffolds as next-generation antibody therapeutics," Curr. Opin. Chem. Biol., 13, 245-255(2009); A. B. van Spriel, et al., "immunotherapeutic perspective for bispecific antibodies," Immunology Today, 21(8), 391-397(2000); P. Chames and D. Baty, "Bispecific antibodies for cancer therapy: The light at the end of the tunnel?," Landes Bioscience, 1(6), 539-546(2009)). Disclosed herein are some design options to resolve this inadequacy in the art.

A more recent example using peptides shows that using flexible and variable length linear dPEG constructs, $dPEG_{12, 24 \text{ and } 36}$ on a native. Fc antibody with just two peptides attached, mimicking the native antibody, shows that in some cases there are up to a $10^5$ increases in the binding of the final construct compared to the single peptide. (Ref.: D. J. Capon, et al., "Flexible antibodies with non-protein hinges," Proc. Jpn. Acad., Ser. B, 87, 603-616 (2011)).

In this disclosure we show that by having the ability to make a variety of key branched dPEG construct core compositions, we disclose the enablement for making the compositions that can control the avidity to a very high degree, but also have the additional option of incorporating other branched dPEG constructs to control the desirable pharmacokinetic and biodistribution properties and retain the binding efficiency of multiple A's, as well as control the orientation and flexibility of the A's. We also disclose options for incorporating more than two peptides or engineered scaffolds or other preferential locators. Additionally these can be incorporated in the construction of nanoparticles.

An additional embodiment for the various options of $A_x$ is where multiples of an engineered antibody are put on to give greater size to the construct as well as potential control of the biologically activity. This can be useful in using the branched dPEG construct to control the pharmacokinetics, especially the serum half-life, as well as the biodistribution.

A particular example to demonstrate certain aspects of these embodiments is work that is in the art with using GLP-1 receptor agonist Exendin-4, which is the active ingredient in several approved drugs for the treatment of Type II diabetes. Exendin-4 has a number of glucoregulatory properties including, enhancing glucose-dependent insulin secretion, suppressing glucagon secretion, reducing gastric mobility and food intake, and improving pancreatic endocrine function. However, Exendin-4 is only about 4.2 kD and 39 amino acid residues, in size and so is excreted very quickly and has to be reinjected frequently into the patient. To date formulation of the Exendin-4 has been the route to finding a dose reduction solution. It has been evaluated in the research literature in a number of conjugation formats, including the use of conventional polymeric PEGs to increase the serum half-life, including a case where two Exendin-4 molecules were used together to also potentially increase the binding, along with the use of a large conventional PEGs for increasing the serum half-life. This format showed a modest increase in the binding of 3.5 times with the two Exendin-4 molecules in a very congested branching format. Additionally, with the 20 kD polymer PEG attached with two Exendin-4 molecules, a very nice serum profile was observed, however, the binding of the Exendin-4 was seriously reduced due to the "shielding effect" of the linear PEG, where the binding is reduced by approximately 67 times to that of the bis-Exendin-4 without the large polymeric PEG! Based on our results with the Fab', using branched PEG constructs with multiple Exendin-4 molecules, should both increase the avidity of the construct, as well as increase the serum half-life, and NOT cause an interference of the branched dPEG with the binding of the Exendin-4 and give a model for a number of similar applications. This is based on the data presented early in the disclosure with the CC49-Fab'-S-MAL-dPEG$_{12}$-Tris(-dPEG$_{24}$ acid)$_3$, in particular, where there is a significant increase in the serum half-life and in a competitive ELISA assay with the CC49-Fab'-S-NEM as the control, the was NO loss in binding.

The examples shown below are built on a lysine core, but this is just an example, and a variety of others can be used. Also, as in another embodiment(s) using our attachment cores, AC's, similar constructs can be manufactured as well.

REFERENCES

1. T. H. Kim, et al., "Mono-PEGylated Dimeric Exendin-4 as High Receptor Binding and Long-Acting Conjugates for Type 2 Anti-Diabetes Therapeutics," Bioconjugate Chemistry, 22, 625-632 (2011);

2. T. H. Kim, et al., "Low Molecular Weight (1 kDa) Polyethylene Glycol Conjugation Markedly Enhances the Hypoglycemic Effects of Intranasally Administered Exendin-4 in Type 2 Diabetic db/db Mice," Biol. Pharm. Bull, 35(7), 1076-1083 (2012.

In the latter reference above, the Lys$^{27}$ in the Exendin-4 is modified with linear polymeric PEGs of MW, 1, 2 and 5 kD, the binding of the resulting construct are almost the same for the 1 kD, then approximately 12 and 37 times lower with the 2 and 0.5 kD, respectively. These results might suggest a more extended chain in solution for the MW range of about 1000. This would on the average be about 24 ethylene oxide units and potentially suggest an optimal length in a branched dPEG construct can be greater than a dPEG$_{24}$.

In the diagram below and in the context of physical parameters shown earlier for the Fab'-branched dPEG construct, where the branched dPEG construct can be easily larger in size and has the ability to dramatically increase the PK of the Fab', and the where with the branched dPEG constructs we do not see the same interference with the binding sites, as well as in the example of Capon, where peptides on a similarly rigid Fc give a synergistic avidity of up to $10^5$ for two peptides over one, and where the difference for the Fab' vs. the whole Ab is about 40, it would seem like a very reasonable and significant advancement in the art would be drawn, from looking at the models of a bis-scFv, a bis-Exendin-4, and a tetra-Exendin-4 shown below. Shown are models of constructs created using branched dPEG constructs, with A's that are biologically active, that would have unexpectedly high avidities, especially when the length of ∿∿∿∿∿ and the configuration around BC are optimized, without losing the binding that is seen when conventional polymeric PEGs are used, and gain the desired PK when the branched dPEG construct is optimized for the PK. This is something that has not been seen in the art and is disclosed herein.

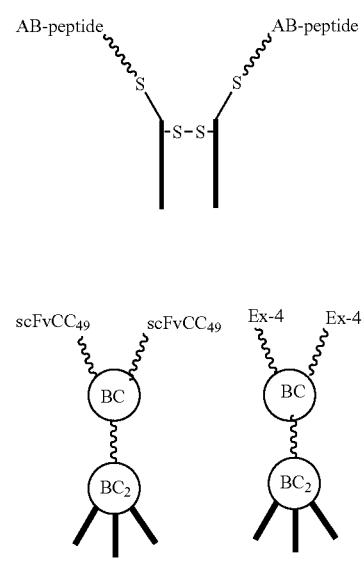

-continued
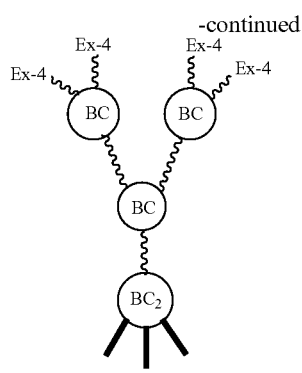
Below are some representative BC's for building the
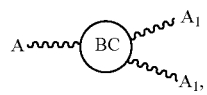
but not limited to this lysine core or the maleimide, with branched dPEG construct compositions, and are herein representative of the general compositions for achieving a multivalent construct.
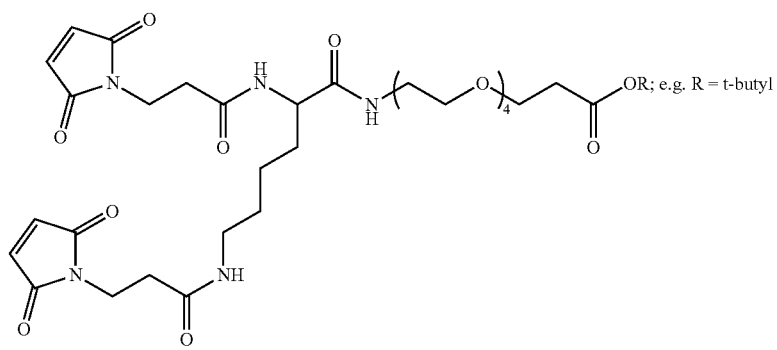
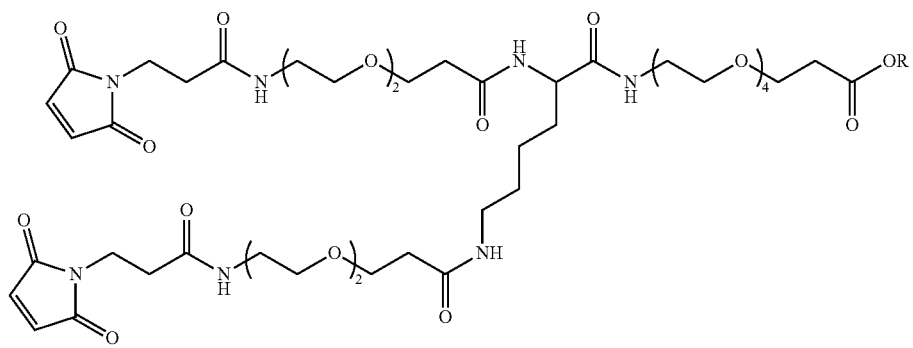
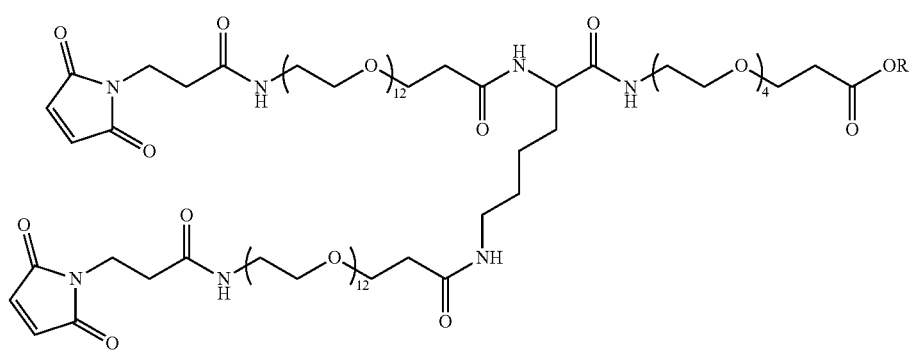

Also shown are two structures showing other useful and preferred composition using a Tris BC, one with a branched protected aminooxy as the t-boc protected chemically reactable group with 3 branches, and the other with the phthimidooxy, in each case with the compatible chemically reactable group on the wavy line with single unique reactivity. In all cases the length of the dPEG in $A_1$∼∼∼ and A∼∼∼ can be varied at will, as can the nature of $A_1$ and A to make them most useful in various synthetic scenarios.

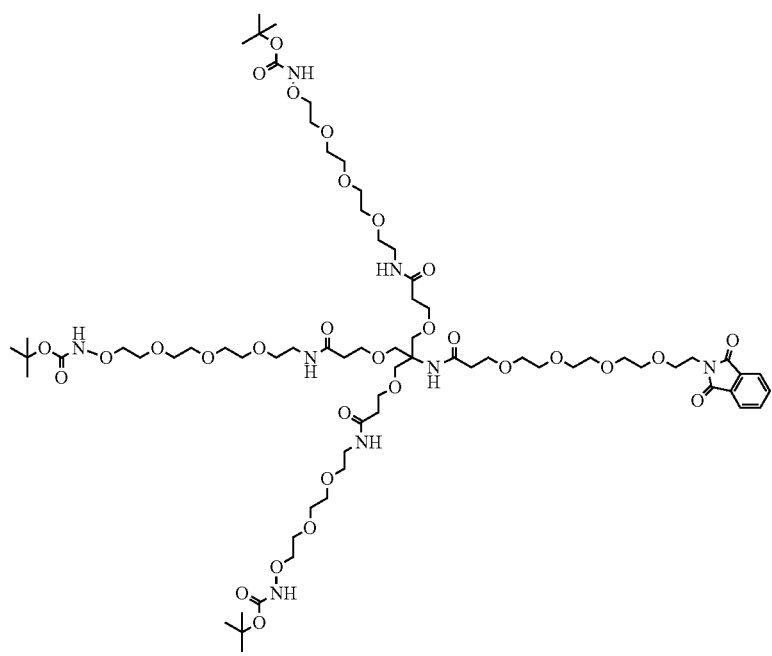

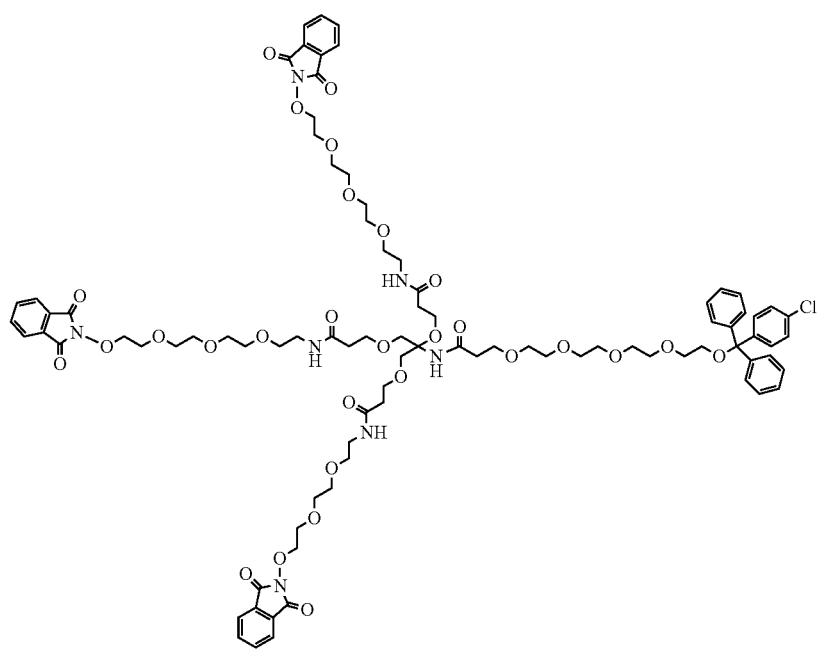

The variables that can be controlled in the construct, but not limited to include:
Optimize the length of the dPEG on
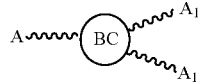
in a method for making
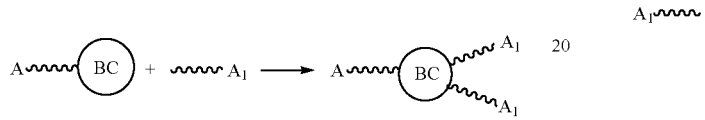
in this equation.
Shown are examples of
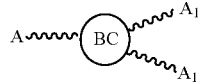
with A1 as the maleimide and the spacer in the wavy line is varied from dPEG=0 to 12. Also is an example where there are 4×
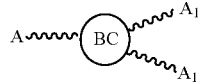
and a wavy line with dPEG length of 12.
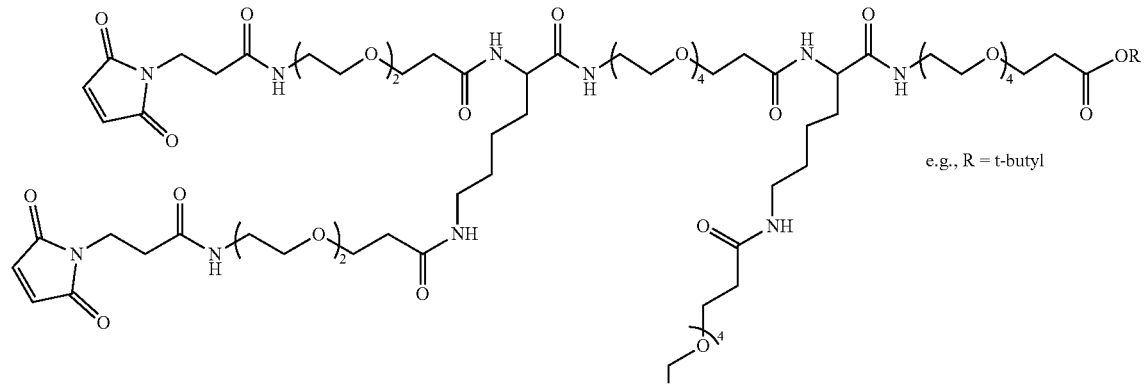
e.g., R = t-butyl
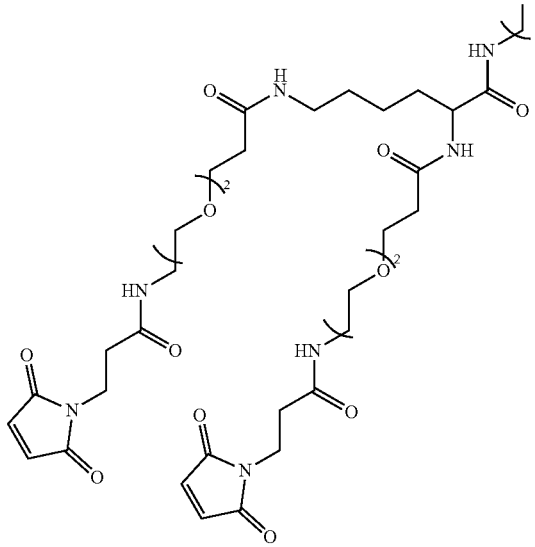

-continued
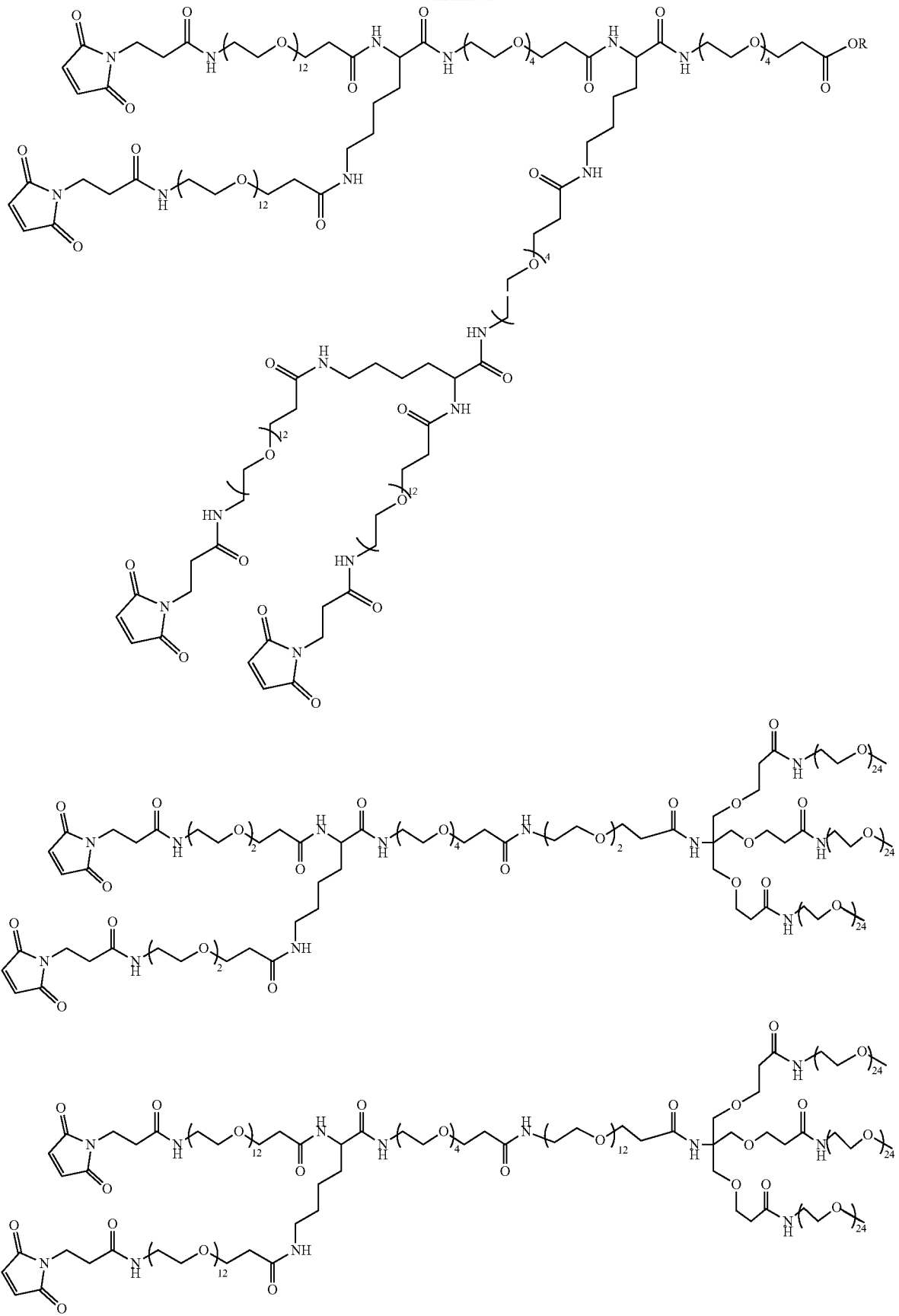

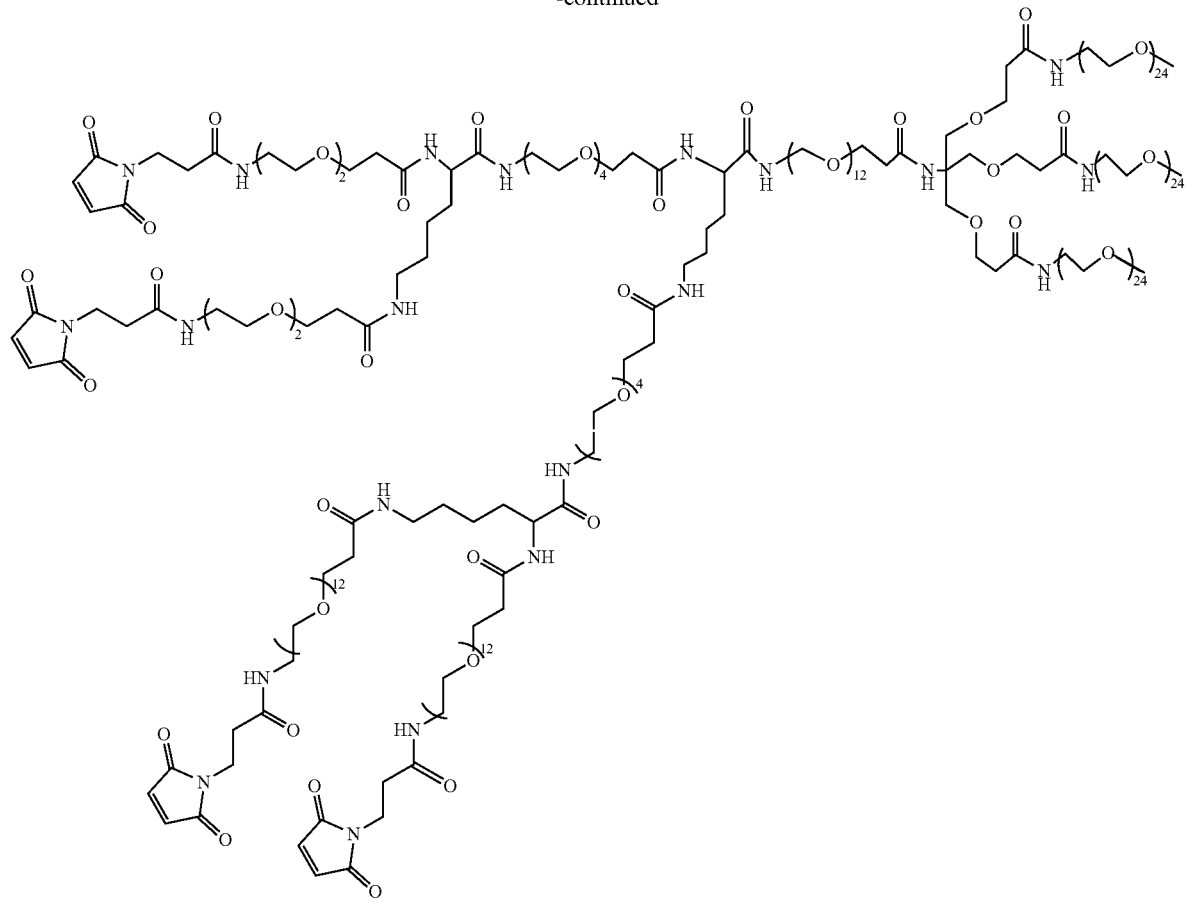

In the experimental examples we show where the -dPEG$_{12}$-Tris(-dPEG$_{24}$-m)$_3$ has been added, but from examples with just a single "A" is extant, the embodiment shown below is also taught.

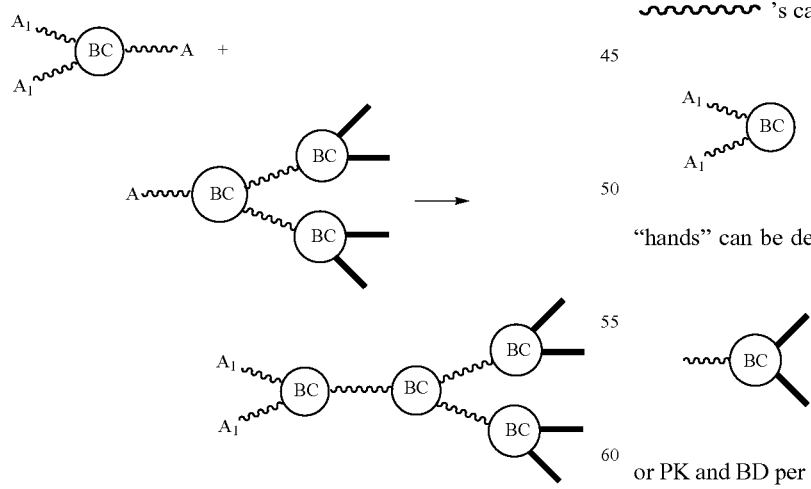

In the equation shown above, A$_1$ could be the same preferential locator, e.g.; a scFv construct, e.g., a fully humanized CC49 scFv with a cysteine engineered into the construct, preferably at the C-terminus (Ref.: J. Schlom, et al., "Variants of Humanized Anti Carcinoma Monoclonal Antibody CC49," U.S. Pat. No. 6,818,749). The ⁓⁓⁓⁓⁓ can be designed such that the nature of the binding of two scFv's can be controlled to give binding characteristics that can change as needed. In the case of a high binding, the flexibility of the two (or more) ⁓⁓⁓⁓⁓'s can be different, such that the avidity of the

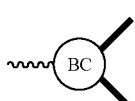

"hands" can be designed to function and the

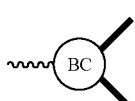

or PK and BD per options disclosed herein. Optionally there could be three scFv's, but higher is likely too large. Optionally, the scFv-CC49 branched dPEG construct disclosed above could be designed as a single A, where high binding is not essential, yet where the branched dPEG construct can be used to control PK and BD, as in an imaging application, more specifically a SPECT/CT imaging application.

Another preferred embodiment is where the "A's" can be different, and where the preferential locator can be $A_1$ or $A_2$ as

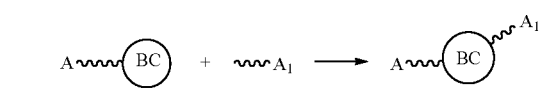

or they can be converted from a chemically reactive moiety to the preferential locator in the order that best suits the chemistry known in the art or useful from the current disclosure. This is diagramed in the scheme below.

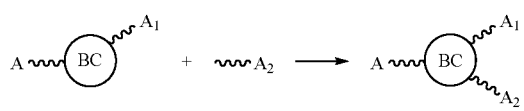

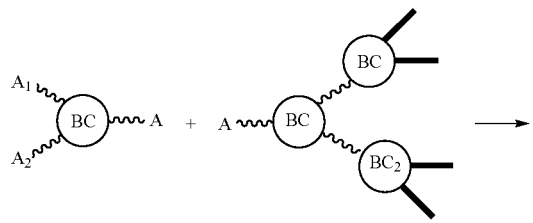

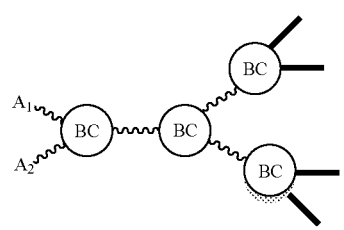

Optionally, $A_1$ and $A_2$ can be different preferential locators, e.g. that target different receptors on the cell surface, the design of the ⁓⁓⁓'s can be adjusted to the nature of the receptors or other bispecific interactions that are being addressed in the biological system, or in other applications, like in a diagnostic assay or nanotechnology.

Examples of $A_1$ and $A_2$ can be two different but not limited to engineered protein scaffolds (Ref.: M. Gebauer and A. Skerra, "Engineered protein scaffolds as next-generation antibody therapeutics," Current Opinion in Chemical Biology, 13, 245-255(2009), preferential locators or two inhibitors that can be distance controlled through

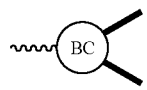

to optimize the level of binding necessary to control the action desired, e.g., the distance between two different receptors or markers for the preferential locators. The distances can vary as a function of the degree of expression. Also the dPEG in the ⁓⁓⁓⁓ gives great flexibility, more than is typical in a peptide spacer. Another extension of this embodiment is where the

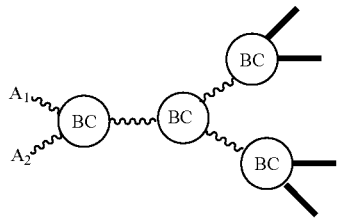

's can be the same or different, as shown in the scheme above. The branched dPEG gives control on the PK and BD on these typically small, 8-20 kDa protein constructs. Also, optionally the wavy line between the BC's in can contain one or more of a DG or TG or both a DG or TG. This is a recent example of a bispecific affibody motif with amino acid spacers. These amino acid spacers can be replaced with a simple heterobifunctional crosslinker, e.g., MAL-dPEG$_x$-ONH-PG, where x can be varied from 2-48 and PG can be t-boc phthalimide or other typical protection groups, or unique to the aminooxy, like methoxysubstituted trityl, preferably dimethoxy or trimethoxy. The engineered protein scaffolds would need an engineered cysteine and an aldehyde or ketone, preferable aryl. Optionally a multifunctional unit can be used to which can be added a

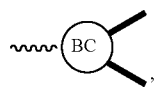

and where optionally the ⁓⁓⁓⁓ can contain a DG or a TG or a combination of each. An example is shown below.

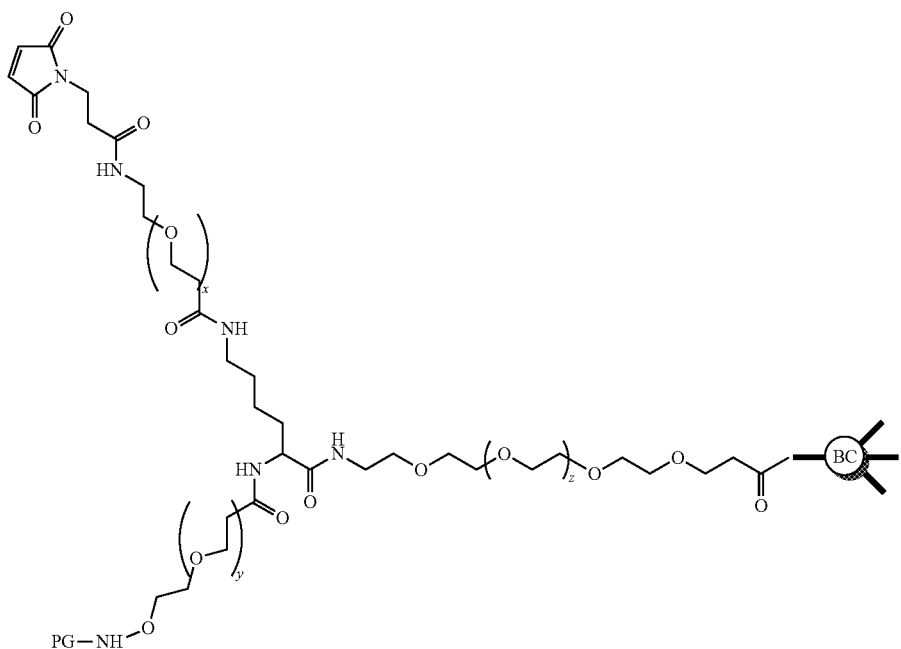

A further embodiment with three biologically active groups in various combinations or configurations, for example. $A_1$, $A_2$ and $A_3$ can be different, or $A_1$ and $A_2$ can be the same and $A_3$ different and this can be made as in the reaction depicted below.

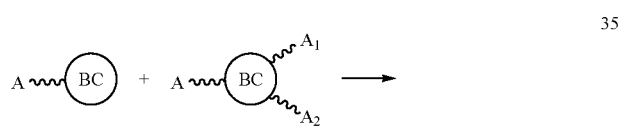

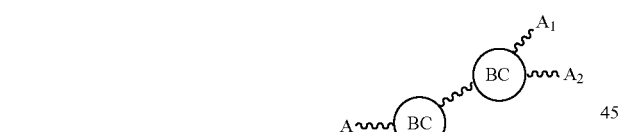

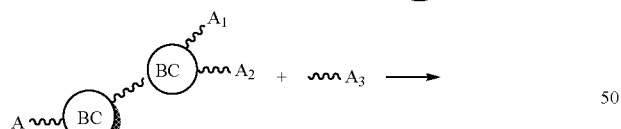

-continued

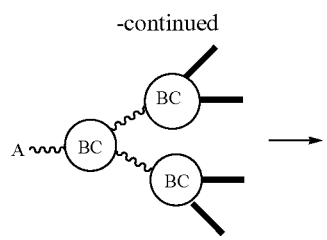

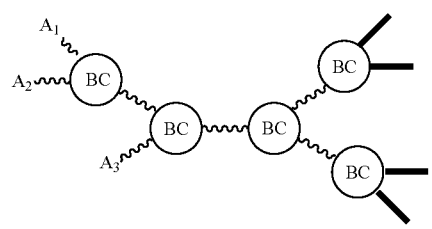

An addition embodiment is where there could be at least 4 or more different biologically active groups. Where $A_3$ can be

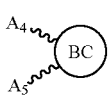

and shown in the diagram below. Other permutations of this basic embodiment are also included as embodiments.

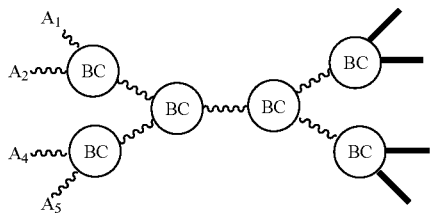

$A_x$, where x is 1, 2, 3, 4 or 5, in

is either a biologically active group or is converted to a biologically active group $A_x$ from a chemically reactive group Ax. The optimal method for making the final branched dPEG constructs shown in any of the equations above will be determined by the normal considerations of process development know in the art, including optimal microreactor technology. Important variables to be incorporated into the wavy line have been discussed above in controlling the relative orientation and biological activity of the $A_x$'s can contain just the functionality, e.g., iodoacetic acid, which can contain a $dPEG_x$ spacer or no dPEG spacer.

An additional preferred embodiment of the branched dPEG constructs is where the wavy line is a template containing attachment cores or attachment cores with dPEG attached functionality in

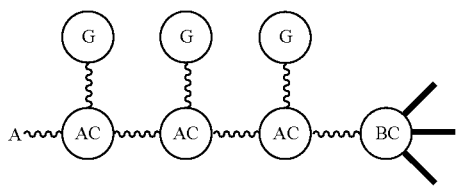

to which can be attached a variety of diagnostic and therapeutic groups, but not limited to such. These template constructs could also be placed on to surfaces or exteriors of various nanoparticles or polymer delivery systems, like gold, PLGA or stealth liposomes.

The general template is shown below. It is shown with 3 AC's but the constructs can have as few as one AC, or as many as 4 or more AC's.

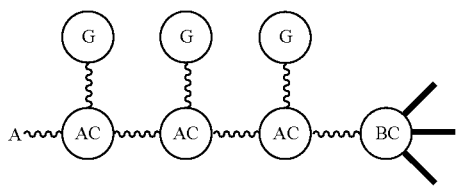

is an attachment core that is also a multifunctional core, with at least three different attachment points so as to be built into this branched dPEG template as part of our general ⁓⁓⁓ in the general branched dPEG construct

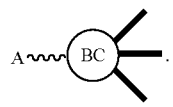

These

are typically going to be functional amino acids, natural or unnatural and in various protected forms, but can also be from a wide variety of other organic cores that can be made trifunctional, e.g. 5-aminoisophthalic acid. Preferred are lysine, tyrosine, aspartic acid, and a range of unnatural amino acids or derivatives of these giving a wider range of functionality to

in order to add the desired diagnostic or therapeutic group, but not limited to these options. The A's can be the same or different, as can the 's. This will be determined by the application. The ⁓⁓⁓ in

can optionally contain a cleavable group.

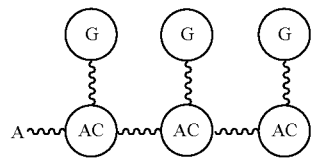

The basic template composition for this preferred embodiment can be synthesized in a variety of ways. Given that the generally preferred AC's are peptides, the option exists to build the basic template to which the BC's, as

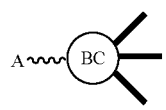

can be added, using with SPPS, solid phase peptide synthesis or standard solution phase chemical methodology, or a combination of each in a convergent fashion (not shown).

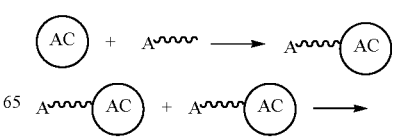

-continued

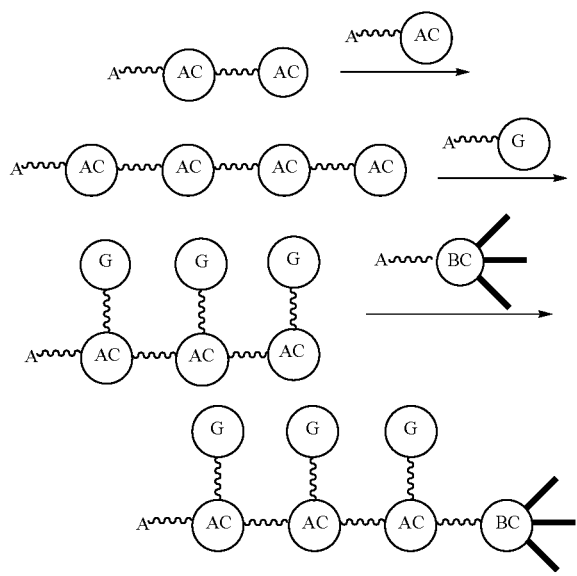

Optionally the

can be added as the template is build up. In the case where AC and G are different at any point along the template chain, this would be a preferred embodiment. An example scheme is shown below to build a tetra-lysine containing template, where the AC's are separated with a dPEG$_4$ spacer.

SPPS (Solid phase peptide synthesis) is one preferred option when all the G's are going to be the same. The basic chain can be built as shown below, but may have to be removed from the resin, as shown in the example, due to the sheer size of the construct, which is a general limitation of the SPPS methodology! Shown is the chemistry using the lysine as the repeating amino acid unit, and we show examples with 3 and 4 lysines with a dPEG$_4$ spacer. However, the lysine can easily could be replaced with other amino acids with a functional side chain that is protected or masked. Preferred are the lysine, tyrosine, aspartic or glutaric acid, optionally with a linear dPEG or a functionality, such as, for example, a ketone or an ester, an unnatural amino acid with an azide.

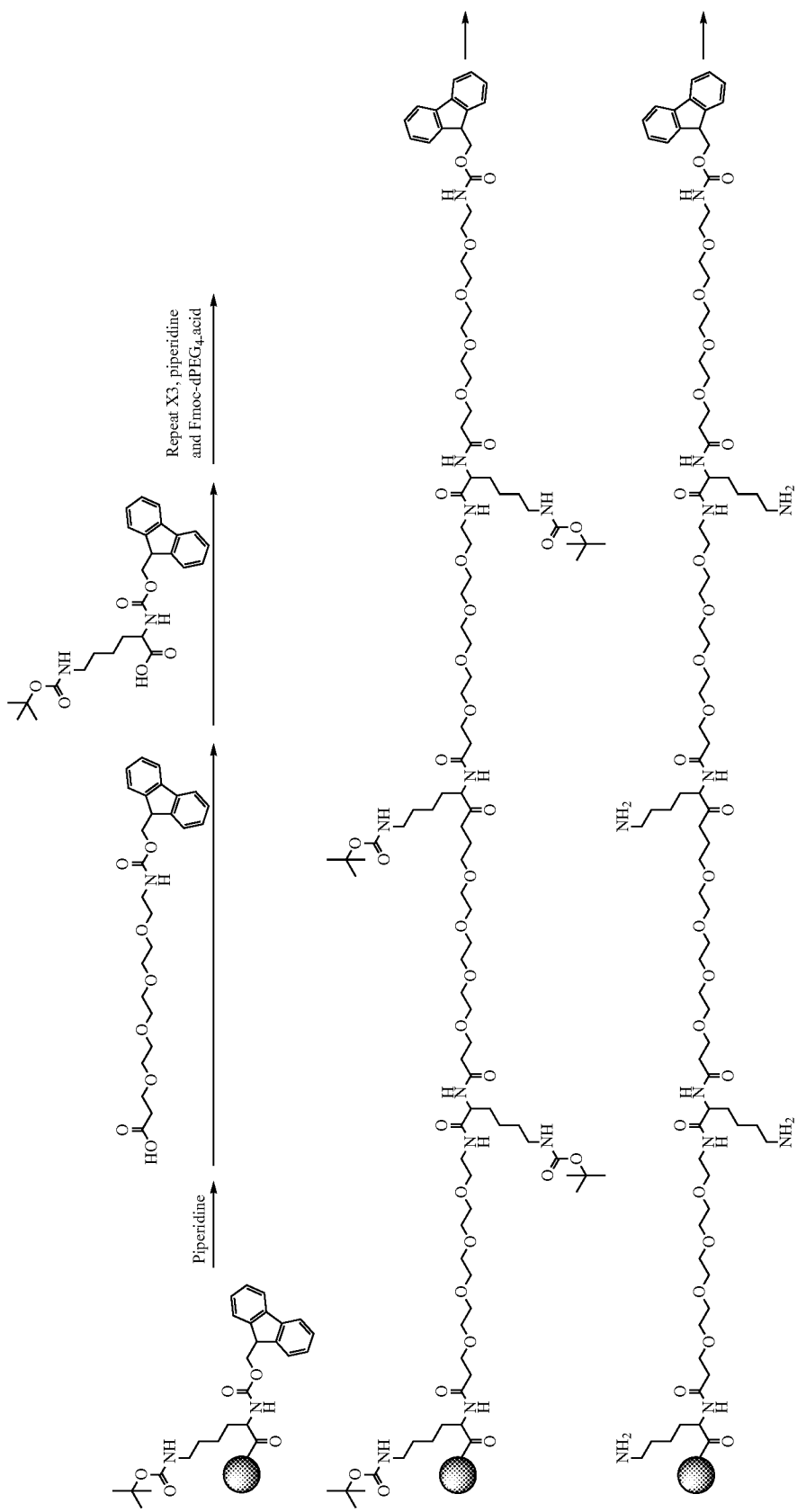

This can be removed from the SPP resin in the protected form, to which can be added a linear dPEG, which would give a form of a branched dPEG, or a
which is shown below.

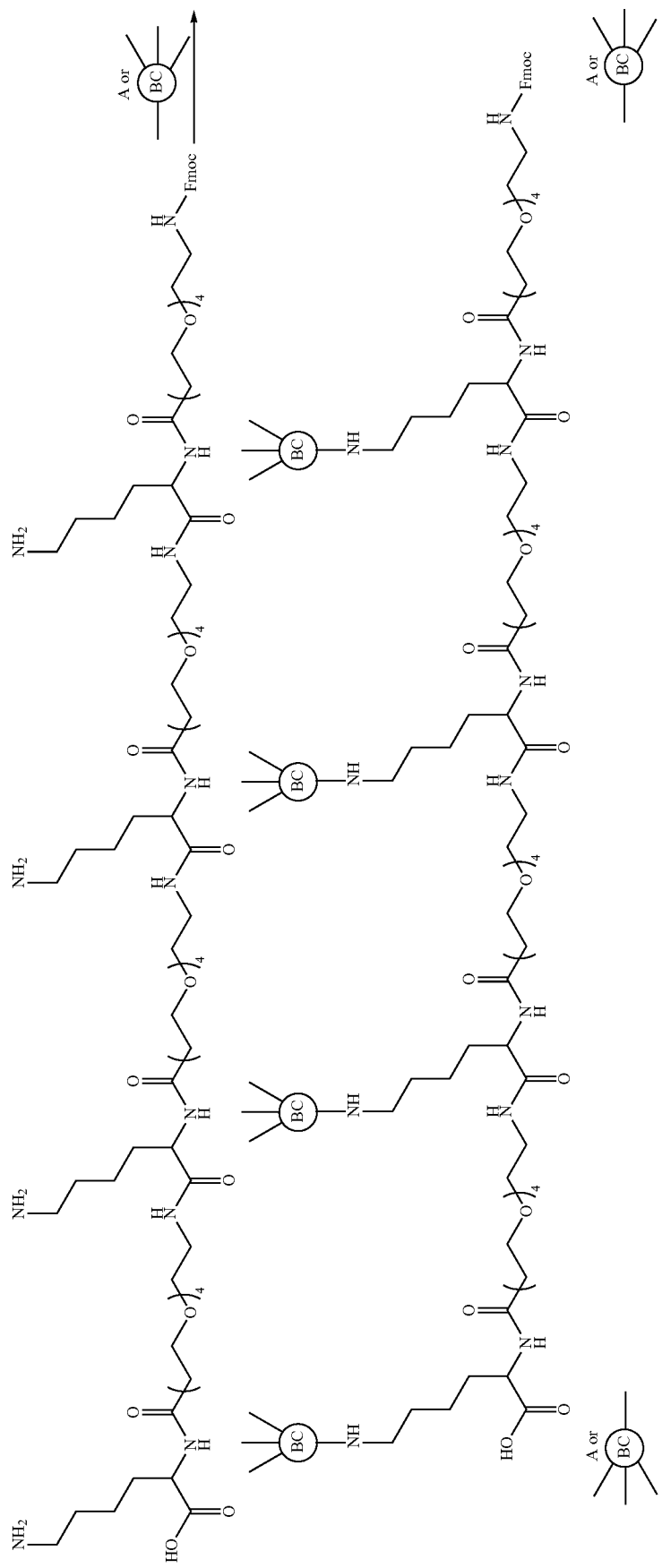

Optionally, the amine can be converted to another functional group, e.g., MAL, ketone, aldehyde, and others (see Table) and reacted to add two or more, in this case 4 G's, from any preferred DG's or TG's. An example is shown below with a novel ketone equivalent, (X). Optionally the conversions taught in Tables 1 and 2 and the related chemistry known in the art. Additionally simple linear dPEG chains at defined by the solid line, ▬▬▬ can also be added to create a novel form of a branched dPEG construct.

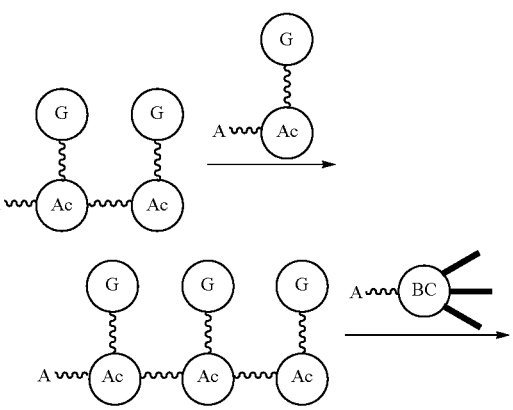

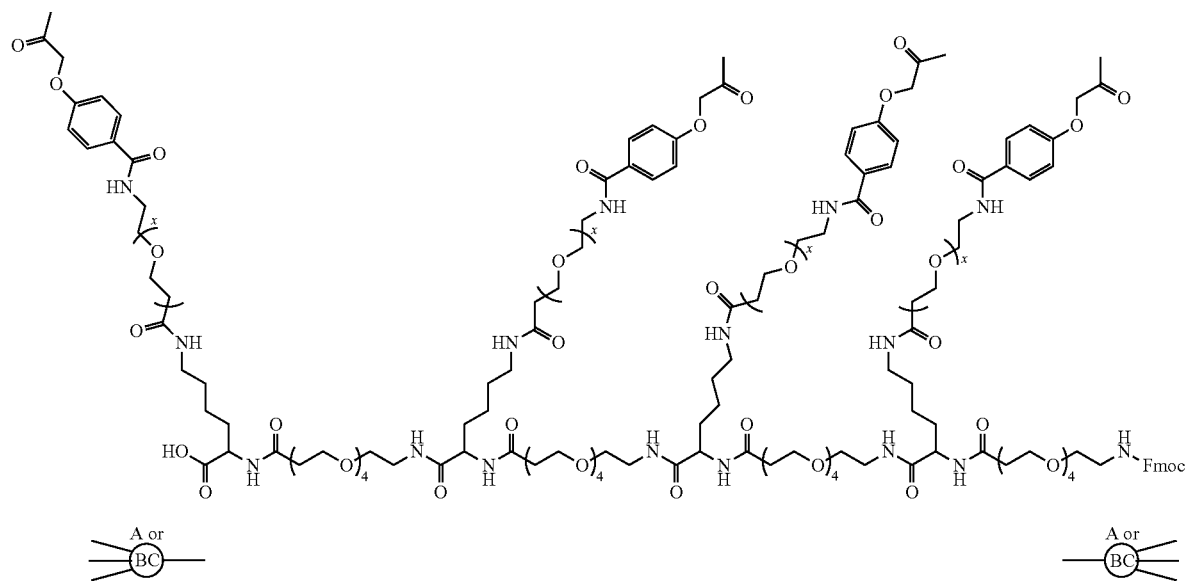

Optionally the template with the attachment cores can be made with the G's already attached, with or without the wavy line. This is preferred when it is desired for the G's to be different. Some of the AC's could be the same, given the variety of protecting groups that can be used for the same group, but removed under selective conditions for each. This is generally outlined in the diagram below.

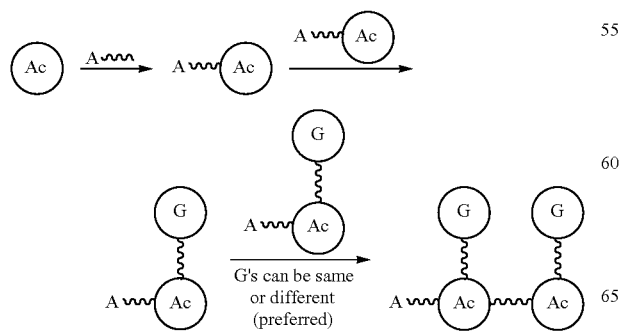

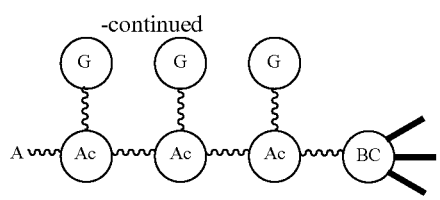

In this approach it is preferred, but not limited to using standard solution based chemical methodology, which optionally includes micro reactor technology (Ref.: C. Wiles and P. Watts, Micro Reaction Technology in Organic Synthesis, CRC Press, 2011; ISBN 978-1-4398-2471-9). There may be conditions that will still be suited for SPPS, when the side chains are smaller and do not create a burden to the solid phase pore size. It is preferred that most often with a preferred

's and the

's are different, this approach is preferred!

A further part of this embodiment is where a combination of SPPS and solution chemistry could make portions of a template of the total branched dPEG construct and they could be combined to a final construct an optimal convergent point in the process.

Shown in the schemes below demonstrate and disclose the versatile nature of the tyrosine as

on a heteromer template, the same could be applied to a homomeric template. It can be seen that within this embodiment many variants can be envisioned based on these basic disclosed examples using tyrosine and its derivatives.

Example of Making a Hetero Template with a Tyrosine AC

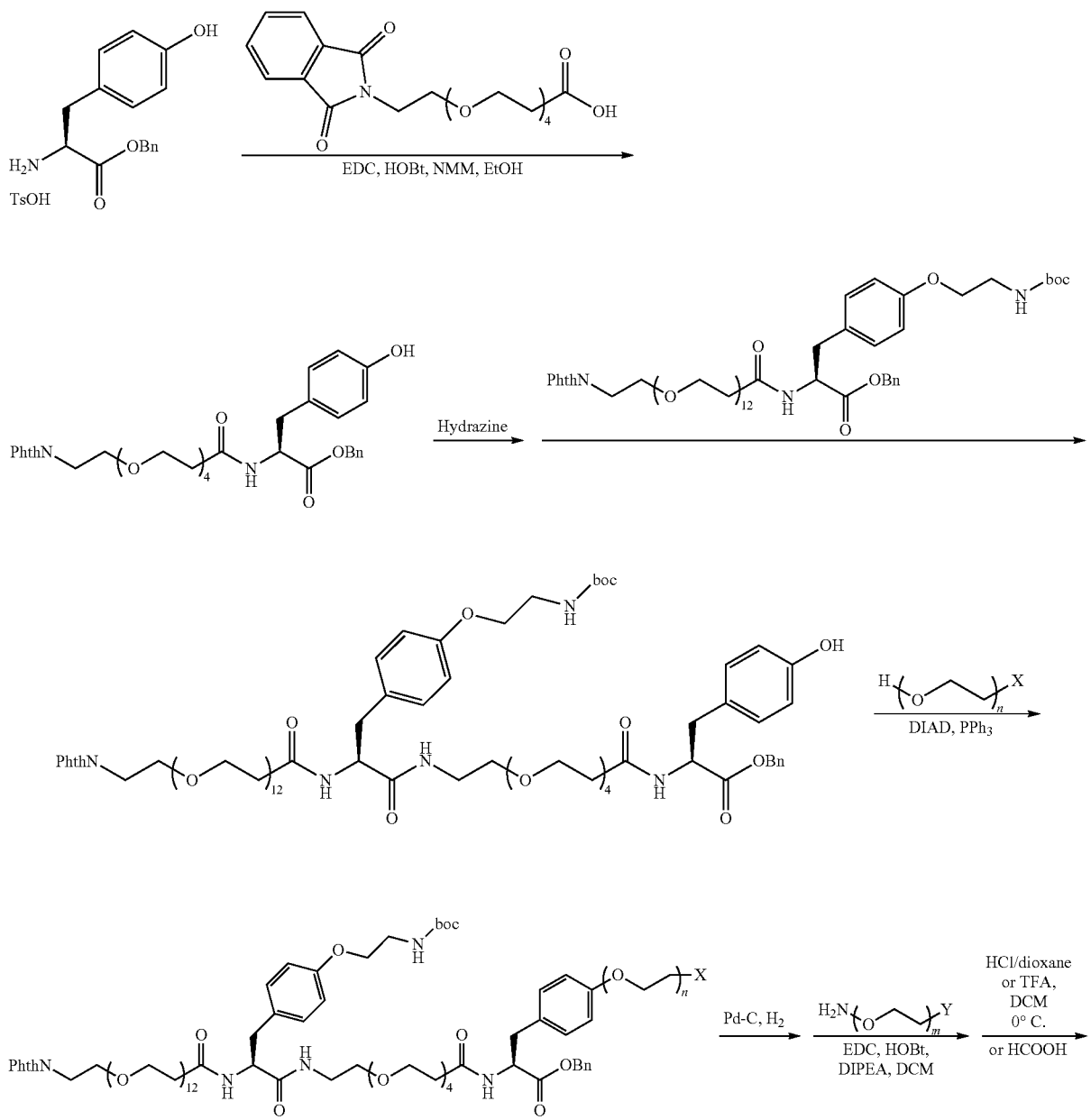

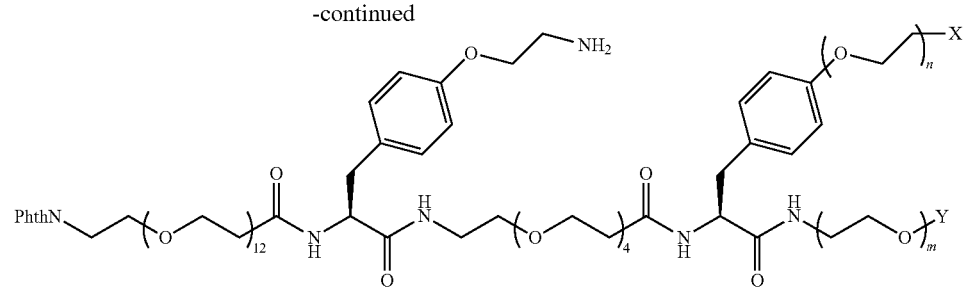
Example of Making a Homo Template with a Tyrosine AC
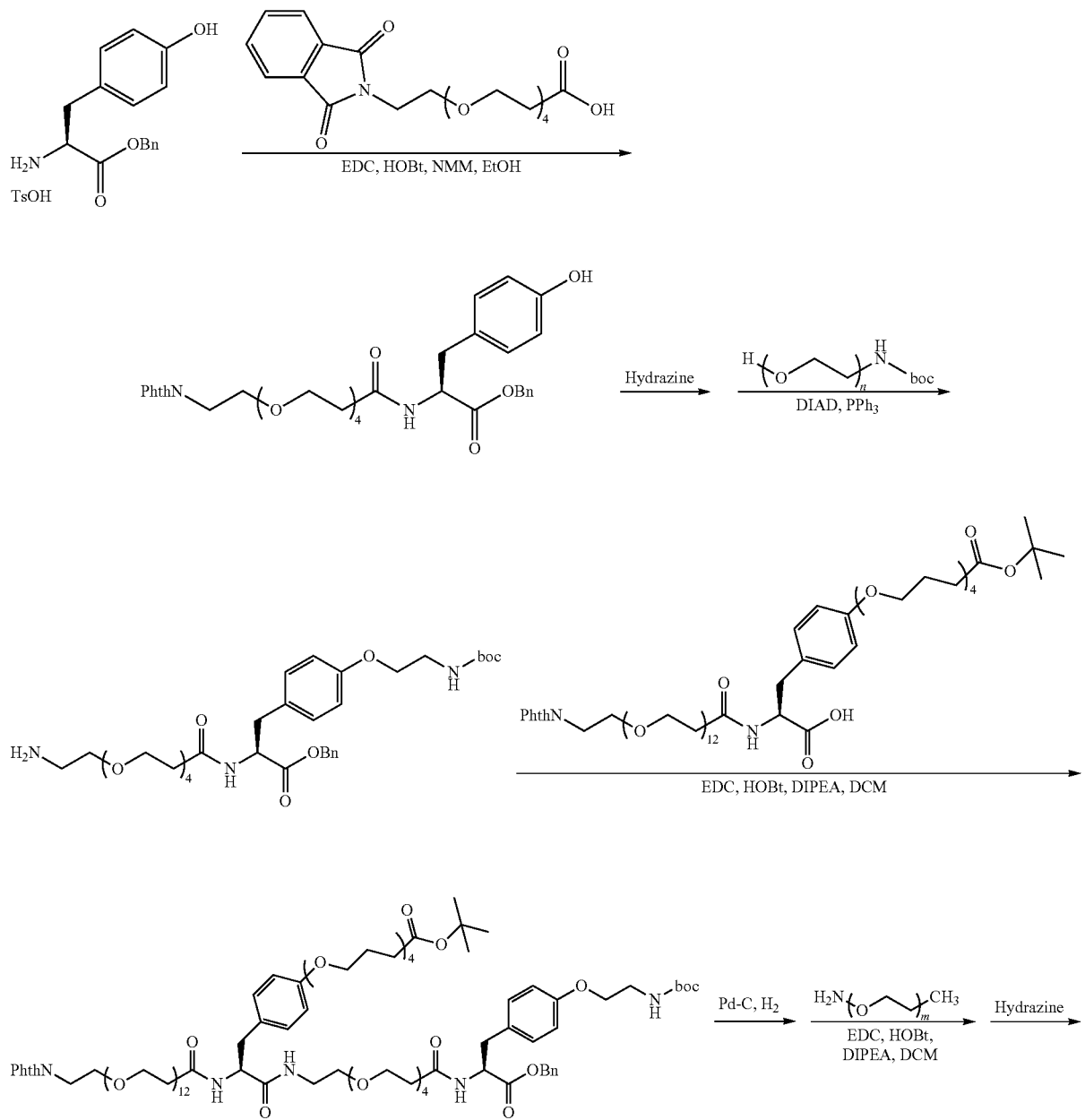

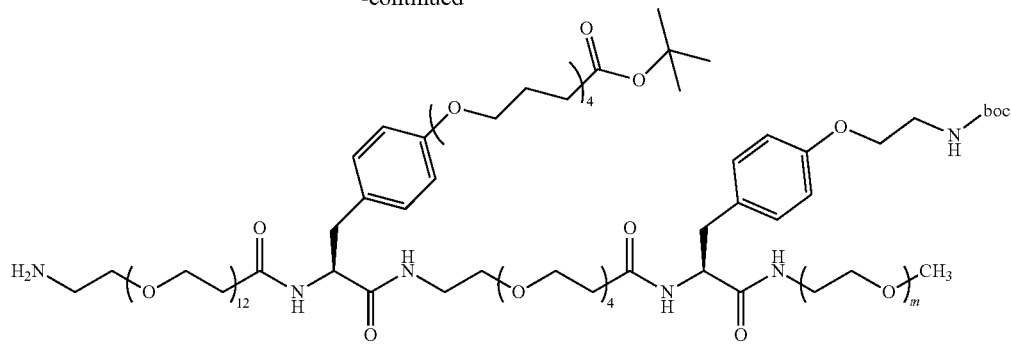
Example of Making a Hetero Template with a Tyrosine AC Using a "Convergent Approach"
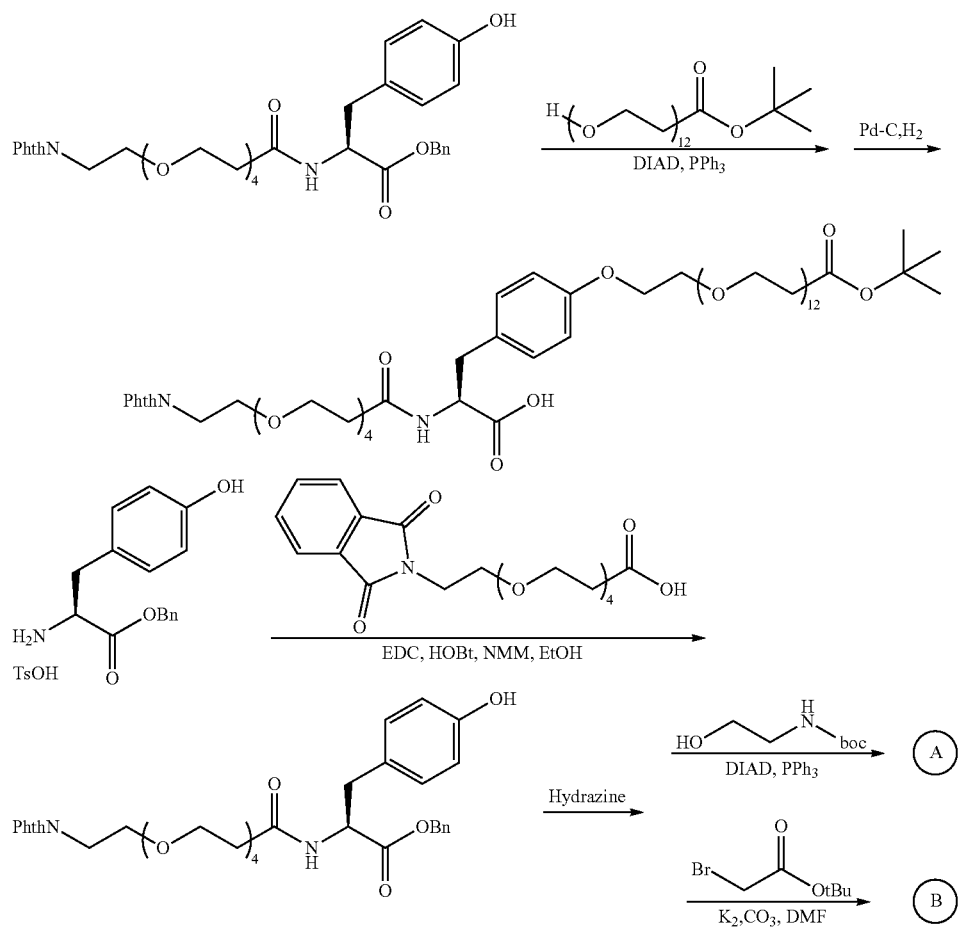
Another example that shows two A's as scFc's, e.g., of CC49, with a tyrosine based DOTA attached to a linear dPEG,
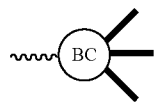
as the -dPEG$_{12}$-Tris(-dPEG$_{24}$-CO$_2$H)$_3$

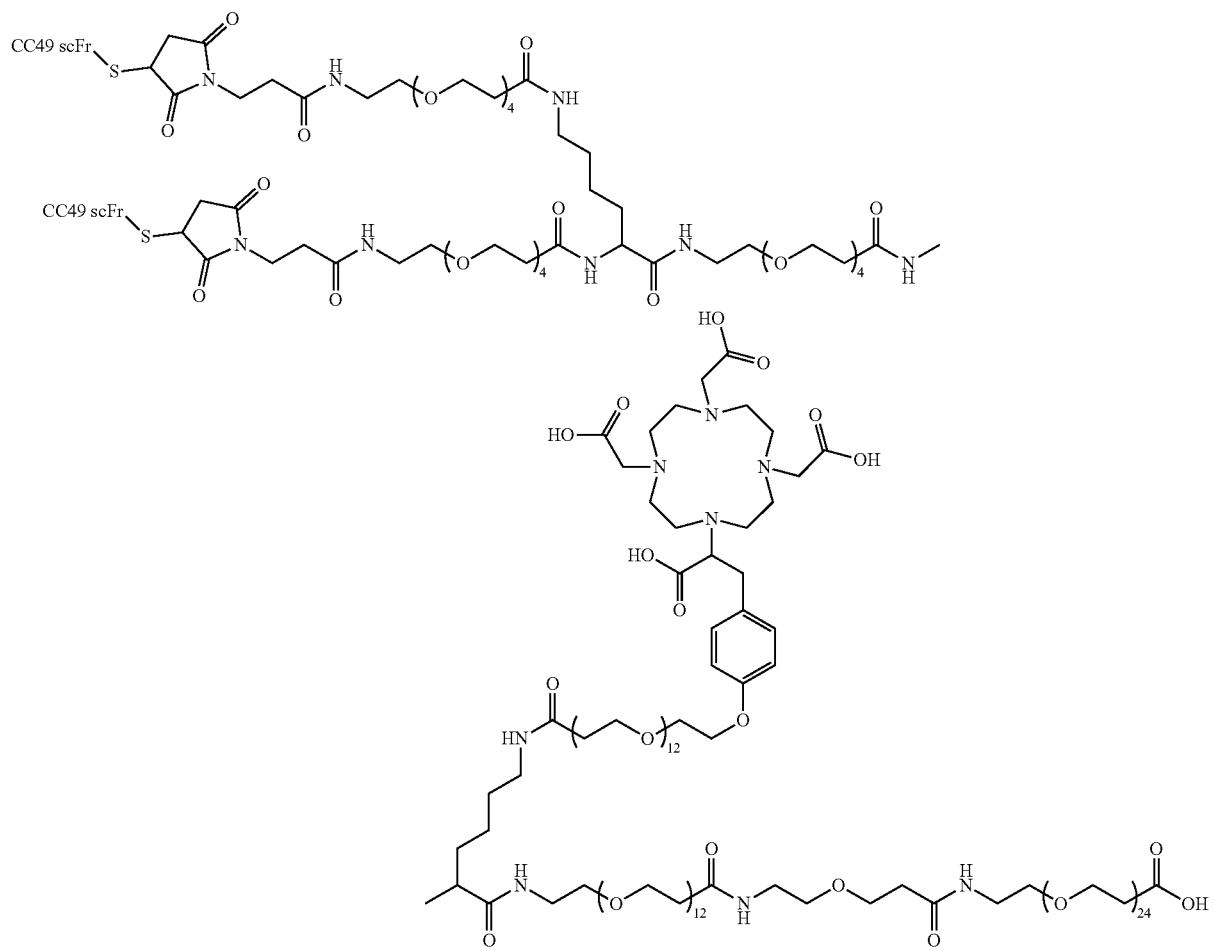

It can be seen that from these few examples a large range of useful branched dPEG constructs can be visualized based on the disclosures herein.

Additional Embodiments of the Branched dPEG Constructs are Shown Below.

Random substitution with branched dPEG constructs: An additional embodiment is the so-called random substitution of a biological at multiple functional sites of reactivity. This embodiment can be visualized in the diagram below. This scheme depicts a very simple "A", a biologically active group, e.g., an enzyme, or an antibody, which has at least four chemically reactive sites, e.g., the epsilon amine of component lysines, and it is reacted with

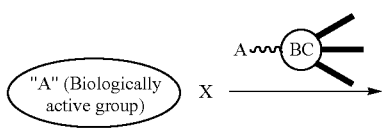

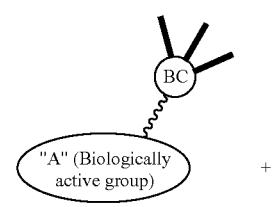

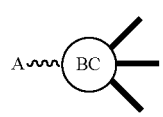

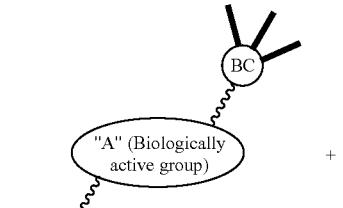

to give a random distribution of products. The distribution is going to depend on the stoichiometry of the reaction, and in theory could drive the reaction to where all four sites are reacted.

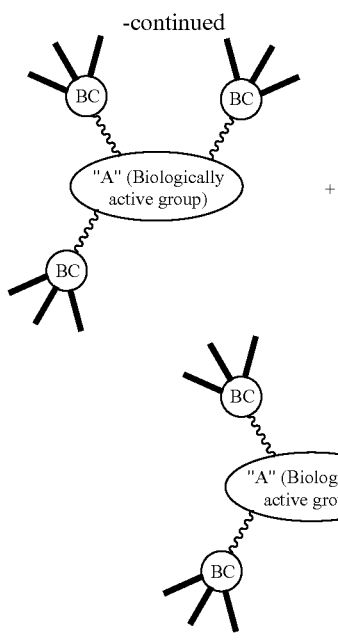

Given the discreteness of the branched dPEG construct, the final distribution can be characterized by mass spectrometry. This is confirmed in the data shown in the work published by Avipep, Inc. and the City of Hope (Ref.: See FIG. 4. in L. Li, et al., J. Nucl. Med., 51, 1139-1146(2010)). In the mass spectrum of the dPEGylated diabody, the individual and increasing number of dPEGs can clearly be seen and distinguished. In the equivalent situation with a conventional polymeric PEG reagent, there would be a continuum of peaks and the individual species would be exceedingly difficult, though more likely, impossible to be distinguished one from another. Hence, it is disclosed herein that if careful process control is put in place for the dPEGylation with a branched dPEG construct(s), that a controlled distribution of substitution could be reproduced and achieved. And in cases like this where the biological activity is largely maintained, this could be a much simpler solution than the complexity of engineering in site-specific sites for substitution. For, conventional polymeric PEGylation, there is a paradigm to technologically transition completely to site-specific substitution, away from the original products on the market, e.g., PEG INTRON and PEGASYS®, which were made from random substitution. This also led to additional loss of biological activity, which may not generally be the case for the branched dPEG constructs, as suggested in the data presented in the next example. Additionally, this could be applied to an engineered protein or, other biological construct where a specific number of thiols, disulfides or aldehydes of ketones, preferably aryl, could be engineered. These are more reactive to maleimides, vinyl sulfones and iodoacetamides or aminooxy compounds, optionally alkynes or alkenes (thiol-yne and thiol-ene reactions) and could more easily be completely substituted to the extent of the number of sites engineered for these particular chemically reactive moieties. In the schematic below is shown an example of a biologically active group with just a thiol, ketone and azide engineered into it, then potentially three different branched dPEG constructs as indicated by the different BC designations, $BC_1$, $BC_2$ and $BC_3$, respectively, and their complementary "A" (chemically reactive moieties) can be used to modify the biologically active group. The branched constructs can carry a large range of terminal groups on ■■■■■■■ and diagnostic and therapeutic groups on ⌇⌇⌇⌇⌇, as disclosed herein. This approach either in a single engineered functionality or in multiplicity, could be applied to develop an entire range of drugs and other useful compounds based on biologics that are heretofore not useful for reasons of toxicity, immunogenicity, BD or PK, which could easily addressed through the tremendous advances in the current state of protein and other biologic design and engineering.

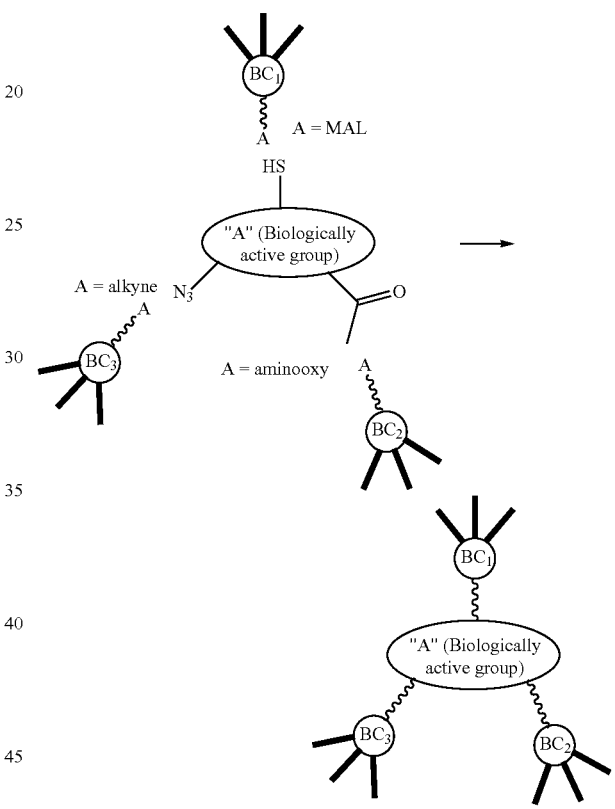

Controlling, Reducing, or Eliminating Immunogenicity with Branched DPEG Constructs:

In 2010 Wild, et al., published a paper looking at the effects of various dPEGs on the activity and the immunogenicity of an enzyme, OPH (organophosphorus hydrolase), including an a very small and early version of a branched dPEG (Ref.: James R. Wild, et al., "Improved pharmacokinetics and immunogenicity profile of organophosphorus hydrolase by chemical modification with polyethylene glycol," Journal of Controlled Release, 146, 318-325 (2010)). It appeared from SDS-PAGE that they were able to get complete modification of the six available lysines, but with the NHS-dPEG$_4$-Tris(m-dPEG$_{12}$)$_3$, that they could only get an average of about 3 onto the enzyme, though using an 800 mole excess of the reagent (demonstrating the limitations of a short single point attachment on the branched compound). Regardless they were able to see a dramatic increase in the enzyme half-life in guinea pigs serum from about 1 hR for the unmodified enzyme to almost 48 hR for the enzyme with the branched dPEGs. This was due to the protective effect the dPEGs had on the enzyme against the immune system of the guinea pigs and NOT the apparent size created by the branched dPEGs. This is confirmed in the tremendous reduction that is seen in the immunogenicity of the unmodified and branched modified enzyme of nearly 70%.

If this is generally true in using branched dPEG constructs, this could be an extremely valuable and unexpected property of the branched dPEG constructs. And this could be additionally important given the growing concern by some of the immunogenicity of methoxy terminated conventional polymeric PEGylation reagents, e.g., Ref.: M. R. Sherman, et al., "Role of the Methoxy Group in Immune Responses to m-PEG-Protein Conjugates," Bioconjugate Chemistry, 23, 485-499(2012). Enzo Life Sciences sells an ELISA kit for monitoring the PEGylation of proteins using anti-PEG antibodies. We have evaluated the kit using a range of both linear and branched dPEG constructs and have seen ZERO response. The largest branched dPEG construct has a MW of about 4 kD where there is expected to be a very large response, and there was none. See Example 10. These data may suggest that there is something unique about the dPEG construct in general and the branched dPEG construct in particular with respect to their ability to be completely transparent to the immune system. It may be a function of the flexibility of the PEG chains as well, which in the case of the branched dPEG constructs is minimal. This would also suggest that doing multiple branched dPEG construct additions to a single "A", biologically active group would be advantageous.

Further Embodiments Look to the Growth of Protein Engineering.

Another embodiment is given based on the growing ability to engineer a range of functionality into the biological construct. And discloses the ability to incorporate into the protein a linear dPEG functionality during its engineering in media, then to which can be attached a branched dPEG construct. The reference below shows data where linear dPEG compounds up to at least $dPEG_{12}$ can be engineered in to the protein in very high yields. (Ref.: "Site-specific incorporation of PEGylated amino acids into proteins using non-natural amino acid mutagenesis," Naoki Shozen, Issei Iijima, Takahiro Hohsaka, Bioorganic & Medicinal Chemistry Letters 19 (2009) 4909-4911.)

Attaching specifically the linear dPEG alone has the potential, of changing the pharmacokinetic properties just with the linear dPEG that are methyl and methoxy terminated, while also modifying the solubility properties. The former properties may give the protein a stealth nature, much the way PEGylate liposomes do, and are actually called stealth liposomes. Given these researchers results it is reasonable to believe that a tyrosine may be as effective in getting the amino acid placed with a linear dPEG side chain, but with one that has a chemically reactable group at the terminus that can be deprotected or activated for chemistry which the branched dPEGs can be attached to. Optionally groups like the azide and propargyl could react directly with the various "Click" partners, with or without copper catalysis, which are well known in the art. (Ref.: Bertozzi, ibid.).

The successful compounds in this reference may best be those with an "A" at the terminus of dPEG chains of 4, 8 and 12 and longer in the aminophenylalanine format, as shown.

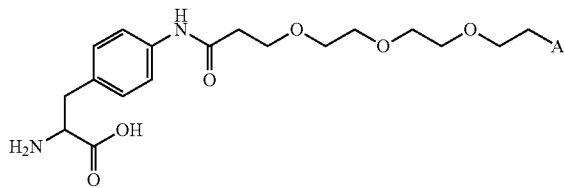

However, potentially more preferably and more versatile would be those shown for the A-dPEG$_x$-tryrosine derivatives. Optionally, one could use compounds like cysteine and other amino acids, including azides containing dPEG chains, including the tyrosine where A is azide or other unnatural functionality as defined for A. This is heretofore not disclosed.

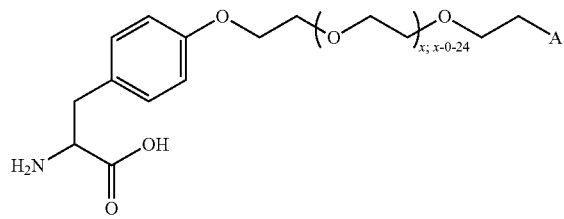

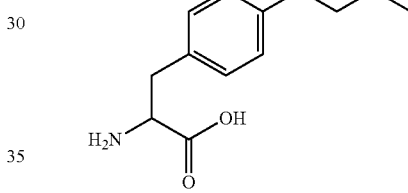

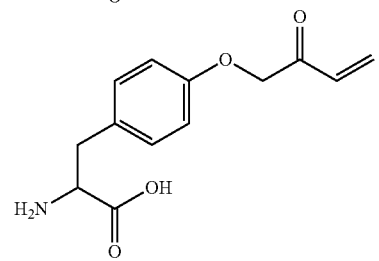

Another embodiment disclosed is based on the current ability of building the engineered scaffolds with many options of incorporating a disulfide into the architecture of the protein scaffold. Above we showed the ability to make bismaleimides, these could also be other chemistries known to react quickly with thiols. We disclose the option to introduce a branched dPEG construct at these disulfides using the bisMAL and other bis-thiol reactive species with a branched dPEG construct attached to it. Given that it may be more optimal to have a shorter spacer, even the bisMAL as shown below may be most preferred, so as not to disturb the natural or non-natural disulfide and the surrounding tertiary structure. Many of these will be in regions where the secondary hydrogen bonding forces within the tertiary structure will cause these forces to bring the sulfurs of the original disulfide back into a close proximity, and thereby not disturb the 3° structure to the detriment of the inherent avidity of the protein. Optionally, the flexibility of having variable length dPEG spacers, may be preferred in certain cases.

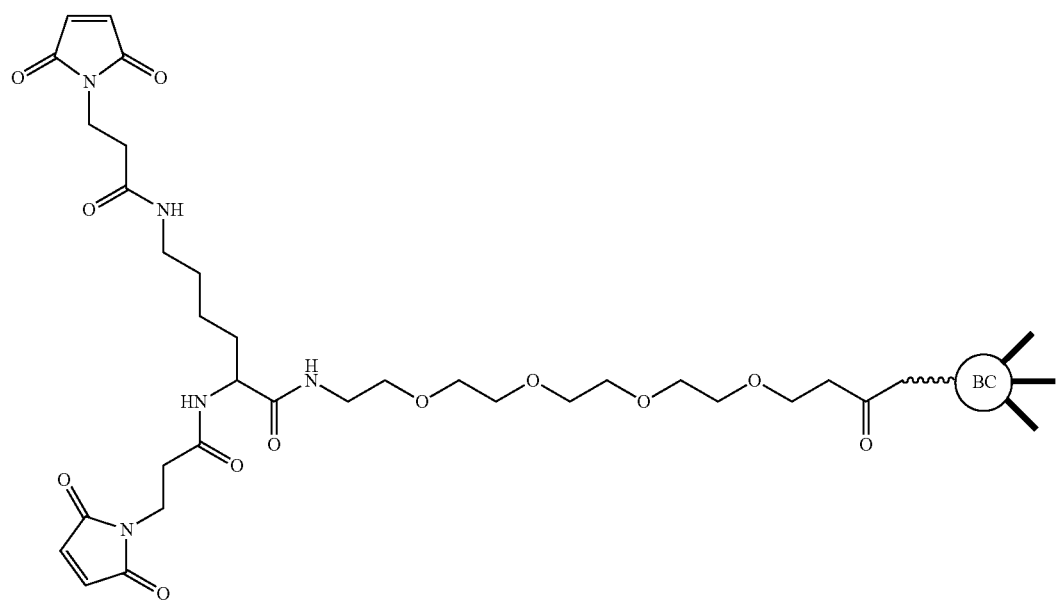
The range of applications is very large given the natural biologically active groups, like many of the cytokines, that have natural disulfide bridges, all of the natural disulfides in whole antibodies, as well that the new generations of protein engineering with disulfides.
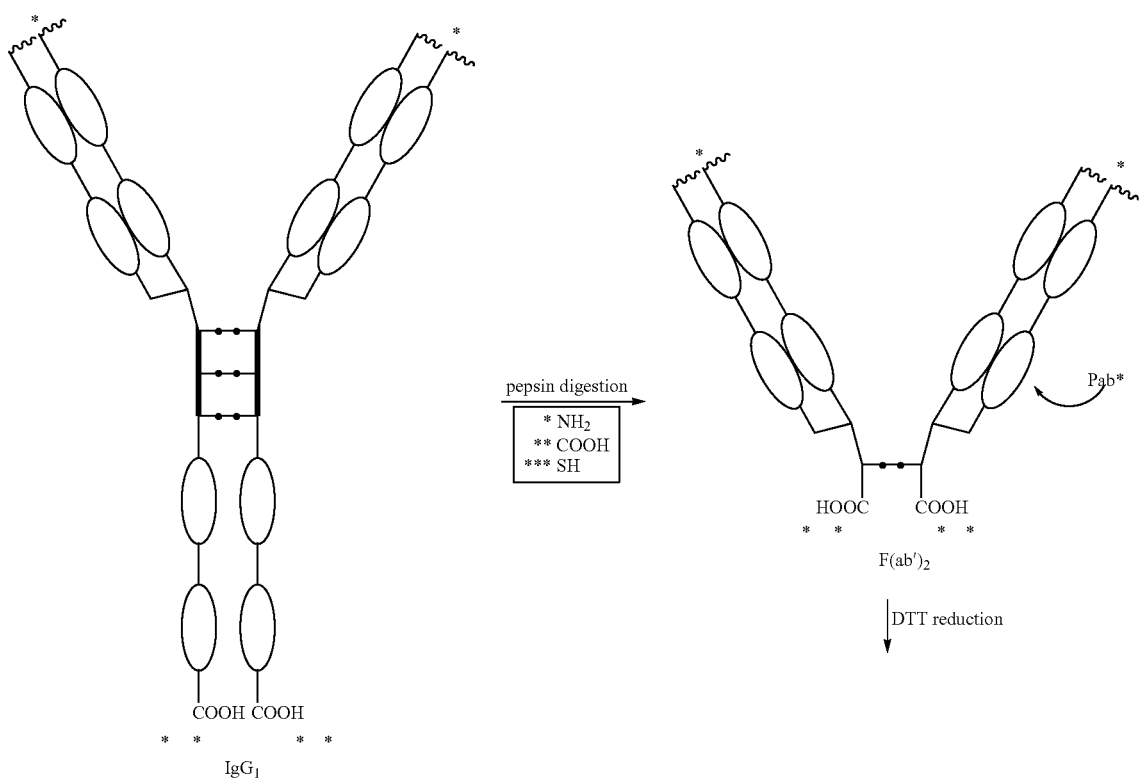

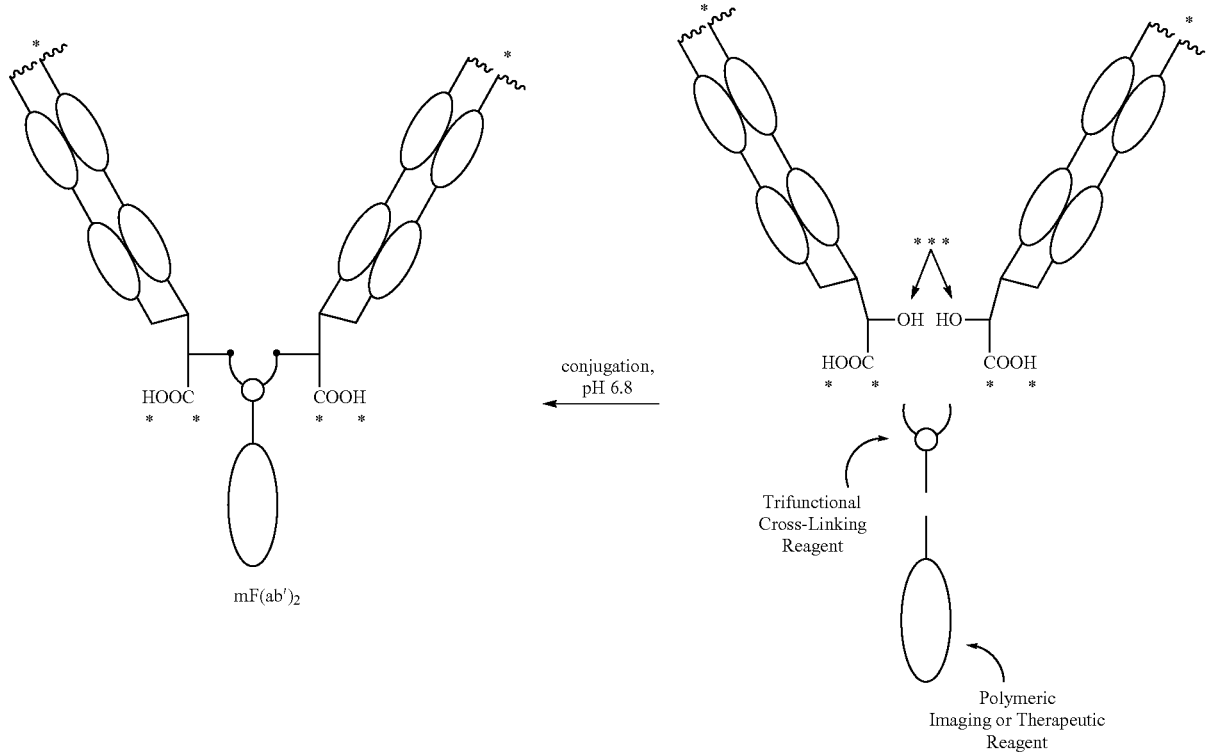

Strategy for site specific conjugation of polymeric diagnostic and therapeutic reagents to antibody F(ab')₂ fragments.

Ref: "Monoclonal Antibody Fab' Fragment Cross-Linking Using Equilibrium Transfer Alkylation Reagents. A Strategy for Site-Specific Conjugation of Diagnostic and Therapeutic Agents with F(ab')₂ Fragments," D. Scott Wilbur, et al., Bioconjugate Chemistry, 1994, 5, 220-235.

This reference figure was published by one of the inventors many years ago. In this disclosure, there is the potential to apply a wide range of very useful branched dPEG constructs to the F(ab')2, as well as the wide spectrum of biologics, natural and designed, which contain the disulfide, including proteins, and in particular, the diabody used as an example in the background information. And as well, the ETAC can be reacted in a way that two different thiols can optionally be attached to the ETAC, creating a bispecific or multispecific preferential locator. The ETAC is also known to bind to the His-tag label.

With proteins, e.g., the disulfide and cysteines have been engineered in for a number of years now. More recently a range of unnatural amino acids, e.g., with azide and aldehyde/ketone functionality have been engineered and technologies are available to make them commercially viable, but ALL of the applications have used the conventional polymeric PEGylation. Site specific PEGylation is achieved with some advantage in activity and the normal advantages of serum half-life, but ALL of the other disadvantages of conventional polymeric PEGylation are extant, and all have the potential to be replaced with the technology disclosed herein and are hereby disclosed.

Below is a list of references showing some examples of this. Further, there is precedent for the linear application in the diabody example from Avipep (above) where they are using linear dPEG constructs onto engineered disulfide loops. Disulfide loops can also be kept intact by bridging them with an ETAC-branched dPEG construct (shown below).

References for Protein Engineering in Functionality:
a. "Chemistry in living systems," Jennifer A Prescher and Carolyn R Bertozzi, Nature Chemical Biology, 2005, 1, 13-21.
b. "Site-specific incorporation of PEGylated amino acids into proteins using endron ralral amino acid mutagenesis," Naoki Shozen, Issei Iijima, Takahiro Hohsaka, Bioorganic & Medicinal Chemistry Letters 19 (2009) 4909-4911.
c. "GlycoPEGylation of recombinant therapeutic proteins produced in Escherichia coli," David Zopf, et al., Glycobiology 2006, 16, 833-843
d. "Introducing genetically encoded aldehydes into proteins," Carolyn R Bertozzi, et al., Nature Chemical Biology 3, 3-1-322 (2007)
e. Function and Structure of a Prokaryotic Formylglycine-generating Enzyme Carolyn R. Bertozzi, et al., THE JOURNAL OF BIOLOGICAL CHEMISTRY VOL. 283, NO. 29, pp. 20117-20125, Jul. 18, 2008
f. "New Aldehyde Tag Sequences Identified by Screening Formylglycine Generating Enzymes in Vitro and in Vivo," Jason S. Rush and Carolyn R. Bertozzi, J. Am. Chem. Soc., 2008, 130 (37), pp 12240-12241
g. "Site-specific chemical modification of recombinant proteins produced in mammalian cells by using the genetically encoded aldehyde tag," Carolyn R. Bertozzi, et al., PNAS, 2009, 106(9), 0.3000-3005.
h. "Microscale to Manufacturing Scale-up of Cell-Free Cytokine Production—A New Approach for Shortening Protein Production Development Timelines," Christopher J. Murray, et al., Biotechnology and Bioengineering, 2011, 108(7), 1570-1578.
i. Peter Schultz and Lei Wang, "Expanding the Genetic Code," Angew. Chem. Int. Ed., 44, 34-66(2005).

j. Chang C. Liu and Peter G. Schultz, "Adding to the Genetic Code," Annu. Rev. Biochem., 79, 413-444(2010).
k. "Unnaturally Productive," c&ENews, Aug. 22, 2011, pg. 40.

Additionally the use of nanoparticles as core carriers for a range of branched constructs provides a novel source of embodiments in this disclosure. As referred to above, a range of microparticles has been coated with, reacted with on their surface a range of dPEGs, all to date have been linear in nature. The nanoparticles include gold, silica, polymers, and liposomes. It has been shown that the dPEG constructs impact a range of properties from the toxicity of silica and gold particles, to the stealth and targeting nature of the same. Some of these results have been seen for other nanoparticles like liposomes and could also be applied to other nanoparticles, including PLGA and related constructs, as well as quantum dots (QDs) and nanotubes, but is possible with ANY microparticle that has a surface functionality, whether it be naturally extant, incorporated via modification or through a coating or series of coatings, so as to make hybrid nanoparticles. Additionally, the PLGA's could benefit in their construction through the use of linear HO-dPEGx-acids as well, and the design and control of many of the coatings that currently incorporate conventional polymeric PEGs, can be replaced with dPEG constructs, linear and branched.

The chemistries of attachment to the microparticles are going to be mostly the thiol and lipoic acid for the gold, however, with their being so many options for surface modifications. See Tables 1 and 2 for combination's that can be applicable to nanoparticle design using dPEGs.

Listed below are a number of references from which we can draw to find many significantly better solutions using one or more of a range of branched dPEG constructs, and in combination with the properly chosen linear dPEG constructs.

Nanoparticle References:
a) "Cellular Uptake and the Fate of PEGylated Gold Nanoparticles Is Dependent on Both Cell-Penetration Peptide and Particle Size," Eunkeu Oh; et al., ACSNano, 2011, 5 (8), pp 6434-6448; DOI: 10.1021/nn201624c.
b) "Cyclic RGD Functionalized Gold Nanoparticles for Tumor Targeting," Daniela Arosio, et al., Bioconjugate Chemistry, 2011, 22, 664-672.
c) "Short Chain PEG Mixed Monolayer Protected God Clusters Increase Clearance and Red Blook Cell Counts," David Cliffel, et al., ACSNano, 2011, 5, 3577-3584.
d) "Conjugation of Peptides to the Passivation Shell of Gold Nanoparticles for Targeting of Cell-Surface Receptors," ACSNano, 2010, 4, 6617-6628.
e) "Multimodal silica nanoparticles are effective cancer-targeted probes in a model of human melanoma," Steven M. Larsen, J Clin Invest doi:10.1172/JCI45600
f) "Biomimetic approach to the formatin of gold nanoparticle/silic core/shell structures and subsequent bioconjugation," Sung Min Dang, et al., Nanotechnology, 2006, 17, 47194725.
g) "Novel Synthetic Route to Peptide-Capped Gold Nanoparticles," Takeshi Serizawa, et al., Langmuir, 2009, 25(20), 12229-12234.
h) "Conjugation of Peptides to the Passivation Shell of god Nanoparticles for Targeting of Cell-Surface Receptors," Roberto Fiammengo, et al., ACSNano, 2010, 4(1.1), 6617-6628.
i) "PEGylation strategies for active targeting of PLA/PLGA nanoparticles," Lisa Brannon-Peppas, et al., Journal of Biomedical Materials Research Part A., 2008, pp. 263-276; DOI: 10.1002/jbm.a.32247.
j) "A Review on Composite Liposomal Technologies for Specialized. Drug Delivery," Viness Pillay, et al., Journal of Drug Delivery, 2011, pp. 1-19; DOI: 10.1155/2011939851.
k) "The Controlled Display of Biomolecules on Nanoparticles: A Challenge Suited to Bioorthogonal Chemistry," Igor L. Medintz, et al., Bioconjugate Chemistry, 2011; 22: 825-858.
l) "Chemical nature and structure of organic coating of quantum dots is crucial for their application in imaging diagnostics," Rumiana Bakalova, et al., International Journal of Nanomedicine, 2011, 6, 1719-1732.
m) "Selective Covalent Protein Immobilization: Strategies and Applications," Jason Micklefield, et al., Chemical Reviews, 2009, 109, 4025-4053.
n) "Functional Improvement of an IRQ-PEG-MEND for delivering genes to the lung," Taichi Ishitsuka, et al., Journal of Controlled Release, 2011, 154(1), 77-83.
o) "Antistaphylococcal Nanocomposite. Films Based on Enzyme Nanotube Conjugates, "ACS Nano, 2010, 4 (7), pp 3993-4000.
p) "Development of a sensitive surface plasmon resonance immunosensor for detection of 2,4-dinitrotoluene with anovel oligo (ethylene glycol)-based sensor surface," Kiyoshi Matsumoto, et al., Talanta, 2009, 79, 1142-1148.

Shown below are some specific structural examples of the various components of the branched dPEG construct compositions by definition. These as shown by example, as well as visual clarification of the above detailed but are only represented of what is generally taught in this disclosure to cover the full range of possible for the branched dPEG constructs given the range of chemistries known that can be applied by one skilled in the art to that can be built onto the key ability to make the linear high purity dPEGs (U.S. Pat. No. 7,888,536 B2) of this disclosure. They are intended to be by example only, but not intended to be limiting.

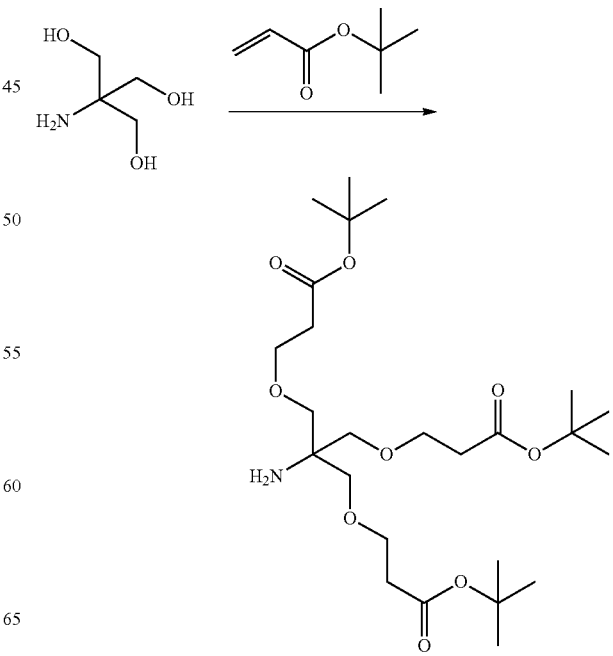

161
-continued
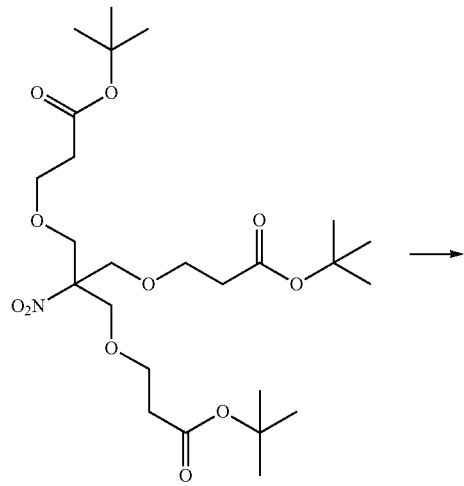
162
-continued
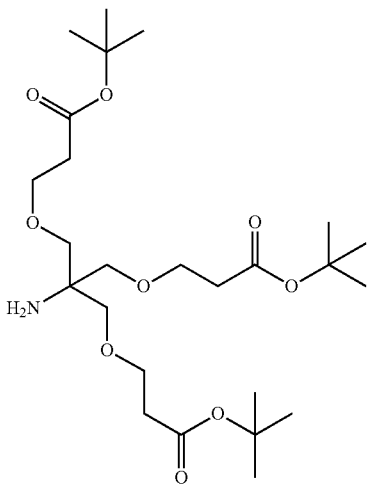
Other Examples of Cores could Include the Following:
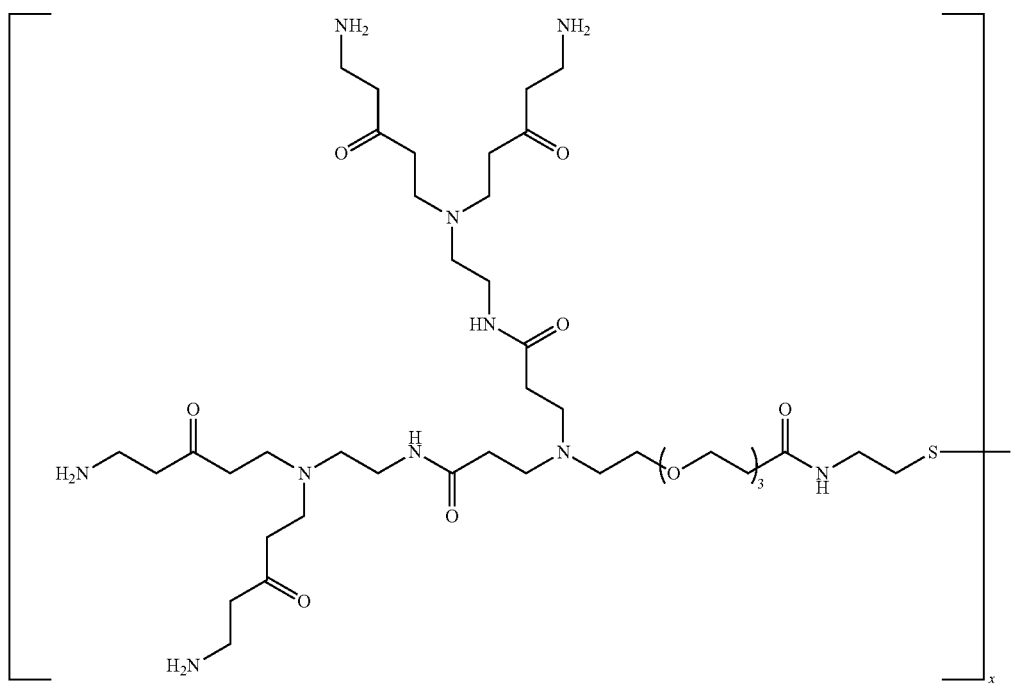

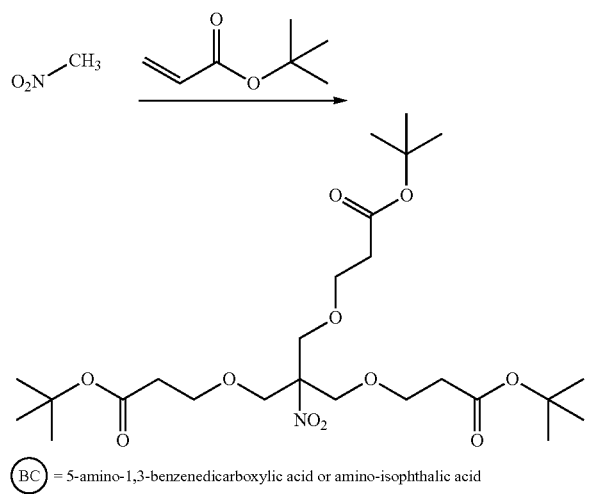

(BC) = 5-amino-1,3-benzenedicarboxylic acid or amino-isophthalic acid

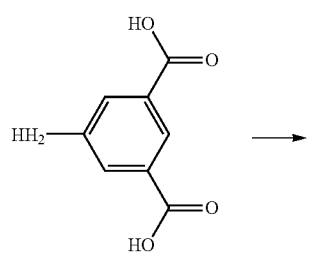

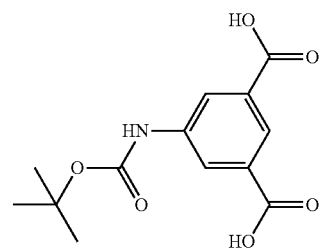

In the examples shown above, other cleavable centers other than the disulfide could be incorporated in the chemistry.

Additional cores can include the various amino acid cores, e.g., lysine, aspartic and glutaric acids, tyrosine, as well as a range of potentially useful compositions from the extensive literature in the dendron and dendrimer areas, as exemplified by the following review.

Ref "Dendrimers Derived from—1-3 Branching Motifs," George R. Newkome and Carol Shreiner, *Chem. Rev.* 2010, 110, 6338-6442.

"A" as a Chemically Reactive or Reactable Moiety: Some Examples of

A〰️

Making

A〰️
PhthN-dPEG$_{12}$—TFP ester

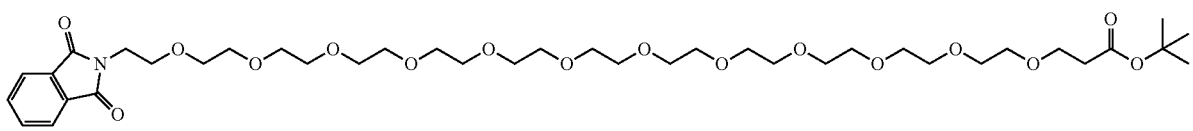

PhthN-dPEG$_{12}$—TBE (t-butyl ester)

↓ Formic acid or TFA

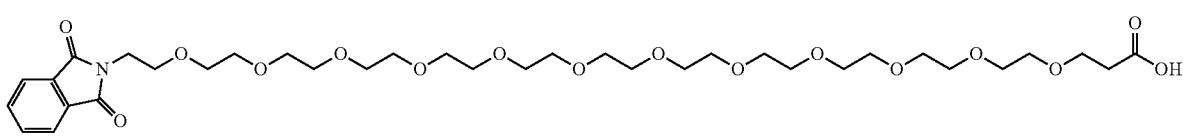

PhthN-dPEG$_{12}$—CO$_2$H

↓ Tetrafluorophenol w/ EDC or DCC

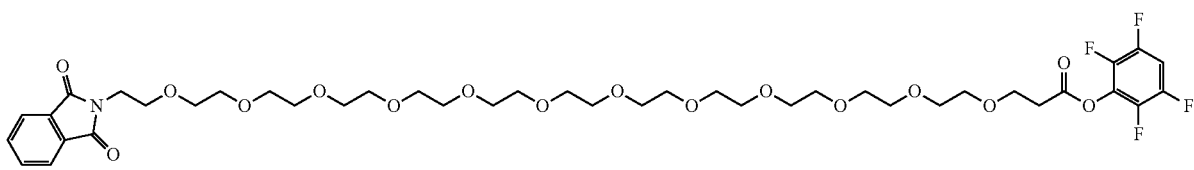

PhthN-dPEG$_{12}$—TFP ester p-ClTrt-O-dPEG$_{12}$—TFP ester

-continued

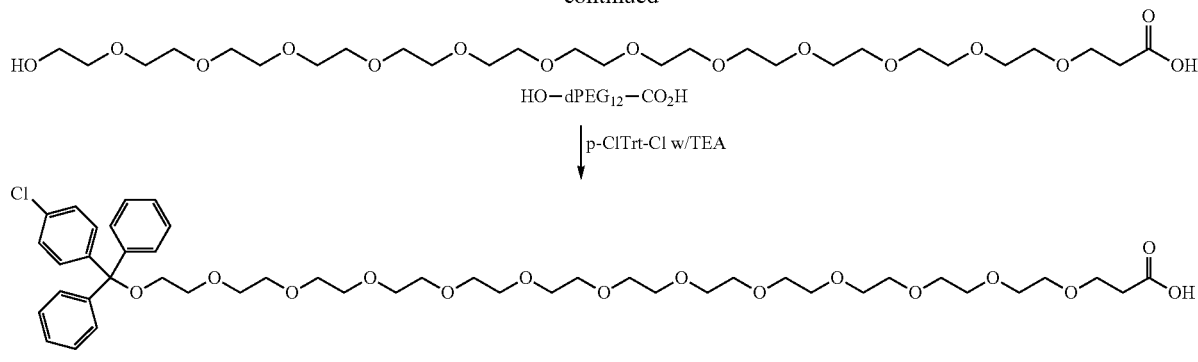

HO—dPEG$_{12}$—CO$_2$H

↓ p-ClTrt-Cl w/TEA p-ClTrt—O-dPEG$_{12}$—CO$_2$H

↓ Tetrafluorophenol w/ EDC or DCC p-ClTrt—O-dPEG$_{12}$—TFP ester

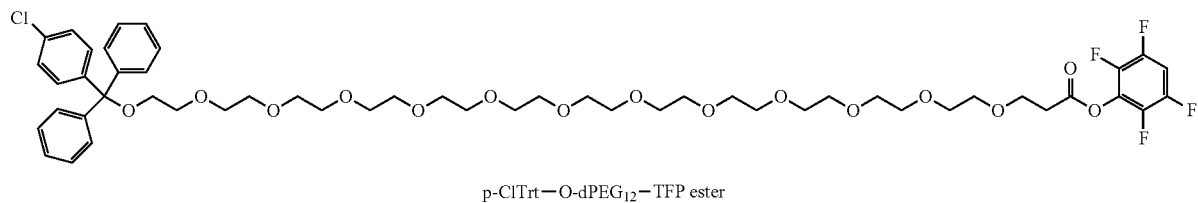

A〜(BC); PhthN-dPEG$_{12}$-Tris(TBE)$_3$

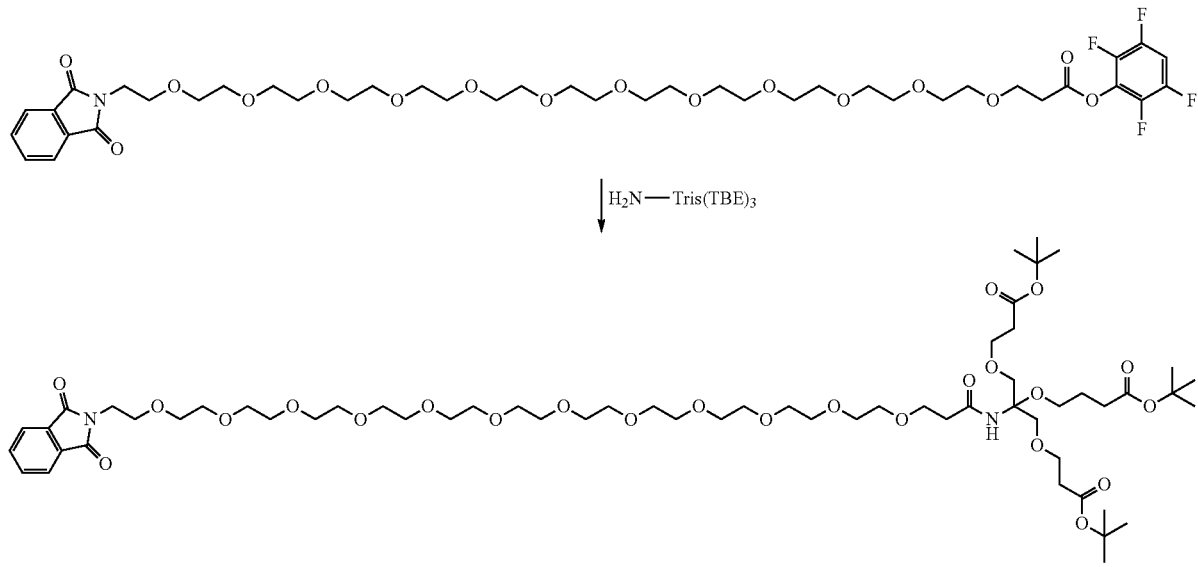

↓ H$_2$N—Tris(TBE)$_3$

Shown below is just one of many possible options for

A〜(BC)

with 〜 containing a cleavable group that can be considered. Others include those with peptides or disulfide, or those with the self-immolative linkers. The hydrazone is cleavable via acid, and this can be controlled by the nature of the R group on the aromatic. Optionally the linkage can be derived from a phenol derivative as opposed to the benzoic acid derivative shown. The art offers a significant landscape of options for control, as the application requires this option.

167
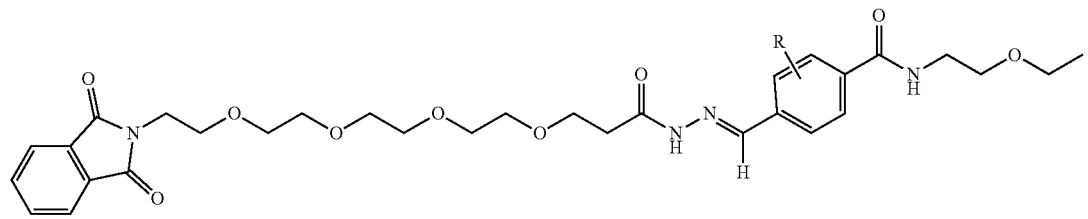
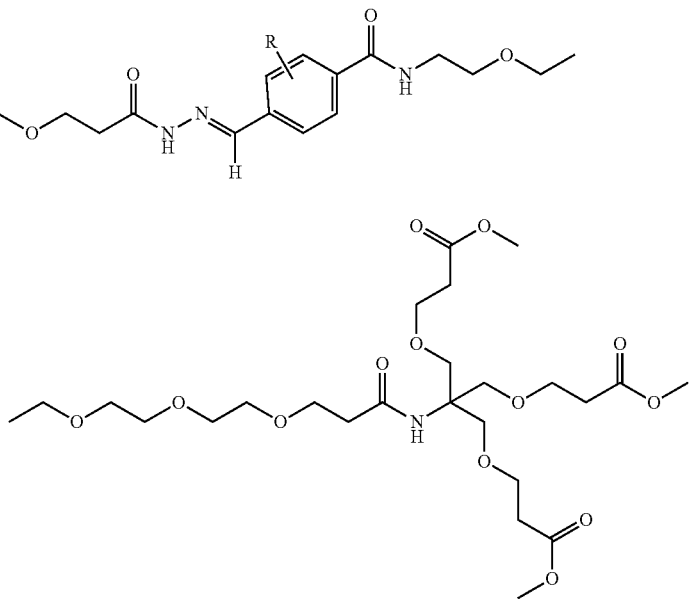
And additional example for the preparation of an
;
PhthN-dPEG₁₂-Tris(TFP)₃
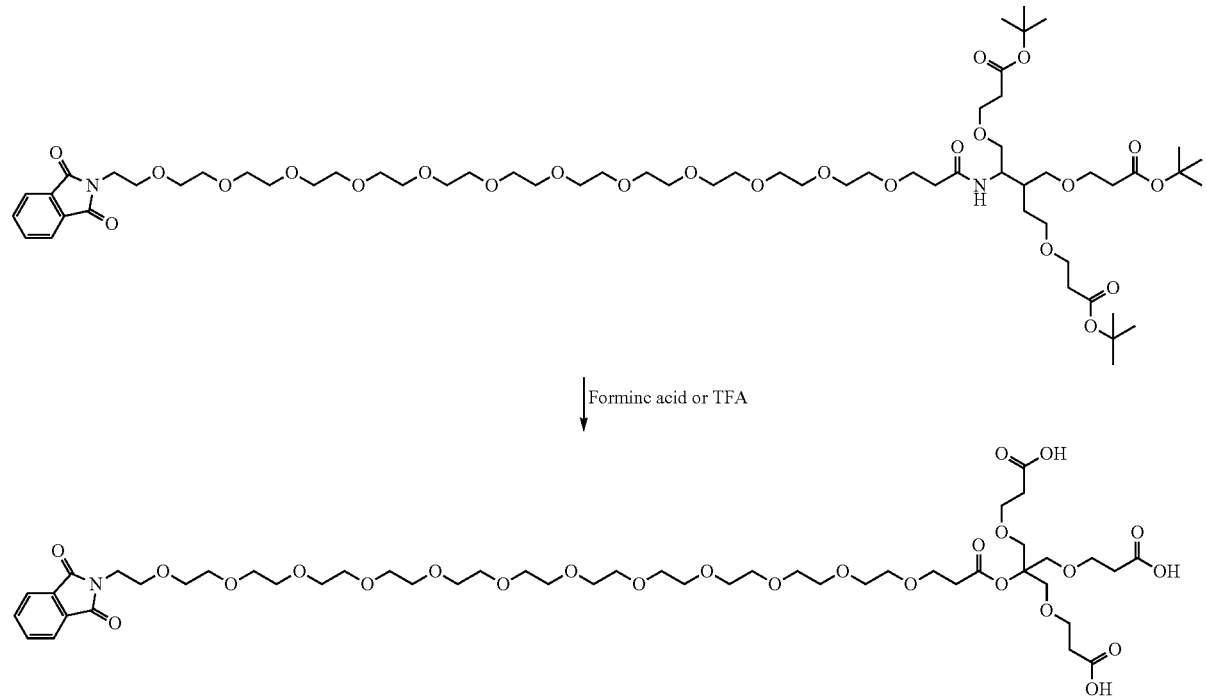

-continued
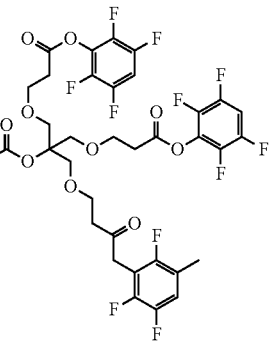
Some examples of the key solid lines, ▬▬▬ e.g., where the terminal group is=m-(methoxy), carboxyl, sulfonate, azide (convertible to positively charged amine), Tris(triacid)$_3$.
(m-dPEG$_8$ amine)
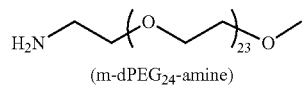
(m-dPEG$_{24}$-amine)
(Amino-dPEG$_{12}$ t-butyl ester)
(Amino-dPEG$_{12}$-SO$_3$-Na$^+$)
(Amino-dPEG$_{23}$-azide)
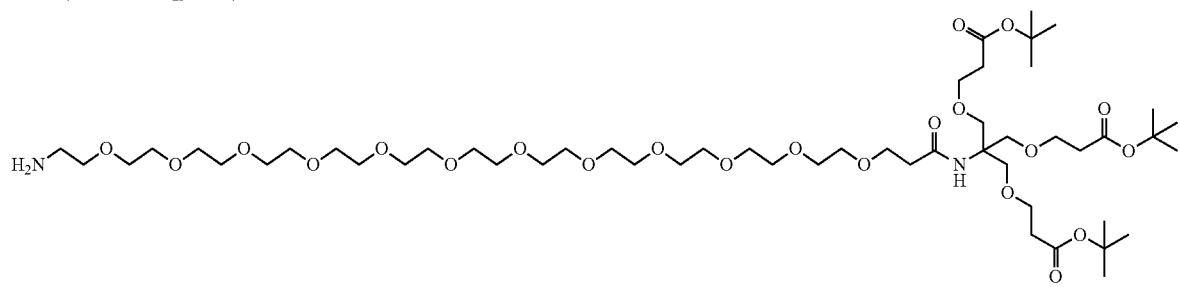
(amino-dPEG$_{12}$-Tris(TBE)$_3$)
Below are examples of making a range of
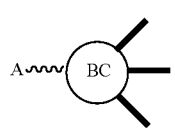

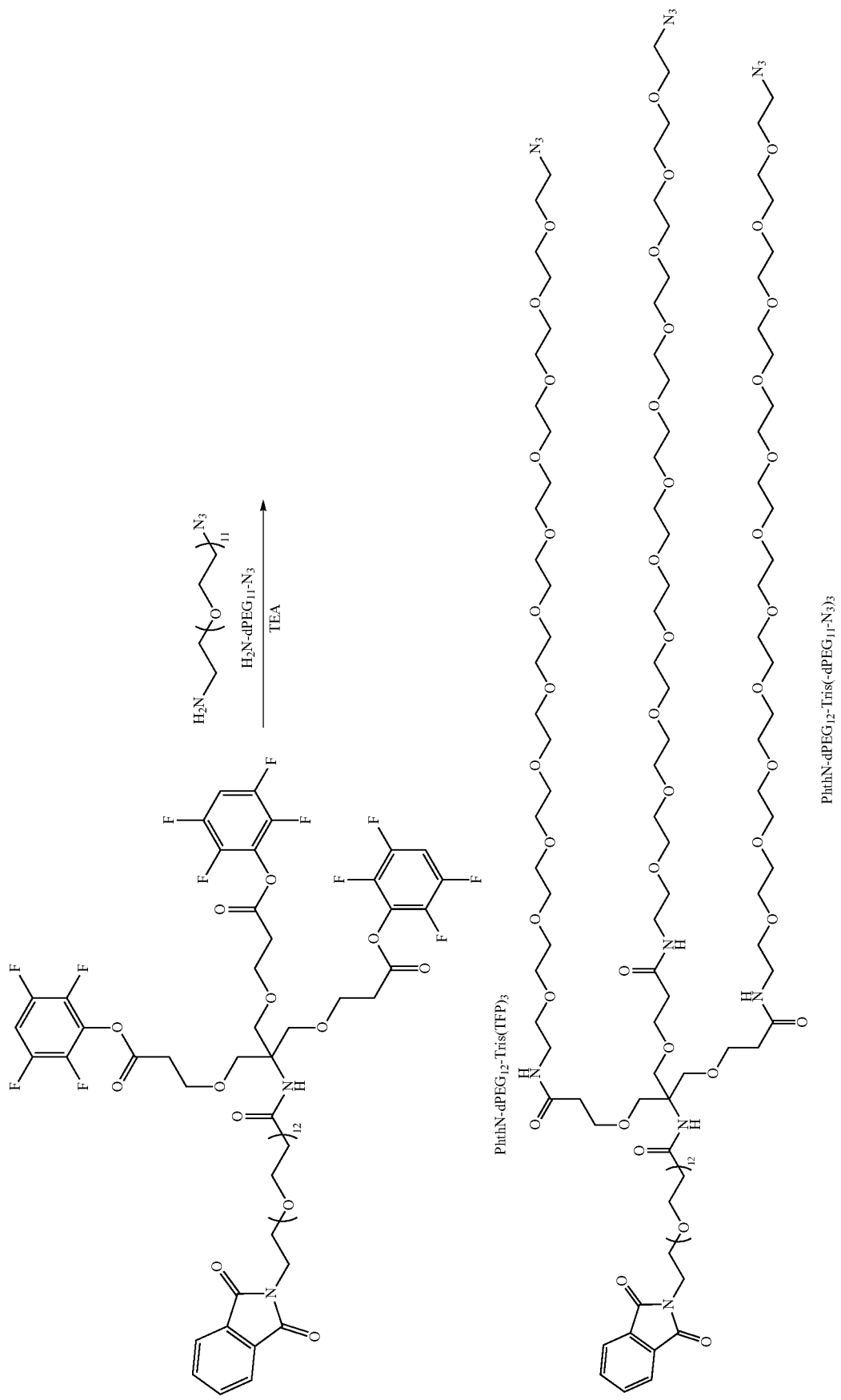

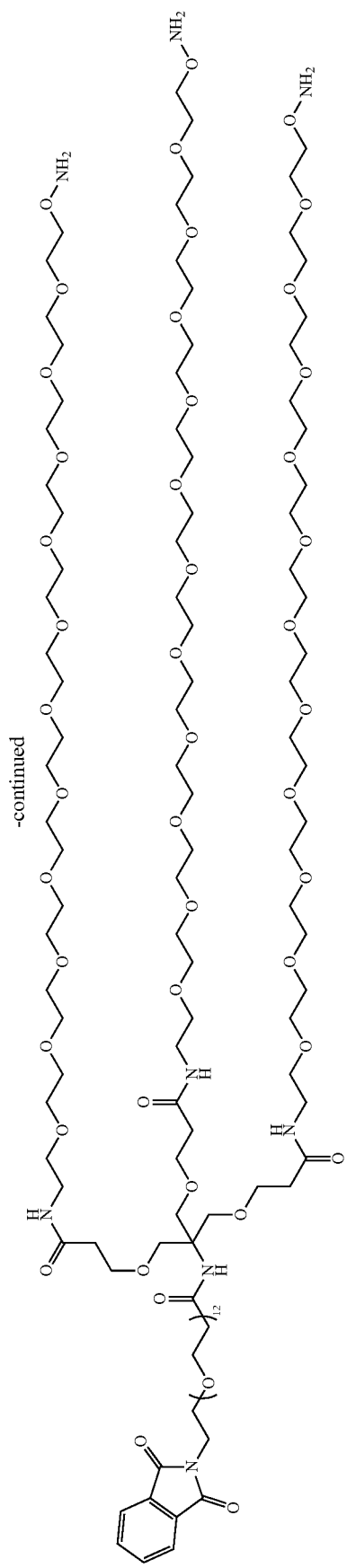
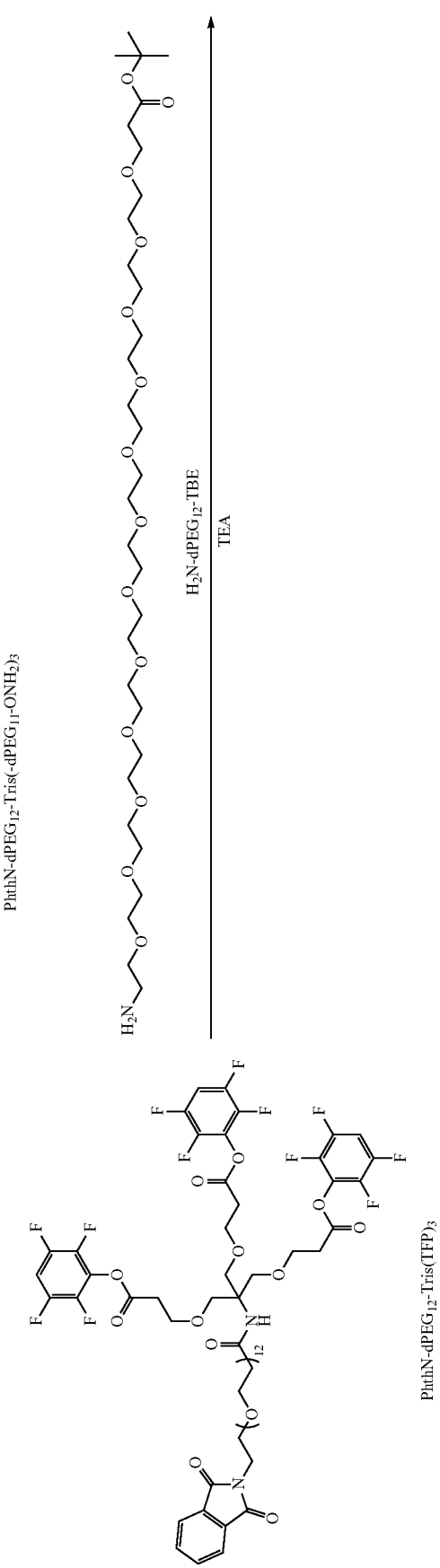

-continued
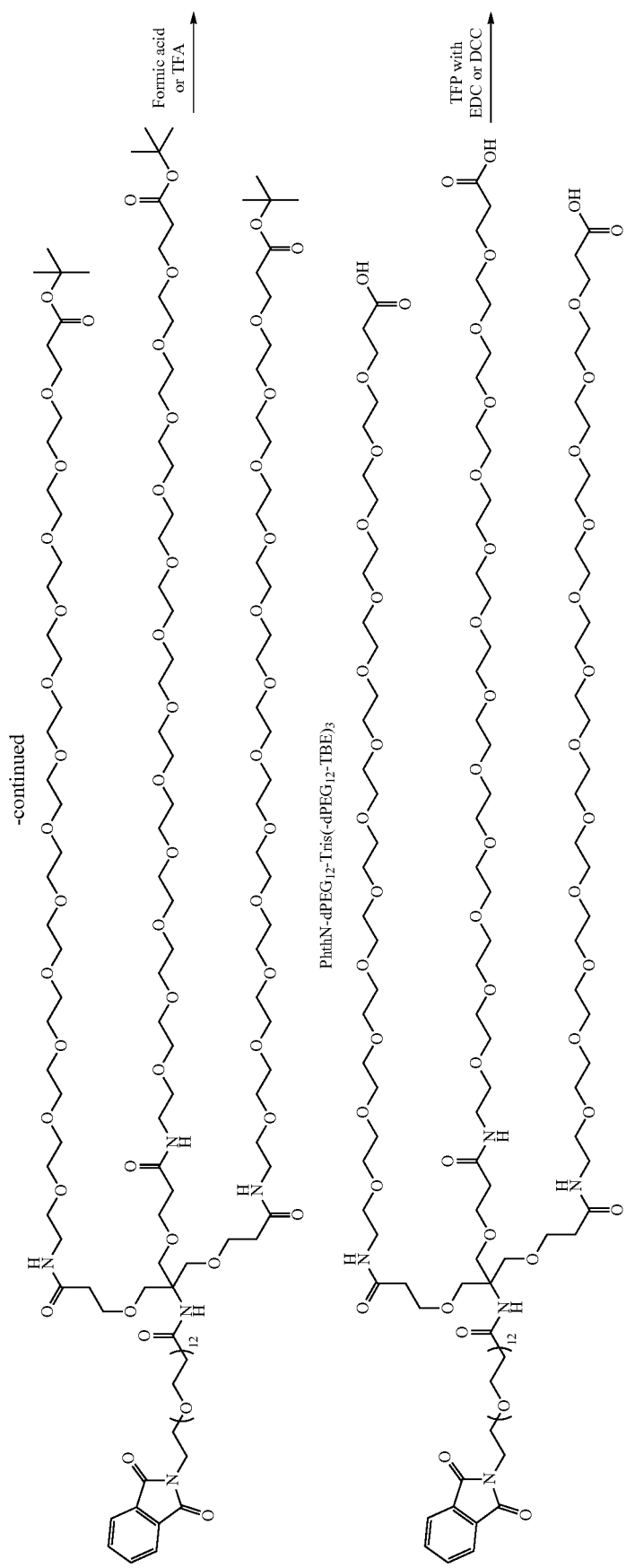
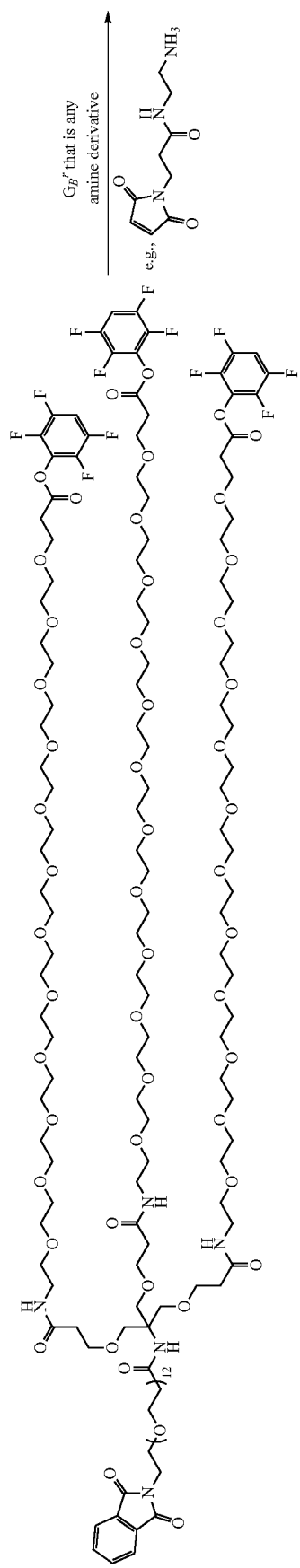

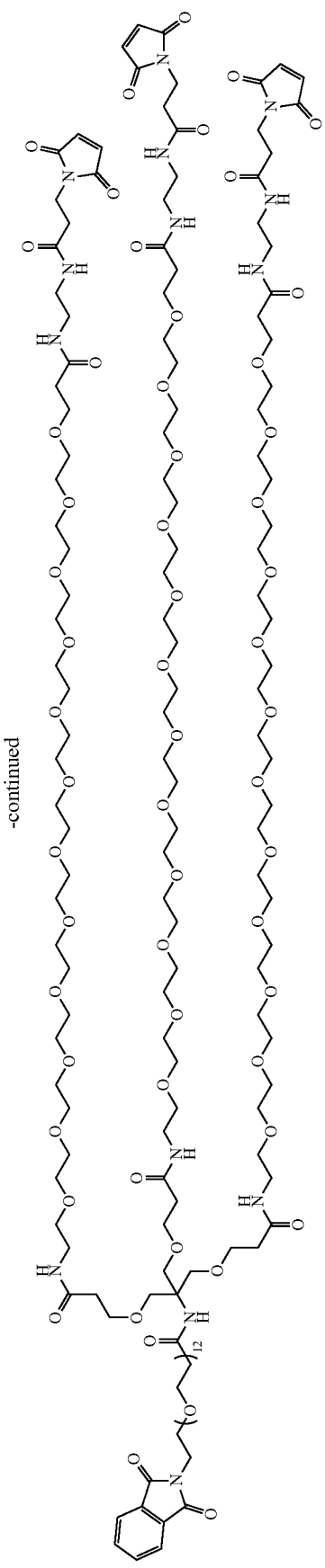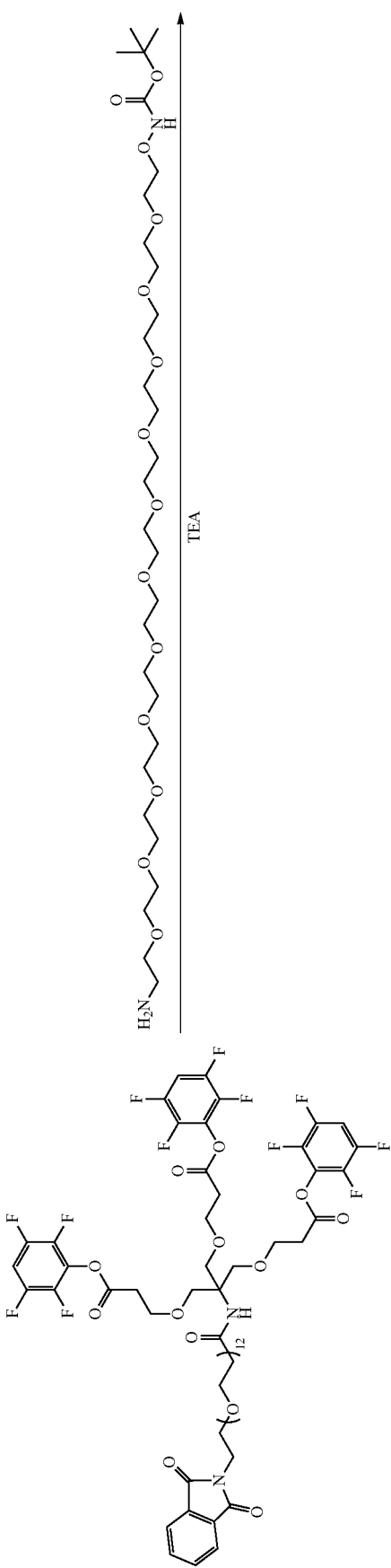

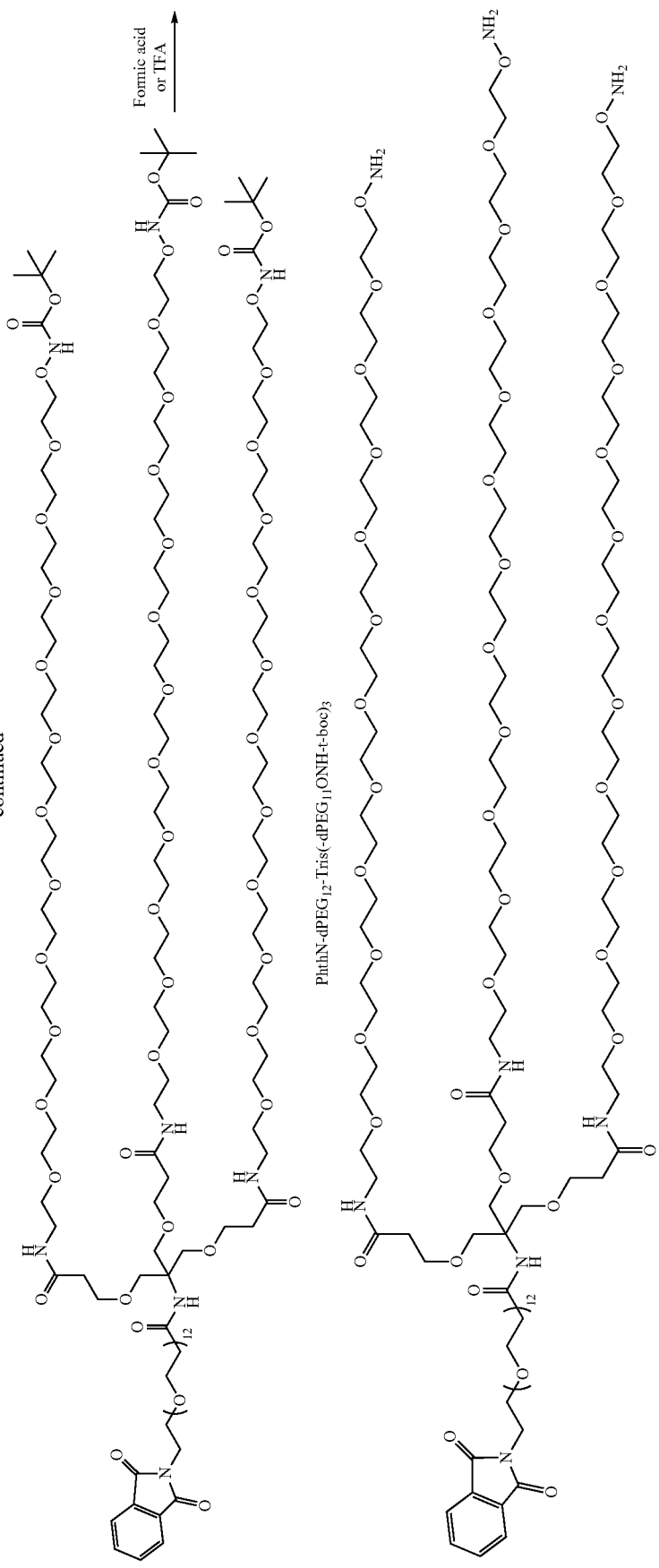

This compound is an extremely versatile intermediate, with the option of being reacted with a large range of aromatic aldehydes or aliphatic ones, including putting on important peptides, including cleavable ones where the terminal peptide is the oxidizable serine or for attaching "A" as larger engineered protein scaffolds with carbonyls site specifically incorporated. This same intermediate can be made in a sequence below where there are 9 terminal groups, or the product of this 3 branched can be put into the 1:3 stoichiometric chemistry, replacing the linear amino-dPEG$_{11}$-ONH-t-boc in this sequence, hence, a very versatile and preferred chemistry.

chemistry that the azide, can undergo, or the azide can simply be reduced to the amine and this Chemistry can be implemented to convert to a wide range of functionality or detectable probes, cleavable peptides, etc. can be incorporated as well. The azide can be reacted in a standard copper catalyzed click, the variety of copper free click reagents, the various Staudinger ligations, as well as the triazine chemistries. Also in this case, as would be the option above in 2, there is a simple change of functional group, or even in another area of disclosure, a higher branched can be reacted to give the next higher generation of branched compound,

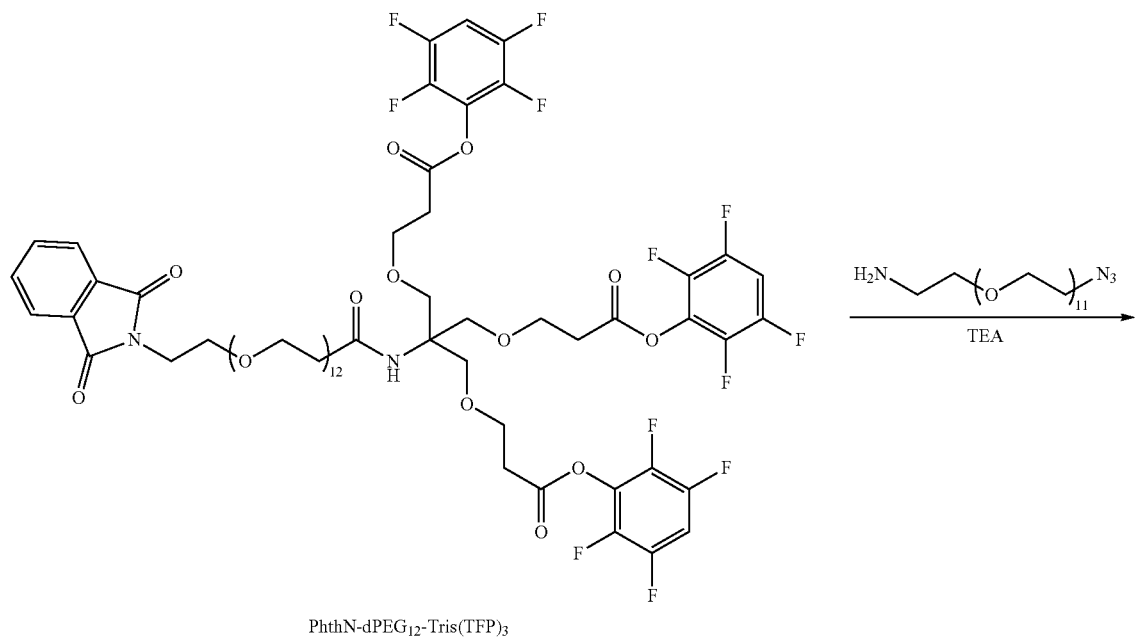

PhthN-dPEG$_{12}$-Tris(TFP)$_3$

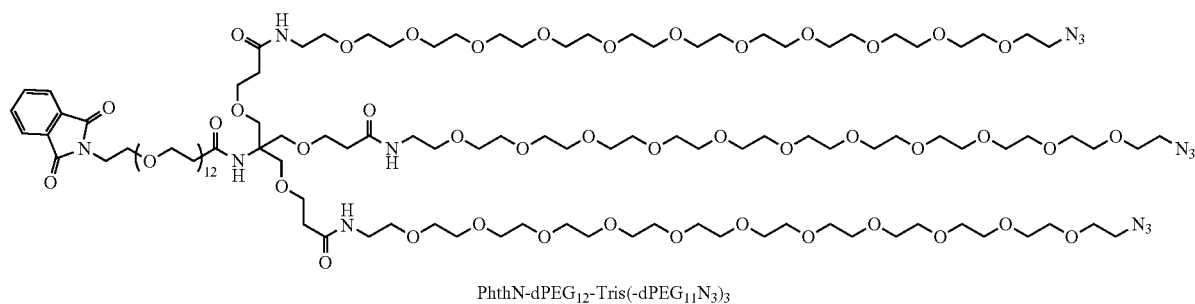

PhthN-dPEG$_{12}$-Tris(-dPEG$_{11}$N$_3$)$_3$

Once again this 3-branched dPEG azide (which can be made below as the 9- or 27- or other intermediate multiple), is highly versatile, give the wide range of biorthogonal either with multiple functionality, or with a detectable group, or with the inclusion of a cleavable construct to which can be attached a biologically useful compound.

The following are some key building blocks for higher branched dPEG constructs as indicated by
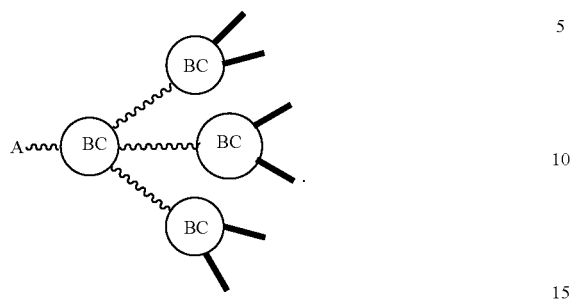
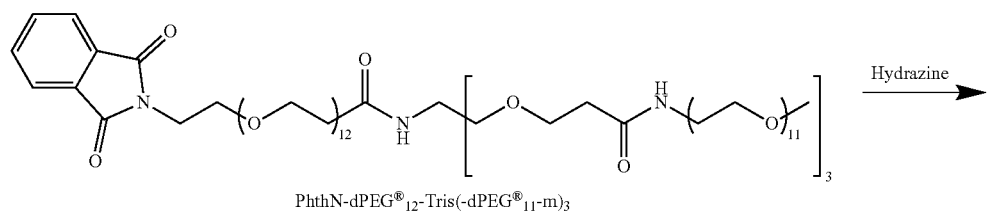
PhthN-dPEG®12-Tris(-dPEG®11-m)3
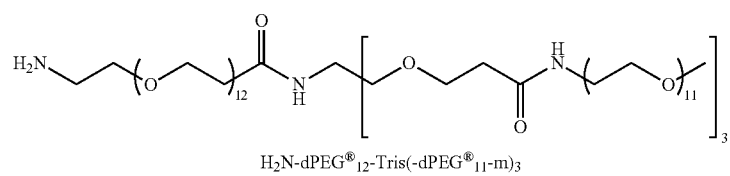
H2N-dPEG®12-Tris(-dPEG®11-m)3
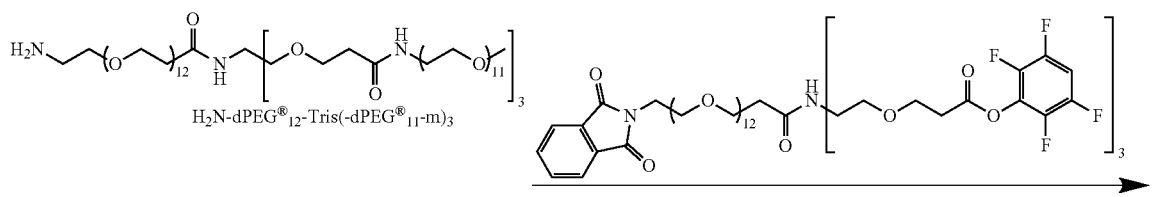
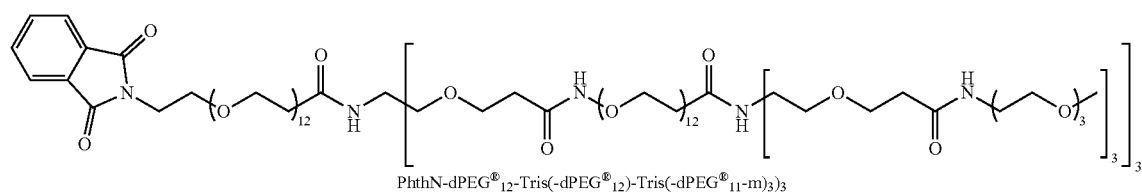
PhthN-dPEG®12-Tris(-dPEG®12)-Tris(-dPEG®11-m)3)3

An Example of Changing the Reactivity of "A", as a Chemically Reactive Moiety.

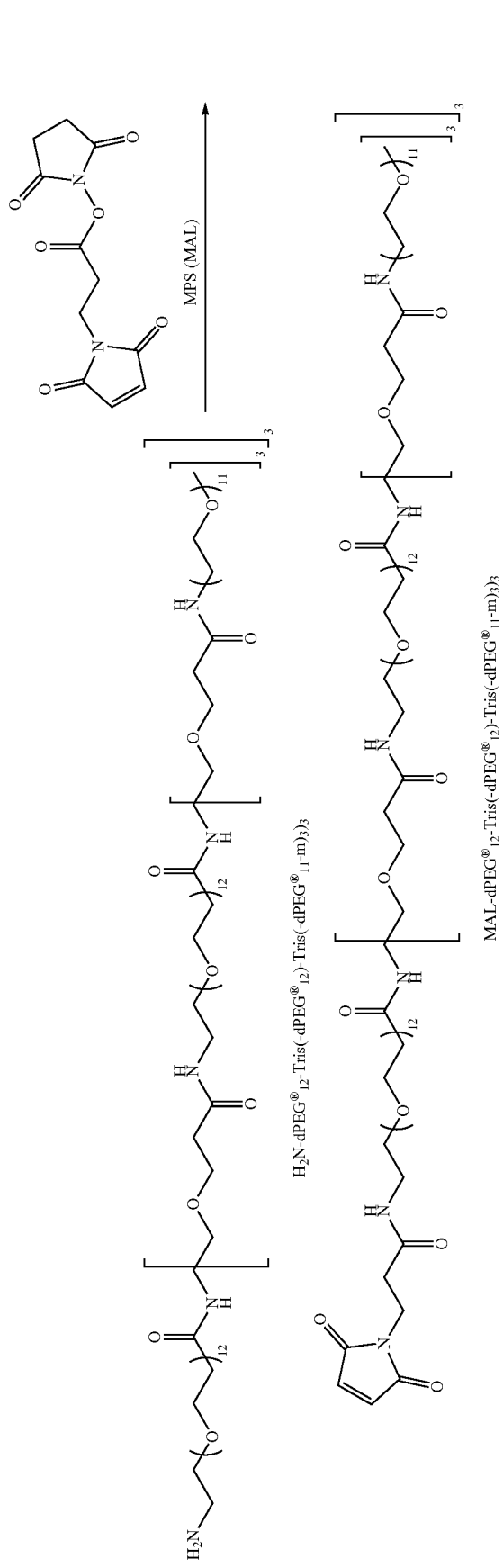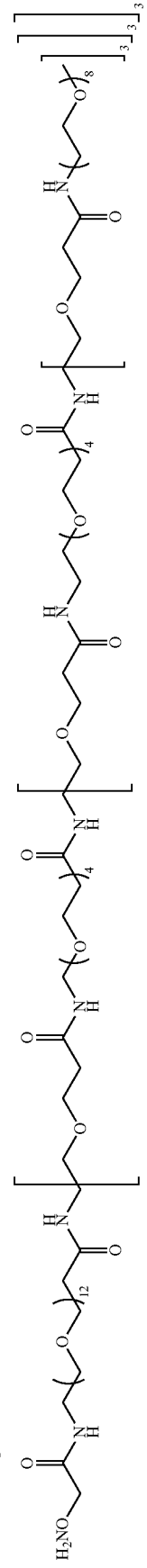

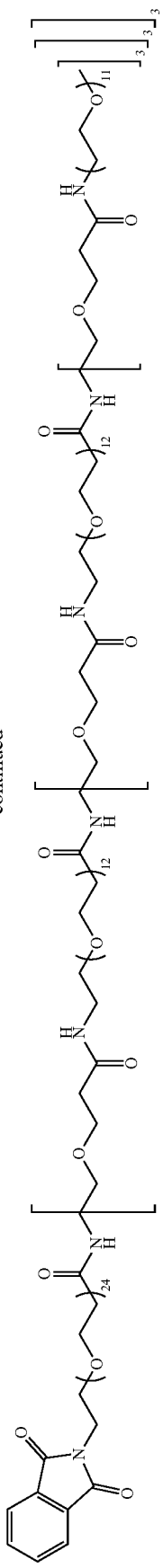
-continued
PhthN-dPEG®24-(Tris(-dPEG®12-(Tris(-dPEG®11-m)3)3)3)3
Chemical Formula: $C_{1173}H_{2283}N_{53}O_{556}$
Molecular Weight: 26059.70

Examples of varying the length of the single point of attachment in a key 3-branched dPEG construct. This is a case where the length can be adjusted in the base process or can be adjusted from a single intermediate to the particular application. The length can control things from the efficiency of the chemistry on to B/BG to the range of motion the branched construct has on the biological or nanoparticle.

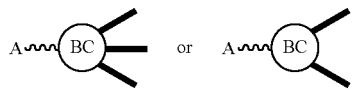

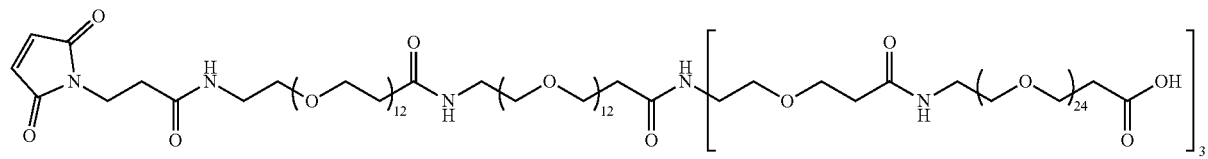

MAL-dPEG®$_{12}$-acetamido-dPEG®$_{12}$-Tris(-dPEG®$_{24}$-CO$_2$-H)$_3$
Chemical Formula: $C_{227}H_{437}N_7O_{113}$
Molecular Weight: 5072.88

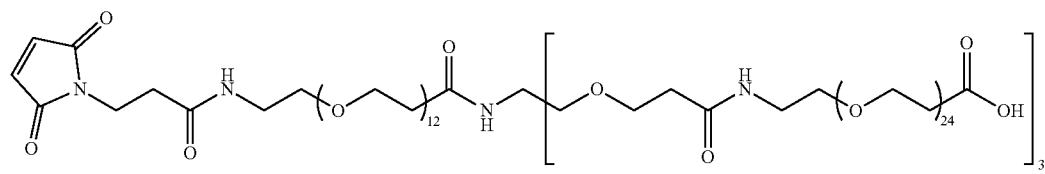

MAL-dPEG®$_{12}$-Tris(-dPEG®$_{24}$-CO$_2$-H)$_3$
Chemical Formula: $C_{200}H_{384}N_6O_{100}$
Molecular Weight: 4473.17

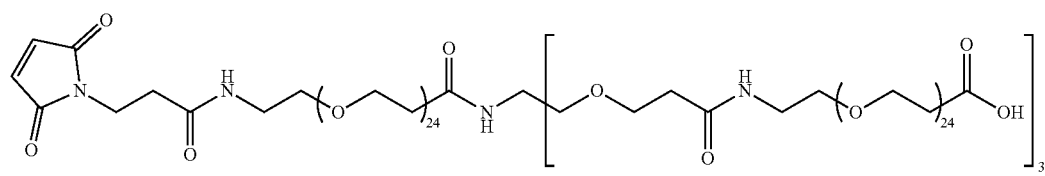

MAL-dPEG®$_{24}$-Tris(-dPEG®$_{24}$-CO$_2$-H)$_3$
Chemical Formula: $C_{224}H_{432}N_6O_{112}$
Molecular Weight: 5001.80

Optionally the branched dPEG construct can be built up by connecting the branched chains away from the core. This strategy can also be used to introduce points of cleavage, multi-functionality, including a drug or probe/label.

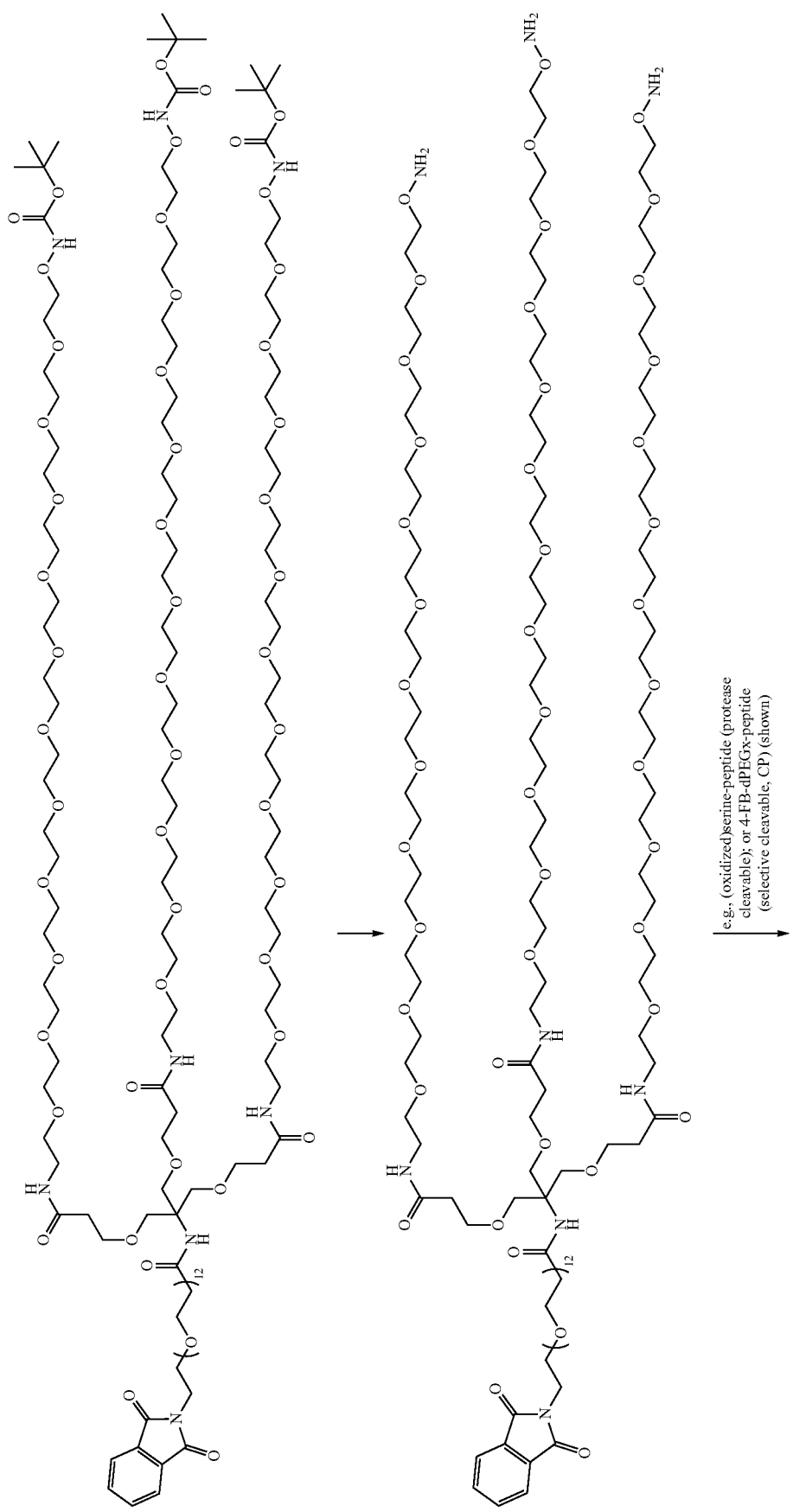

-continued
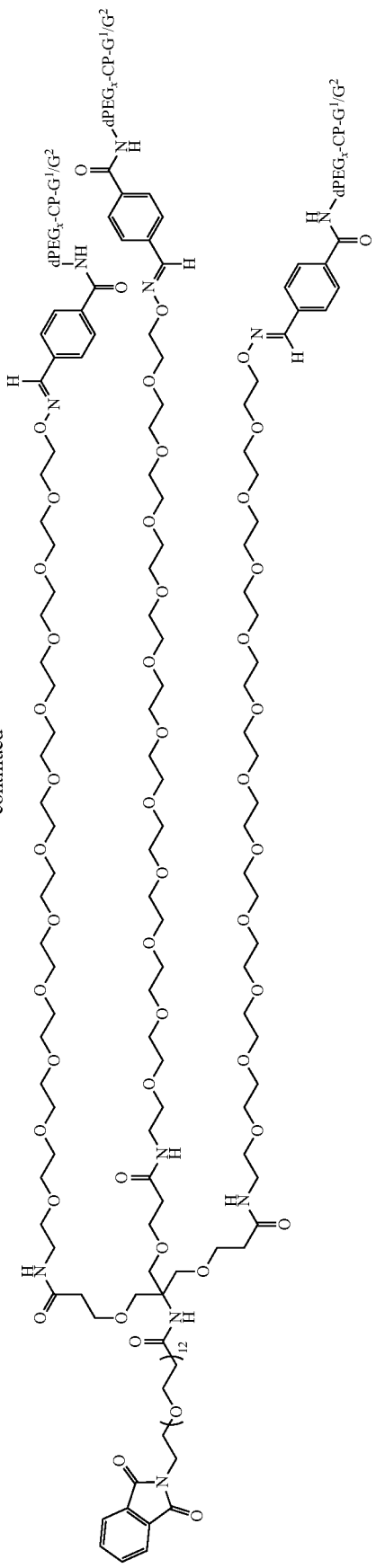

Examples of Various Options for a on an Optional 3-Branched dPEG Construct:
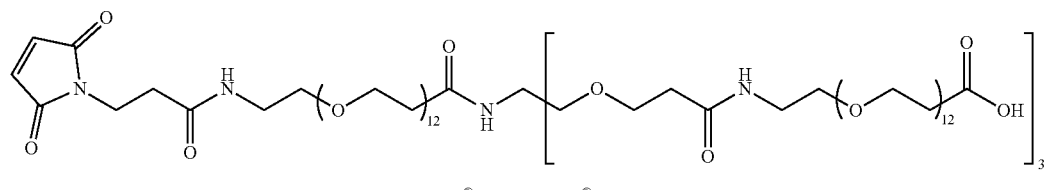
MAL-dPEG®12-Tris(-dPEG®12-CO2H)3
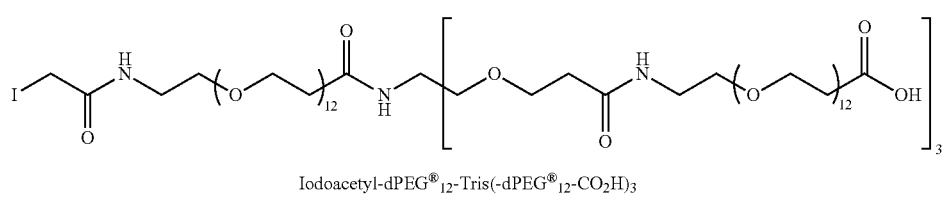
Iodoacetyl-dPEG®12-Tris(-dPEG®12-CO2H)3
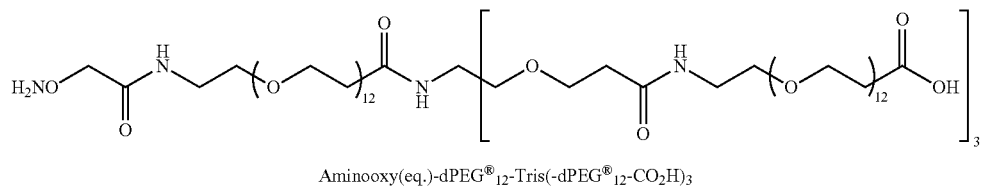
Aminooxy(eq.)-dPEG®12-Tris(-dPEG®12-CO2H)3
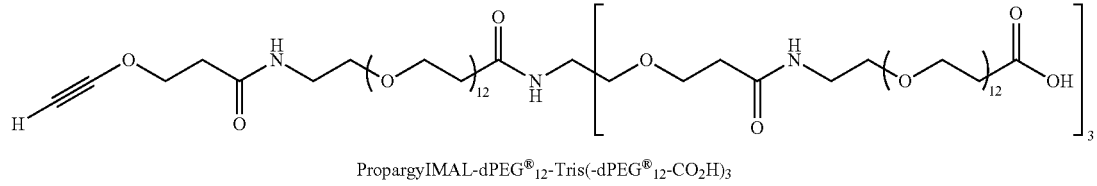
PropargylMAL-dPEG®12-Tris(-dPEG®12-CO2H)3
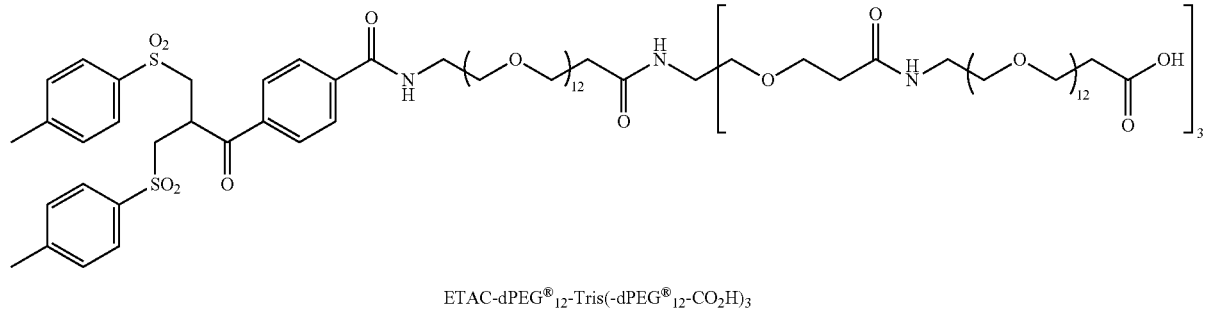
ETAC-dPEG®12-Tris(-dPEG®12-CO2H)3
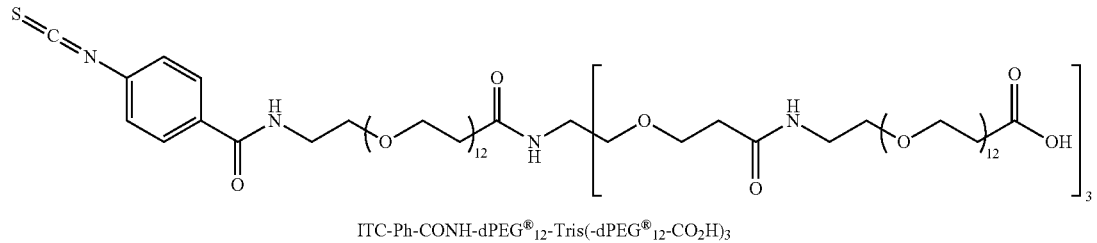
ITC-Ph-CONH-dPEG®12-Tris(-dPEG®12-CO2H)3

Example of a multifunctional branched dPEG construct with it designed into ⌇⌇⌇⌇ as In this case we have a fluorescent probe, FITC, and a tag or handle, biotin. This is something that could be made on a peptide synthesizer, or in solution. Optionally other functionality, including a cleavable point, also a peptide, could be incorporated into the single point attachment. A second branched dPEG construct, as well as a linear dPEG can be incorporated as well.

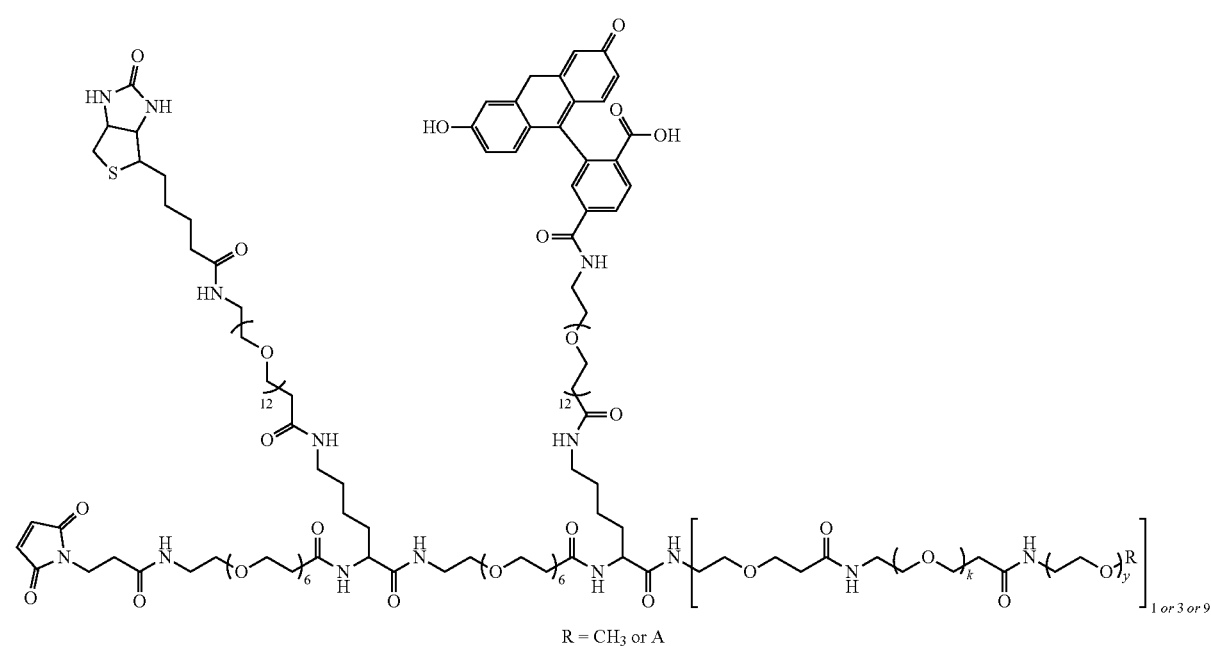

R = CH₃ or A

Example of making a composition

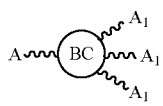

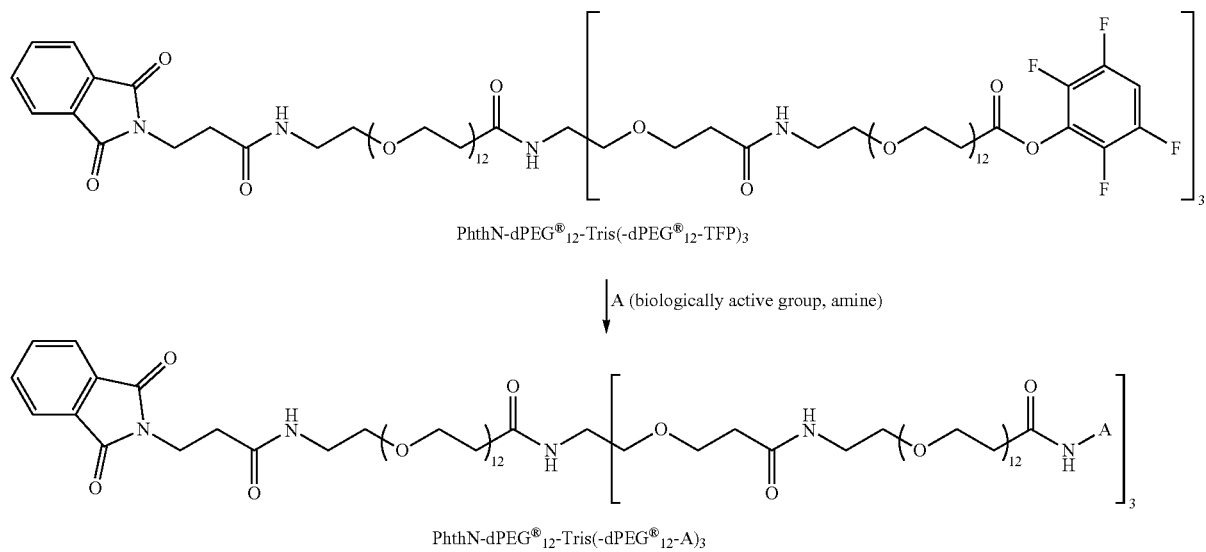

The example below is an important intermediate and an extension of the above 3-branched, but showing that it may be optional to incorporate into a 9 (or with a different core size, 4 or 6 branched) branching dPEG construct. The terminal group here is the carboxyl, convertible into an active ester as in the 3-branched above, but can also as above for the 3-branched incorporate the aminooxy, azide, or a PG-O-, among others as the terminal group as a chemically reactable or reactive group.

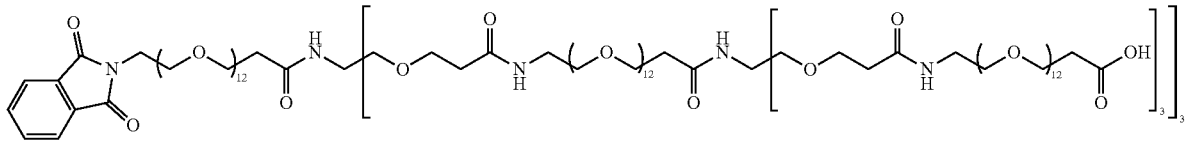

Chemical Formula: $C_{411}H_{777}N_{17}O_{204}$
Molecular Weight: 9221.56

PhthN shown as "A" with is optionally OPG and covertible to maleimide, iodoacetamide, NCS(ITC), aminooxy, azide, acetylide (preferred)

EXAMPLES

Example 1

Basic Branched Core, Branched dPEG Constructs and Hetero, BC1, BC2

203
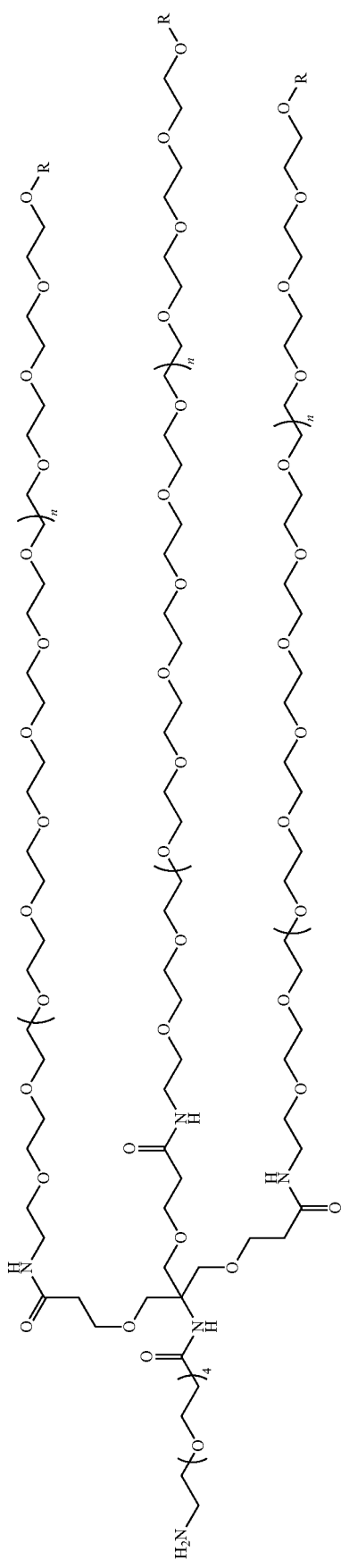
NH$_2$-dPEG$_4$-Tris(-dPEGx-m)$_3$; x = 24, n = 1 and R = CH$_3$;
NH$_2$-dPEG$_4$-Tris(-dPEG$_{24}$ acid)$_3$; n = 3 and R = CH$_2$CH$_2$-CO$_2$H
↓ MPS
204
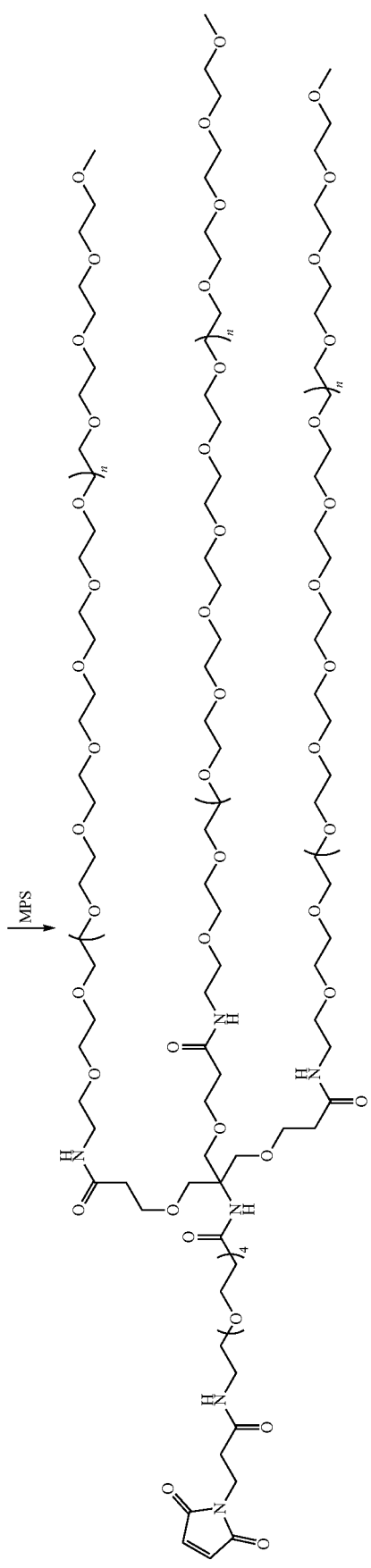
MAL-dPEG$_4$-Tris(-dPEGx-m)$_3$; x = 24, n = 1 and R = CH$_3$;
MAL-dPEG$_4$-Tris(-dPEG$_{24}$ acid)$_3$; n = 3 and R = CH$_2$CH$_2$-CO$_2$H

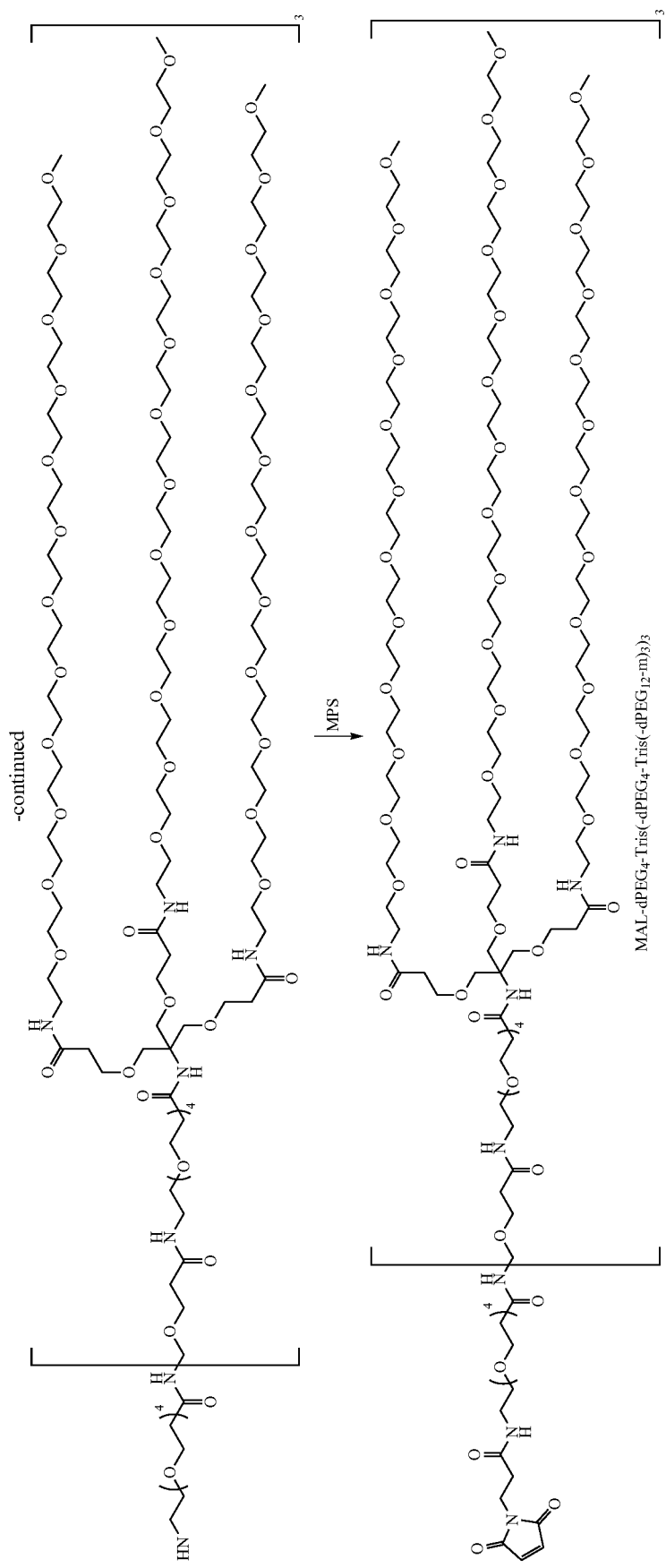

Preparation of Maleimide Derivatives MAL-dPEG$_4$-Tris(m-dPEG$_{24}$)$_3$; MAL-dPEG$_4$-Tris(-dPEG$_{24}$ acid)$_3$; MAL-dPEG$_4$-Tris(-dPEG$_4$-Tris(m-dPEG$_{12}$)$_3$)$_3$.

To a solution of each of the amines (0.5 g) dissolved in glacial HOAc (5 mL) was added maleimidopropionate N-hydroxysuccinimide ester (2 equiv.). That solution was stirred and heated under microwave at 150° C. for 30 min. Upon completion of reaction, 5 mL of water was added: The crude reaction solution (10+mL) was purified on a Biotage C18 FLASH (25+M) column via a gradient elution. The gradient mixture was composed of MeOH and 0.1% aqueous HOAc (pH 3.25). Starting with 25% MeOH/75% 1% HOAc solution. The initial solvent mixture was held for 2 min, increased to 100% MeOH over the next 15 min, and then held at 100% MeOH for 8 min). Isolated yields of the purified and respective MAL-branched dPEGs were in the range 67-91%.

PhthN-dPEG$_4$-Tris(TFP)$_3$:

and a cooling ice bath. In a separate 0.5 L three-neck round bottom flask equipped with a magnetic stirrer, thermocouple, and cooling ice bath a slurry of EDC (51.1 g, 267 mmol) in 200 mL of anhydrous dichloromethane was prepared under a nitrogen blanket. A solution of TFP (43.5 g, 262 mmol) in 60 mL of anhydrous dichloromethane was added to the EDC slurry via syringe at 6° C. with the rate to maintain temperature at about 5-10° C. The resulting clear solution stirred for an additional 10 min at 5° C. and then was added drop wise to the pre-chilled solution of Phth-dPEG4-tris-acid in CH$_2$Cl$_2$ at 0° C. The reaction mixture stirred at 0° C. for an additional 30 min. The cooling bath was then removed, and the reaction was allowed to warm to ambient temperature and stirred overnight. The reaction was monitored by TLC (R$_f$=0.4 for product while the Phth-dPEG-4-tris acid stays at origin in 50% CH$_2$Cl$_2$-50% EtOAc) or by HPLC. After the starting tris-acid disappeared, the reaction was quenched with cold saturated NH$_4$Cl

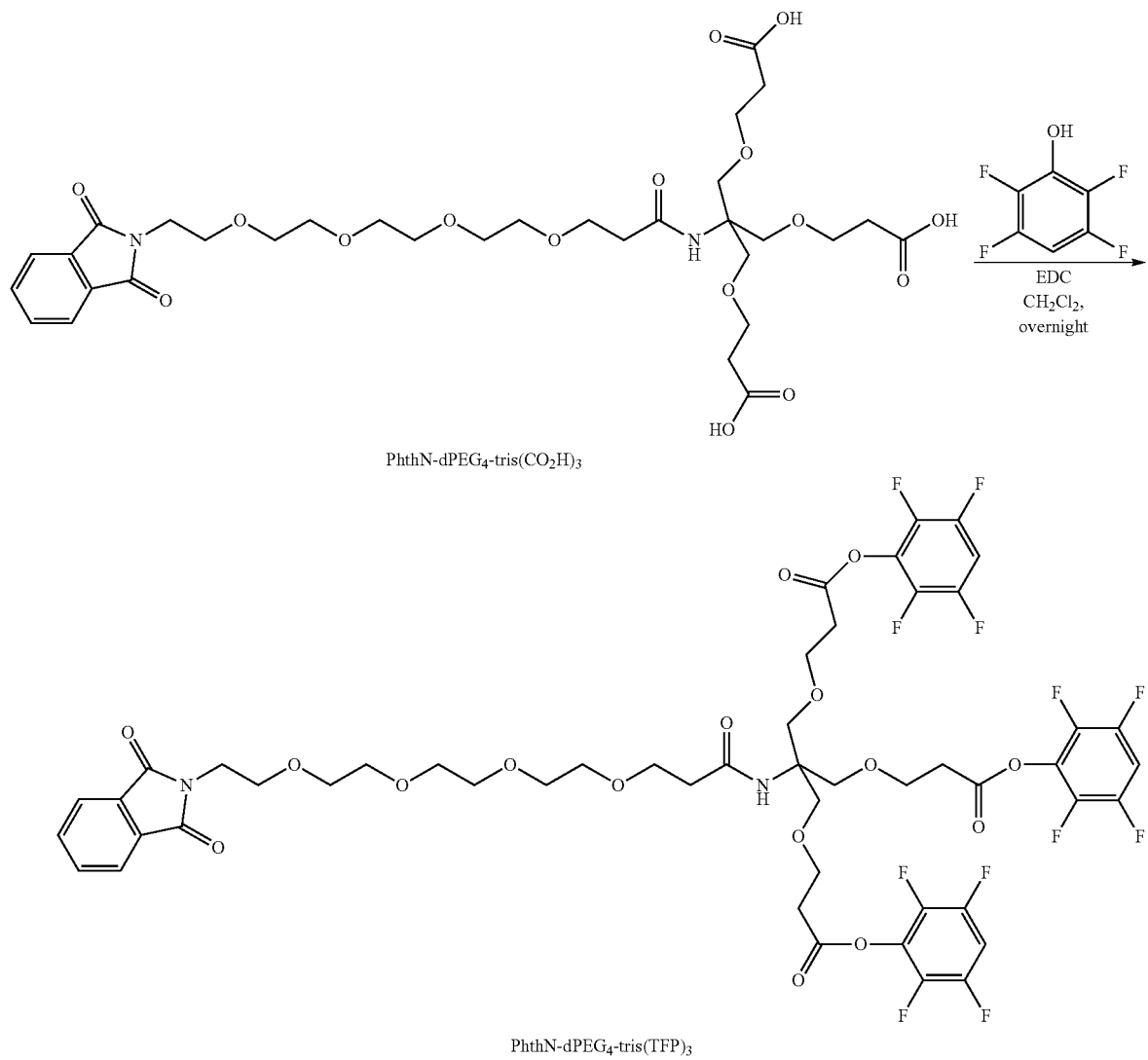

A solution of Phth-dPEG4-tris acid (36:6 g, 51.2 mmol) in 220 mL of anhydrous dichloromethane was placed in a 1 L three-neck round bottom flask equipped with a magnetic stirrer, additional funnel, thermocouple, nitrogen balloon, (3×200 mL) and extracted with dichloromethane (3×20 mL). The combined extracts were dried over anhydrous Na$_2$SO$_4$ and concentrated under reduced pressure to give 79 g of viscous yellow oil. An excess of TFP was removed by precipitation on 105 g of celite from its solution in EtOAc-hexane=1/5 (160 mL) by dropwise addition of 200 mL of hexane. Resulting suspension was filtered, and the cake was washed with hexane-MTBE=5:1 (250 mL) and the filtrate was discarded. The product was washed from celite with $CH_2Cl_2$ (5×120 mL), solvent was removed on rotavap to give 55.7 g of very viscous yellow oil with HPLC purity of 97%. This material was further purified by column chromatography on silica gel. Gradient elution with a mixture of dichloromethane with ethyl acetate from 0% to 60% of EtOAc gives 34.14 g (57% yield) of product. An additional 14.2 g were isolated by chromatography from washes from the TFP removal stage resulting in a total recovery 48.3 g (81% yield) of target compound as clear viscous oil. HPLC (3045FF acid method): RT 40.14 min, purity 100%. $^1$H NMR (400 MHz, $CDCl_3$, δ): 7.85 (m, 2H, phthalimide), 7.72 (m, 2H, phthalimide), 7.01. (m, 3H, TFP), 6.22 (s, 1H, NH), 3.90 (t, 2H, $CH_2N$), 3.87-3.78 (m, 12H, $CH_2O$), 3.74 (t, 2H, $CH_2CO$), 3.70 (t, 2H, $CH_2O$), 3.62-3.55 (m, 10H, $CH_2O$), 2.92 (t, 6H, $CH_2CO$).
PhthN-dPEG$_{12}$-Tris(TFP)$_3$:

stirred overnight. HPLC (Acid 60 method) indicated complete consumption of sm (TR=6.385) and formation of tri-TFP (TR=18.7). The reaction mixture was diluted with DCM (1.5 L), washed with sat aq $NH_4Cl$ (3×500 mL), washed with sat aq $NaHCO_3$ (5×500 mL), again with $NH_4Cl$ (500 mL), brine, dried, over $Na_2SO_4$, filtered over celite, and concentrated under reduced pressure to give 174.7 g of a yellow viscous oil. TLC (60:40 EtOAc: 4/1 DCM/EtOH) indicated a single major product, TFP, and some baseline material: HPLC (Acid60 method) indicated a major, product with 99% purity. The residue was preabsorbed on to 200 g $SiO_2$ and was purified on an Isco Torrent using a RediSep Rf 750 g column, EtOAc (A), and 4:1 DCM:EtOH (B). The column was equilibrated with EtOAc and a gradient was run with 4CV of 0% B then ramping up to 60% B over 6CV and holding at 60% for 2 CV. The appropriate fractions were spotted on TLC, fractions 1-26 and the carboy were pooled, and concentrated to give 124.3 g of a pale yellow oil. The oil was dissolved in DCM, dried over Na2SO4, filtered over celite, and concentrated under reduced pressure to give 116.1 g (68%) of a pale yellow viscous oil. TLC (40:60

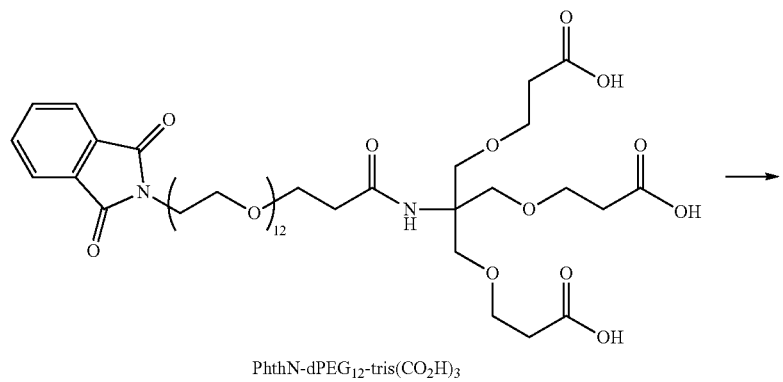

PhthN-dPEG$_{12}$-tris(CO$_2$H)$_3$

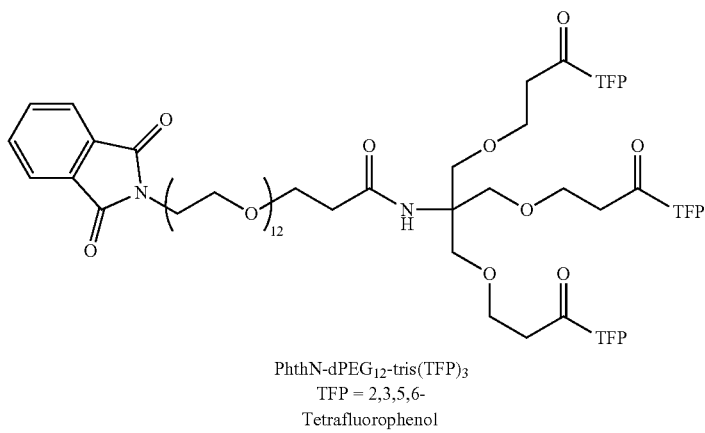

PhthN-dPEG$_{12}$-tris(TFP)$_3$
TFP = 2,3,5,6-Tetrafluorophenol

A 2.5 L oven dried RBF fitted With nitrogen blanket, cooling bath, and addition funnel was set up for this reaction. The flask was charged with PhthN-12-tris(acid)$_3$ (120.61 g, 113 mmol) and DCM (565 ml) and cooled to 0° C. TFP (94 g, 565 mmol) and EDC (108 g, 565 mmol) were dissolved in DCM (565 ml) and placed in the addition funnel. The reaction was cooled and the TFP/EDC mixture was added dropwise and the reaction was warmed to room temp and EtOAc:4/1 DCM/EtOH) indicated a single spot with a trace of residual TFP visible near the solvent front. HPLC (Acids5545FF method): RT 32.14 min, purity 100%. $^1$H NMR (400 MHz, $CDCl_3$, δ): 7.84 (m, 2H), 7.71 (m, 2H), 7.01 (m, 3H), 6.23 (s, 1H), 3.91 (t, 2H), 3.82-3.72 (m, 12H), 3.79-3.55 (m, 50H), 3.74 (t, 2H), 2.92 (t, 6H), 2.4 (t, 2H). PhthN-dPEG$_4$-tris(-dPEG$_{11}$-m)$_3$ and NH$_2$-dPEG$_4$-tris(-dPEG$_{11}$-m)$_3$:

211 212
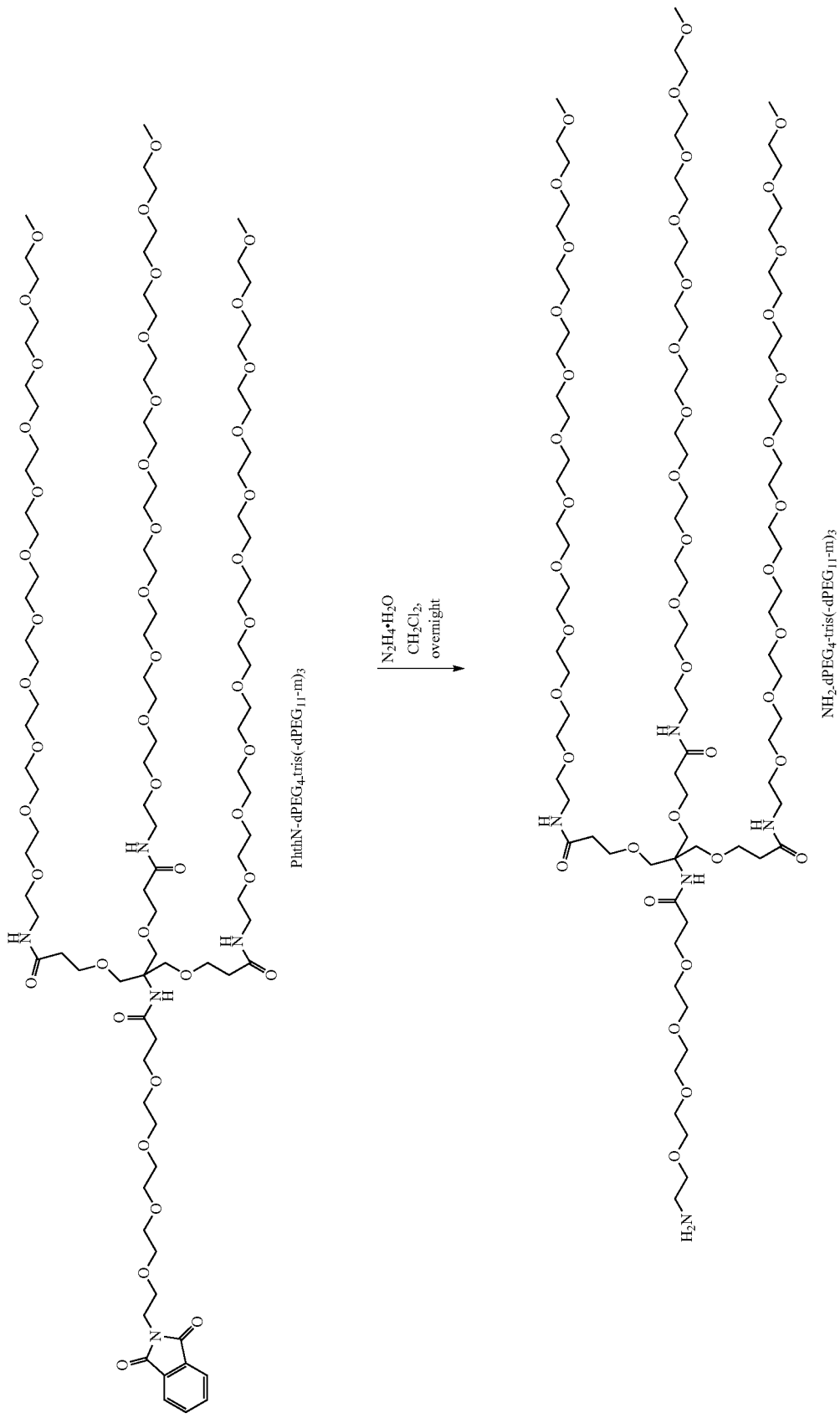

A solution of NH$_2$-dPEG11-m (17.8 g, 34.5 mmol) in 50 mL of anhydrous dichloromethane was placed in a 500 mL three-neck round bottom flask equipped with a magnetic stirrer, thermocouple, balloon filled with nitrogen, and ice-methanol cooling bath. Lutidine (4.59 g, 42.8 mmol) was added to this solution, and the resulting mixture was cooled to 0° C. A solution of Phth-4-tris-TFP ester (11.11 g, 9.59 mmol) in 25 mL of anhydrous dichloromethane was added dropwise to the reaction within 45 min, stirred for an additional 20 min at 0° C., and allowed to warm to ambient temperature and stirred overnight. The reaction was monitored by TLC (R$_f$=0.68 for Phth-4-tris(TFP)$_3$ and R$_f$=0.34 for product, in 90% DCM-10% EtOH) or HPLC, and after consumption of the TFP-ester it was quenched with cold 10% HCl (2×200 mL). The organic materials were extracted with dichloromethane (3×80 mL), the combined extracts were washed with cold 2% NaHCO$_3$ (100 mL), and the organic phase was separated and dried over anhydrous Na$_2$SO$_4$. The solvent was removed on rotavap, and the obtained yellow viscous oil (26 g, ~100% pure by HPLC) was flushed by column chromatography on silica gel. The excess of side product—TFP was removed first with 50/50 mixture of CH$_2$Cl$_2$-EtOAc, following by gradient elution using EtOH—CH$_2$Cl$_2$ from 0 to 20% EtOH. Pure fractions were concentrated under reduced pressure give 11.8 g (55.8%) of clear oil. An additional 7.5 g of material was recovered from impure fractions by column chromatography on silica gel resulting in which gives total 19.3 g (91% yield) of the target compound. HPLC (3045FF acid method): RT 27.93 min, purity 100%. $^1$H NMR (400 MHz, CDCl$_3$, δ): 7.85 (m, 2H, phthalimide), 7.73 (m, 2H, phthalimide), 6.92 (t, 3H, NH), 6.61 (s, 1H, NH), 3.89 (t, 2H, CH$_2$N), 3.84-3.50 (m, 160H, CH$_2$O), 3.49-3.40 (m, 6H, CH$_2$O), 3.38 (s, 9H, CH$_3$O), 2.50-2.36 (m, 10H, CH$_2$CO).

PhthN-dPEG$_{12}$-Tris(-dPEG$_{11}$-m)$_3$:

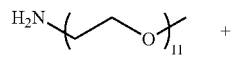

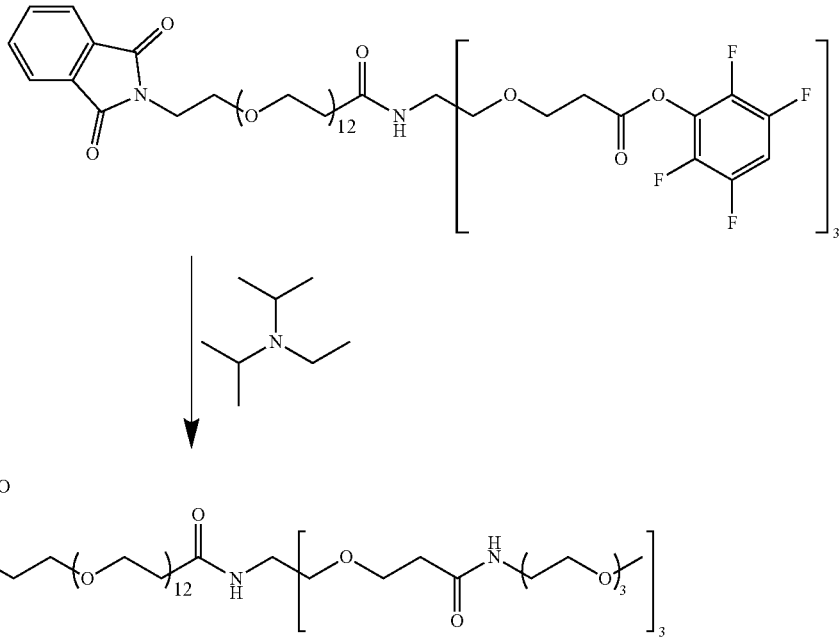

Using m11 amine, the amine is dripped into solution of TFP ester and DIIPEA in DCM cooled to OC. HPLC after one hour. HPLC following morning. The rxn is washed 2×200 ml sat bicarb, 2×200 ml 10% HCL, 1×200 ml sat brine, and dried over sod sulfate. It is azeotroped 2× with 50 ml ACN after evap DCM to weigh 56 gm. This is dissolved in ACN/TBME 65 ml/475 ml and heated to ~50C and filtered through glass fiber. The soln is cooled to ~10C which gives an hazy mixture which is stirred overnight. The mixture oils out so the solvents are removed and the oil is dissolved in 1 to 10 oil to solvent ratio with 10% acetone-TBME. After stirring overnite it also oils but not completely but there is no solid so it is seeded with some 95% solid from a previous batch. Stirring all day does not solidify it but when the solutions is cooled to OC with ice the oil solidifies. This stirs overnight to give a milky solid which is diluted with 500 ml 5% acetone-TBME and then filtered. The solid is very light and comes initially through the coarse filter. It is washed with 500 ml 5% acetone/TBME and is a caramel solid with some solvent present, 35 gm (56%). HPLC (acid60 method): RT 1.0.12 min, purity 93%.
$NH_2$-$dPEG_4$-Tris(-$dPEG_{11}$)$_3$:

217 218
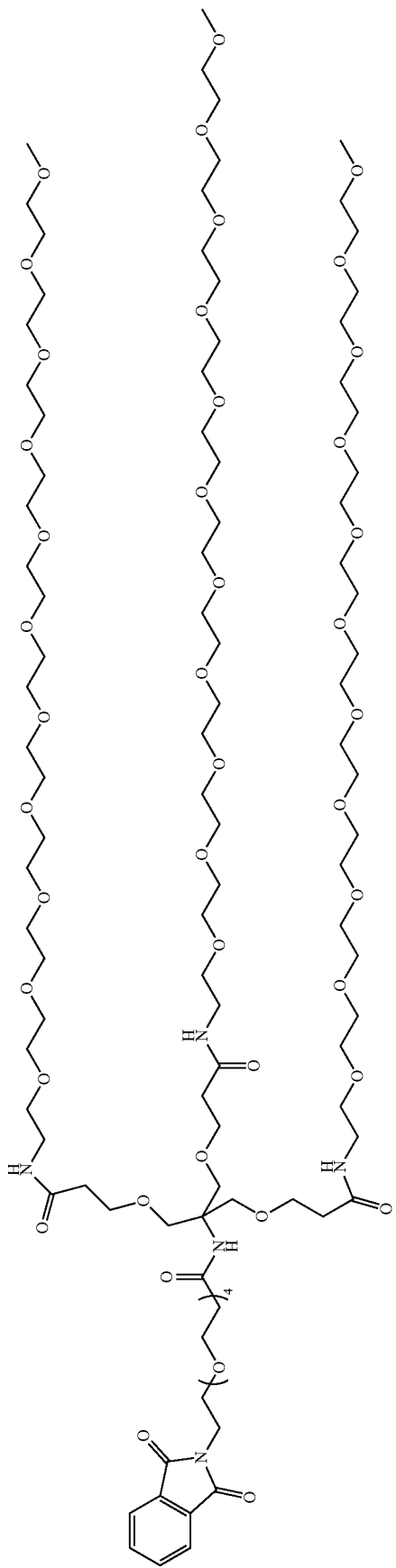 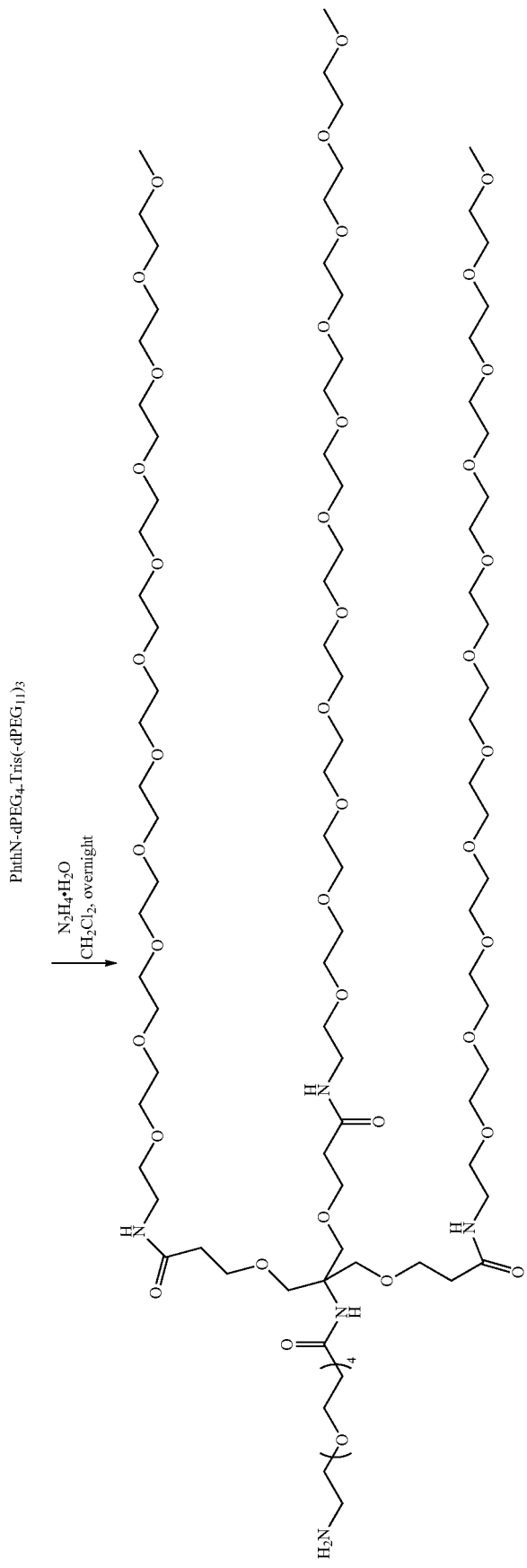

A solution of Phth-4-tris(11-m)$_3$ (11.7 g, 5.3 mmol) in 30 mL of anhydrous dichloromethane was placed in a 100 mL one neck round bottom flask equipped with magnetic stirrer, thermocouple, cooling ice bath, and nitrogen balloon. This solution was chilled to 0° C., and hydrazine hydrate (3.12 g, 62.3 mmol) was added dropwise to the flask. The resulting mixture stirred for an additional 30 min at 0° C. and allowed to warm to ambient temperature and stirred overnight. The reaction was monitored by TLC, and disappearance of the starting material ($R_f$=0.36 for the ester and $R_f$=0.08 for the product in 90% CH$_2$Cl$_2$-10% EtOH with 10% NH$_4$OH) indicated completion of the reaction. The white precipitate was filtered, washed with CH$_2$Cl$_2$ (3×20 mL), and the combined filtrates were washed with 20 mL of diluted cold NaHCO$_3$. The aqueous phase was back extracted with dichloromethane (2×30 mL), and the combined organic phases were dried over anhydrous Na$_2$SO$_4$. The solvent was removed under reduced pressure, and the obtained clear oil (10.9 g) was purified by column chromatography on silica gel. Gradient elution with a mixture of dichloromethane with ethanol from 0% to 20% of EtOH containing 10% of ammonia hydroxide gives 9.85 g of clear oil. This material was re-dissolved in dichloromethane and washed with 20 mL of a 1:1 mixture of water and brine, the organic layer was separated, dried over anhydrous Na$_2$SO$_4$, and then concentrated on rotavap. After an additional drying under high vacuum 9.77 g (89% yield) of clear oil was obtained which slowly solidifies into a white solid. HPLC (3045FF amine method): RT 22.78 min, purity 100%. $^1$H NMR (400 MHz, CDCl$_3$, δ): 6.84 (t, 3H, NH), 6.60 (s, 1H, NH), 3.85-3.58 (m, 150H, CH$_2$O), 3.57-3.52 (m, 13H, CH$_2$O); 3.51 (t, 2H, CH$_2$N), 3.47-3.39 (m, 6H, CH$_2$O), 3.38 (s, 9H, CH$_3$O), 2.86 (t, 2H, CH$_2$CO), (m, 8H, CH$_2$CO).

H$_2$N-dPEG$_{12}$-Tris(-dPEG$_{11}$-m)$_3$:

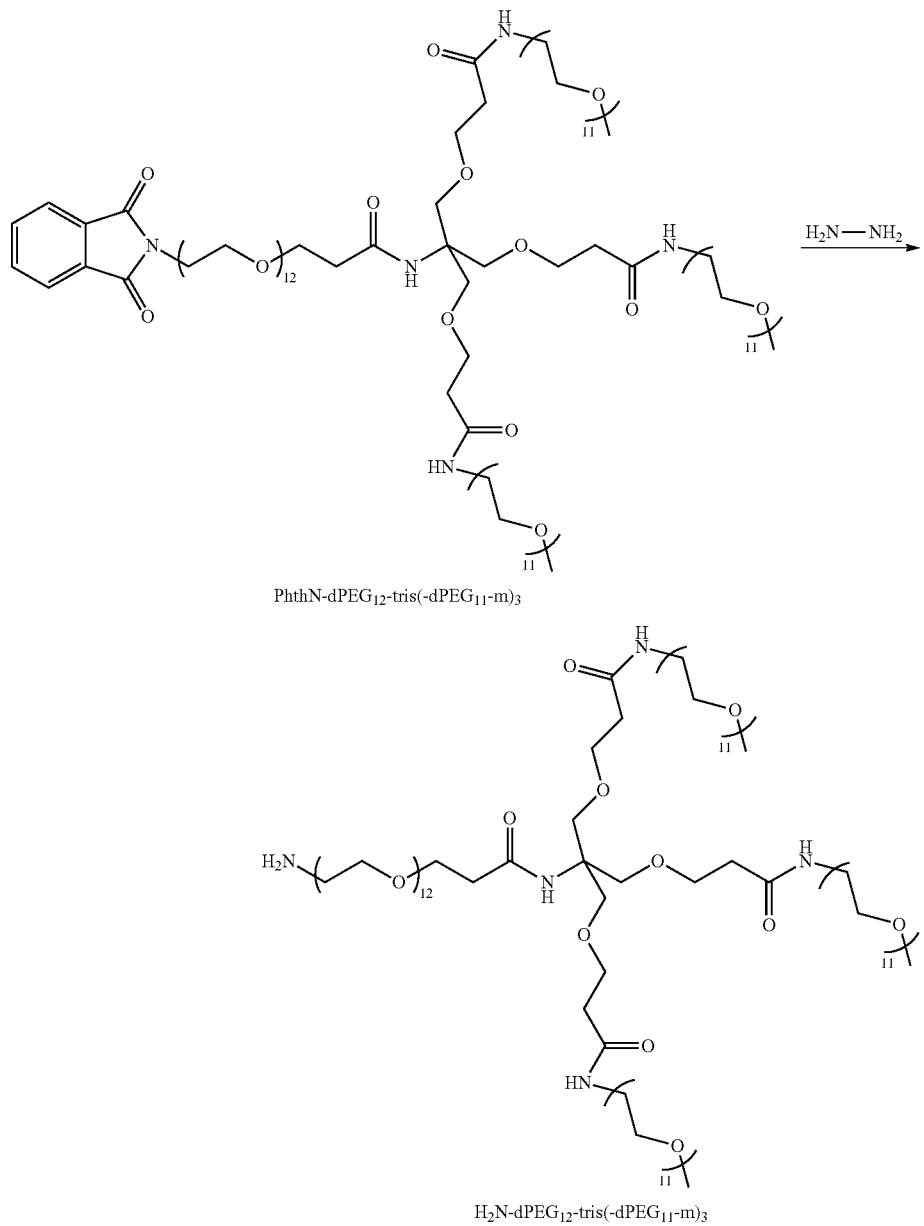

PhthN-dPEG$_{12}$-tris(-dPEG$_{11}$-m)$_3$

H$_2$N-dPEG$_{12}$-tris(-dPEG$_{11}$-m)$_3$

A solution of Phth-12-tris(11-m)$_3$ (35 g, 13.67 mmol) in anhydrous dichloromethane was treated with hydrazine hydrate (6 mL) and was stirred overnight. Solid is filtered off through fluted filter paper and washed with DCM then DCM is removed and oil is dried twice with ACN to weigh 32 g (96%). HPLC (amines4020 method): RT 13.59 min, purity 92%.

HO$_2$C-dPEG$_4$-Tris(-dPEG$_{11}$)$_3$:

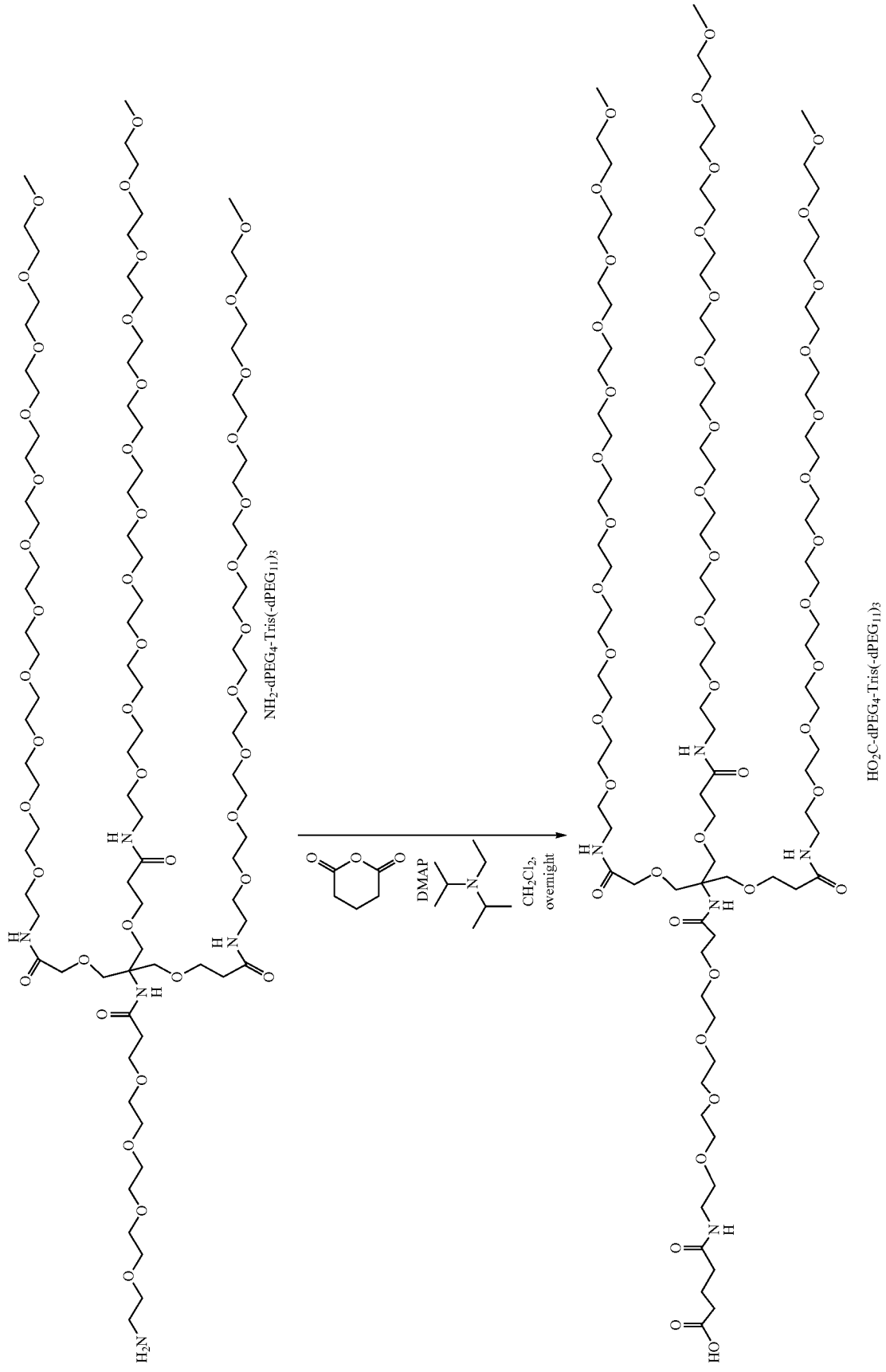

A solution of $NH_2$-$dPEG_4$-tris($dPEG_{11}$-m)$_3$ (8.77 g, 4.22 mmol) in 30 mL of anhydrous dichloromethane was placed in a 500 mL three-neck round bottom flask equipped with a magnetic stirrer, thermocouple, balloon filled with nitrogen, and ice-methanol cooling bath. Diisopropylethyl amine (1.1 g, 8.51 mmol) and DMAP (0.33 g, 2.7 mmol) were added to this solution, and the resulting mixture was cooled to 0° C. A solution of glutaric anhydride (10.578 g, 5.07 mmol) in 8 mL of anhydrous dichloromethane was added dropwise to the reaction with the rate to maintain temperature around 0° C., stirred for an additional 30 min at 0° C., and allowed to warm to ambient temperature and stirred for 7 hours. The reaction was monitored by TLC ($R_f$=0.36 for product, in 90% DCM-10% MeOH) or HPLC, and after consumption of the TFP-ester it was quenched with cold 10% HCl (50 mL). The organic materials were extracted with dichloromethane (3×20 mL), and the combined extracts were dried over anhydrous $Na_2SO_4$. The solvent was removed on retavap, and the obtained white semisolid (9.66 g, 99% pure by HPLC) was flushed on silica gel using gradient elution with MeOH—$CH_2Cl_2$ from 0 to 15% MeOH. The fractions were concentrated under reduced pressure to constant weight to give 8.45 g (91%) of glassy white material. HPLC (3045FF acid method): RT 24.1 min, 100%. $^1$H NMR (400 MHz, $CDCl_3$, δ): 6.90 (t, 4H, NH), 6.67 (s, 1H, NH), 3.85-3.58 (m, 152H, $CH_2O$), 3.58-3.51 (m, 14H, $CH_2O$), 3.48-3.39 (m, 8H, $CH_2O$), 3.37 (s, 9H, $CH_3O$), 2.50-2.40 (m, 8H, $CH_2CO$), 2.37 (t, 2H, $CH_2CO$), 2.29 (t, 2H, $CH_2CO$), 1.95 (quintet, 2H, $CH_2$).

TFP-$dPEG_4$-Tris(-$dPEG_{11}$-m)$_3$:

227            228
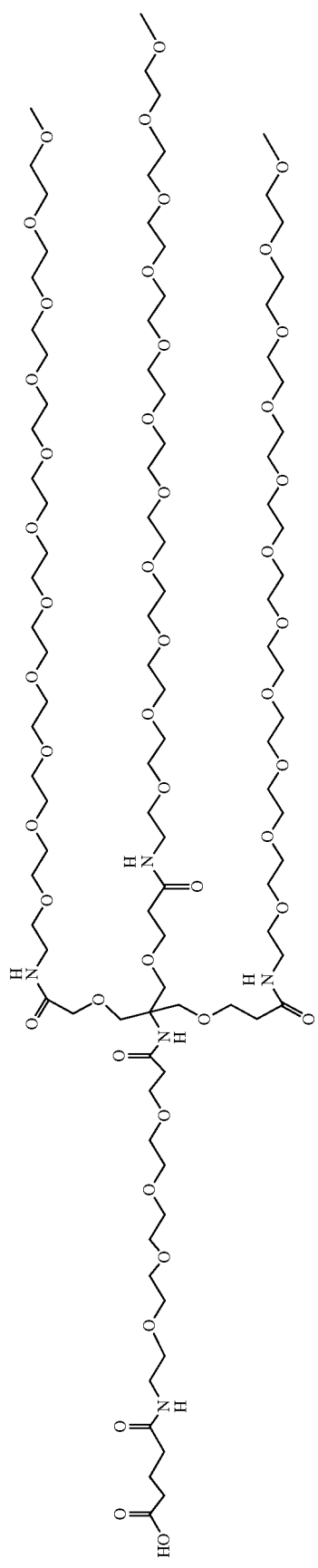
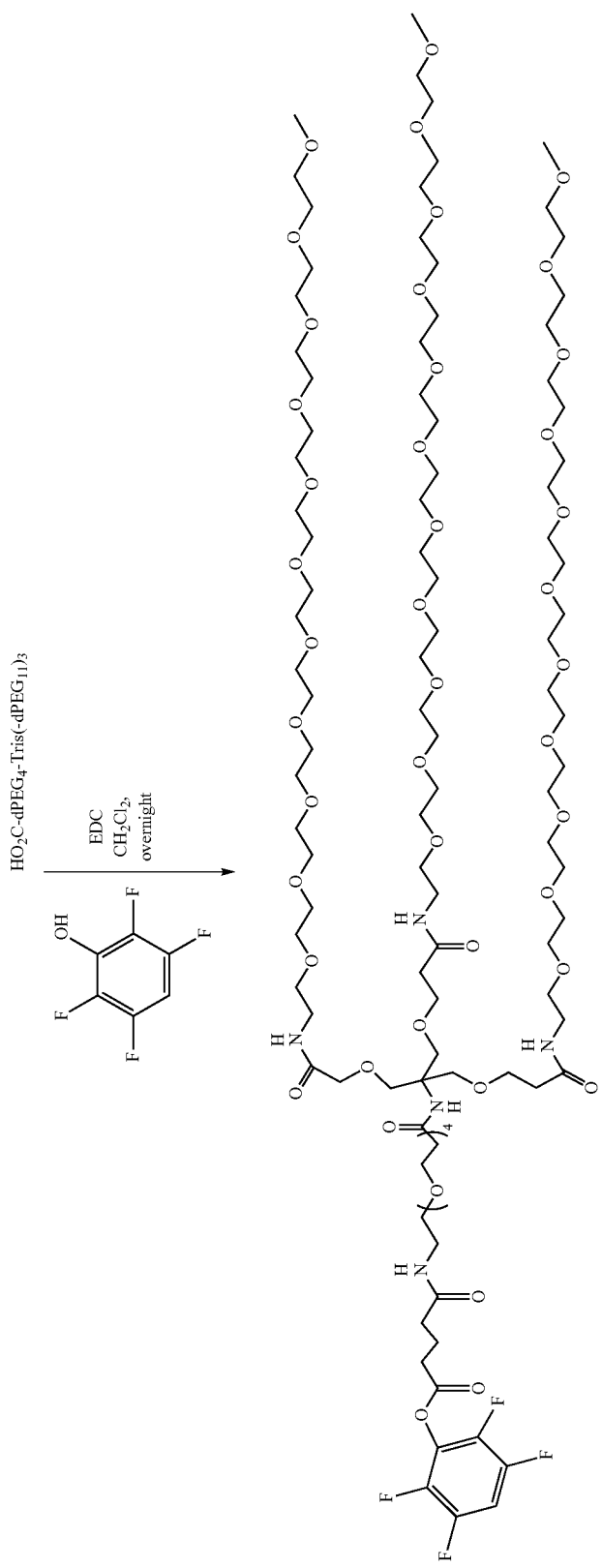

A solution of HCO₂-Glu-NH-dPEG₄-tris-(dPEG₁₁-m)₃ acid (7.75 g, 3.54 mmol) in 30 mL of anhydrous dichloromethane was placed in a 200 mL three-neck round bottom flask equipped with a magnetic stirrer, thermocouple, nitrogen balloon, and a cooling ice bath. In a separate 50 mL one-neck round bottom flask equipped with a magnetic stirrer, thermocouple, and cooling ice bath a slurry of EDC (1.28 g, 6.69 mmol) in 15 mL of anhydrous dichloromethane was prepared under a nitrogen blanket. A solution of TFP (1.1 g, 6.62 mmol) in 6 mL of anhydrous dichloromethane was added to the EDC slurry via syringe at 6° C. with the rate to maintain temperature at about 5-10° C. The resulting clear solution stirred for an additional 5 min at 5° C. and then was added dropwise via syringe to the solution of the above acid in CH₂Cl₂ at 0° C. The reaction mixture stirred at this temperature for an additional 30 min. The cooling bath was then removed, and the reaction was allowed to warm to ambient temperature and stirred overnight. The reaction was monitored by TLC (R$_f$=0.25 for HOCO₂-Glu-NH-dPEG4-tris(dPEG11-m)₃, and R$_f$=0.38 for product in 90% CH₂Cl₂-10% MeOH) or by HPLC. After the starting tris-acid disappeared, the reaction was quenched with cold with 1:1 diluted NaHCO₃ (80 mL) containing 10 mL of brine, and extracted with dichloromethane (3×30 mL). The organic phase was washed with cold water (80 mL) containing 10 mL of brine, dried over anhydrous Na₂SO₄ and concentrated under reduced pressure to give 10.2 g of clear viscous oil with HPLC purity of ~100%. An excess of TFP was removed by precipitation 12 g celite from its solution in EtOAc-MTBE=1:1 (50 mL) by dropwise addition of hexane-MTBE=4:1 mixture (100 mL). Resulting suspension was filtered, and the cake was washed with hexane-MTBE=5:1 (60 mL) and the filtrate was discarded. The product was washed from celite cake with dichloromethane (4×30 mL), and this filtrate was concentrated under reduced pressure until constant weigh to give 7.7 g (93% yield) of viscous clear oil which slowly solidifies into a paraffin-like white solid. HPLC (3045FF acid method): RT 30.32 min, 99%. ¹H NMR (400 MHz, CDCl₃, δ): 7.01 (m, 1H, TFP), 6.78 (t, 3H, NH), 6.56 (s, 1H, NH), 6.46 (broad t, 1H, NH), 3.86-3.48 (m, 182H, CH₂O), 3.49-3.39 (m, 9H, CH₂d), 3.37 (s, 9H, CH₃O), 2.7.7 (t, 2H, CH₂CO), 2.47-2.38 (m, 8H, CH₂CO), 2.34 (t, 2H, CH₂CO), 2.10 (quintet, 2H, CH₂).

MAL-dPEG₁₂-Tris(-dPEG₁₁-m)₃:

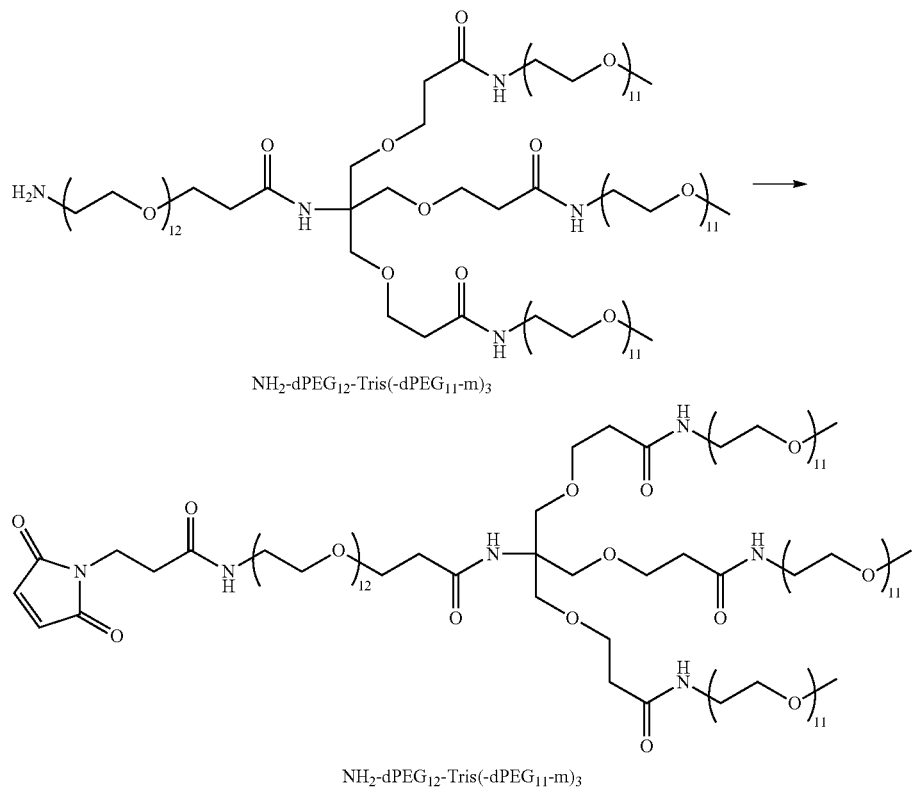

NH₂-dPEG₁₂-Tris(-dPEG₁₁-m)₃

NH₂-dPEG₁₂-Tris(-dPEG₁₁-m)₃

A 50 mL 3-neck RBF fitted with nitrogen blanket, cooling bath, and addition funnel was set up for this reaction. The flask was charged with MPS (0.657 g, 2.469 mmol) and DCM (12.86 ml) and cooled in an ice bath. Amino-dPEG12-tris(m-11)₃ (5 g, 2.058 mmol) was dissolved in DCM (12.86 ml) and 2,6-Lutidine (0.312 ml, 2.68 mmol) was added via pipette and the mixture was placed in the addition funnel. The amine mixture was added dropwise and the reaction was allowed to warm to room temp and stirred for 2 h. HPLC (Amines4020 method) indicated complete consumption of sm. TLC (90:10 and 80:20 DCM:MeOH) indicated complete consumption of sm and formation of a major product. The reaction was diluted with DCM (75 mL), washed with 10% HCl (2×10 mL), washed with sat aq bicarb (2×10 mL), washed with brine (15 mL), dried over Na₂SO₄, filtered over celite, and concentrated under reduced pressure to give 5.005 g of a cloudy viscous yellow oil. HPLC (amines4020 method) indicated a single major product with 100% purity by ELSD. TLC indicated one major spot with a very small amount of MPS NHS remaining. The sample was purified via chromatography on a 50 g column using DCM (A) and MeOH (B). The column was primed with 1CV 5% B and then 2CV of 0% B. The sample was preabsorbed onto 10 g $SiO_2$ and a gradient was run at 0% B for 1CV then ramping to 15% B over 10CV then holding at 15% B.

The fractions were run on a TLC plate and 18-29 were pooled and concentrated to give 2.65 g (50%) of a clear colorless oil that solidified to a white solid after the weekend on high vac. TLC (85:15 DCM:MeOH) indicated a single spot. HPLC (amines3045FF method): RT 25.5 min, 96%. $^1$H NMR (400 MHz, $CDCl_3$, δ): 6.71 (m, 5H), 6.54 (s, 1H), 6.28 (s, 1H), 3.83 (m, 2H), 3.72-3.38 (m, 190H), 3.37 (s, 9H), 2.51 (t, 2H), 2.41 (m, 8H).

PthN-dPEG$_{12}$-Tris(-dPEG$_{24}$-m)$_3$:

mL), washed with brine (75 mL), dried over $Na_2SO_4$, filtered over celite, and concentrated under reduced pressure to give 29.2 g of a viscous orange liquid that started to solidify. TLC indicated a single major product with residual TFP. The residue was dissolved in ACN (15 mL) and $Et_2O$ was dripped in until cloudiness was just observed (80 mL). 25 g of celite was added and more $Et_2O$ was dripped in (160 mL). The celite was filtered off, rinsed with $Et_2O$ (2×50 mL), and the product was then washed off with DCM (4×100 mL). TLC indicated most of the TFP in the breakthrough and washes. The product was in the DCM flushes. The flushes were concentrated under reduced pressure to give 31.3 g of an orange oil. The solid was preabsorbed on to 40 g of silica

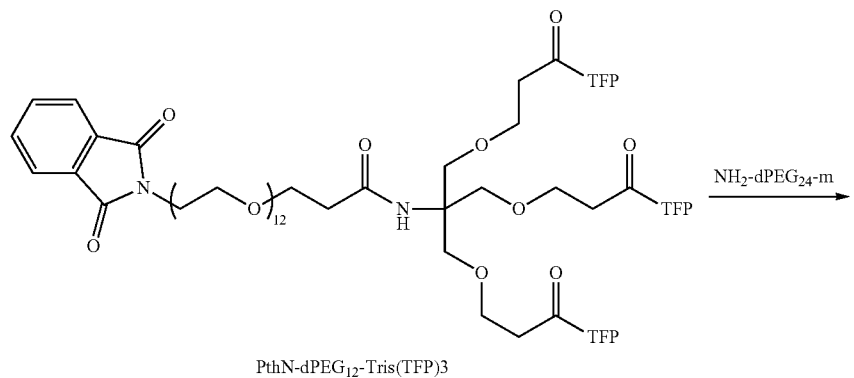

PthN-dPEG$_{12}$-Tris(TFP)3

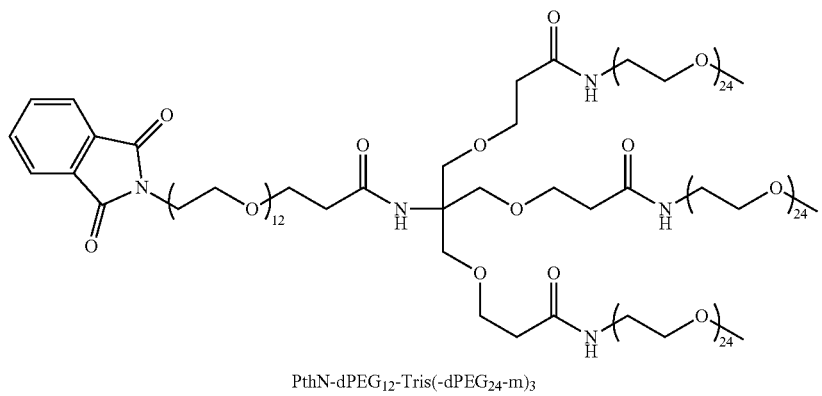

PthN-dPEG$_{12}$-Tris(-dPEG$_{24}$-m)$_3$

A 250 mL 3-neck RBF fitted with addition funnel, nitrogen blanket, and cooling bath was set up for this reaction. The flask was charged with m-24-amine (23.04 g, 21.17 mmol), dichloromethane (52.9 ml), and N-Ethyldiisopropylamine (3.70 ml, 21.17 mmol) and cooled to 5° C. in an ice bath. PhthN-12-tris(TFP)3 (8 g, 5.29 mmol) was dissolved in dichloromethane (52.9 ml), placed in the addition funnel, added drop wise to the amine mixture, warmed to room temperature, and allowed to stir overnight. HPLC (Acid60method) indicated complete conversion of sm and formation of a single major product. HPLC (Amines3045FF method) also indicated a single major product and some excess amine. TLC (85:15 DCM:MeOH) indicated complete consumption of tris-TFP and formation of a major product. The reaction was diluted with DCM (300 mL), washed with 10% HCl (3×75 mL), washed with sat aq $NaHCO_3$ (3×75 and purified on a Isco Rf on a 220 g column using DCM (A) and MeOH (B) and taking 100 mL fractions. The column was primed with 10% B for 1CV and then 0% B for 2CV. The solid load cartridge was inserted and a gradient was run at 0% B for 3CV then ramping to 15% B over 10CV and then holding at 15% B. Small fractions were taken as the peak began to elute to avoid a large amount of mixed product. The fractions were run on a TLC plate and 25-54 were pooled, concentrated, and triturated with hexanes then $Et_2O$ to give 15.854 g (70%) of a white powdery solid. TLC (85:15 DCM:MeOH) indicated a single spot. HPLC (amines3045FF method): RT 31.01 min, 100% purity. $^1$H NMR (400 MHz, $CDCl_3$, δ): 7.84 (m, 2H), 7.72 (m, 2H), 6.78 (5, 3H), 6.55 (s, 1H), 3.92-3.30 (m, 352H), 2.41 (m, 14H, water of hydration inflating integral value from 8).

$H_2N$-dPEG$_{12}$-Tris(-dPEG$_{24}$-m)$_3$:

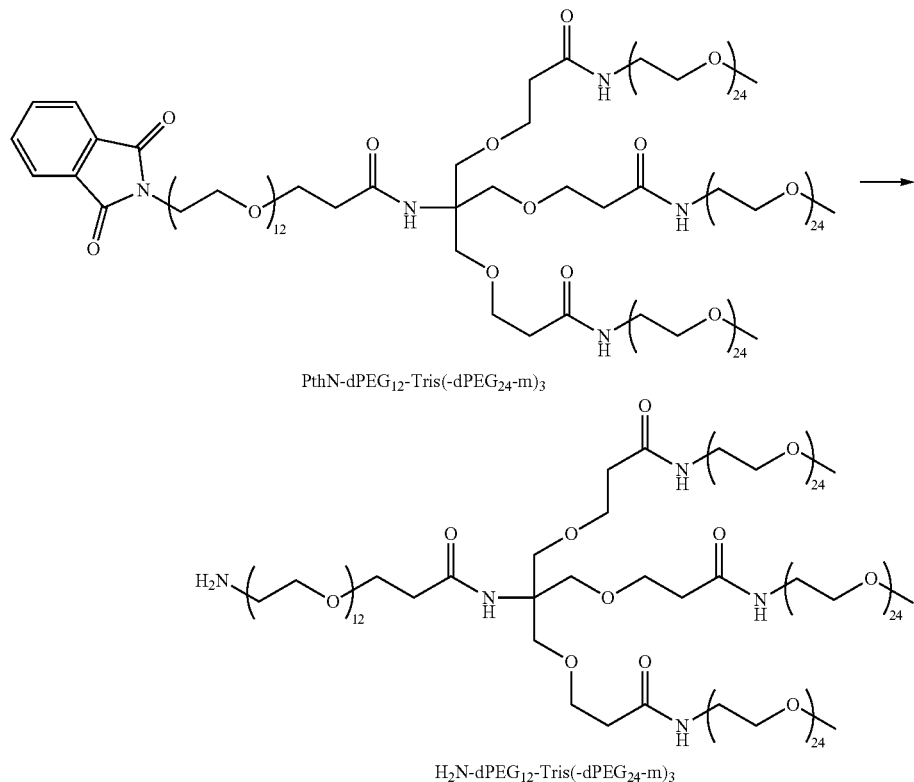

PthN-dPEG₁₂-Tris(-dPEG₂₄-m)₃

H₂N-dPEG₁₂-Tris(-dPEG₂₄-m)₃

A 200 mL RBF was charged with PhthN-12-tris(amido-24-m)3 (15.854 g, 3.71 mmol) and dichloromethane (37.1 ml). Hydrazine monohydrate (1.799 ml, 37.1 mmol) was added via syringe and the reaction was allowed to stir overnight at room temperature. HPLC (Amines3045FFmethod) indicated complete conversion of sm and formation of a single major product. TLC (90:10 DCM: 4/1 MeOH/NH₄OH) indicated complete conversion of sm and formation of a single product. The precipitate was filtered off over celite and the solvent was removed under reduced pressure to give 15.6 g of a pale yellow solid. The residue was subjected to flash filtration on a 50 g plug of $SiO_2$ using DCM (A) and 4/1 MeOH/NH₄OH (B) and taking 100 mL fractions. The residue was preabsorbed on to 30 g of silica then eluted over a 50 g plug of $SiO_2$ in a glass funnel. The fractions were concentrated, taken up in DCM (400 mL), washed with brine (2×50 mL), dried over $Na_2SO_4$, filtered over celite, and concentrated under reduced pressure to give 14.5 g of a sticky off white solid. The solid was dissolved in 12 mL ACN and dripped in to 120 mL $Et_2O$. The solution was then cooled and another 25 mL $Et_2O$ was dripped in. The cloudy supernatant was decanted and the residual semi-solid dried under high vac and triturated with $Et_2O$ to give 13.8 g (90%) of a white powdery solid. HPLC (amines3045FF method): RT 28.80 min, 100% purity. ¹H NMR (400 MHz, CDCl₃, δ): 6.79 (s, 3H), 6.56 (s, 1H), 3.84-3.38 (m, 350H), 3.36 (s, 9H), 2.87 (t, 2H), 2.39 (m, 8H).

MAL-dPEG₁₂-Tris(-dPEG₂₄-m)₃:

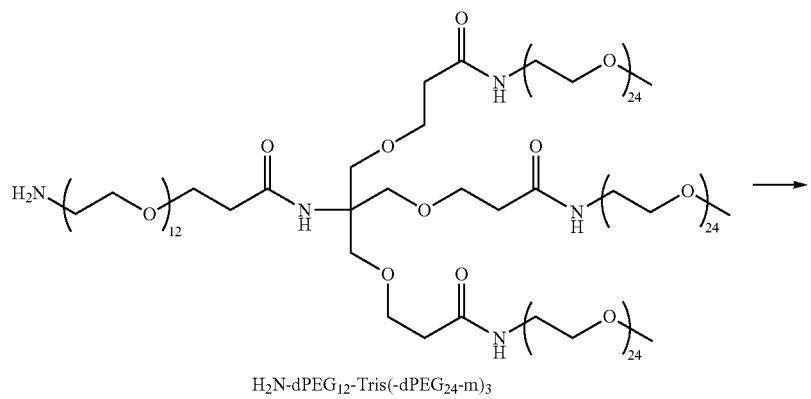

H₂N-dPEG₁₂-Tris(-dPEG₂₄-m)₃

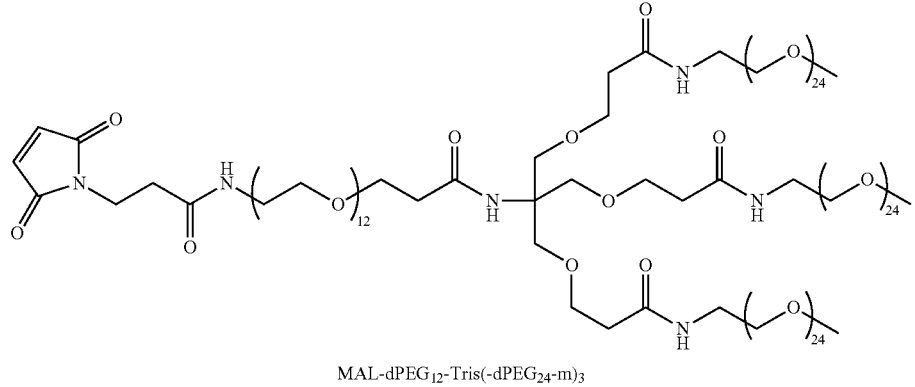

MAL-dPEG₁₂-Tris(-dPEG₂₄-m)₃

A 100 mL 3-neck RBF was charged with MPS (0.422 g, 1.587 mmol) and dichloromethane (13.22 ml) and cooled to 0° C. Amino-12-tris(amido-24-m)3 (5.484 g, 1.322 mmol) was dissolved in dichloromethane (13.22 ml) and 2,6-Lutidine (0.200 ml, 1.719 mmol) was added via pipette. The amine mixture was added dropwise to the MPS solution and allowed to warm to 22° C. The reaction was stirred for 3 h. HPLC (Amines4020) indicated a single product; however the retention time was indistiguishable from the starting amine. TLC (85:15 DCM:MeOH) indicated complete consumption of sm and formation of a single major product. The reaction was diluted with DCM (100 mL), washed with 10% HCl (2×10 mL), washed with sat aq NaHCO₃ (2×10 mL), washed with brine (15 mL), dried over Na₂SO₄, filtered over celite, and concentrated under reduced pressure to give 5.011 g (88%) of an oily off-white solid. TLC (85:15 DCM:MeOH) indicated a single, major product and many of the impurities were removed in the workup.

The residue was preabsorbed on to 8 g of silica and purified on a 50 g SNAP cartridge on a Biotage Isolera using DCM (A) and MeOH (B) taking 22 mL fractions. The column was primed with 10% B for 1CV and 0% B for 2CV. The SLSC was inserted and a gradient was run at 0% B for 2CV then ramping to 20% B over 10CV and holding at 20% B. When the product began to elute the fractions were reduced to 10 mL for the first 3. Fractions 15-27 were pooled and concentrated to give 3.292 g (58%) of a white sticky solid. TLC (85:15 DCM:MeOH) indicated a single spot. HPLC (amines3045FF method): RT 29.19 min, 99% purity. ¹H NMR (400 MHz, CDCl₃, δ): 6.72 (s, 3H), 6.69 (s, 2H), 6.53 (s, 1H), 6.31 (2, 1H), 3.86-3.37 (m, 352H), 3.35 (s, 9H), 2.49 (t, 2H), 2.40 (m, 8H).

PthN-dPEG₁₂-Tris(dPEG₁₂-TBE)₃:

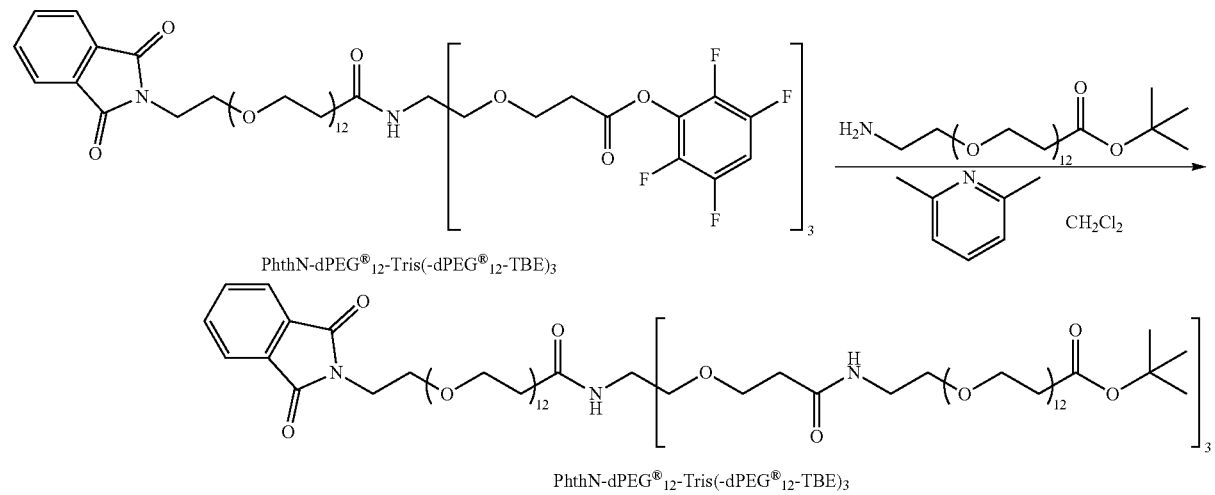

PhthN-dPEG®₁₂-Tris(-dPEG®₁₂-TBE)₃

PhthN-dPEG®₁₂-Tris(-dPEG®₁₂-TBE)₃

A solution of NH₂-dPEG12-TBE (13.82 g, 20.51 mmol) in 35 mL of anhydrous dichloromethane was placed in a 250 mL three-neck round bottom flask equipped with a magnetic stirrer, thermocouple, balloon filled with nitrogen, and ice-methanol cooling bath. Lutidine (2.71 g, 25.3 mmol) was added to this solution, and the resulting mixture was cooled to 0° C. A solution of Phth-dPEG12-tris(TFP)₃ ester (8.06 g, 5.33 mmol) in 25 mL of anhydrous dichloromethane was added dropwise to the reaction within 20 min, stirred for an additional 30 min at 0° C., and allowed to warm to ambient temperature and stirred overnight. The reaction was monitored by TLC ($R_f$=0.66 for Phth-12-tris(TFP)₃ and $R_f$=0.25 for product, in 90% DCM-10% EtOH) or HPLC, and after consumption of the TFP-ester it was quenched with cold 10% HCl (2×200 mL). The organic materials were extracted with dichloromethane (3×50 mL), the combined extracts were washed with cold 2% NaHCO₃ (1×200 mL), and the organic phase was separated and dried over anhydrous Na₂SO₄. The solvent was removed on rotavap, and the obtained yellow viscous oil (22 g, 90% pure by HPLC) was purified by column chromatography on silica gel. The excess of side product—TFP was removed first with 50/50 mixture of $CH_2Cl_2$-EtOAc, following by gradient elution using EtOH—$CH_2Cl_2$ from 0 to 20% EtOH. Pure fractions were concentrated under reduced pressure give 10.24 g (63% yield) of Phth-12-tris(12-TBE)$_3$ as a yellow oil which slowly solidifies into a yellow solid in a freezer. An additional 2.85 g of material was recovered from impure fractions by column chromatography on silica gel resulting in 81% total yield of the target compound. HPLC (3045FF acid method): RT 37.05 min, purity 98.3%. $^1$H NMR (400 MHz, $CDCl_3$, δ): 7.85 (m, 2H, phthimide), and 7.72 (m, 2H, phthalimide), 6.86 (t, 3H, NH), 6.59 (s, 1H, NH), 3.90 (t, 2H, $CH_2N$), 3.84-3.5 (m, 218H, $CH_2O$), 3.48-3.40 (m, 8H, $CH_2O$), 2.5 (t, 6H, $CH_2CO$), 2.48-2.38 (m, 8H, $CH_2CO$), 1.45 (s, 27H, $CH_3$).

$H_2N$-dPEG$_{12}$-Tris(-dPEG$_{12}$-TBE)$_3$:

and stirred overnight. The reaction was monitored by TLC, and disappearance of the starting material ($R_f$=0.28 for the ester and $R_f$=0.06 for the product in 90% $CH_2Cl_2$-10% EtOH with 10% $NH_4OH$) indicated completion of the reaction. The white precipitate was filtered, washed with $CH_2Cl_2$ (3×20 mL), and the combined filtrates were washed with 20 mL of water. The aqueous phase was back extracted with dichloromethane (3×30 mL), and the combined organic phases were dried over anhydrous $Na_2SO_4$. The solvent was removed under reduced pressure, and the obtained clear oil (5 g) was purified by column chromatography on silica gel. Gradient elution with a mixture of dichloromethane with ethanol from 0% to 30% of EtOH containing 10% of ammonia hydroxide gives 4.6 g of clear oil. This material was re-dissolved in dichloromethane and washed with 20 mL of a 1:1 mixture of water and brine, the organic layer was

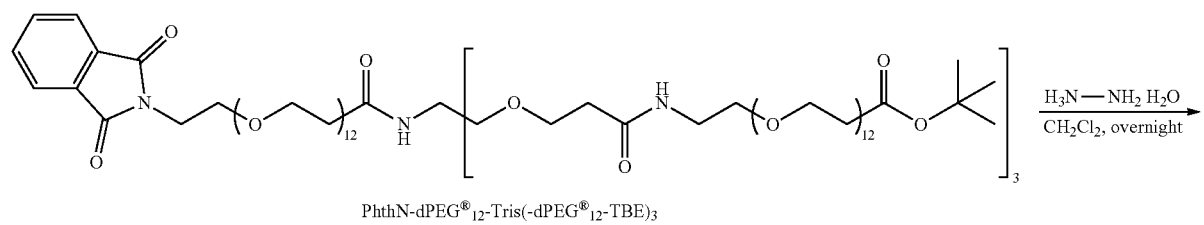

PhthN-dPEG®$_{12}$-Tris(-dPEG®$_{12}$-TBE)$_3$

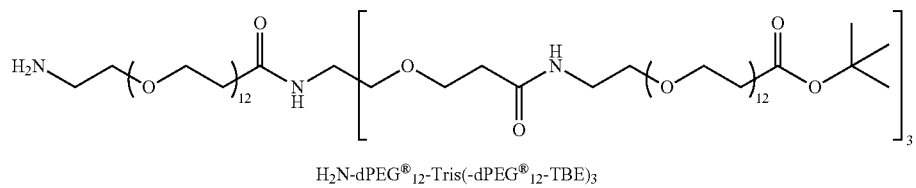

$H_2N$-dPEG®$_{12}$-Tris(-dPEG®$_{12}$-TBE)$_3$

A solution of Phth-12-tris(12-TBE)$_3$ (5.079 g, 1.674 mmol) in 25 mL of anhydrous dichloromethane was placed in a 100 mL one neck round bottom flask equipped with magnetic stirrer, thermocouple, cooling ice bath, and nitrogen balloon. This solution was chilled to 0° C., and hydrazine hydrate (0.95 g, 18.98 mmol) was added dropwise to the flask. The resulting mixture stirred for an additional 30 min at 0° C. and allowed to warm to ambient temperature separated, dried over anhydrous $Na_2SO_4$, and then concentrated on rotavap. After an additional drying under high vacuum 4.55 g (94% yield) of clear oil was obtained which slowly solidifies into a white solid. HPLC (3045F amines method): RT 35.14 min, purity 99.4%. $^1$H NMR (400 MHz, $CDCl_3$, δ): 6.82 (t, 3H, NH), 6.57 (s, 1H, NH), 3.84-3.38 (m, 230H, $CH_2O$, $CH_2N$), 2.87 (t, 2H, $NH_2$), 2.52-2: 38 (m, 14H, $CH_2CO$), 1.45 (s, 27H, $CH_3$).

MAL-dPEG$_{12}$-Tris(-dPEG$_{12}$-TBE)$_3$:

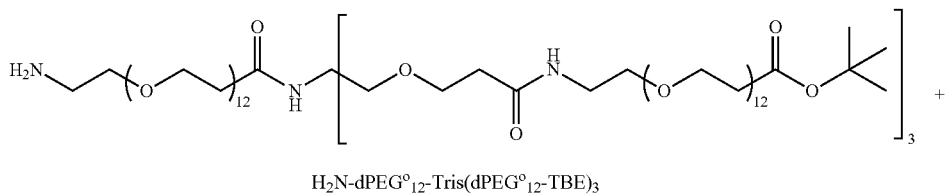

H$_2$N-dPEG$^o$$_{12}$-Tris(dPEG$^o$$_{12}$-TBE)$_3$

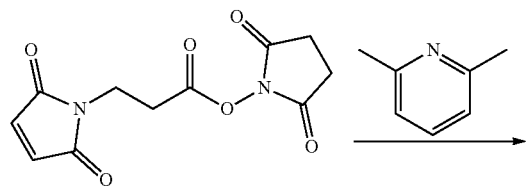

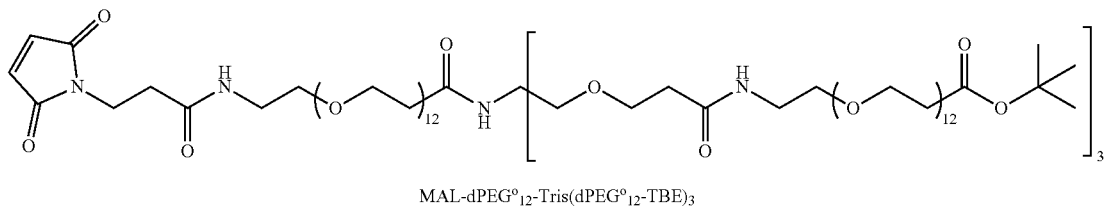

MAL-dPEG$^o$$_{12}$-Tris(dPEG$^o$$_{12}$-TBE)$_3$

The amine (24.6 g, 8.47 mmol) is cooled in an ice bath in dry DCM along with the lutidene (1.09 g, 10.16 mmol). The MPS (2.48 g, 9.32 mmol) is added and the rxn stirs overnite at rt. The rxn is diluted to 400 ml DCM and then washed with sat bicarb, 10% HCl, and sat brine, dried over sod sulfate and rotovaped azeotroping twice with ACN to weigh 22 gm. This is cc on the Biotage using a 350 gm column with a 50 gm forecolumn as a guard. The 350 gm column is equilibrated with 2 CV 5% ethanol/DCM then 1CV back to 100% DCM and another 100% CV DCM before the 50 gm guard column is attached with the maleimide loaded in DCM. After 1CV isocratic 100% DCM the gradient is over 12CV to 20% ethanol. The product elutes in fractions 43-70 of which fractions 46-58 are pooled and concentrated to give 22 g (85%) of an off-white waxy solid. HPLC (acid6015 method): RT 12.89 min, purity 100%.

MAL-dPEG$_{12}$-Tris(-dPEG$_{12}$-CO$_2$H)$_3$:

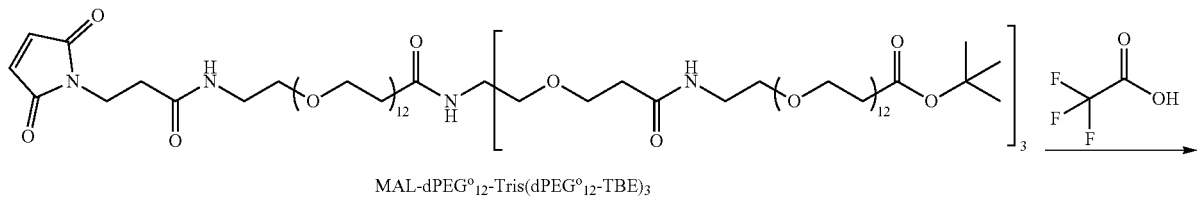

MAL-dPEG$^o$$_{12}$-Tris(dPEG$^o$$_{12}$-TBE)$_3$

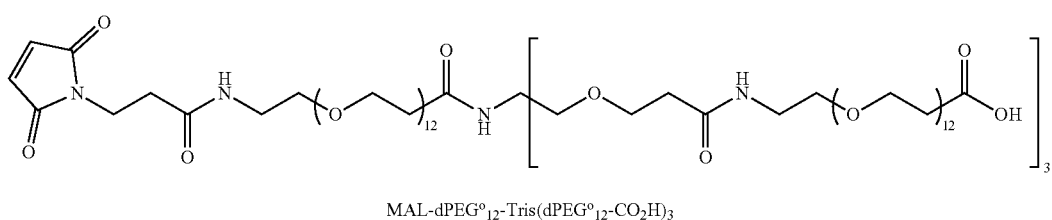

MAL-dPEG$^o$$_{12}$-Tris(dPEG$^o$$_{12}$-CO$_2$H)$_3$

The t-butyl ester (9 g, 2.5 mmol) is cooled in an ice bath with dry DCM and then the TFA (30 mL) is added neat. The deprotection is run for 12 hr at rt with mag stirring with a drying tube attached. HPLC confirms deprotection. The rxn is diluted w/DCM and then washed 1× with water then 5×1% brine, sat brine, then sod sulfate, rotovapped with oil pump. Material is a light brown paste. The material is chromatographed on the Biotage to give 5 g (59%) of a cream colored solid. HPLC (acid6015 method): RT 6.22 min, purity 93%. $^1$H NMR (400 MHz, CDCl$_3$, δ): 6.90 (br t, 3H), 6.71 (2H), 6.62 (br, 1H), 6.49 (br, 1H), 3.92-3.36 (m, 217H), 2.60 (t, 6H), 2.52 (t, 2H), 2.49-2.39 (overlapping t, 8H).

PhthN-dPEG$_{12}$-Tris(-dPEG$_{12}$-acid)$_3$:

disappearing of starting Phth-12-tris-TBE-ester (R$_f$=0.72 for the ester, R$_f$=0.4 for product in CH$_2$Cl$_2$-MeOH=9/1), and after completion the excess of formic acid was removed on rotavap at 35° C. to give a viscous yellow oil. This material was dissolved in 80 mL of CH$_2$Cl$_2$ and washed with a mixture of water (30 mL) and brine (10 mL). The product was extracted with dichloromethane (3×30 mL), and the combined organic phases were dried over anhydrous Na$_2$SO$_4$. Solvent was removed on rotavap, and the obtained yellow viscous oil in ~100% yield (4.97 g, 96% pure by HPLC) was flashed by column chromatography on silica gel with gradient elution using MeOH—CH$_2$Cl$_2$ from 0 to 15% methanol to give after drying under high vacuum 3.78 g (86% yield) of product as a yellow oil. HPLC (3045FF acid

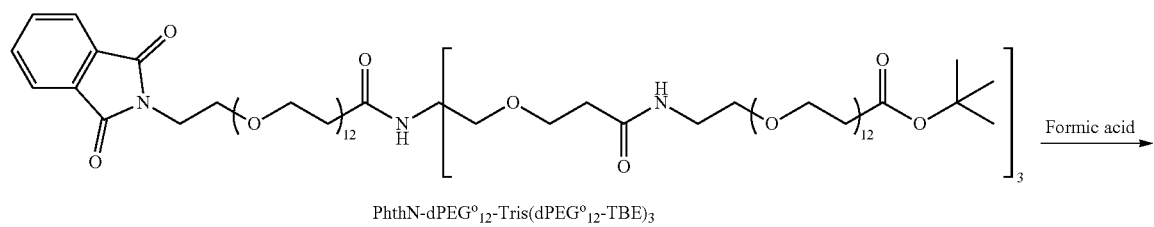

PhthN-dPEG°$_{12}$-Tris(dPEG°$_{12}$-TBE)$_3$

Formic acid

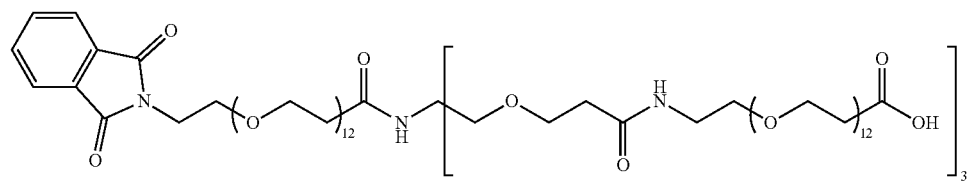

PhthN-dPEG°$_{12}$-Tris(dPEG°$_{12}$-CO$_2$H)$_3$

A mixture of Phth-12-tris(12-TBE)$_3$ (4.63 g, mmol) and formic acid (18.7 g, mmol) was placed in a 100 mL one-neck round bottom flask equipped with a magnetic stirrer, heating mantle, thermocouple, and nitrogen balloon. The temperature was maintained at 35° C., and the resulting mixture stirred overnight. The reaction was monitored by TLC (by method): RT 27.14 min, purity 96.97%. $^1$H NMR (400 MHz, CDCl$_3$, δ): 7.84 (m, 2H, phthalimide), 7.71 (m, 2H, phthalimide), 6.88 (t, 3H, NH), 6.61 (s, 1H, NH), 3.89 (t, 2H, CH$_2$N), 3.85-3.5 (m, 218H, CH$_2$O), 3.48-3.37 (m, 8H, CH$_2$O), 2.59 (t, 6H, CH$_2$CO), 2.50-2.38 (m, 8H, CH$_2$CO)

H$_2$N-dPEG$_{12}$-Tris(-dPEG$_{12}$-acid)$_3$:

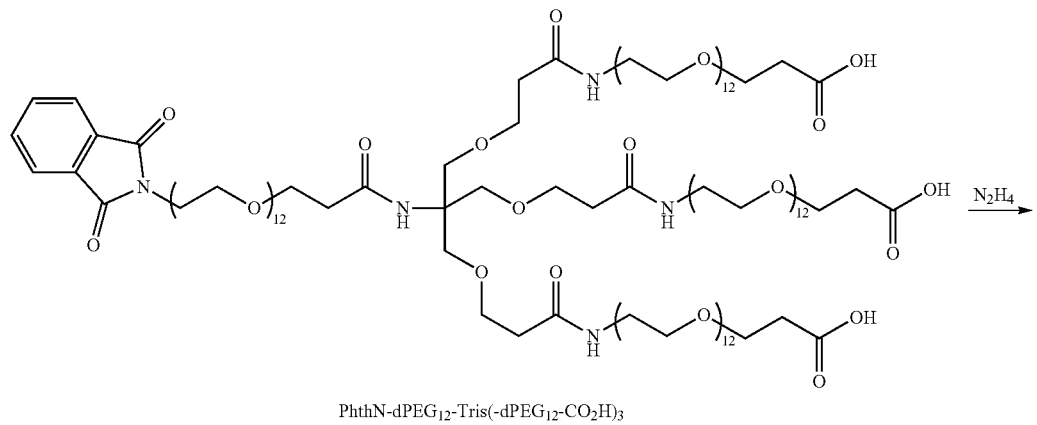

PhthN-dPEG$_{12}$-Tris(-dPEG$_{12}$-CO$_2$H)$_3$

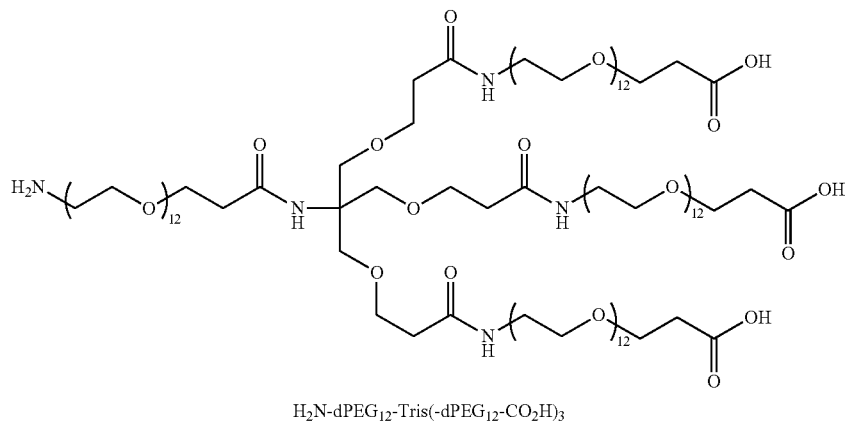

H$_2$N-dPEG$_{12}$-Tris(-dPEG$_{12}$-CO$_2$H)$_3$

A 25 mL RBF was charged with PhthN-12-tris(amido-12-acid)3 (2.211 g, 0.771 mmol) and DCM (7.71 ml). Hydrazine monohydrate (0.374 ml, 7.71 mmol) was added via pipette. The reaction became very thick after about 1 hour so additional DCM (7.71 ml) was added and the reaction was held at room temp overnight. The reaction was filtered on a buchner and concentrated under reduced pressure to give a yellow oil. TLC (85:15 DCM 3/1 MeOH/HCOOH) indicated complete conversion of sm and formation of a single major product along with some minor 12 positive spots. The oil was dissolved in 2 mL Me2CO, chilled to −20C and 20 mL Et2O was added. The solvent was decanted from the resulting oil and drying under reduced pressure provided 1.341 g (64%) of a clear yellow viscous oil. HPLC (amines4020 method): RT 9.77 min, 97% purity. $^1$H NMR (400 MHz, CDCl$_3$, δ): 6.98 (m, 3H), 6.67 (m, 1H), 3.87-3.35 (m, 212H), 3.19 (m, 2H), 2.60 (m, 6H), 2.44 (m, 8H).

BocHNO-α-amido-dPEG$_{12}$-Tris(-dPEG$_{12}$-acid)$_3$:

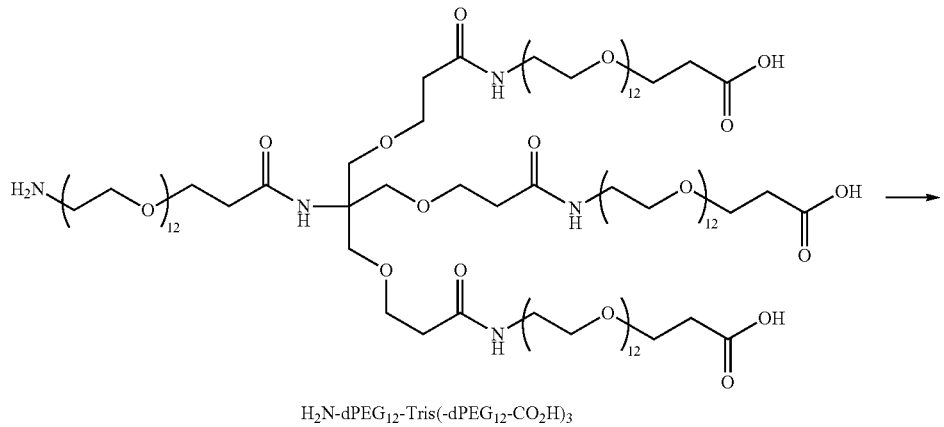

H$_2$N-dPEG$_{12}$-Tris(-dPEG$_{12}$-CO$_2$H)$_3$

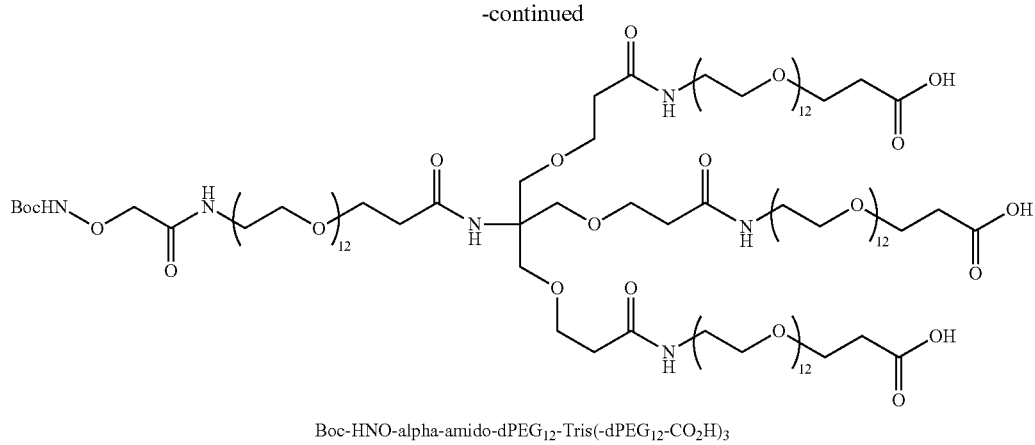

Boc-HNO-alpha-amido-dPEG$_{12}$-Tris(-dPEG$_{12}$-CO$_2$H)$_3$

A 25 mL RBF fitted with addition funnel, nitrogen blanket, and cooling bath was set up for this reaction. The RBF was charged with amino-12-tris(amido-12-acid)$_3$ (1.341 g, 0.490 mmol), water (1.508 ml), triethylamine (0.276 ml, 1.960 mmol), and acetonitrile (3.77 ml). The mixture was cooled to 0° C. in an ice bath. N-Boc-alpha(aminoxyacyl)Bt (0.172 g, 0.588 mmol) was dissolved in acetonitrile (4.52 ml) and added dropwise via addition funnel. The reaction was stirred at 10 C for 4 h. TLC (85:15 DCM: 3/1 MeOH/HCOOH) indicated complete consumption of sm and a single major product. HPLC (Amines4020 and Acid60 methods) indicated a single major product. The solvent was removed under reduced pressure and the residue was taken up in water (30 mL). The aq layer was washed with EtOAc (2×10 mL). The pH was adjusted to 3 by the slow addition of 20% conc HCl and the aq layer was washed again with EtOAc (2×10 mL). The aq layer was extracted with DCM (3×30 mL). TLC indicated no product and only Bt was washed out with the EtOAc, and while some I$_2$ positive material in the aq layer, but it did not appear to be product based on the Rf value. The organic extracts were combined, washed with brine, dried over Na$_2$SO$_4$, filtered over celite, and concentrated under reduced pressure to give 799 mg (56%.) of a pale yellow oil. HPLC (Amines4020 method): RT 11.97 min, 97% purity. $^1$H NMR (400 MHz, CDCl$_3$, δ): 6.98 (m, 3H), 6.67 (m, 1H), 3.87-3.35 (m, 212H), 3.19 (m, 2H), 2.60 (m, 6H), 2.44 (m, 8H), 1.488 (s, 9H).

PhthN-dPEG$_{12}$-Tris(-dPEG$_{12}$-TFP)$_3$:

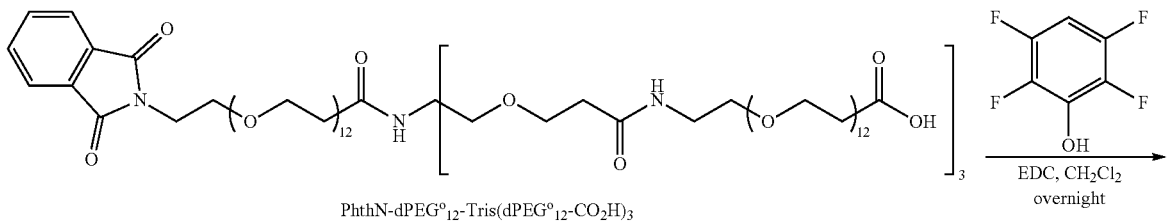

PhthN-dPEG°$_{12}$-Tris(dPEG°$_{12}$-CO$_2$H)$_3$

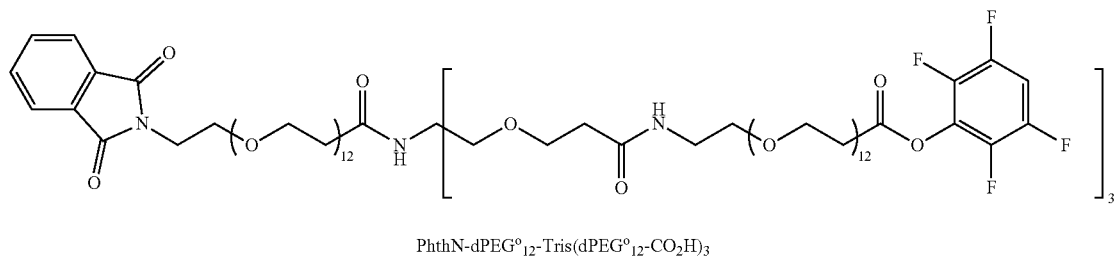

PhthN-dPEG°$_{12}$-Tris(dPEG°$_{12}$-CO$_2$H)$_3$

A solution of Phth-dPEG$_{12}$-tris-(dPEG$_{12}$-CO$_2$H)$_3$ acid (2.14 g, 0.747 mmol) in 12 mL of anhydrous dichloromethane was placed in a 50 mL three-neck round bottom flask equipped with: a magnetic stirrer, thermocouple, nitrogen balloon, and a cooling ice bath. In a separate 25 mL one-neck round bottom flask equipped with a magnetic stirrer, thermocouple, and cooling ice bath a slurry of EDC (0.805 g, 4.2 mmol) in 15 mL of anhydrous dichloromethane was prepared under a nitrogen atmosphere. A solution of TFP (0.812 g, 4.89 mmol) in 6 mL of anhydrous dichloromethane was added to the EDC slurry via syringe at 5° C. The resulting clear solution stirred for an additional 5 min at 5° C. and then was added dropwise via syringe to the solution of the above acid in CH$_2$Cl$_2$ at 0° C. The reaction mixture stirred at this temperature for an additional 20 min. The cooling bath was then removed, and the reaction was allowed to warm to ambient temperature and stirred overnight. The reaction was monitored by TLC ($R_f$=0.07, tailing from the origin for Phth-dPEG12-tris(dPEG12-$CO_2$)$_3$, and $R_f$=0.43 for product, in 90% $CH_2Cl_{2-10}$% MeOH) or by HPLC. After the starting tris-acid disappeared, the reaction was quenched with cold with 1:1 diluted $NaHCO_3$ (50 mL) containing 10 mL of brine, and extracted with dichloromethane (3×50 mL). The organic phase was washed with cold water (80 mL) containing 10 mL of brine, dried over anhydrous $Na_2SO_4$ and concentrated under reduced pressure to give 3.04 g of clear yellowish oil. This crude material was purified by column chromatography on silica gel. Gradient elution with a mixture of dichloromethane-isopropyl alcohol from 0 to 30% IPA gives 1.85 g of product as yellowish oil. It further was re-dissolved in 15 mL of EtOAc, slowly diluted with MTBE-hexane=2:1 (30 mL) and precipitated from this solution on 4 g of celite with 50 mL of hexane. Resulting slurry stirred for 20 min, filtered, celite cake washed with MTBE-hexane-1:1 (3×25 mL) and filtrates were discarded. The product was washed from celite with dichloromethane (3×80 mL), and this filtrate was concentrated under reduced pressure to constant weight to give 1.76 g (71% yield) of target TFP-ester. This material slowly crystallizes to off-white solid. HPLC (3045FF acid method): RT 38.72 min, purity 96.3%. $^1$H NMR (400 MHz, $CDCl_3$, δ): 7.84 (m, 2H, phthimide), and 7/2 (m, 2H, phthalimide), 7.0 (m, 3H, TFP), 6.78 (t, 3H, NH), 6.56 (s, 1H, NH), 3.91-3.85 (m, 8H, $CH_2O$), 3.81-3.52 (m, 206H, $CH_2O$), 3.45-3.39 (m, 7H, $CH_2O$), 2.95 (t, 6H, $CH_2CO$), 2.48-2.38 (m, 8H, $CH_2CO$).

PhthN-dPEG$_{12}$-Tris(-dPEG$_{24}$-TBE)$_3$:

The flask was charged with $H_2$N-24-TBE (22.91 g, 19.06 mmol) and DCM (52.9 ml). 2,6-Lutidine (2.466 ml, 21.17 mmol) was added via syringe and the mixture was cooled to 0° C. PhthN-12-tris(TFP)3 (8 g, 5.29 mmol) was dissolved in DCM (52.9 ml) and placed in the addition funnel. The tris TFP ester was added dropwise, the ice bath was removed, and the reaction was allowed to stir at room temperature overnight. TLC (85:15 DCM:EtOH) indicated complete conversion. HPLC (Amines3045FF method) indicated a single major product with a small leading impurity. HPLC (Acids5545FF method) also indicated the desired product with the small leading impurity. The solvent was removed under reduced pressure and the residue was taken up in 250 mL $H_2O$ and washed with 2/1 EtOAc/hexanes (75 mL). This resulted in an emulsion, so 150 mL 10% HCl was added. The organic layer was removed and the acidic aq layer was washed again with 2/1 EtOAc/hexanes (75 mL), $Et_2O$ (75 mL), and hexanes (75 mL). TLC analysis indicated the organic washes extracted essentially all of the TFP and no product. The aq layer was saturated with salt and extracted with DCM (4×100 mL). TLC analysis indicated a UV active spot remained in the aq layer, but it appeared all the product had been extracted into the DCM. The organics were combined, washed with 10% HCl (50 mL), brine (50 mL), dried over $Na_2SO_4$, filtered over celite, and concentrated under reduced pressure to give 36.9 g of viscous yellow oil. TLC analysis indicated product and starting amine. It appeared that a solvent system of 2/1 DCM/EtOAc and MeOH would be appropriate for separation. The residue was then preabsorbed on to 50 g of SiO2 and purified on the Rf using a 330 g column and 2/1 DCM/EtOAc (A) and MeOH (B). The

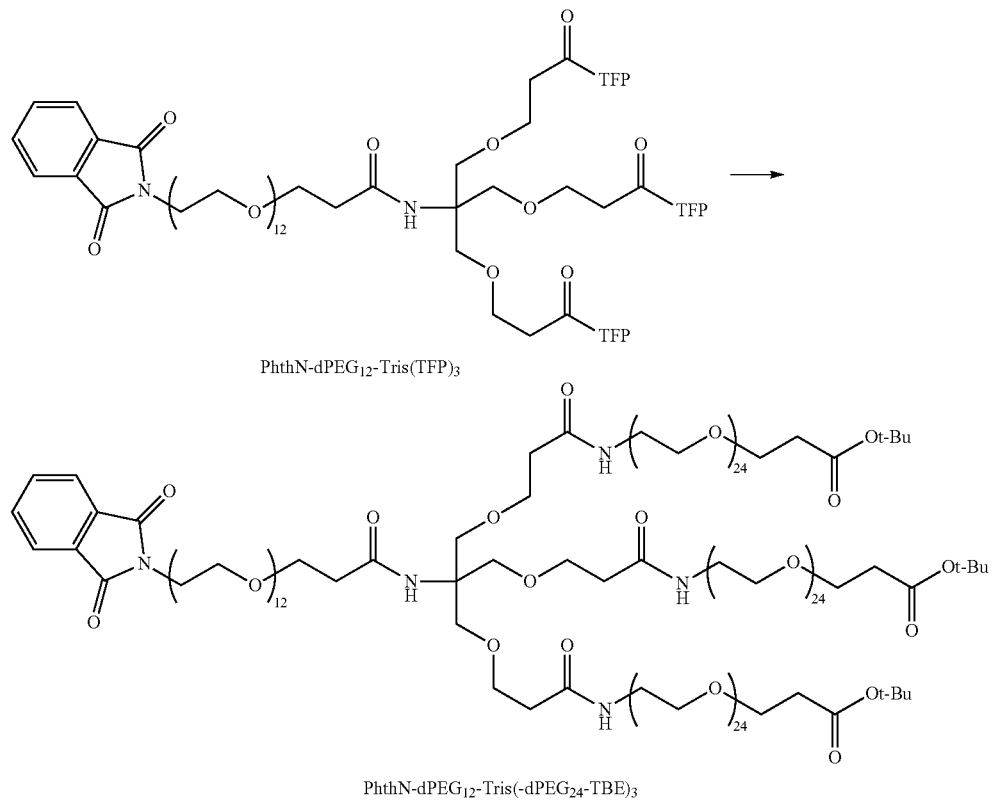

A 250 mL 3-neck RBF fitted with addition funnel, nitrogen blanket, and cooling bath was set up for this reaction.

column was primed with 15% B for 1CV and 0% B for 2CV. The SLSC was inserted and a gradient was run at 2% B g for 1CV and then ramping to 12% B over 10CV. Fractions 59-114 were pooled and concentrated, taken up in DCM, dried over Na2SO4, and filtered over celite. Concentration and trituration with Et2O and hexanes provided 13.17 g (54%) of an off-white powdery solid. HPLC (Acids5545FFmethod): RT 37.03 min, purity 100%. HPLC (Amines3045FFmethod): RT 36.88 min, purity 99.7%. $^1$H NMR (400 MHz, CDCl$_3$, δ): 7.81 (m, 2H), 7.69 (m, 2H), 6.73 (m, 3H), 6.52 (s, 1H), 3.88-3.29 (m, 356H), 2.49-2.32 (m, 14H), 1.41 (s, 27H).

H$_2$N-dPEG$_{12}$-Tris(-dPEG$_{24}$-TBE)$_3$:

was filtered off over celite and the solvent was removed under reduced pressure to give 5.987 g of a pale yellow solid. The residue was then preabsorbed on to 15 g of SiO$_2$ and purified on an Isco Rf using an 80 g column, DCM (A), and 9/1 MeOH:NH4OH (B). The column was primed with 15% B for 1CV and 0% B for 2CV. The SLSC was inserted and a gradient was run at 0% B g for 1CV and then ramping to 15% B over 4CV and holding at 15% B. TLC analysis indicated fractions 14-27 were pure product so the fractions were concentrated, taken up in DCM (200 mL), washed with

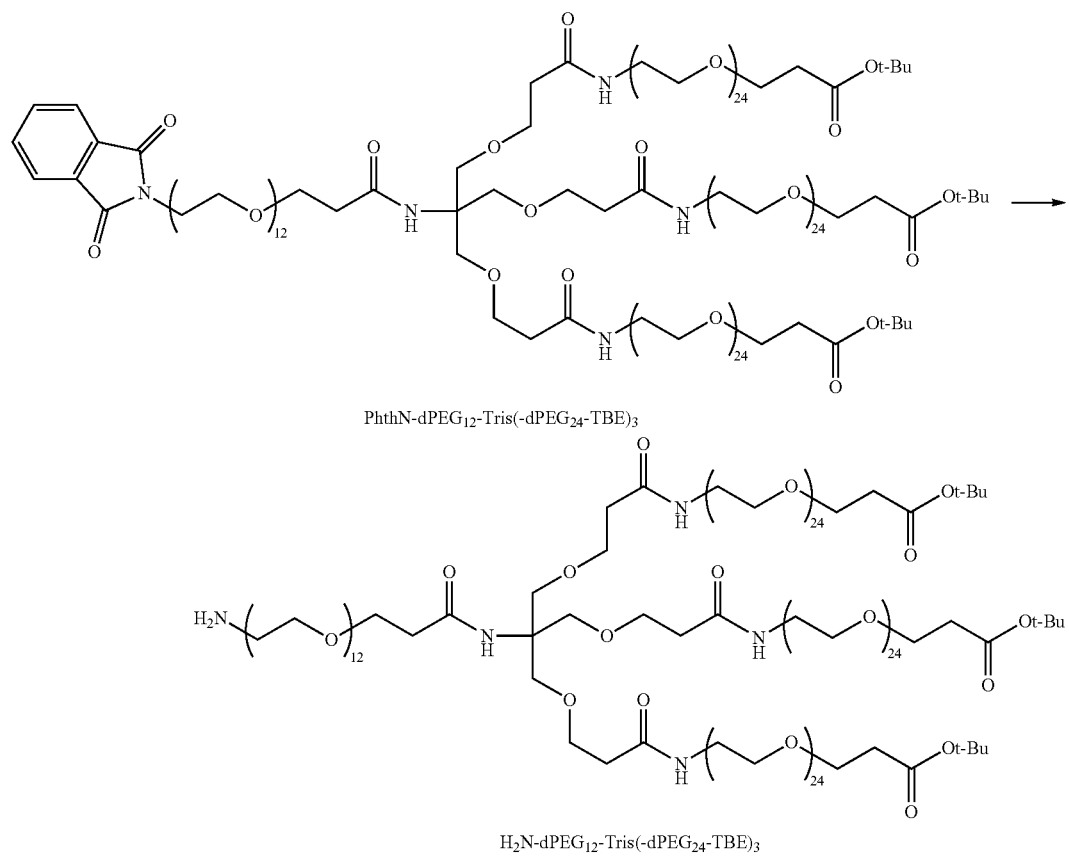

PhthN-dPEG$_{12}$-Tris(-dPEG$_{24}$-TBE)$_3$

H$_2$N-dPEG$_{12}$-Tris(-dPEG$_{24}$-TBE)$_3$

A 100 mL RBF fitted with nitrogen blanket was set up for this reaction. The flask was charged with PhthN-12-tris(24-TBE)3 (6 g, 1.299 mmol) and Dichloromethane (12.99 ml). Hydrazine monohydrate (0.630 ml, 12.99 mmol) was added via syringe and the reaction was allowed to stir at room temp overnight. TLC (90:10 DCM:MeOH) indicated complete consumption of sm. TLC (90:10, 85:15, and 80:20 DCM 9/1 MeOH/NH$_4$OH) indicated a single major product with a minor ninhydrin-positive spot near baseline. The precipitate water (25 mL) brine (2×25 mL), dried over Na$_2$SO$_4$, filtered over celite, and concentrated under reduced pressure to give 5.225 g (90%) of a sticky off white solid. HPLC (Amines3045FFmethod): RT 37.13 min, purity 100%. $^1$H NMR (400 MHz, CDCl$_3$, δ): 6.77 (m, 3H), 6.54 (s, 1H), 3.86-3.30 (m, 354H), 2.86 (t, 2H), 2.51-2.28 (m, 14H), 1.41 (s, 27H).

MAL-dPEG$_{12}$-Tris(-dPEG$_{24}$-TBE)$_3$:

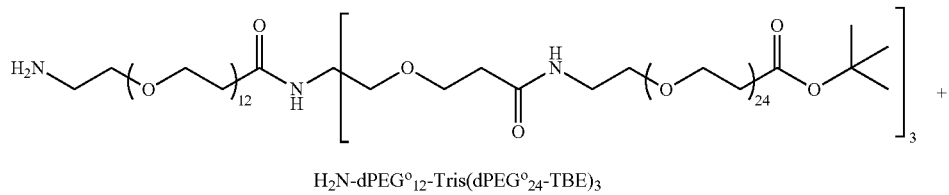

H$_2$N-dPEG°$_{12}$-Tris(dPEG°$_{24}$-TBE)$_3$

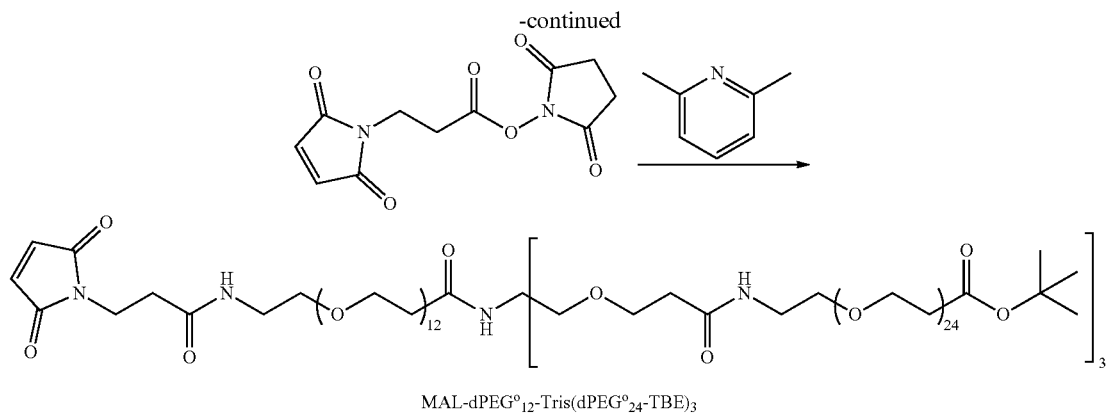

MAL-dPEGº₁₂-Tris(dPEGº₂₄-TBE)₃

In scintillation vial is added the MPS (1.435 g, 5.39 mmol) and lutidene (0.668 g, 6.24 mmol) with 10 ml dry DCM. This is cooled to ice temp and then the amine (20 g, 4.45 mmol) is added incrementally. The rxn is washed with sat bicarb, then 10% HCl then sat brine, followed by sod sulfate, filtered and dried, azeo 2× with ACN. HPLC (Acids60 method): RT 15.43 min, purity 96%.
MAL-dPEG₁₂-Tris(-dPEG₂₄-CO₂H)₃:

rxn is diluted w/DCM and then washed 1× with water then 5×1% brine, sat brine, then sod sulfate, rotovapped with oil pump to give 18 g of a brown paste. The material is dissolve din acetonitrile and dripped into cold hexanes to give 14 g (78%) of a cream colored waxy solid. HPLC (acid6015 method): RT 8.03 min, purity 100%. ¹H NMR (400 MHz,

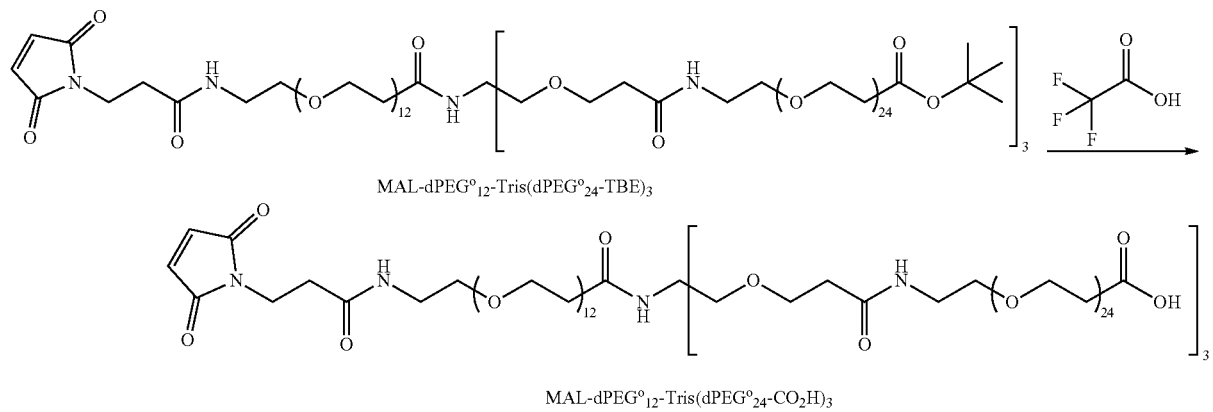

MAL-dPEGº₁₂-Tris(dPEGº₂₄-TBE)₃

MAL-dPEGº₁₂-Tris(dPEGº₂₄-CO₂H)₃

The t-butyl ester (17.9 g, 3.86 mmol) is cooled in an ice bath with dry DCM and then the TFA (30 mL) is added neat. The deprotection is run for 12 hr at rt with mag stirring with a drying tube attached. HPLC confirms deprotection. The CDCl₃, δ): 6.85 (br t, 3H), 6.72 (s, 2H), 6.61 (br, 1H), 6.53 (br, 1H), 3.92-3.36 (m, 363H), 2.61 (t, 6H), 2.53 (t, 2H), 2.50-2.41 (overlapping t, 8H).

PthN-dPEG₁₂-Tris[-dPEG₁₂-Tris(-dPEG₁₁-m)₃]₃:

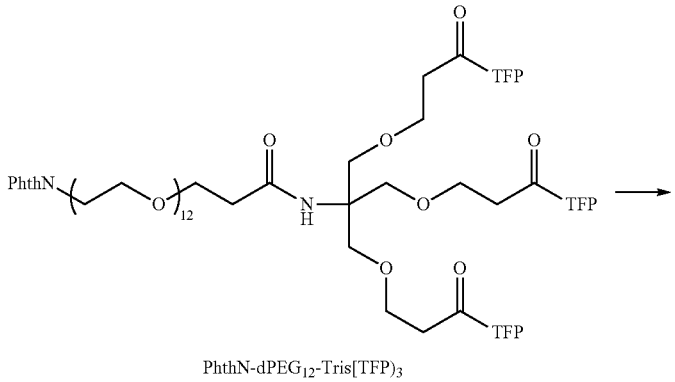

PhthN-dPEG₁₂-Tris[TFP]₃

-continued

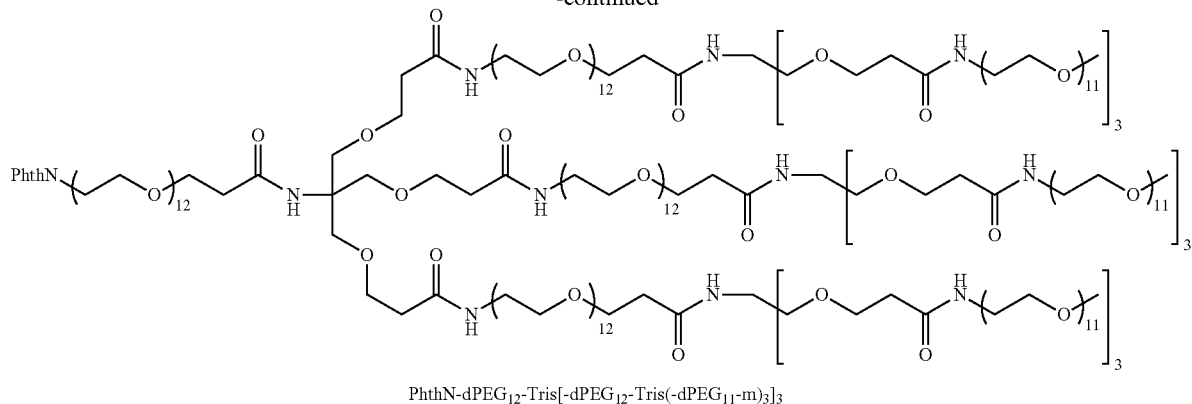

PhthN-dPEG$_{12}$-Tris[-dPEG$_{12}$-Tris(-dPEG$_{11}$-m)$_3$]$_3$

The triNHS ester (5 g, 3.68 mmol) is added to the amine (51 g, 20.98 mmol) in dry DCM. The reaction is allowed to stir for 2 days. The volume is tripled by adding DCM and it is washed with two portions of 5% HCl to remove excess amine and then rotovapped The viscous liquid is dissolved in 300 ml water and extracted with DCM. Concentration provided 11 g (38%) of a yellowish sticky solid. HPLC (Acids4020method): RT 18.82 min, purity 69%.
H$_2$N-dPEG$_{12}$-Tris[-dPEG$_{12}$-Tris(-dPEG$_{11}$-m)$_3$]$_3$:

A solution of the phthalimide (8.2 g, 0.99 mmol) in anhydrous dichloromethane was treated with hydrazine hydrate (0.7 mL) and was stirred overnight. Solid is filtered off through fluted filter paper and washed with DCM then DCM is removed and oil is dried twice with ACN to give 6.2 g (77%). HPLC (amines4020 method): RT 15.78 min, purity 92%
Mal-dPEG$_{12}$-Tris[-dPEG$_{12}$-Tris(-dPEG$_{11}$-m)$_3$]$_3$:

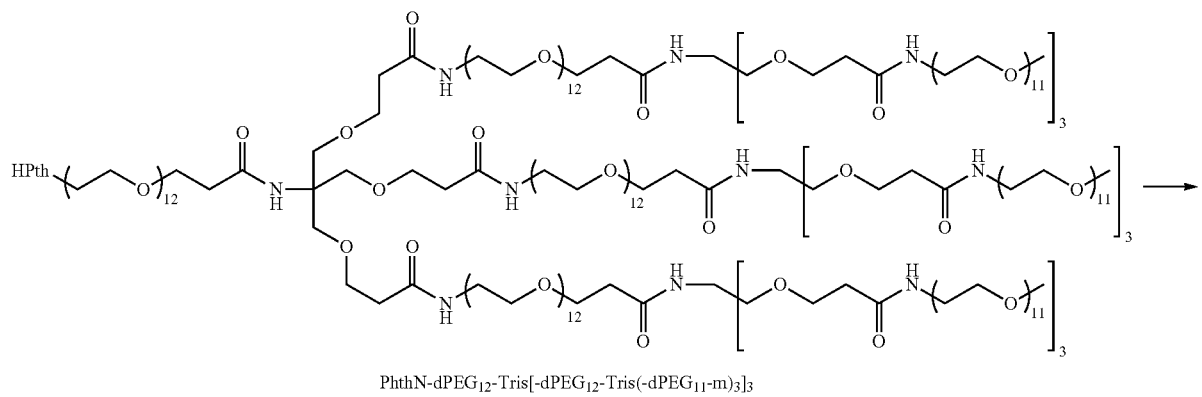

PhthN-dPEG$_{12}$-Tris[-dPEG$_{12}$-Tris(-dPEG$_{11}$-m)$_3$]$_3$

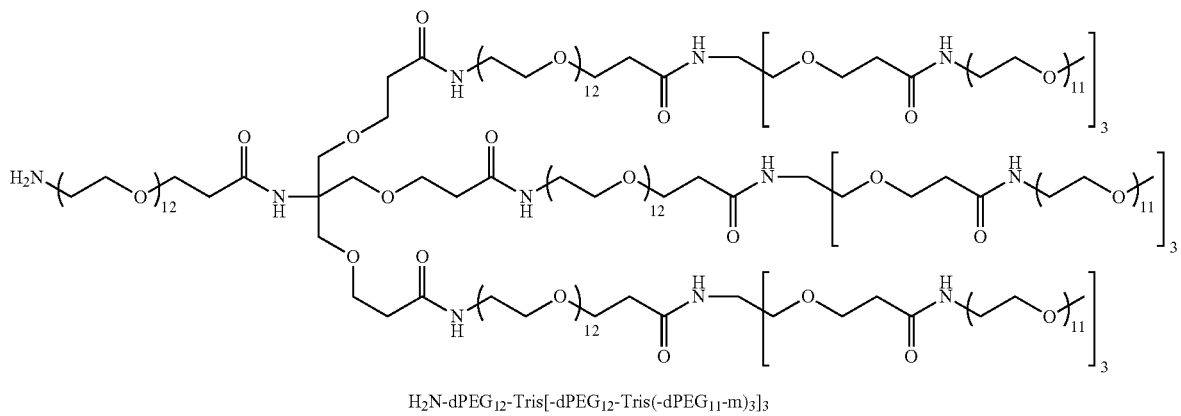

H$_2$N-dPEG$_{12}$-Tris[-dPEG$_{12}$-Tris(-dPEG$_{11}$-m)$_3$]$_3$

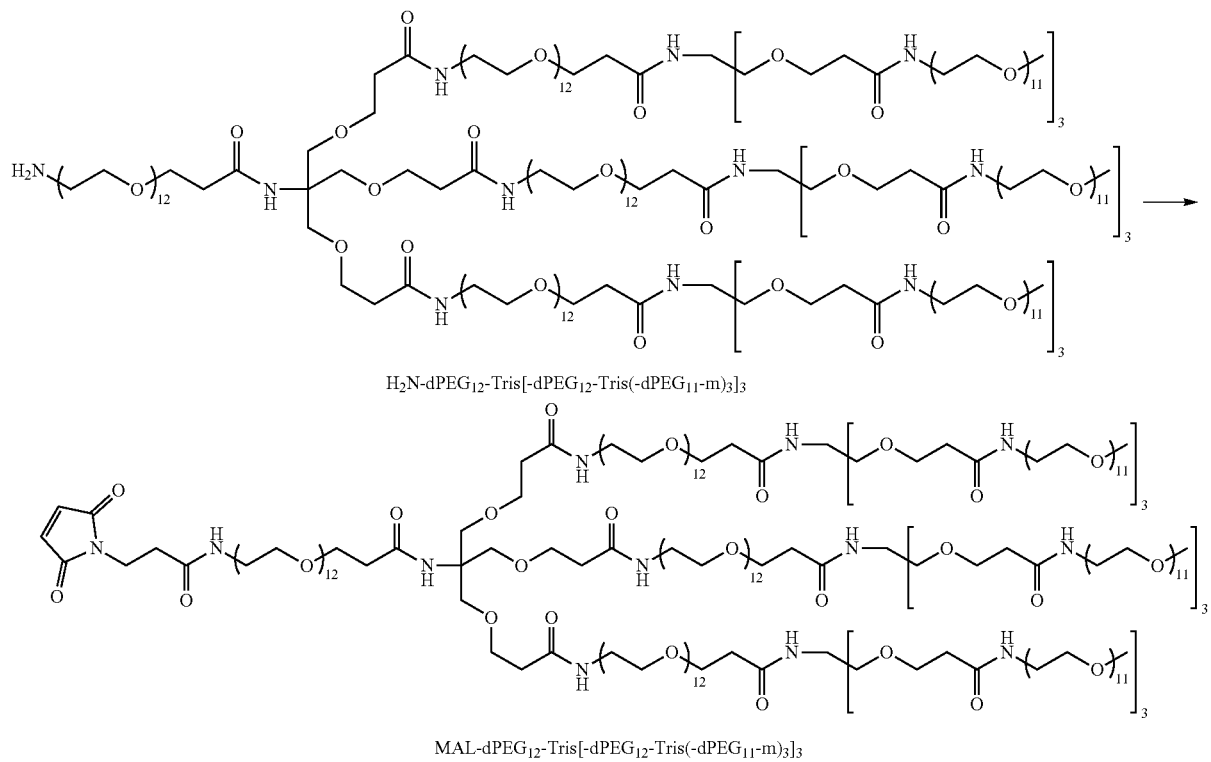

H₂N-dPEG₁₂-Tris[-dPEG₁₂-Tris(-dPEG₁₁-m)₃]₃

MAL-dPEG₁₂-Tris[-dPEG₁₂-Tris(-dPEG₁₁-m)₃]₃

A 25 mL 3-neck RBF fitted with nitrogen blanket, cooling bath, and addition funnel was set up for this reaction. The flask was charged with MPS (0.156 g, 0.587 mmol) and DCM (8.16 ml) and cooled to 0 C in an ice/salt water bath. Amino-12-tris(amido-12-tris(amido-m-11)₃)₃ (4 g, 0.489 mmol) was dissolved in DCM (8.16 ml) and 2,6-lutidine (0.074 ml, 0.636 mmol) was added via pipette. The amine mixture was placed in the addition funnel and added dropwise to the flask and the reaction was allowed to warm to room temp and stirred for 2 h. TLC (85:15 and 80:20 DCM:MeOH, visualized with I2 and ninhydrin) seemed to indicate consumption of sm. HPLC (Amines4020 method) also indicated consumption of sm and formation of a major product, but both had very close retention times. The reaction was diluted with DCM (100 mL), washed with 10% HCl (2×10 mL), washed with sat aq NaHCO₃ (2×10 mL), washed with brine (20 mL), dried over Na₂SO₄, filtered over celite, and concentrated under reduced pressure to provide 4.48 g of a clear yellow viscous oil. HPLC (Amines4020 method) indicated a major product with 88% purity. The residue was purified on a Biotage Isolera with a 50 g column using DCM (A) and MeOH (B). The column was primed with 1CV 5% B then with 2CV 0% B. The sample was preabsorbed on to 5 g SiO2 and a gradient was run at 0% B for 1CV then ramping to 20% B over 12CV and holding at 20% B. The fractions were run on a TLC plate and 36-60 were pooled and concentrated to give 1.905 g (47%) of a clear pale yellow oil that slowly solidified to an off-white solid. TLC (85:15 DCM:MeOH) indicated a single spot. HPLC (Acids545FF method): RT 19.36 min, purity 90%. ¹H NMR (400 MHz, CDCl₃, δ): 6.80-6.69 (m, 15H), 6.55 (m, 4H), 3.86-3.39 (m, 644H), 3.37 (s, 27H), 2.54-2.37 (m, 36H).

31: PthN-dPEG₁₂-Tris[-dPEG₁₂-Tris(TBE)₃]₃:

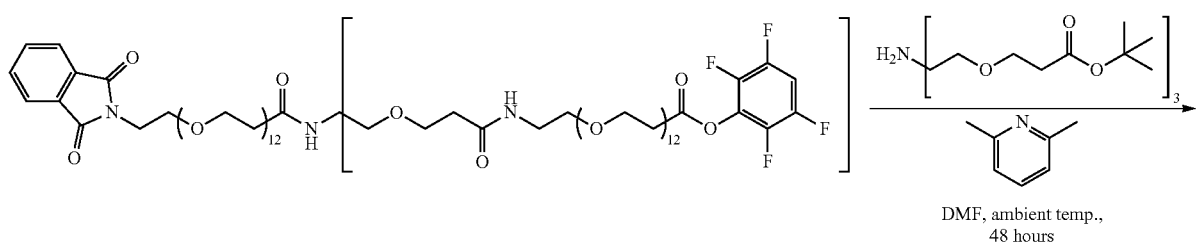

DMF, ambient temp., 48 hours

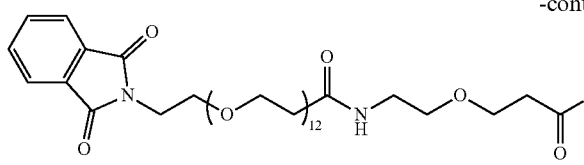
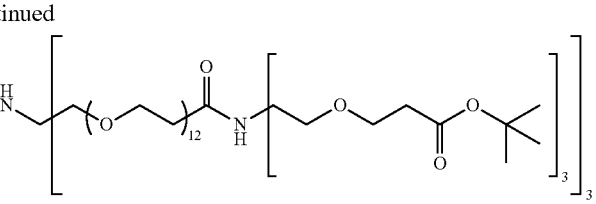

A solution of NH2-tris(CH2OCH2CH2-TBE)3 (0.254 g, 0.502 mmol) in 3 mL of anhydrous DMF was placed in a 25 mL one-neck round bottom flask equipped with a magnetic stirrer, thermocouple, balloon filled with nitrogen, and ice cooling bath. Lutidine (58 mg, 0.541 mmol) was added to this solution, and the resulting mixture was cooled to 10° C. A solution of Phth-dPEG12-Tris(NH-dPEG12-TFP)3 ester (0.268 g, 0.081 mmol) in 2 mL of anhydrous DMF was added dropwise via syringe to the reaction mixture within 5 min, and the reaction was allowed to warm to ambient temperature and stirred 48 hrs. Due to identical Rf-values for TFP-ester and product, the stepwise replacement of the TFP-groups was monitored by HPLC until all TFP-groups were replaced by the amine moiety (RT's: TFP-ester=38.7 min, for mono-substituted 43.1 min, di-substituted 43.14 min, and for fully tri-substituted 44.5 min). After complete conversion, the reaction was quenched with cold 10% HCl (2×30 mL), the organic materials were extracted with CH2Cl2 (5×25 mL) and combined extracts were washed with cold saturated sodium bicarbonate solution (2×30 mL). The organic phase was separated, dried over anhydrous sodium sulfate and concentrated under reduced pressure to give 0.56 g of colorless oil.

This crude material was purified by column chromatography on silica gel by gradient elution using MeOH—CH2Cl2 from 0 to 15% MeOH. Pure fractions were concentrated under reduced pressure resulting in 0.295 g (84% yield) of target compound as glassy looking material.

HPLC (3045FF acid method): RT 44.41 min, purity 100%.

1H NMR (400 MHz, CDCl3, δ): 7.86-7.82 (m, 2H, phthimide), and 7.74-7.69 (m, 2H, phthalimide), 6.94 (m, 3H, NH), 6.61 (s, 1H, NH), 6.30 (s, 3H, NH), 0.3.92-3.86 (m, 2H, CH2N), 3.75-3.53 (m, 242H, CH2O), 3.45-3.38 (m, 6H, CH2O), 2.48-3.38 (m, 36H, CH2CO), 2.48-2.38 (m, 14H, CH2CO), 1.44 (s, 81H, CH3).

32: PthN-dPEG$_{12}$-Tris[-dPEG$_{12}$-Tris(CO$_2$H)$_3$]$_3$:

A mixture of Phth-12-Tris(12-tris-TBE)3 (0.253 g, 0.058 mmol) and formic acid (2.51 g, 54.5 mmol) was placed in a 25 mL one-neck round bottom flask equipped with a magnetic stirrer, heating mantle, thermocouple, and nitrogen balloon. The temperature was maintained at 35° C., and the resulting mixture stirred overnight. The reaction was monitored by TLC (by disappearing of starting Phth-12-tris-12-trisTBE-ester with Rf=0.4 in CH2Cl2-MeOH=9/1), and after completion the excess of formic acid was removed on rotavap at 35° C. to give a viscous yellow oil. This material was dissolved in 50 mL of CH2Cl2 and washed with a mixture of water and brine (3/1, 2×30 mL). The product was extracted with dichloromethane (3×30 mL), and the combined organic phases were dried over anhydrous Na2SO4. Solvent was removed on rotavap to yield 0.214 g (96% yield) of "nona-acid" as white semisolid material and 95% purity by HPLC. This crude product was flashed on silica gel with gradient elution using MeOH—CH2Cl2 from 0 to 25% methanol, concentrated on rotavap and re-dissolved in 20 mL of dichloromethane. The obtained cloudy solution was filtered via a 0.45 PTFE membrane filter in order to remove silica gel, and concentrated on rotavap. The residue was dried further under high vacuum to give 0.168 g (75% yield) of product as colorless viscous oil.

HPLC (3045FF acid method): RT 26.5 min, purity 96%.

1H NMR (400 MHz, CDCl$_3$, δ): $^1$H NMR (400 MHz, CDCl$_3$, δ): 8.40-7.40 (very broad, 8H, CO$_2$H), 7.88-7.80 (m, 2H, phthimide), and 7.76-7.68 (m, 2H, phthalimide), 7.06 (m, 3H, NH), 6.69 (s, 1H, NH), 6.56 (s, 3H, NH), 3.88 (m, 2H, CH$_2$N), 3.84-3.33 (m, 246H, CH$_2$O), 2.60-2.48 (m, 18H, CH$_2$CO), 2.47-2.35 (m, 14H, CH$_2$CO).

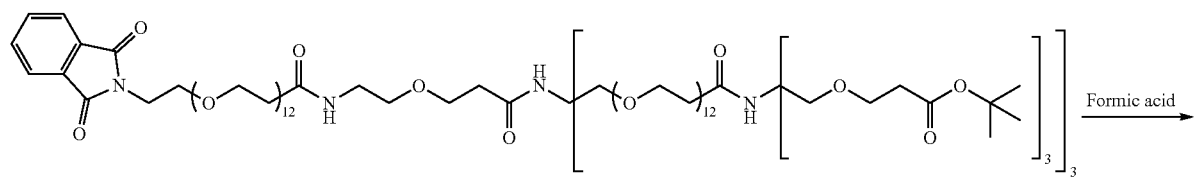

Formic acid →

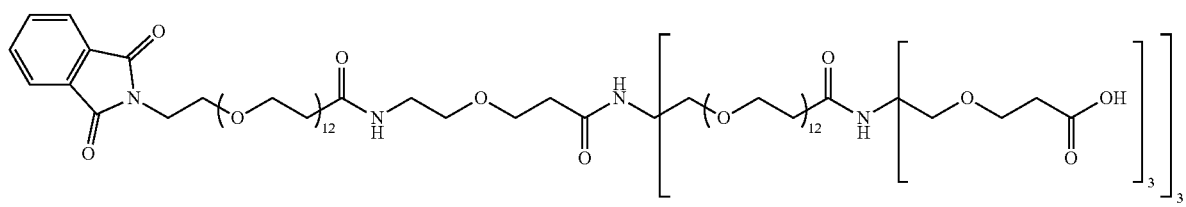

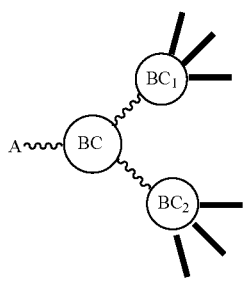

PhthN-dPEG$_{12}$-Tyr(-dPEG$_4$-amido-dPEG$_{12}$-Tris(-dPEG$_{24}$-TBE)$_3$)-OBn:

product. The reaction was diluted with DCM, washed with 10% HCl (3×15 mL), washed with sat aq NaHCO$_3$ (3×15 mL), washed with brine, dried over Na$_2$SO$_4$, filtered over celite, and concentrated under reduced pressure to give 5.19 g of an off-white solid. TLC (90:10 DCM:MeO) indicated a single major product with some baseline impurities. HPLC (Acid5545FF method) indicated one major product and complete consumption of the acid. HPLC (Amines3045FF method) indicated one major and one minor product along with complete consumption of the amine. The residue was preabsorbed onto 12 g of SiO$_2$ and purified on an Ism Rf using an 80 g RediSep, DCM (A), and MeOH (B). The column was primed with 10% B for 2CV and 0% B for 2CV. The SLSC was, inserted and a gradient was run at 0% B for 1 CV and then ramping to 12% B over 12CV and holding at

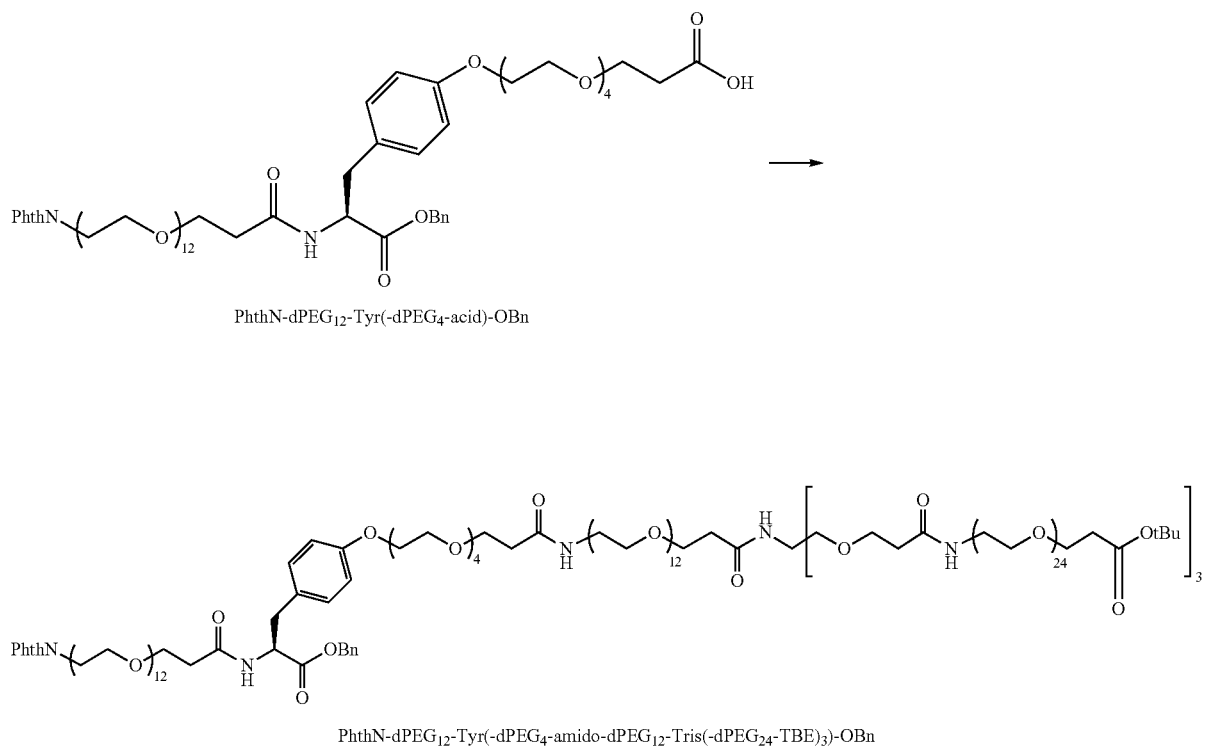

PhthN-dPEG$_{12}$-Tyr(-dPEG$_4$-acid)-OBn

PhthN-dPEG$_{12}$-Tyr(-dPEG$_4$-amido-dPEG$_{12}$-Tris(-dPEG$_{24}$-TBE)$_3$)-OBn A 25 mL RBF fitted with nitrogen blanket and cooling bath was charged with PhthN-12-Tyr(O-4-acid)-OBn (1 g, 0.800 mmol) and Dichloromethane (40.0 ml). N,N-Diisopropylethylamine (0.168 ml, 0.960 mmol) was added followed by HOBt hydrate (0.176 g, 1.041 mmol) and the mixture was cooled to 0° C. EDC (0.199 g, 1.041 mmol) was added and the reaction was stirred for 5 minutes. H2N-12-tris(24-TBE)3 (4.31 g, 0.960 mmol) (MG1-B1200-041) was added in a single portion and the reaction was warmed to room temp and stirred overnight. TLC (90:10 DCM:MeOH) indicated complete conversion of starting acid and some residual amine present. HPLC (Acid5545FF and Amines3045FF methods) also both indicated a single major 12% B for 5CV then increasing to 15% B. Analysis by TLC indicated 5-28 were a single spot so they were pooled, concentrated, triturated with Et2O/hexanes, and dried under high vac overnight to give 3.454 g (75%) of an off-white waxy solid. HPLC (Acids5545FF method): RT 29.85 min, purity 100%. HPLC (Amines3045FF method): RT 37.67 min, purity 100%. $^1$H NMR (400 MHz, CDCl$_3$, δ): 7.82 (m, 2H), 7.70 (m, 2H), 7.35 (m, 3H), 7.28 (m, 2H), 6.93 (dd, 2H), 6.85-6.61 (overlapping m, 7H), 6.55 (br, 1H), 5.11 (m, 2H), 4.83 (m, 1H), 4.09 (m, 2H), 4.00-3.27 (m, 422H), 3.01 (m, 2H), 2.54-2.30 (overlapping t, 23H, note residual water of hydration peak caused this to integrate higher than 18H), 1.42 (s, 27H).

PhthN-dPEG$_{12}$-Tyr(-dPEG$_4$-amido-dPEG$_{12}$-Tris(-dPEG$_{24}$-TBE)$_3$)-OH:

pressure to give 2.227 g (66%) of a pale yellow oil that solidified upon standing under high vac and after trituration

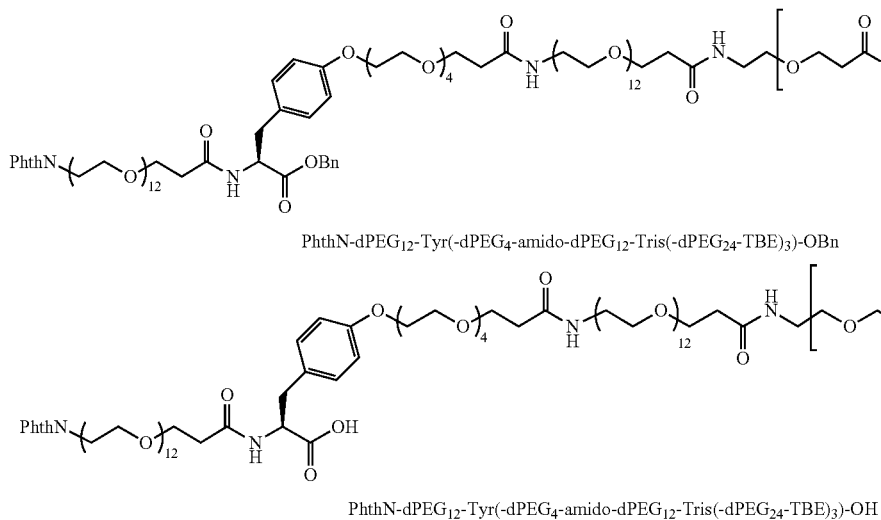

PhthN-dPEG$_{12}$-Tyr(-dPEG$_4$-amido-dPEG$_{12}$-Tris(-dPEG$_{24}$-TBE)$_3$)-OBn PhthN-dPEG$_{12}$-Tyr(-dPEG$_4$-amido-dPEG$_{12}$-Tris(-dPEG$_{24}$-TBE)$_3$)-OH A 100 mL RBF was charged with PhthN-12-Tyr[O-4+12-tris(24-TBE)3]-OBn (3.454 g, 0.604 mmol), THF (2.415 ml), and 2-Propanol (9.66 ml). Charcoal (10× the weight of Pd(OAc)$_2$, 67 mg) was added followed by Palladium(II) acetate (6.78 mg, 0.030 mmol). The mixture was placed under a balloon of Hydrogen (1.217 mg, 0.604 mmol) with vigorous stirring for 4 hours. TLC (90:10 DCM:MeOH) indicated complete conversion of sm to a single spot. HPLC (Acids5545FFmethod) also indicated complete conversion to a single major product. The reaction was filtered over celite, rinsed with DCM, and concentrated to give a dark brown oil. The oil was taken up in water (60 mL), washed with Et2O (10 mL), hexanes (10 mL), the aq layer was acidified with 6 mL 10% HCl, salt was added, and it was extracted with DCM (3×40 mL). TLC indicated most of the product had been extracted. The organic layer was dried over Na$_2$SO$_4$, filtered over celite, and concentrated under reduced with Et2O/hexanes. The material was used without further purification. TLC (90:10 DCM:MeOH) indicated a single spot. HPLC (Acids5545FF method): RT 27.67 min, purity 100%. $^1$H NMR (400 MHz, CDCl$_3$, δ): 7.79 (m, 2H), 7.67 (m, 2H), 7.04 (dd, 2H), 6.87-6.71 (overlapping m, 7H), 6.54 (br, 1H), 4.73 (m, 1H), 4.03 (m, 2H), 3.90-3.28 (m, 422H), 3.04 (m, 2H), 2.49-2.31 (overlapping t, 18H), 1.39 (s, 27H).

PhthN-dPEG$_{12}$-Tyr(-dPEG$_4$-Amido-dPEG$_{12}$-Tris(-dPEG$_{24}$-TBE)$_3$)-dPEG$_{12}$-Tris(-dPEG$_{24}$-m)$_3$:

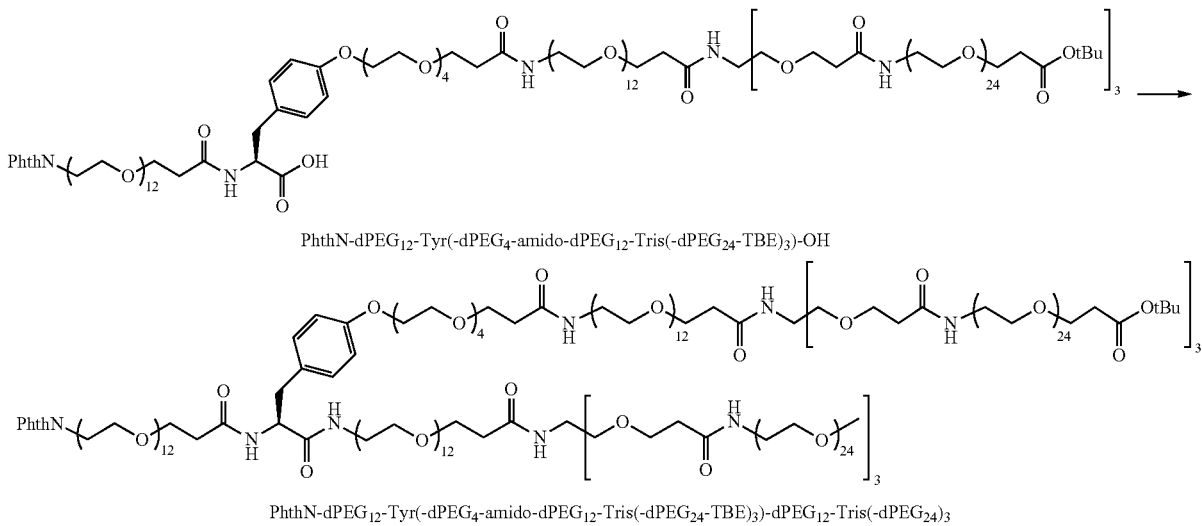

PhthN-dPEG$_{12}$-Tyr(-dPEG$_4$-amido-dPEG$_{12}$-Tris(-dPEG$_{24}$-TBE)$_3$)-OH PhthN-dPEG$_{12}$-Tyr(-dPEG$_4$-amido-dPEG$_{12}$-Tris(-dPEG$_{24}$-TBE)$_3$)-dPEG$_{12}$-Tris(-dPEG$_{24}$)$_3$ A 50 mL RBF fitted with nitrogen blanket was charged with PthN-12-Tyr(O-4+12-tris(24-TBE)3)-OH (1.83 g, 0.325 mmol) and DCM (6.50 ml). N,N-Diisopropylethylamine (0.074 ml, 0.422 mmol) was added via pipette followed by HOBt hydrate (0.066 g, 0.390 mmol). The mixture was cooled to 0° C., EDC (0.075 g, 0.390 mmol) was added, and the reaction was stirred for 5 minutes. H2N-12-tris(24- m)3 (1.617 g, 0.390 mmol) was added in a single portion and the reaction was warmed to room temp and stirred overnight. HPLC (Ac5545FF method) indicated consumption of and formation of a single major product, but the RTs were very close. Am3045FF method also indicated consumption of most of the amine and formation of a single major product. The reaction was diluted with DCM (100 mL), washed with 10% aq HCl (2×10 mL), washed with sat aq bicarb (2×10 mL), washed with brine (10 mL), dried over $Na_2SO_4$, filtered over celite, and concentrated under reduced pressure to give 3.149 g of a pale yellow solid. The residue was pre-absorbed onto 7 g of $SiO_2$ and purified on an Isco Rf using a 40 g RediSep, DCM (A), and MeOH (B). The column was primed with 10% B for 2CV and 0% B for 2CV. The SLSC was inserted and a gradient was run at 0% B for 1 CV and then ramping to 15% B over 15CV and holding at 15% B for 5CV. Analysis by TLC indicated 18-46 were a single spot so they were pooled, concentrated, triturated with $Et_2O$/hexanes, and dried under high vac overnight to give 2.358 g (74%) of an off-white waxy solid. HPLC (Acids545FF method): RT 28.12 min, purity 99.4%. HPLC (Amines3045FF method): RT 38.65 min, purity 99.9%.

$^1$H NMR (400 MHz, $CDCl_3$, δ): 7.75 (m, 2H), 7.63 (m, 2H), 7.02 (br d, 2H), 6.86 (br d, 2H), 6.81-6.60 (m, 9H), 6.50 (br, 3H), 4.48 (m, 1H), 3.99 (t, 2H), 3.84-3.18 (overlapping m and MeO s, 781H), 2.89 (m, 2H), 2.44-2.26 (overlapping t, 26H), 1.35 (s, 27H).

Multi "A" Branched dPEG Constructs

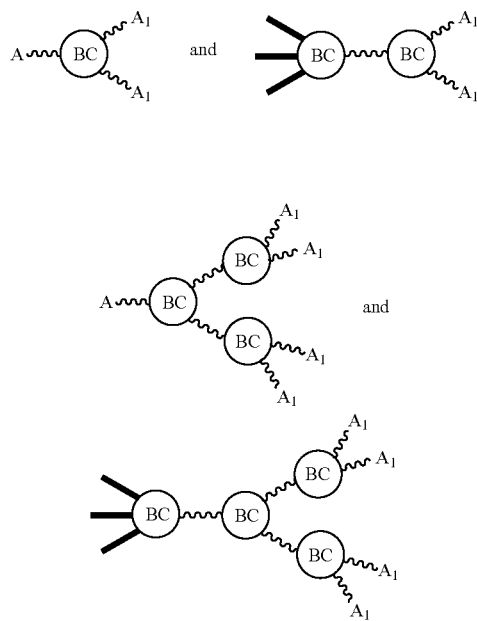

Z—NH-Lys(-Z)-dPEG$_4$-TBE:

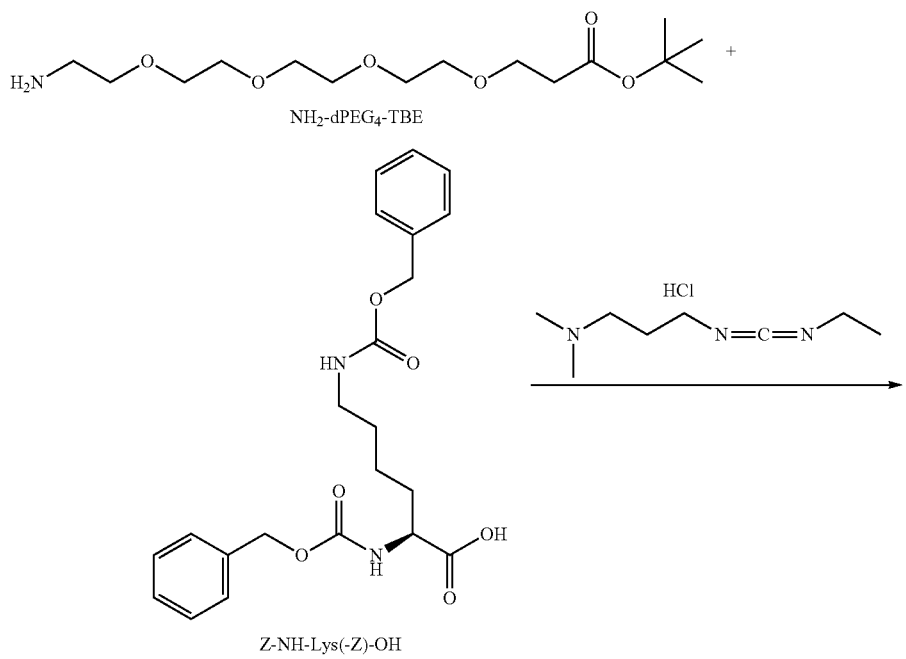

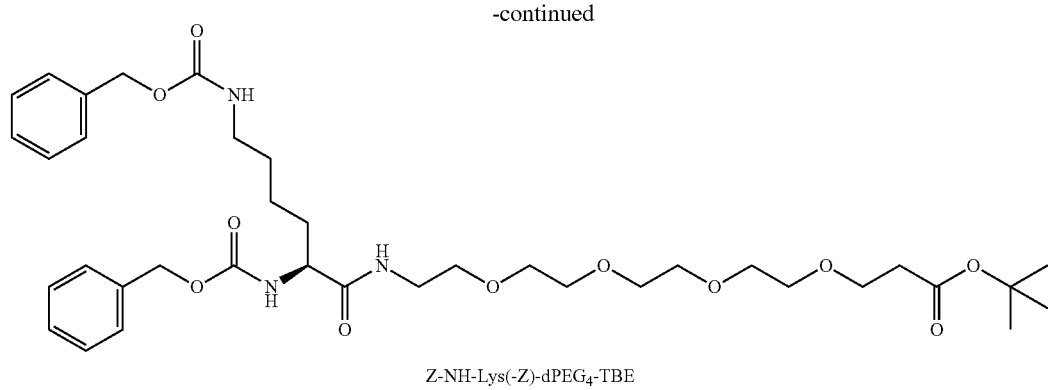

Z-NH-Lys(-Z)-dPEG₄-TBE

In the glove box under an atmosphere of dry nitrogen, a 3000 mL, 4-necked flask was charged with bis-CBZ-Lysine (200.0 g, 483 mmol), EDC (139 g, 724 mmol), and 1500 mL of 2:1 tetrahydrofuran:tert-butyl methyl ether. The flask was fitted with an immersion well; the remaining joints were stoppered, and the flask was transferred to the fume hood where one of the stoppers was replaced with an addition funnel connected by a gas inlet adapter to a bleed of dry nitrogen. The flask was placed in a salted ice-water bath, fitted with an overhead stirring apparatus, and stirred until 0° C. was attained. In the glove box under a dry nitrogen atmosphere, amino-dPEG®₄-TBE (163 g, 507 mmol) was dissolved in tetrahydrofuran (170 ml). The PN10221 was then poured into the addition funnel under a nitrogen shower and added slowly by drop, keeping the temperature as close to ° C. as possible. The reaction was allowed to continue overnight, warming slowly to ambient. The reaction appeared complete the next morning by TLC and RP-HPLC. Stirring of the reaction mixture was stopped, and the EDU was allowed to settle for several hours. The solution was then decanted from the EDU goo. The reaction solvent was removed by rotary evaporation under reduced pressure at 45° C. The residue was then dissolved in dichloromethane to a final volume of 1400 mL and washed once with 250 mL with 10% aqueous HCl, then once with 400 mL of 5% brine. The DCM was removed by rotary evaporation at 35° C., and the residue was dried by rotary evaporation at 45° C. under high vacuum for about 0.1 hour. Yield: 330 gms (95.4%) HPLC (AMINES3045FF METHOD): 96.2% purity by ELSD. TLC: Ethyl Acetate:Methanol 8:2. Major spot at Rf=0.69 with both UV quench at 254 nm and iodine-positive reaction. One minor UV quenching spot (no iodine reaction) near solvent front. No ninhydrin-positive spot. NMR: (400 MHz, CDCl₃, δ): 7.322 (m, 11H, 2 CBZ rings & NH); 6.737 (s, 1H, amide); 5.762 (s, 1H, amide); 5.084 (m, 4H, 2x CH₂O from CBZ); 4.153 (q, 1H, CHN on lysine); 3.526 (t, 2H, CH₂ β to N on lysine sidechain); 3.425 (t, 2H, CH₂ β to N on dPEG®); 3.164 (t, 2H, CH₂N on PEG); 2.478 (t, 2H, CH₂CO on PEG); 1.467 (m, 15H, lysine side chain alkyl methylene groups plus t-butyl ester). Quantitative NMR purity=96.8%

H₂N-Lys(H₂N)-dPEG₄-TBE

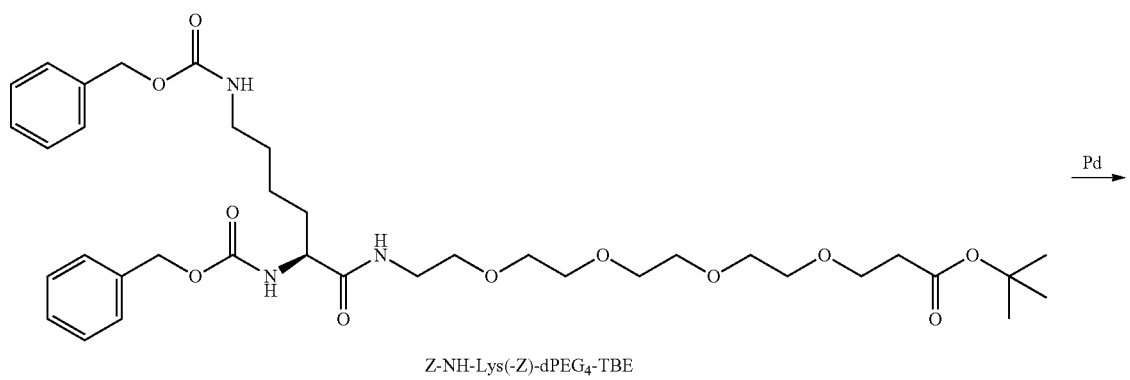

Z-NH-Lys(-Z)-dPEG₄-TBE

-continued

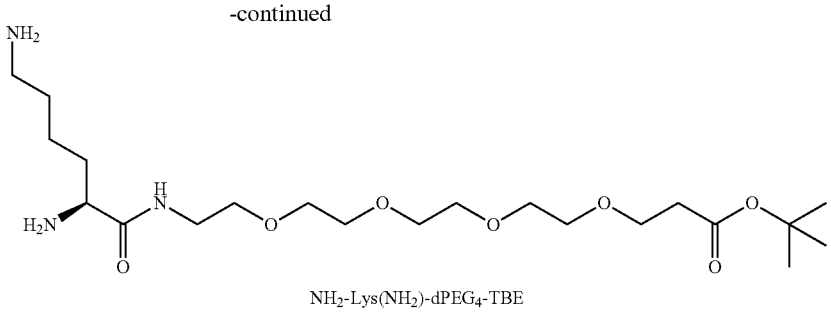

NH₂-Lys(NH₂)-dPEG₄-TBE

All solvents were degassed with nitrogen for at least 20 minutes and either used immediately or sealed in a flask for later use. In the glove box under an atmosphere of dry nitrogen, to a 2000 mL, 4-necked RB flask fitted with an immersion well and PTFE stoppers was added bis-CBZ-Lysine-dPEG®₄-TBE (328 g, 457 mmol) dissolved in Methanol (700 ml) and Palladium 10% on carbon (37.7 g, 354 mmol). The palladium residue left on the plastic funnel was rinsed into the flask using small portions of degassed methanol. The flask was transferred to the fume hood where it was placed in a heating mantle and fitted with a Friedrich condenser, overhead stirring apparatus, and glass tube passing through a septa stopper, which tube could be connected to a gas line. The tube was connected to hydrogen gas and the reaction was stirred with heating (in 5° C. steps) to 55° C. The reaction was incomplete after 6 hours by NP-TLC and RP-HPLC. Therefore, under a nitrogen, shower, to the reaction mixture was added Palladium 10% on carbon (20.0 g, 188 mmol) and Methanol (500 ml). The reaction was continued for 1 hour and checked again by TLC and RP-HPLC and was found to be complete: The reaction mixture was degassed for 1 hour by vigorously bubbling nitrogen through the reaction mixture. The reaction mixture was filtered through 3 layers of glass fiber in a Büchner funnel into a filter flask. The filter cake in the funnel was rinsed with three portions each of 300 mL degassed methanol. The palladium was quenched by dumping the filter into a bucket of water. The methanol was removed by rotary evaporation under reduced pressure at 45° C. The product was dried under high vacuum on the rotary evaporator at 25° C. for 16 hours to give 193.6 grams (94%) at 98.5% purity (quantitative NMR). TLC: 10% (9:1 Methanol:Ammonium Hydroxide): 90% Dichloromethane. Plates were eluted 7 minutes in solvent, dried by hot air gun, visualized under UV light at 254 nm (marking UV quenching spots), and then developed either in iodine or with ninhydrin solution. HPLC: AMINES3045FF NMR: (400 MHz, CDCl₃, δ). 7.557 (br s, 1H, amide); 3.646 (t, 2H, CH₂ β to CO); 3.483 (t, 2H, CH₂ β to N on dPEG®); 3.383 (t, 2H CH₂N, on PEG); 3.282 (t, 1H, CHN on lysine); 2.648 (t, 2H, CH₂N on lysine); 2.424 (t, 2H, CH₂CO on dPEG®); 1.767 (br s, 4H, 2x NH₂ on lysine); 1.372 (m, 15H, lysine side chain alkyl plus tert-butyl ester).

bis(MAL)₂-Lys-4-TBE or MAL-Lys(MAL)-dPEG₄-TBE:

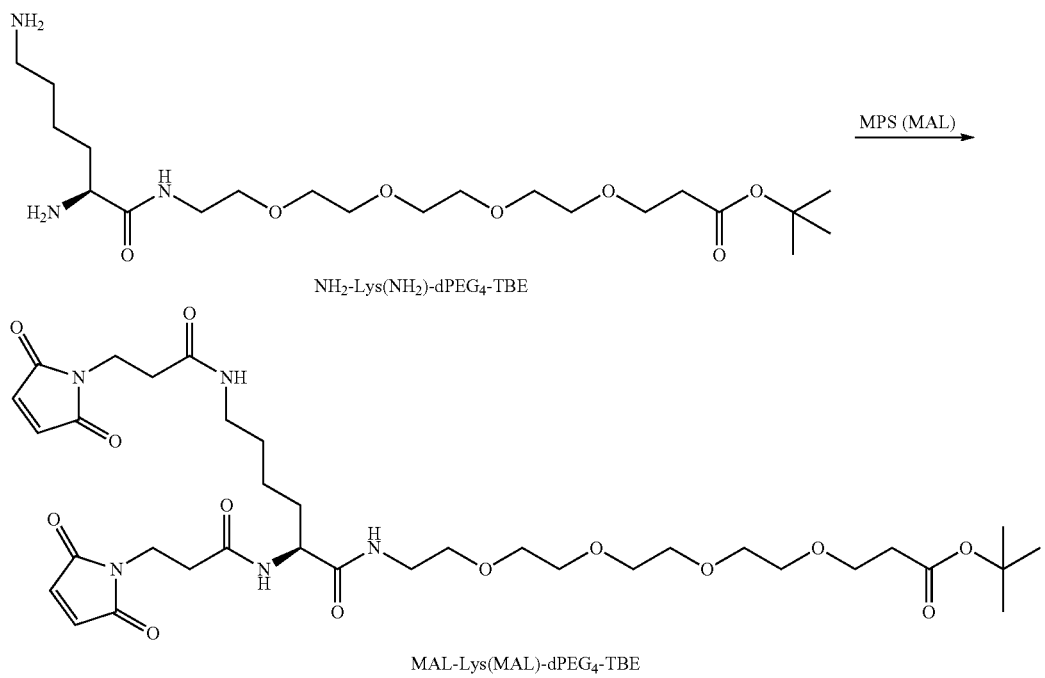

In the glove box under an atmosphere of dry nitrogen, to a 250 mL, 4-necked RB flask fitted with an immersion well, egg-shaped magnetic stir bar, and PTFE stoppers was added MPS (35.0 g, 131 mmol) and dry (over sieves) dichloromethane (75 ml) to form a white slurry. Separately, in an Erlenmeyer flask, Lysine-dPEG4-TBE (30.0 g, 66.7 mmol) and 2,6-Lutidine (20 ml, 172 mmol) were dissolved in dry (over sieves) dichloromethane (25 ml) to form a yellow solution. The reaction vessel (RB flask) was transferred to the fume hood, placed in an ice-water bath atop a magnetic stir plate, and fitted with an addition funnel connected by a gas inlet adapter to a bleed of dry nitrogen. A thermocouple was inserted in the immersion well to monitor temperature. The Lysine-dPEG®$_4$-TBE solution was poured under a nitrogen shower into the addition funnel and then added slowly by drop. The reaction mixture exothermed strongly. When about ⅔ of the lysine-dPEG®$_4$-TBE solution had added, the reaction suddenly congealed into an off-white paste. Added dry (over sieves) Dichloromethane (100 ml), placed the reaction vessel in a heating mantle set at 35° C., broke up the paste into small chunks so that stirring could resume, and then continued adding the lysine-dPEG®$_4$-TBE solution. By the time all of the amine had added, the temperature of the reaction mixture was at 42° C., and the dichloromethane was boiling. Reaction mixture was yellow solution, a bit darker than before the reaction began. Removed the heating mantle and continued stirring at ambient until the reaction mixture cooled to 35° C. Added back the heating mantle, set at 30° C. and continued the reaction overnight at 30° C. The reaction had lost ½ of solvent and was an amber gel the next day. The heat was turned off, and 200 mL dry dichloromethane were added with stirring. All of the product went into solution, then gelled again. The gel was transferred to an Erlenmeyer flask and diluted with stirring to 700 mL with dichloromethane (not dry). Checked reaction by HPLC and TLC. Reaction was not complete. Additional attempts to force the reaction to completion were unsuccessful. TLC using ninhydrin showed no primary amine present, but on extended heating the impurity slowly turned red, suggesting that the amine had reacted but not coupled with a maleimide. The solvent was partially removed by rotary evaporation at 25° C. under reduced pressure, then dichloromethane was added to 700 mL volume followed by 35 mL methanol. The reaction mixture was washed 1×100 mL with ambient temperature saturated aqueous sodium bicarbonate. Time in contact with this wash solution was kept to a minimum. The reaction mixture was then placed in a salted ice-water bath and chilled with stirring. The mixture was washed 4×100 mL with 600 mM aqueous HCl (ice cold) then washed 2×250 mL with distilled water. The solvent was removed by rotary evaporation, and 55 grams (110%) of crude, impure material was recovered. This material was purified by normal phase flash chromatography on a Teledyne-Isco Torrent flash chromatography system to give 16 grams (31.9%). TLC: 10% Methanol, 90% DCM. HPLC: ACID60FF, 4.747 minutes (ELSD), column is Supelco Discovery HS C18 column, 4.6 mm×25 cm. ACID3045FF, 21.247 minutes (ELSD), same column as above.

Bis(MAL)$_2$-Lys-4-Acid or MAL-Lys(MAL)-dPEG$_4$-Acid:

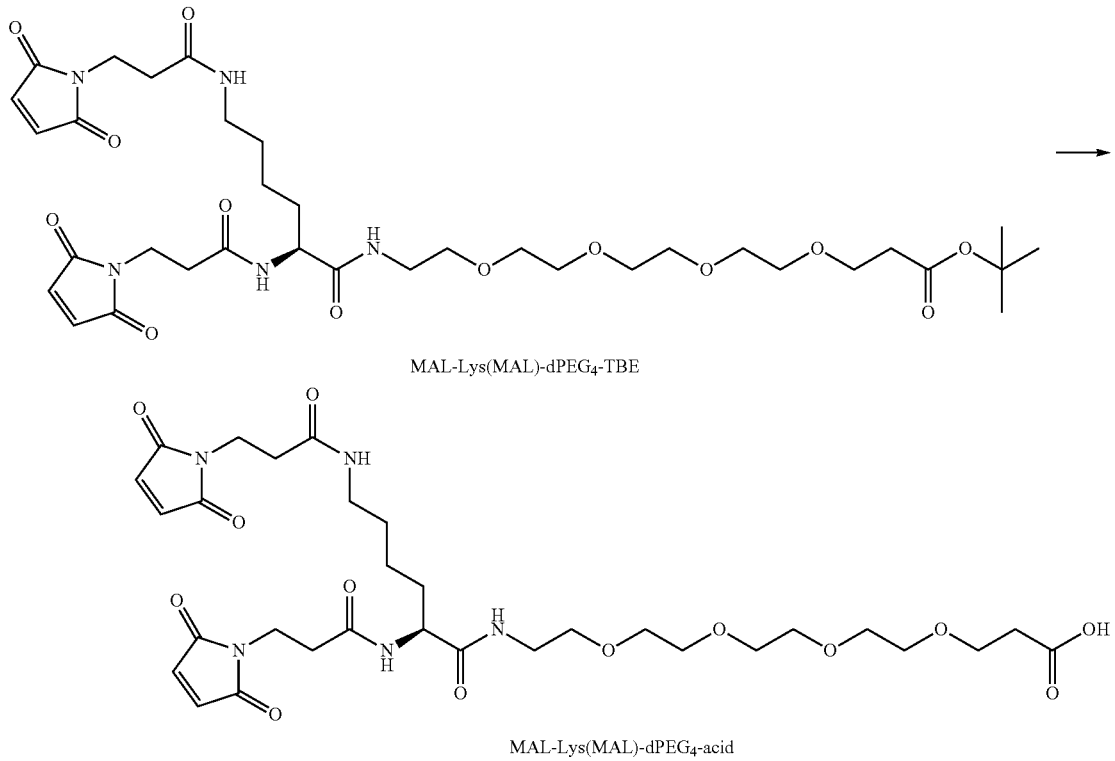

MAL-Lys(MAL)-dPEG$_4$-TBE

MAL-Lys(MAL)-dPEG$_4$-acid

A 1000 mL, 4-necked RB flask fitted with an immersion well and PTFE stoppers was charged with Bis-MAL-Lys-dPEG®$_4$-TBE (15 g, 19.95 mmol) dissolved in dichloromethane (430 ml) forming a light yellow, highly viscous solution. The flask was placed in a salted ice-water bath and fitted with an addition funnel connected by a gas inlet adapter to a bleed of dry nitrogen and an overhead stirring apparatus. The addition funnel was charged with trifluoroacetic acid (TFA) (250 ml, 3245 mmol), which was then added by drop over 4 hours. The reaction was allowed to continue overnight, warming slowly to ambient, and appeared by RP-HPLC to be complete the next morning. DCM and TFA were removed by rotary evaporation at 30° C. under reduced pressure using a water aspirator. To the TFA was added to 3×1000 mL portions of DCM, and the DCM was then removed by rotary evaporation as before. After the third portion was removed, the residue was placed under high vacuum at 40° C. on the rotary evaporator and kept there with 12 rpm rotation for 3 hours. The residue (a brown goo) was taken up in. 250 mL of 75:25 hexanes:TBME. The flask containing the residue was placed in a secondary container and stirred 26 hours using vigorous overhead stirring. The solvent was decanted, stored, and replaced with 100 mL of 75:25 hexanes:TBME and stirred for 38 hours. The product during this second stirring became mostly white powder with some small chunks of brown goo. The first and second Hexanes:TBME solutions were filtered through 3 layers of filter paper, and the residue was collected. In the glove box under a nitrogen atmosphere, the gooey brown lumps were separated from the white powder. The white powder was labeled "crop 1", and the gooey brown lumps were labeled "crop 2". Each crop was recrystallized separately three times by dissolving in a minimum volume of dry acetonitrile and then recrystallizing from 3:1 Hexanes:TBME while slowly lowering the temperature from ambient to −20° C. The second crop (about 5 grams) failed to give a product with the expected NMR structure and was discarded. Yield (1$^{st}$ crop only): 8.8 grams (63.4%) at 92.2% purity by quantitative NMR, 1.00% by RP-HPLC. TLC: 10% Methanol, 90% DCM, with 4 drops/mL acetic acid added. HPLC: Column is Supelco Discovery HS C18, 25 cm×4.6 mm. HPLC retention times are given for 3× recrystallized material. ACID60FF: 2.346 minutes (ELSD), ACID4020: 5.745 minutes (ELSD), ACID3045FF: 8.816 minutes (ELSD). NMR: (400 MHz, DMSO, δ): 8.058 (br s, 1H, amide); 7.914 (br s, 2H, 2 amides); 7.007 (s, 4H, 2 maleimides); 4.144 (t, 1H, CHN on lysine); 3.594 (m, 6H, 3x CH$_2$ β to CO); 3.399 (t, 2H, CH$_2$ β to N on PEG); 3.195 (t, 2H, CH$_2$N on PEG); 2.950 (t, 2H, CH$_2$N on lysine); 2.441 (overlapping triplets, 4H, 2x CH$_2$CO on maleimides); 2.314 (t, 2H, CH$_2$CO on PEG); 1.535 (m, 1H, lysine alkyl); 1.425 (m, 1H, lysine alkyl), 1.298 (m, 2H, lysine alkyl); 1.162 (m, 2H, lysine alkyl).

Bis(MAL)$_2$-Lys-4-TFP or MAL-Lys(MAL)-dPEG$_4$-TFP:

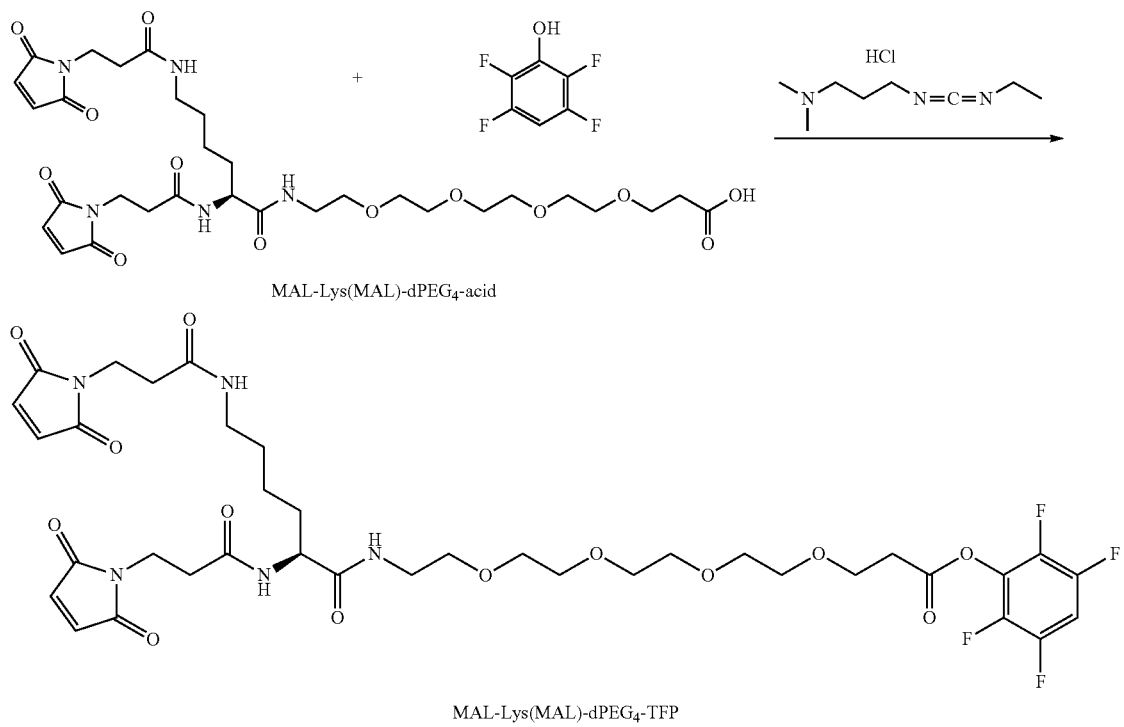

MAL-Lys(MAL)-dPEG$_4$-acid

MAL-Lys(MAL)-dPEG$_4$-TFP

In the glove box under an atmosphere of dry nitrogen, to a 250 mL, 4-necked RB flask fitted with an immersion well, PTFE stoppers, and an egg-shaped stir bar was added Bis-MAL-LYS-dPEG$_4$-acid (8.2 g, 11.79 mmol) slurried in Dichloromethane (60 ml). Separately, in the glove box in an Erlenmeyer flask, 2,3,5,6-tetrafluorophenol (2.689 g, 16.19 mmol) and EDC (2.891 g, 15.08 mmol) were dissolved in Dichloromethane (15 ml). The RB flask was transferred to the fume hood and placed in an ice water bath. The flask was fitted with an addition funnel connected by a gas inlet adapter to a bleed of dry nitrogen. The slurry was stirred. When the temperature reached 10.5° C., the slurry suddenly gelled and seized, making further stirring impossible. Removed the RB flask from the ice water bath and placed in a heating mantle at 25° C. The slurry was heated, and the stir bar was left on to start stirring as soon as possible. The stirring resumed when the temperature in the flask reached 19.7° C. The flask continued to be stirred until the temperature stabilized at 25° C. During the warm up, the temperature in the flask reached 36.8° C. At 30.2° C., the material started to dissolve in the dichloromethane, and by 30.9° C., it was fully dissolved. As the solution cooled back to 25° C., it became very cloudy as product started falling out of solution. The EDC-TFP solution was transferred to the addition funnel under a nitrogen shower, then added dropwise to the acid slurry/solution at ambient temperature. Once all of the EDC-TFP was added, the heating mantle was set to 30° C., and the reaction was allowed to proceed overnight at this temperature. Reaction was complete the next day by RP-HPLC and TLC (see data). Stored the reaction mixture in the freezer overnight. Transferred the reaction mixture to a 125 mL filter flask and diluted to 100 mL with dichloromethane. Placed the filter flask under a steady flow of nitrogen. Added a stir bar. Washed the reaction mixture 2×20 mL with 1.2 molar aqueous HCl (cold). Observed each wash some clear crystals clogging up the stopcock. Required work to get the crystals to pass through the stopcock into the funnel. Washed the reaction mixture 1×25 mL with saturated brine. Dried over 10 grams $Na_2SO_4$ for 30 minutes under nitrogen with vigorous stirring, then filtered and washed filter cake with dry DCM. Removed solvent by rotary evaporation and checked by TLC and HPLC. Product was extremely overweight (28 grams) indicating retained solvent. Removed solvent by overnight rotary evaporation under high vacuum at 35° C. to give 9.3 g of an amber solid. The sample was preabsorbed onto 4 g of $SiO_2$ and purified on an Isco Rf on an 80 g RediSep column using DCM (A) and EtOH (B). A gradient was run at 0% B for 2CV then ramping to 10% B over 11CV and holding at 10% B. Fractions 16-34 were pooled and concentrated to give a white solid. The solid was suspended in hexanes, filtered, and dried, under high vac to provide 7.4 g (74%) of a white powdery solid. TLC (95:5 DCM:EtOH) indicated a single spot. HPLC (Acids4020 method): RT 13.75 min, purity 99%. $^1$H NMR (400 MHz, $CDCl_3$, δ): 7.02 (m, 1H), 6.83 (m, 1H), 6.80-6.67 (m, 5H), 6.30 (m, 1H), 4.36 (m, 1H), 3.92-3.79 (m, 6H), 3.74-3.51 (m, 16H), 3.44 (m, 2H), 3.20 (t, 2H), 2.63-2.46 (m, 4H), 1.77 (m, 1H), 1.64 (m, 1H), 1.48 (m, 2H), 1.31 (m, 2H).

Bis(MAL)$_2$-Lys-dPEG$_4$-Amido-dPEG$_{12}$-Tris(-dPEG$_{24}$-m)$_3$ or MAL-Lys(MAL)-dPEG$_4$-Amido-dPEG$_{12}$-Tris(-dPEG$_{24}$-m)$_3$:

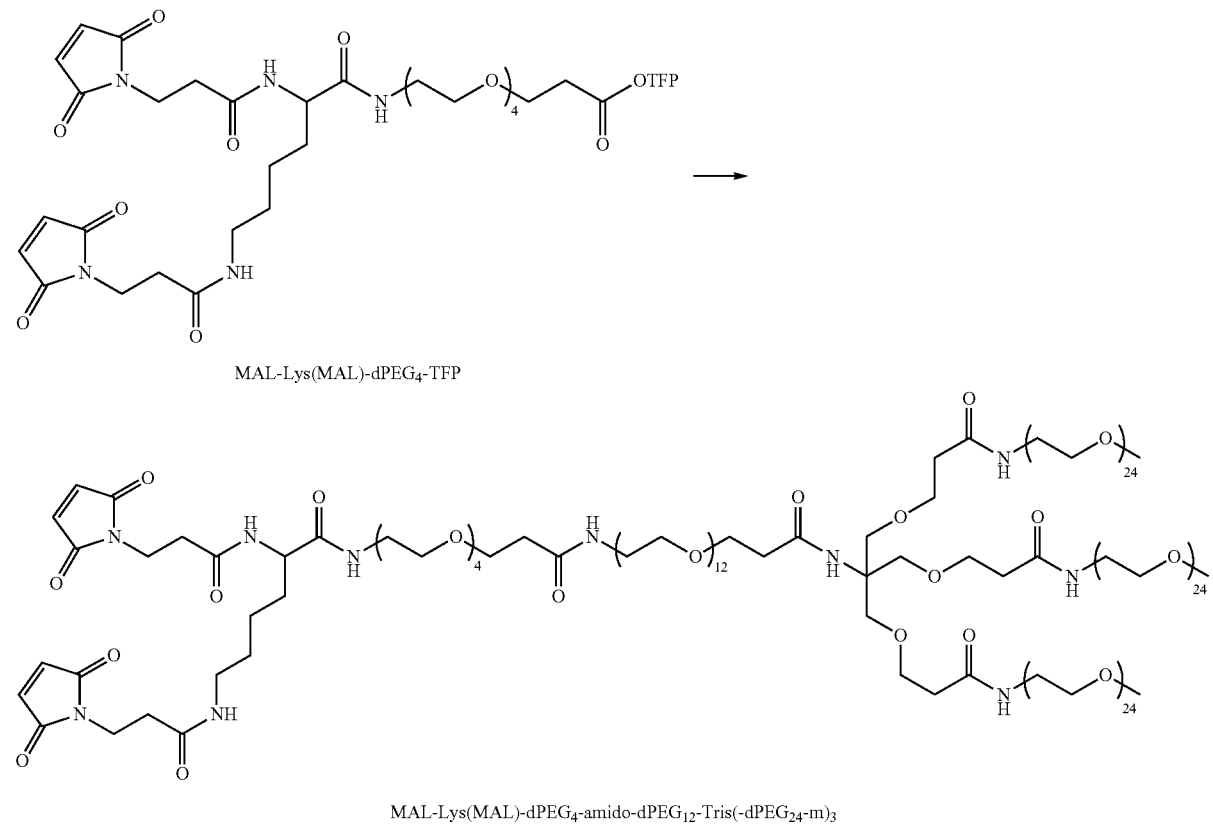

MAL-Lys(MAL)-dPEG$_4$-TFP

MAL-Lys(MAL)-dPEG$_4$-amido-dPEG$_{12}$-Tris(-dPEG$_{24}$-m)$_3$

A 100 mL RBF fitted with addition funnel, cooling bath, and nitrogen blanket was set up for this reaction. The RBF was charged with bis(mal)-Lys-4-TFP (0.854 g, 1.013 mmol) and DCM (18.08 ml) and was cooled to 0° C. in an ice bath. H2N-12-tris(amido-24-m)3 (3 g, 0.723 mmol) was dissolved in DCM (18.08 ml) and 2,6-Lutidine (0.135 ml, 1.157 mmol) was added via pipette. The amine mixture was added dropwise to the TFP ester, the cooling bath was removed, and the reaction was stirred at room temp overnight. HPLC (Amines3045FFmethod) indicated complete conversion of branched amine. TLC (85:15 DCM:MeOH) indicated a major spot. The reaction was diluted with DCM (100 mL), washed with 10% HCl (2×20 mL), brine (20 mL), dried over $Na_2SO_4$, filtered over celite, and concentrated under reduced pressure to give 4.8 g of of an oily yellow solid. The residue was preabsorbed on to 10 g of $SiO_2$ and purified on an Isco Rf using an 80 g RediSep, DCM (A,) and EtOH (B). Collection was done using 220 nm. The column was primed with 30% B for 2CV and 0% B for 2CV. The SLSC was inserted and a gradient was run at 5% B for 4CV then ramping to 14% B over 5CV. The gradient was held at 14% until the peak eluted and was then ramped to 30% over 8CV and held at 30%. The fractions were run on a TLC plate and 16-36 were pooled and concentrated under reduced pressure to give 2.739 g (78%) of a white powdery solid.

TLC (85:15 DCM:MeOH) indicated a major spot. HPLC (Amines3045FF method): RT 28.89 min, purity 99.7%. $^1$H NMR (400 MHz, CDCl₃, δ): 7.01 (m, 1H), 6.84-6.72 (m, 5H), 6.70 (s, 2H), 6.69 (s, 2H), 6.53 (br, 1H), 6.40 (m, 1H), 4.33 (m, 1H), 3.98-3.67 (m, 370H), 3.35 (s, 9H), 3.17 (m, 2H), 2.57-2.35 (m, 14H), 1.77 (m, 1H), 1.64 (m, 1H), 1.48 (m, 2H), 1.31 (m, 2H).

Bis(MAL-dPEG$_2$)$_2$-Lys-dPEG$_4$-TBE or MAL-dPEG$_2$-Lys(MAL-dPEG$_2$)-dPEG$_4$-TBE:

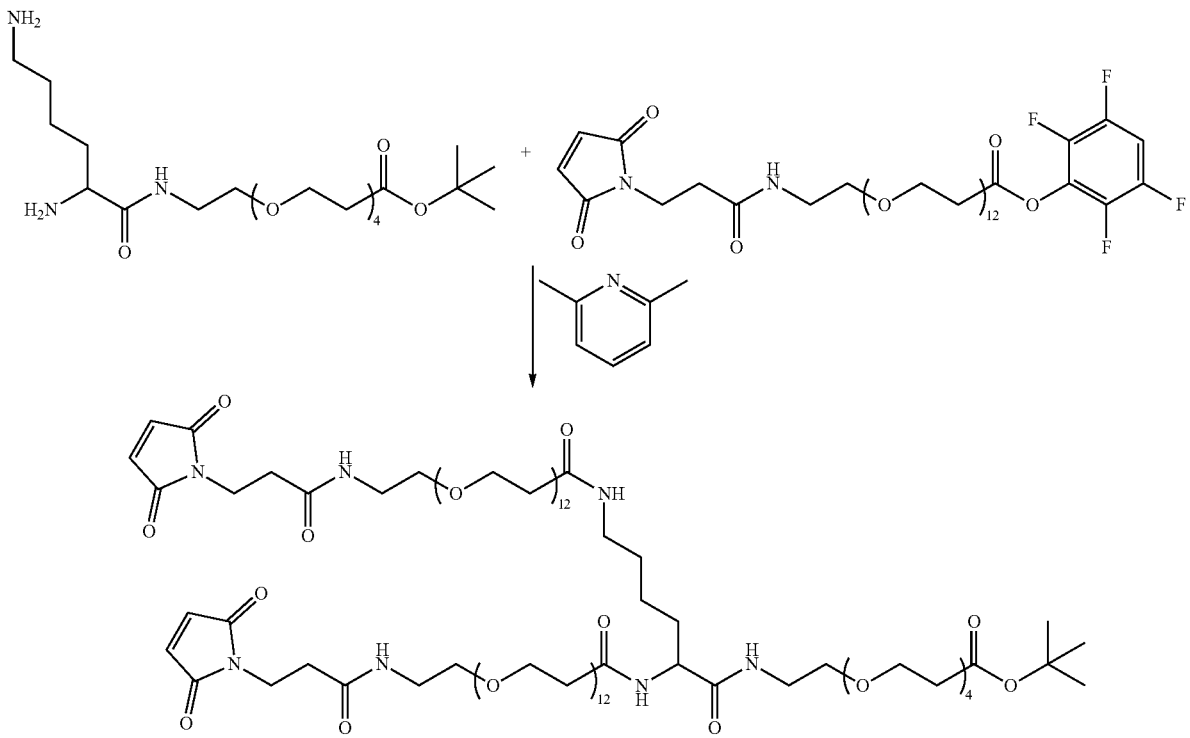

In the glove box under at atmosphere of dry nitrogen, a 250 mL, 4-necked RB flask ("reaction vessel") fitted with an immersion well and PTFE stoppers and containing an egg-shaped magnetic stir bar was charged with MAL-dPEG®2-TFP ester (65.5 g, 137 mmol) dissolved in dichloromethane (65 ml). Separately, a 250 mL Erlenmeyer flask was charged with Lysine-dPEG®4-TBE (20.6 g, 45.8 mmol), 2,6-Lutidine (19 ml, 163 mmol), and dichloromethane (40 ml). This mixture was stirred until dissolved. The reaction vessel was transferred to the fume hood where it was placed in an ice water bath and fitted with an addition funnel connected by a gas inlet adapter to a bleed of dry nitrogen. The flask was stirred until 0° C. The lysine solution was then poured under a nitrogen shower into the addition funnel and was added by drop to the reaction vessel. The reaction began to gel in the cold temperature as more lysine solution was added. Stirring had to be turned up to maximum, and the rate of addition had to be slowed so that the lysine-PEG solution was added over 2 hours. At the end of the reaction, the mixture was completely gelled, so dry dichloromethane (80 ml) was added in 10 mL portions until the solution would stir again. After each portion was added, the flask was shaken by hand to incorporate the solvent and mix the reagents. The flask was then placed back on the stir plate to see if it could be stirred magnetically. Because the solution had gelled, once all of the lysine solution was added, the flask was removed from the ice-water bath and was placed in a heating mantle set at 30° C. The reaction was allowed to continue overnight. The reaction was complete by RP-HPLC. The reaction mixture had gelled again overnight. The gelled reaction mixture was transferred in the glove box under a nitrogen atmosphere to a 500 mL flask. In small portions, the original flask and the transfer funnel were rinsed with dry dichloromethane (150 ml), and the rinses were added to the reaction mixture. The reaction mixture was then heated at 35° C. with vigorous stirring until the gel dissolved. As soon as the heat was turned off, the reaction mixture gelled again. The reaction mixture was diluted to 600 mL with DCM and stirred until the gel dissolved. The reaction mixture was washed 4×100 mL with ice-cold aqueous HCl (17.5 mL concentrated aq. HCl in 400 mL water=0.53 molar HCl). Each wash formed emulsions that were very slow to break, even when gentle stirring was employed; therefore, 25 mL MeOH was added to the DCM. The reaction mixture was washed 2×100 mL with 10% brine, then once with 200 mL saturated brine. The solvent was removed by rotary evaporation at 35° C. under reduced pressure, then dried under high vacuum for 2 hours at 40° C. Yield (crude): 87.5 grams (115%). The crude material was purified by normal phase flash chromatography using a Teledyne-Isco Torrent instrument to give 39.5 grams (51.7%). TLC: 10% Methanol, 90% DCM, 3 drops glacial acetic acid/mL solvent. HPLC: AMINES4020, AMINES3045FF. NMR (400 MHz, CDCl₃, δ): 7.183 (br s, 1H, amide); 7.134 (br s, 1H, amide); 7.055 (br s, 1H, amide); 6.892 (br s, 1H, amide); 6.697 (two singlets, 4H, 2x maleimide); 6.609 (br s, 1H, amide); 4.411 (m, 1H, CHN on lysine); 3.816 (t, 4H, 2x CH₂ β to CO); 3.197 (t, 2H, CH₂N on PEG); 2.536 (t, 4H, CH₂CO on PEG); 2.485 (two triplets, 4H, CH₂CO on branches); 2.427 (t, 2H, CH₂CO on PEG tail); 1.789 (m, 1H, lysine alkyl); 1.622 (m, 1H, lysine alkyl); 1.423 (m, 2H, lysine alkyl); 1.359 (m, 2H, lysine alkyl).

Bis(MAL-dPEG₂)₂-Lys-dPEG₄-Acid or MAL-dPEG₂-Lys(MAL-dPEG₂)-dPEG₄-Acid:

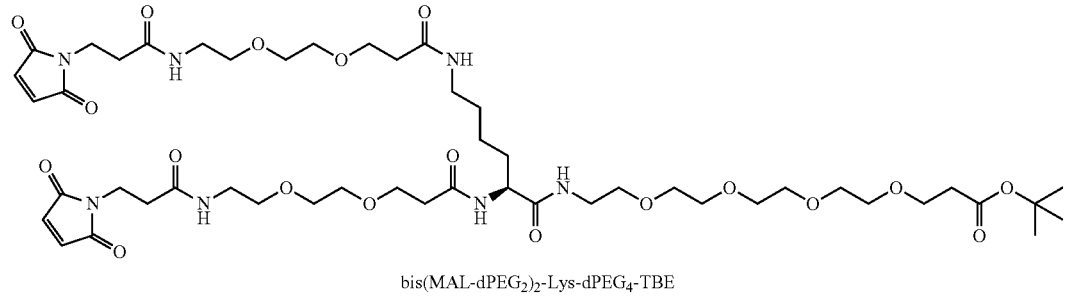

bis(MAL-dPEG₂)₂-Lys-dPEG₄-TBE

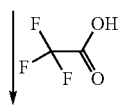

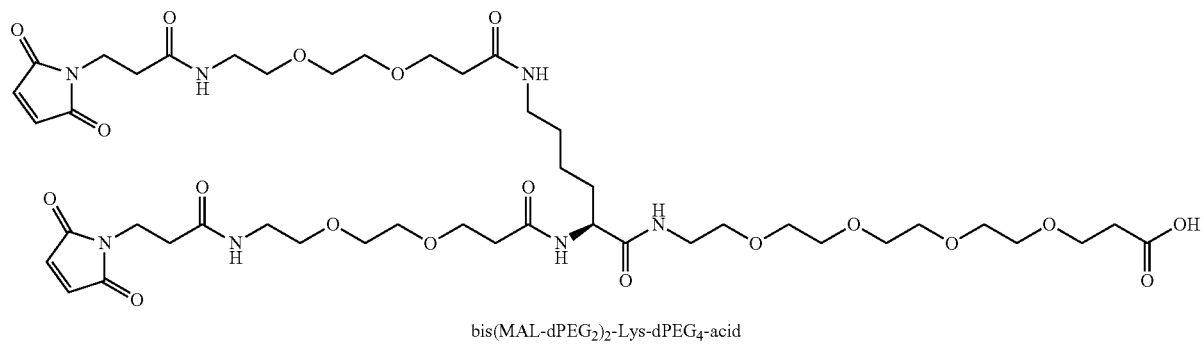

bis(MAL-dPEG₂)₂-Lys-dPEG₄-acid

In a 500 mL, one-necked RB flask was dissolved bis-(MAL-dPEG®₂)₂-Lysine-dPEG®₄-TBE (37.5 g, 35.0 mmol) in dichloromethane (100 ml). An egg-shaped magnetic stir bar was added to the flask, and the flask was fitted with an addition funnel connected by a gas inlet adapter to a drying tube filled with Drierite®. The flask was placed in a salted ice-water bath and stirred for 30 minutes to chill. The solution gelled in 20 minutes, so to the gel was added dichloromethane (100 ml). The gel dissolved in about 1 minute in the additional solvent. The addition funnel was then charged with Trifluoroacetic acid (200 ml, 2596 mmol), which was added by drop to the stirring solution. The reaction was allowed to continue overnight and appeared complete by RP-HPLC the next morning. Stripped solvent from reaction by rotary evaporation at 40° C. using a water aspirator. Dried under high vacuum for 3 hours at 45° C. Crude yield 75.8 grams. The crude material was taken up in a minimal volume of acetonitrile and triturated into 2:1 Hexanes:TBME. The flask containing the trituration was then chilled with stirring to −20° C. in a dry ice-acetone bath to facilitate further precipitation. This process was repeated twice, and each time, the product became more difficult to dissolve in acetonitrile. The recovered solids were taken up in 100 mL of dichloromethane, transferred to a 250 mL Erlenmeyer, flask, and then, diluted to 175 mL final volume with DCM. The DCM solution was then washed 2×25 mL with saturated brine followed by drying for 1 hour over sodium sulfate. The sodium sulfate was filtered away through AW Standard Super Cel NF (Sigma-Aldrich, aka, Celite). The Celite was washed with several small portions of dichloromethane to collect the entire product. The solvent was removed by rotary evaporation at 35° C., then dried under high vacuum for 2 hours. Yield: 28.6 grams (80%) TLC: 10% Methanol, 90% Dichloromethane, 3 drops glacial acetic acid/mL solvent. HPLC: ACID3045FF, NMR: (400 MHz, CDCl₃, δ): 8.656 (br s, 1H, COOH); 7.330 (br t, 1H, amide); 7.235 (br t, 1H, amide), 6.969 (br s, 1H, amide), 6.797 (br s, 1H, amide), 6.686 (2 singlets, 4H, 2x maleimides); 4.412 (m, 1H, CHN on lysine); 3.787 (m, 4H, 2x CH₂₁ β to CO); 3.719 (m, 6H, 3x CH₂ β to CO); 3.174 (t, 2H, CH₂N); 2.522 (overlapping triplets, 6H, 4x CH₂CO); 2.427 (t, 2H, CH₂CO); 1.771 (m, 1H, lysine alkyl); 1.614 (m, 1H, lysine alkyl); 1.476 (m, 2H, lysine alkyl); 1.339 (m, 2H, lysine alkyl).

Bis(MAL-dPEG₂)₂-Lys-dPEG₄-TFP Ester or MAL-dPEG₂-Lys(MAL-dPEG₂)-dPEG₄-TFP Ester:

279 280
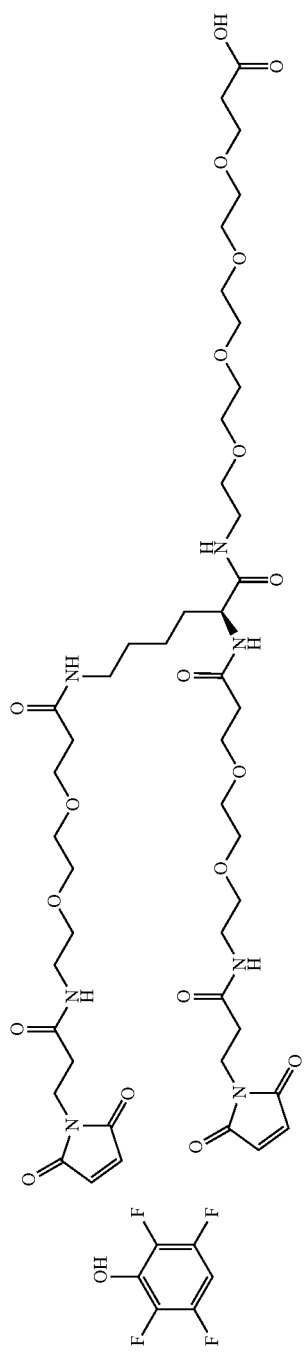
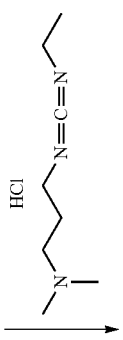
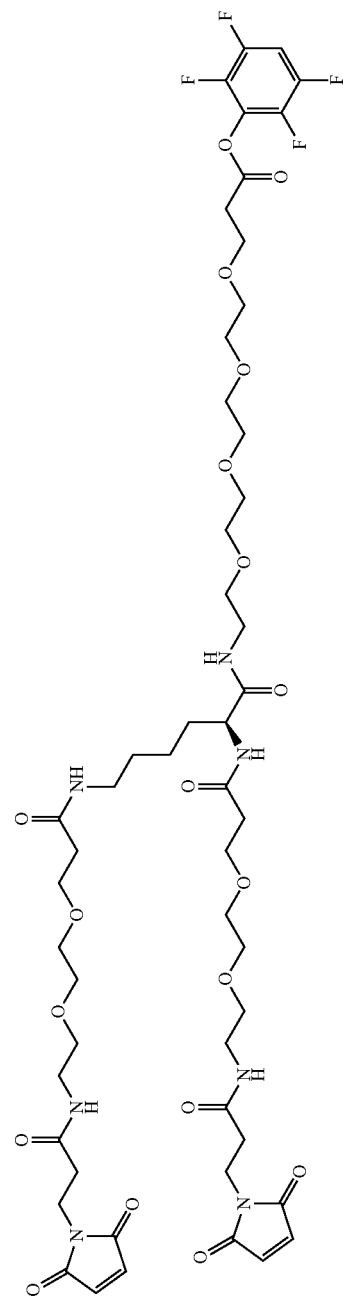

In the glove box under a dry nitrogen atmosphere (rel hum=18%), a 250 mL, 4-necked, RB flask fitted with PTFE stoppers, egg-shaped magnetic stir bar, and immersion well, was charged with EDC (5.7 g, 29.7 mmol), 2,3,5,6-tetrafluorophenol (4.3 g, 25.9 mmol), and dry (over sieves) Dichloromethane (20.00 ml). Separately, also in the glove box, was dissolved bis-MAL-dPEG2-Lysine-dPEG4-acid (22.2 g, 21.89 mmol) in dry (over sieves) Dichloromethane (20.00 ml). After the EDC/TFP solution in the reaction vessel had cooled to 0° C., dripped in the acid solution, keeping the temperature at or below 5° C. After all of the acid solution had dripped in, allowed the reaction to continue on ice for 1 hour, then heated to 30° C. for 2 hours. Reaction was complete by RP-HPLC after 1 hour of heating. Continued stirring overnight at ambient. Transferred the reaction mixture to a 250 mL filter flask. Diluted reaction mixture to 150 mL with dry dichloromethane. Placed the filter flask in an ice bath and connected filter flask to a bleed of dry nitrogen. Washed the reaction mixture 4×25 mL with ice cold 0.363 M aq. HCl (made from concentrated aq. HCl). (NOTE: Stir SLOWLY, just enough to agitate the layers without mixing. Rapid stirring leads to emulsions that are very difficult to break.) Washed the reaction mixture 1×25 mL with 10% brine. Washed the reaction mixture 1×50 mL with saturated brine. Dried the reaction mixture over 40.2 grams of $Na_2SO_4$ for 120 minutes. Filtered away the sodium sulfate through 4 layers of glass fiber in a Buchner funnel under a nitrogen shower. Washed the filter cake with dry DCM. Filtered the reaction mixture through a bed of AW. Standard Super-Cel NF in a fritted glass funnel under a nitrogen shower. Removed the solvent by rotary evaporation at 35° C. under high vacuum. The residue (15 g) was taken up in DCM and preabsorbed onto 30 g of bulk silica and purified on a 120 g RediSep using DCM (A) and EtOH (B). The column was primed with 20% B for 1CV and then 0% B for 2CV. The SLSC was inserted and a gradient was run at 5% B for 5CV then ramping to 17% over 8CV and bumping up to 30% to finish eluting product. A small amount of pink UV active material eluted, followed by TFP, and finally product. Fractions 30-56 were pooled and concentrated to give a viscous pale yellow semi-solid. Trituration with $Et_2O$ gave an off-white solid. This solid was crushed under hexanes, the hexanes decanted, and the off-white powdery solid was dried under high vac overnight to give 10.968 g (43%) of a white powdery solid. TLC (85:15 DCM:EtOH) indicated a single spot. HPLC (Acids4020 method): RT 13.64 min, purity 98.1%. $^1$H NMR (400 MHz, $CDCl_3$, δ): 7.21-6.96 (overlapping m, 4H), 6.83 (br t, 1H), 6.71 (s, 4H), 6.55 (br t, 1H), 4.43 (m, 1H), 3.93-3.29 (m, 42H), 3.21 (br q, 2H), 2.96 (t, 2H), 2.59-2.38 (overlapping t, 8H), 1.77 (m, 1H), 1.64 (m, 1H), 1.48 (m, 2H), 1.31 (m, 2H).

Bis(MAL-$dPEG_2$)$_2$-Lys-$dPEG_4$-Amido-$dPEG_{12}$-Tris(-$dPEG_{24}$-m)$_3$:

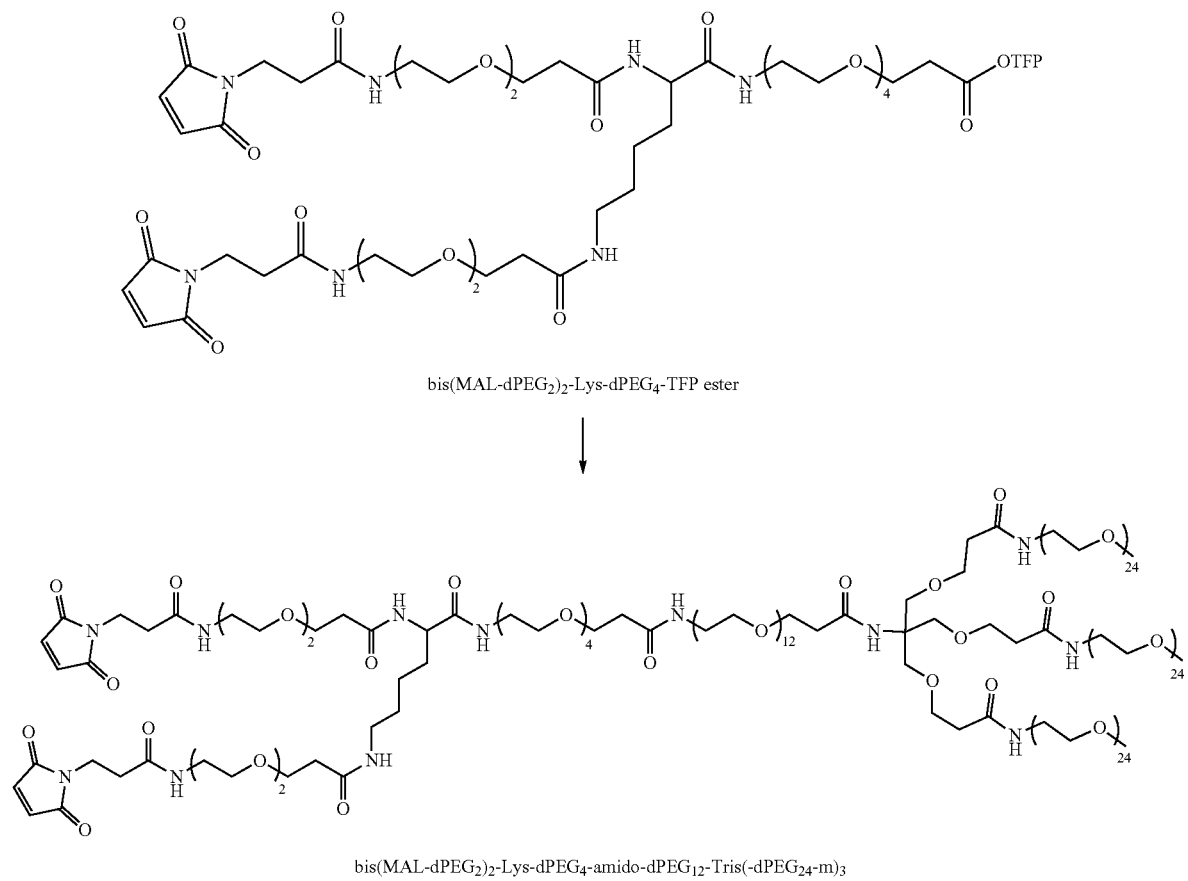

A 100 mL RBF fitted with addition funnel, cooling bath, and nitrogen blanket was set up for this reaction. The RBF was charged with bis(mal-2)-Lys-4-TFP (1.177 g, 1.013 mmol) and DCM (18.08 ml) and the flask was cooled to 0° C. in an ice bath. H2N-12-tris(amido-24-m)3 (3 g, 0.723 mmol was dissolved in DCM (18.08 ml) and 2,6-Lutidine (0.135 ml, 1.157 mmol) was added via pipette. The amine mixture was added dropwise to the TFP ester, the cooling bath was removed, and the reaction was stirred at room temp overnight. HPLC (Amines3045FF method) seemed to indicate complete conversion of branched amine although the retention times were too close to tell. TLC (85:15 DCM: MeOH) indicated a major spot.

The reaction was diluted with DCM (100 mL), washed with 10% HCl (3×20 mL), brine (20 mL), dried over Na$_2$SO$_4$, filtered over celite, and concentrated under reduced pressure to give 5.3 g of an oily yellow solid. The residue MeOH) indicated a single spot, although there was some streaking on the plate. HPLC (Amines3045FF method): RT 28.68 min, purity 98.7%. $^1$H NMR (400 MHz, CDCl$_3$, δ): 7.19 (br t, 1H), 7.12 (m, 2H), 6.92 (br t, 1H), 6.77 (m, 4H), 6.34 (overlapping s and br t, 5H), 6.51 (br t, 1H), 4.33 (m, 1H), 3.78-3.05 (m, 403H), 2.49-2.26 (overlapping t, 18H), 1.77 (m, 1H), 1.64 (m, 1H), 1.48 (m, 2H), 1.31 (m, 2H).

Bis(MAL-dPEG$_{12}$)$_2$-Lys-dPEG$_4$-TBE or MAL-dPEG$_{12}$-Lys (MAL-dPEG$_{12}$)-dPEG$_4$-TBE:

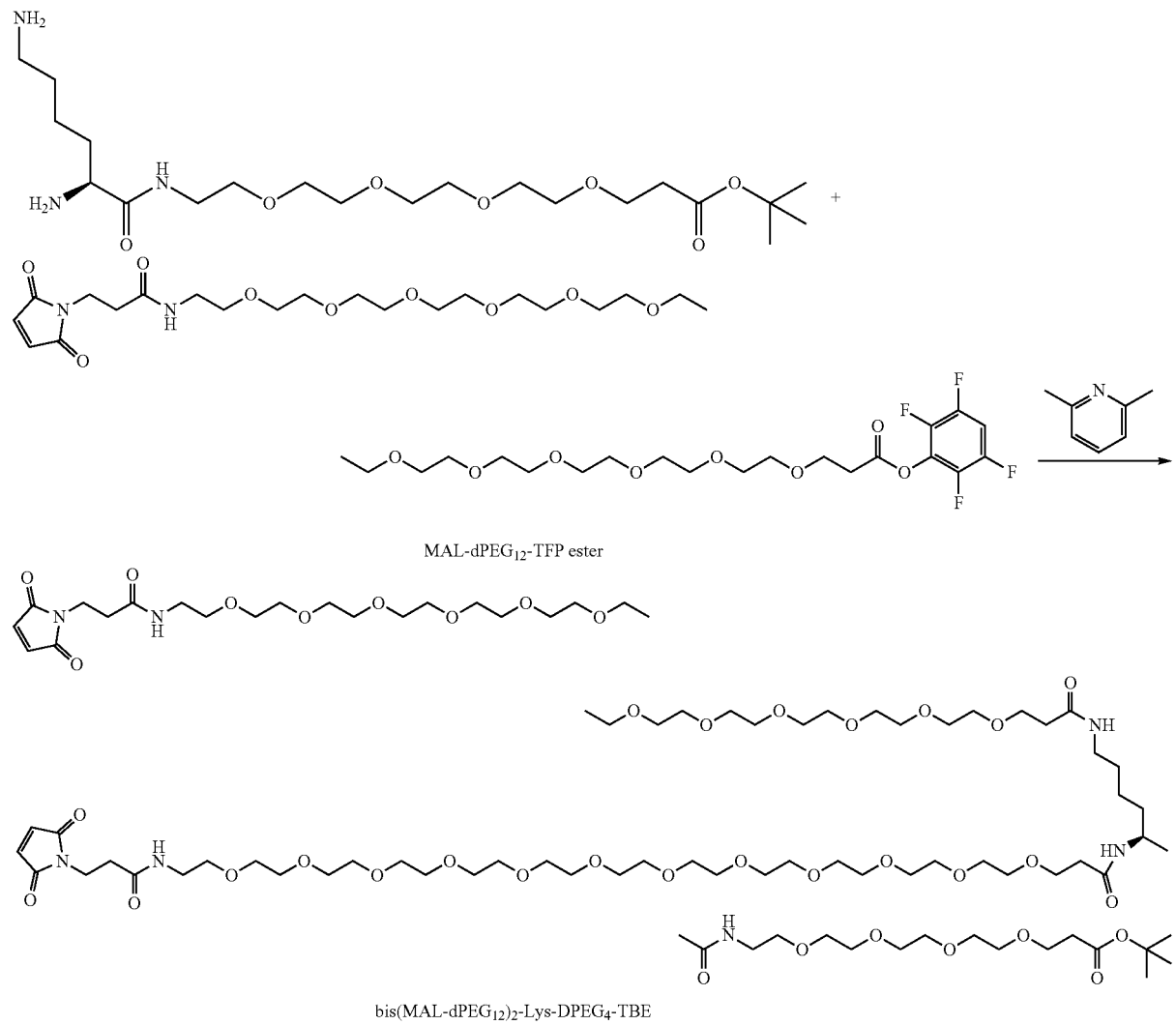

was preabsorbed on to 10 g of SiO$_2$ and purified on an Isco Rf using an 80 g RediSep, DCM (A), and MeOH (B). Collection was done using 220 nm. The column was primed with 15% B for 2CV and 0% B for 2CV. The SLSC was inserted and a gradient was run at 8% B for 4CV then ramping to 15% B over 10CV. The gradient was then bumped to 20% to finish eluting product. The fractions were run on a TLC plate and 16-36 were pooled and concentrated under reduced pressure to give 2.922 g of a white powdery solid. The residue was taken up in DCM, washed with 10% HCl, washed with brine, dried over Na2SO4, filtered over celite, and concentrated under reduced pressure to give 2.67 g (72%) of an off-white powdery solid. TLC (85:15 DCM:

In the glove box under an atmosphere of dry nitrogen, a 50 mL, 4-necked RB flask fitted with septa stoppers, egg-shaped magnetic stir bar, and immersion well was charged with MAL-dPEG®$_{12}$-TFP ester (12.9 g, 14.07 mmol) dissolved in dichloromethane (12 ml). Separately, in a dry 20 mL scintillation vial, Lysine-dPEG®$_4$-TBE (3.0 g, 6.67 mmol) and 2,6-Lutidine (2 ml, 17.17 mmol) were dissolved in dichloromethane (6.00 ml). The RB flask (reaction vessel) was stoppered and transferred to the fume hood where it was fitted with an addition funnel connected by a gas inlet adapter to a bleed of dry nitrogen and placed in a salted ice water bath. The reaction vessel was stirred until chilled to 0° C., then the addition funnel was charged with the lysine solution, which was added by drop (about 1 mL/min) to the reaction vessel. Once all of the lysine solution had been added, the reaction mixture was a dark reddish-brown. The reaction vessel was removed from the ice bath and placed in a heating mantle set at 30° C. The reaction was allowed to continue overnight with stirring at 30° C. under a bleed of dry nitrogen. The reaction was checked by HPLC after 1 hour. Reaction appeared messy but complete by HPLC. For the workup, two separate reactions of this product were combined. The other reaction was run identically to this reaction but at a slightly larger scale. The combined theoretical yield for the two reactions was 47.7 grams (24.46 mmole). The combined reaction mixtures were diluted to 150 mL with dichloromethane in an Erlenmeyer flask. Placed the flask in an ice-water bath and stirred 15 minutes to chill. The reaction mixture was washed 2×50 mL with ice-cold 0.363M aq. HCl, then 1×50, mL with saturated brine, then 2×50 mL with HCl again, then 1×50 mL with saturated brine and let stand for 8 hours to fully separate the layers, then dried over 50 grams of $Mg_2SO_4$ for 10 minutes, then repeated with 75 grams of $Mg_2SO_4$ for 60 minutes, filtering away the $Mg_2SO_4$ each time through Celite and washing the filter cake to recover as much product as possible each time. Recovered 54.3 grams (27.8 mmol) (114%). Material appeared impure by HPLC and NMR. The residue (11.0 grams, 5.6 mmol) was adsorbed onto 25 grams Redi-Sep silica gel in 100 mL dichloromethane and 2.5 mL acetic acid (to protect maleimides). Ran chromatography using Isco Rf. Fractions 1&2, 5-8, 21-30, 36-45, 46-50, and 51-55 were pooled separately. Removed solvent by rotary evaporation to give 4.0 grams from 11.0 grams=36.4% at 96% purity (HPLC). A second lot was purified on the Biotage Isolera. Took 20.0 grams of and purified on a 220 gram Isco Rf column. Recovered 7.9 grams (39.5%) of product in fractions 33-49 at 96% purity (HPLC). TLC: 30% (9:1 Ethanol:Formic acid):70% Dichloromethane HPLC: AMINES3045FF, ACID3045FF. NMR: Spectrum not taken. Bis(MAL-dPEG$_{12}$)$_2$-Lys-dPEG$_4$-Acid or MAL-dPEG$_{12}$-Lys(MAL-dPEG$_{12}$)-dPEG$_4$-Acid:

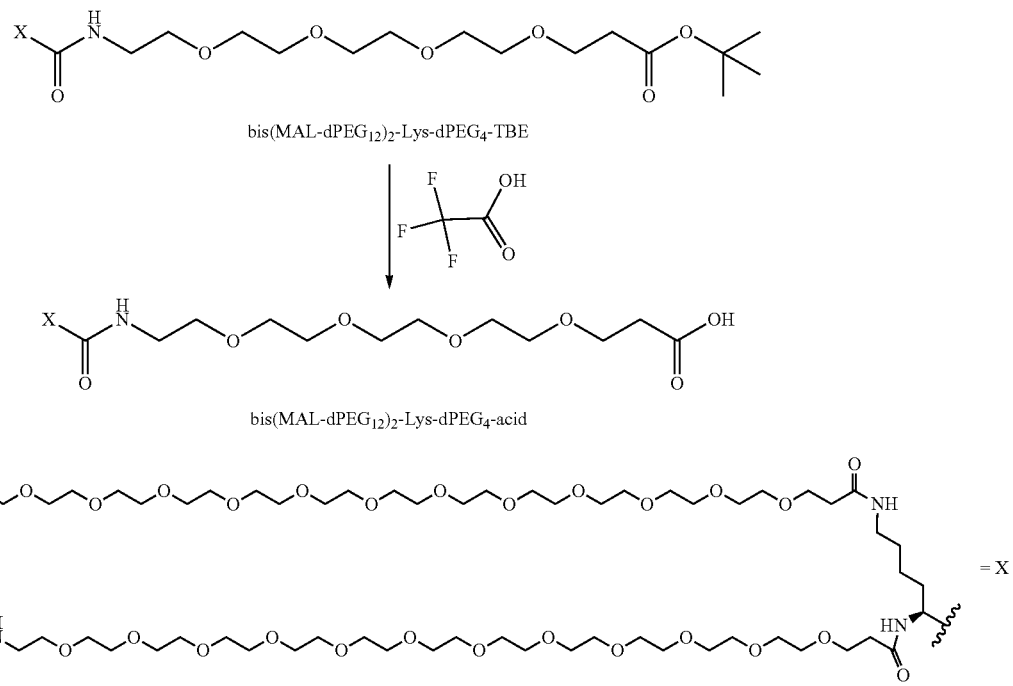

In the glove box under an atmosphere of dry ice and dry nitrogen, to a 50 mL, 4-necked RB flask (septa stoppers, immersion well, egg-shaped magnetic stir bar) was added bis-(MAL-dPEG®$_{12}$)$_2$-Lysine-dPEG®$_4$-TBE (3.8 g, 1.947 mmol) dissolved in dichloromethane (10 ml). The flask was stoppered and transferred to the fume hood where it was placed in a salted ice-water bath and fitted with an addition funnel connected by a gas inlet adapter to a drying tube filled with Drierite®. The mixture was stirred until the temperature reached 0° C. The addition funnel was then charged with Trifluoroacetic acid (10 ml, 130 mmol), which was added by drop to the reaction mix. The reaction was allowed to continue overnight. Reaction was checked by HPLC the next morning and was complete. The solvent was removed by rotary evaporation at 35° C. under reduced pressure. The residue was dissolved in 5 mL of dry acetonitrile, then with stirring, 2.5 grams of Celite was added. To this was added with stirring 30 mL of 2:1 Hexanes:TBME. The Celite was filtered through a fritted glass funnel, then washed with 80 mL of 1:1 Hexanes:TBME. The product was extracted from the Celite with dichloromethane, and the solvent was removed by rotary evaporation at 35° C. under reduced pressure, followed by vacuum drying overnight at ambient temperature to give 2.6 grams (70.4%) as a clear amber gel. This process was repeated on a larger scale with 92% percent recovery; however, the recovered product both times was not pure by HPLC, as compared to the starting material; therefore, it had to be further purified by Biotage. Biotage purification was accomplished by elution on a normal phase flash chromatography column (Teledyne-Isco) using a gradient of 0%-50% 9:1 (Ethanol:Formic Acid) in Dichloromethane. Fractions with pure product were identified by NPTLC and combined. The solvent was removed by rotary evaporation under reduced pressure at 35° C. The residue was taken up in a minimal volume of dichloromethane and washed three times with saturated brine to remove formic acid. Yield from the column varied from 30% to 40% (1.0 gram to 3.3 grams, depending on the scale of the column) as an amber semisolid. TLC: 30% (9:1 Ethanol:Formic Acid), 70% Dichloromethane HPLC: ACID3045FF (94.6% purity after cc and brine wash). NMR (400 MHz, $CDCl_3$, δ): 7.115 (m, 2H, amides), 6.702 (s, 4H, 2x maleimides), 6.347 (br s, 2H, amides), 4.412 (m, 1H, CHN lysine), 3.413 (m, 4H, $CH_2$ β to N), 3.207 (br t, 2H, $CH_2N$), 2.591 (tr, 2H, $CH_2CO$), 2.507 (overlapping triplets, 8H, $CH_2CO$), 1.824 (m, 1H, lysine alkyl), 1.645 (m, 1H, lysine alkyl), 1.501 (m, 2H, lysine alkyl), 1.360 (m, 2H, lysine alkyl).

Bis(MAL-dPEG$_{12}$)$_2$-Lys-dPEG$_4$-TFP Ester or MAL-dPEG$_{12}$-Lys(MAL-dPEG$_{12}$)-dPEG$_4$-TFP Ester:

checked by RP-HPLC. HPLC showed no reaction. Let reaction continue overnight at ambient, but no reaction was seen. To the reaction mixture was added EDC (0.328 g, 1.711 mmol) (dry). After 1 hour, the reaction was checked, and some reaction occurred. To the reaction mixture was added EDC (2.428 g, 12.66 mmol) and 2,3,5,6-tetrafluorophenol (2.103 g, 12.66 mmol) plus dry (over sieves) DCM (15 mL), and allowed reaction to continue overnight. Reaction immediately turned dark green (almost black). The reaction was complete by HPLC within two hours. Allowed the reaction mixture to stir at ambient overnight; however, by morning, the reaction had a reddish tinge to it. This was washed with water, dried over sodium sulfate, filtered, and concentrated to give 1.5 g of a viscous dark amber oil. The sample was preabsorbed on to 4 g of SiO2 and purified on

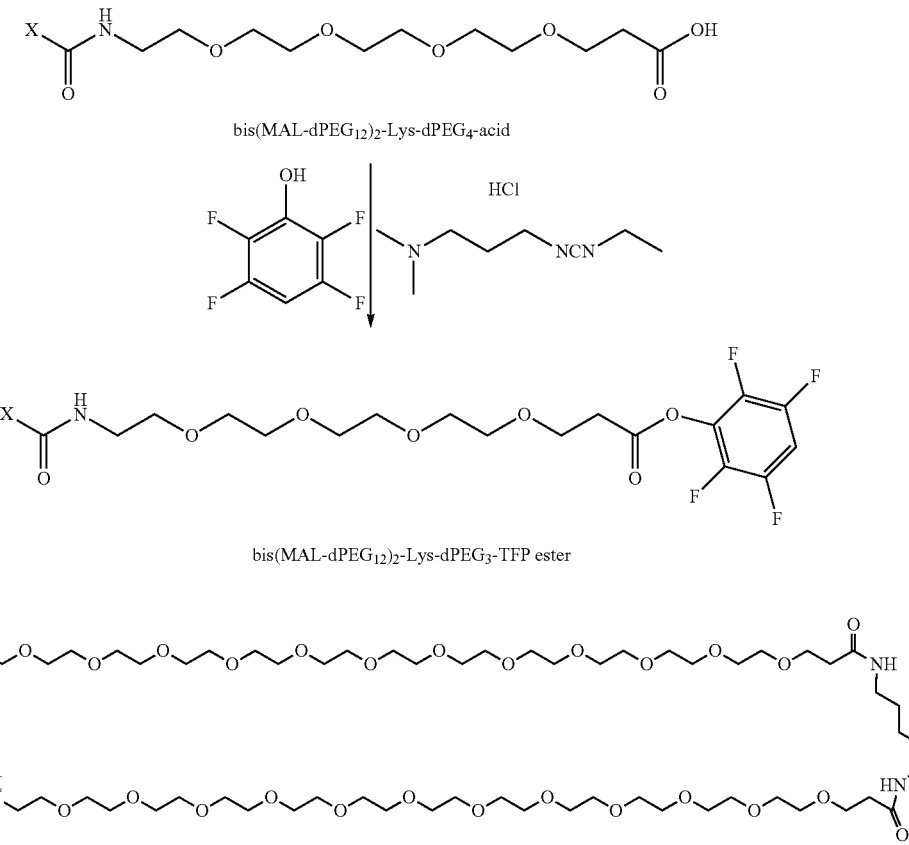

In the glove box under an atmosphere of dry ice and dry nitrogen, a 50 mL, 4-necked RB flask was charged with bis-(MAL-dPEG®12)$_2$-Lysine-dPEG®$_4$-TFP ester (2.4 g, 1.266 mmol) dissolved in dry (over sieves) Dichloromethane (10 ml). The RB flask was fitted with an egg-shaped magnetic stir bar, immersion well, and septa stoppers; transferred to the fume hood; placed in a salted ice-water bath; and fitted with an addition funnel connected by a gas inlet adapter to a bleed of dry nitrogen. Separately, in a 20 mL scintillation vial was dissolved EDC (0.303 g, 1.583 mmol) and 2,3,5,6-tetrafluorophenol (0.263 g, 1.583 mmol) in dry (over sieves) Dichloromethane (1 ml). With stirring, the RB flask was chilled to 0° C. The EDC-TFP solution was then added dropwise. The temperature rose about 4° C., then fell. The solution was stirred in the ice bath for 30 minutes, then removed and heated to 35° C. for 2 hours, before being a 24 g column using DCM (A) and 9:1 EtOH:HCOOH (B). The column was primed with 20% B for 1CV and 0% B for 2CV. A gradient was run at 4% B for 3CV then ramping to 15% B over 10CV and holding at 15% B. The gradient was bumped to 20% B and then 30% B when it appeared the material was tailing off the column. TLC analysis indicated some mixed fractions at the front and the material was tailing at the end. Fractions 6-40 were pooled, concentrated, taken up in DCM, washed with a small amount of brine, dried over MgSO4, filtered over celite, and concentrated under reduced pressure to give 590 mg (19%) of a pale yellow oily solid. HPLC (Acids3045FF method): RT 28.12 min, purity 97.1%. No NMR was obtained for this sample.

Bis(MAL-dPEG$_{12}$)$_2$-Lys-dPEG$_4$-Amido-dPEG$_{12}$-Tris(-dPEG$_{24}$-m)$_3$:

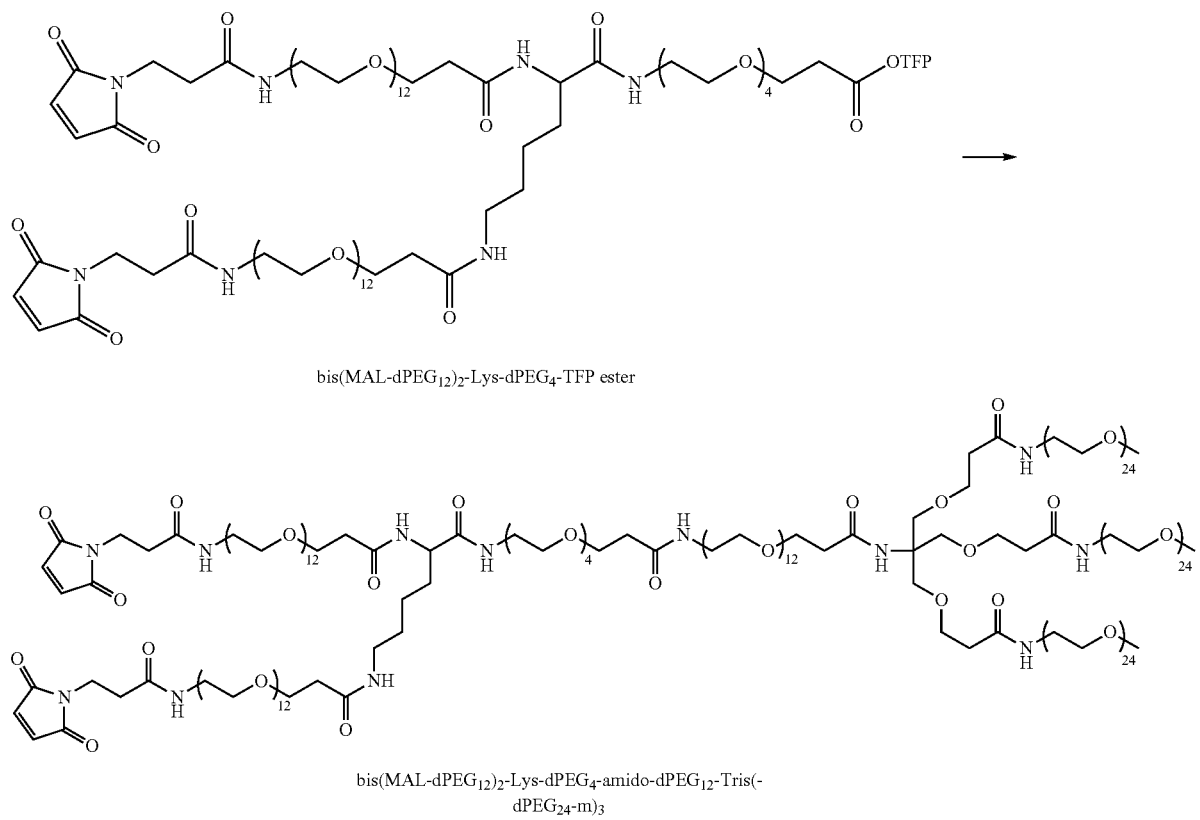
bis(MAL-dPEG₁₂)₂-Lys-dPEG₄-TFP ester
bis(MAL-dPEG₁₂)₂-Lys-dPEG₄-amido-dPEG₁₂-Tris(-dPEG₂₄-m)₃
This material, can be prepared as bis(MAL-dPEG₂)₂-Lys-dPEG₄-amido-dPEG₁₂-Tris(-dPEG₂₄-m)₃.
bis[bis(MAL-dPEG₂)₂-Lys-dPEG₄]₂-dPEG₄-TBE:

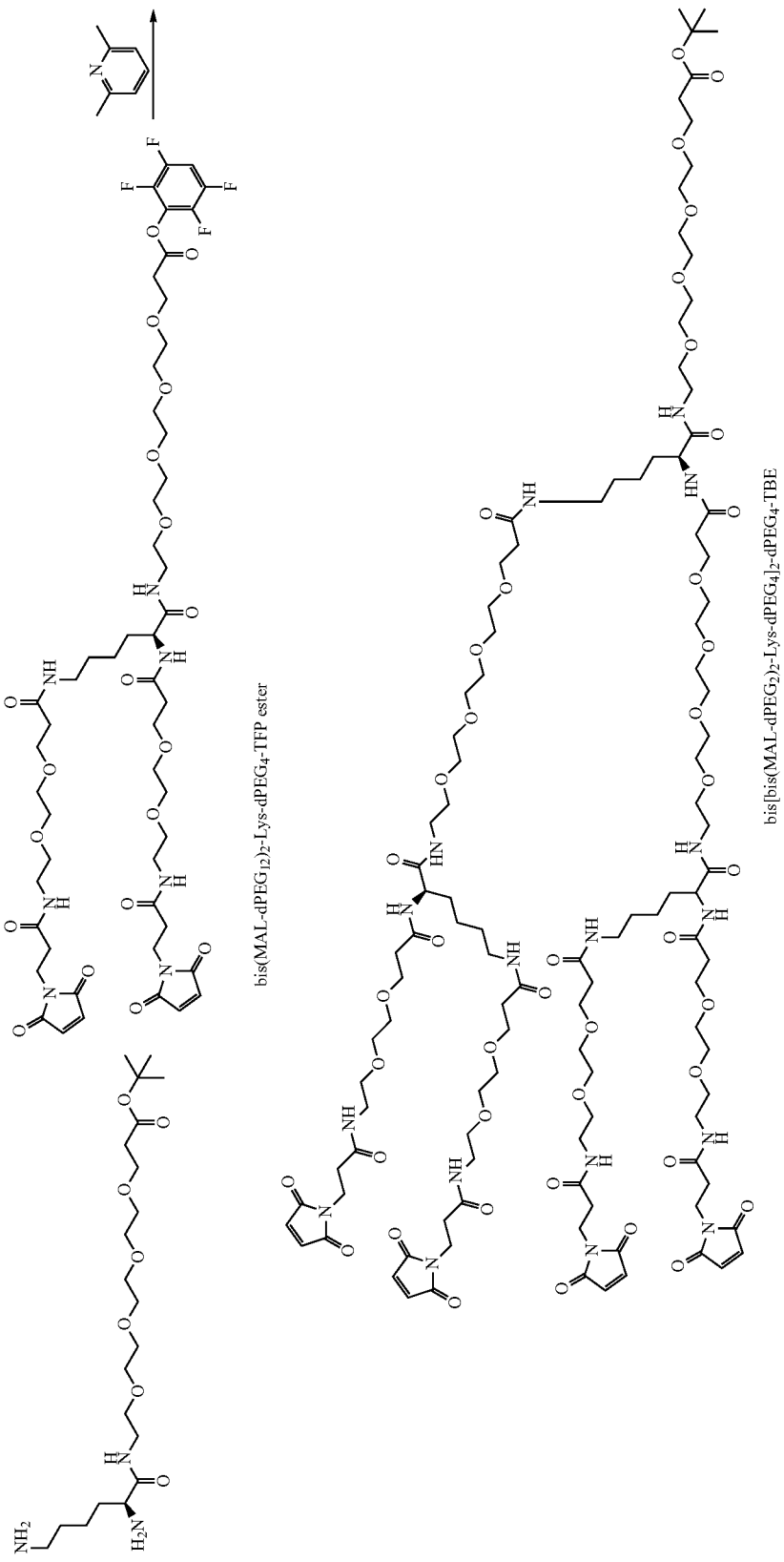

In the glove box under an atmosphere of dry nitrogen, to a 25 mL, 3-necked RB flask fitted with septa stoppers and containing an egg-shaped magnetic stir bar was added bis-(MAL-dPEG®$_2$)-Lysine-dPEG®$_4$-TFP ester (2.741 g, 2.359 mmol) dissolved in dry (over sieves) Dichloromethane (7.0 ml). Separately, in a 7 mL scintillation vial was dissolved Lysine-dPEG®$_4$-TBE (0.507 g, 1.128 mmol) and 2,6-Lutidine (0.350 ml, 3.01 mmol) (dry over sieves) in dry (over sieves) Dichloromethane (1.0 ml). The RB flask (reaction vessel) was transferred to the fume hood and placed in an ambient temperature (20° C.) water bath where it was fitted with an, addition funnel connected by a gas inlet adapter to a bleed of dry nitrogen and an immersion well containing a thermocouple. The amine solution was added by drop. The reaction mixture was stirred another 10 minutes in the ice-water bath, then removed from the bath and placed in a heating mantle set at 35° C., where it was heated and stirred for another hour. The reaction mixture was then checked by RP-HPLC. The reaction appeared complete by RP-HPLC. Returning to check on the reaction, however, it had gelled completely. To the reaction mixture was then added 10 mL of dry (over, sieves) dichloromethane. The reaction was allowed to continue stirring overnight at, ambient temperature. The reaction was completely gelled again the next morning. The reaction mixture was stored in the freezer at −20° C. overnight. The reaction mixture was transferred to a 50 mL Erlenmeyer flask and diluted to 30 mL final volume with dichloromethane. The reaction mixture was washed 3×10 mL with 1.2 M HCl, then 1×10 mL with saturated brine. By TLC, it was clear that some of the product went into the HCl, but not into the saturated brine. The HCl solution containing product was saturated with NaCl, then extracted 3×10 mL with DCM. By TLC no product remained in water. The DCM extracts were combined, and solvent was removed by rotary evaporation at 35° C. Yield: 3.0 grams (109%) Product was stored at −20° C. No further work was done on this product. TLC: 15% MeOH, 85% DCM, 3 drops glacial acetic acid/mL solvent HPLC: ACID3045FF, product elutes at 22.8 minutes. No NMR was obtained for this sample.

Bis[Bis(MAL-dPEG$_2$)$_2$-Lys-dPEG$_4$]$_2$-dPEG$_4$-Acid:

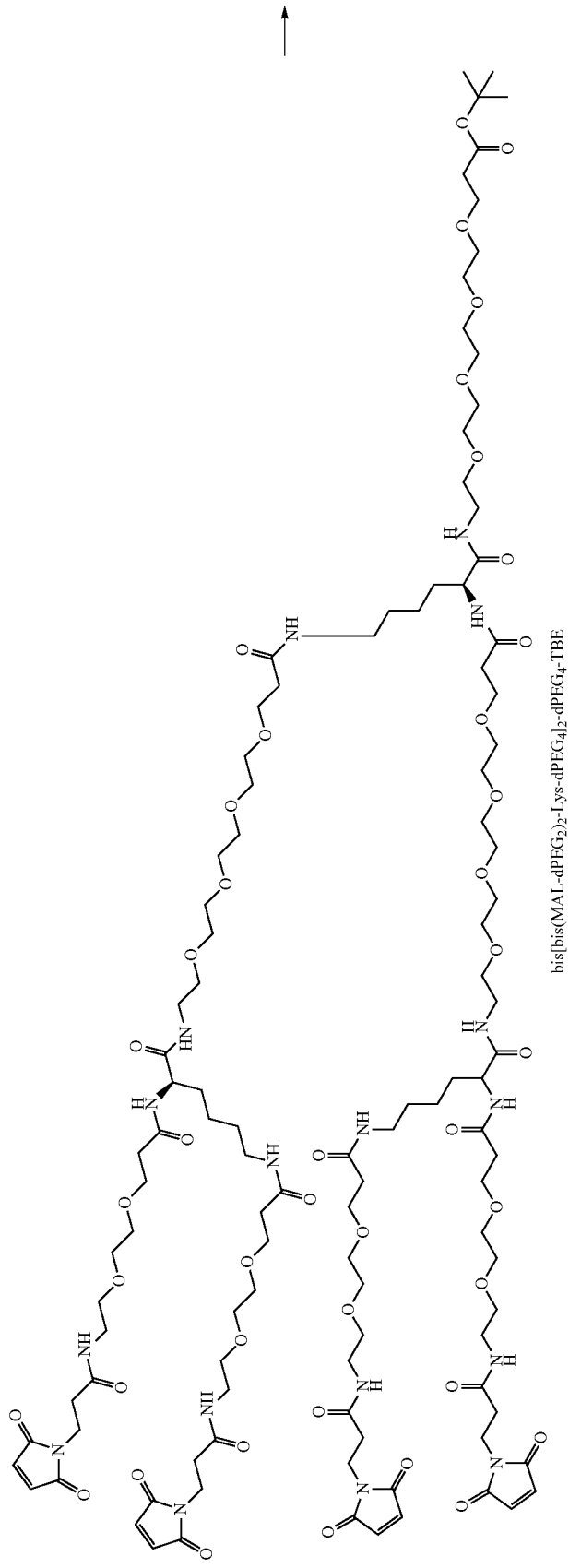
bis[bis(MAL-dPEG₂)₂-Lys-dPEG₄]₂-dPEG₄-TBE

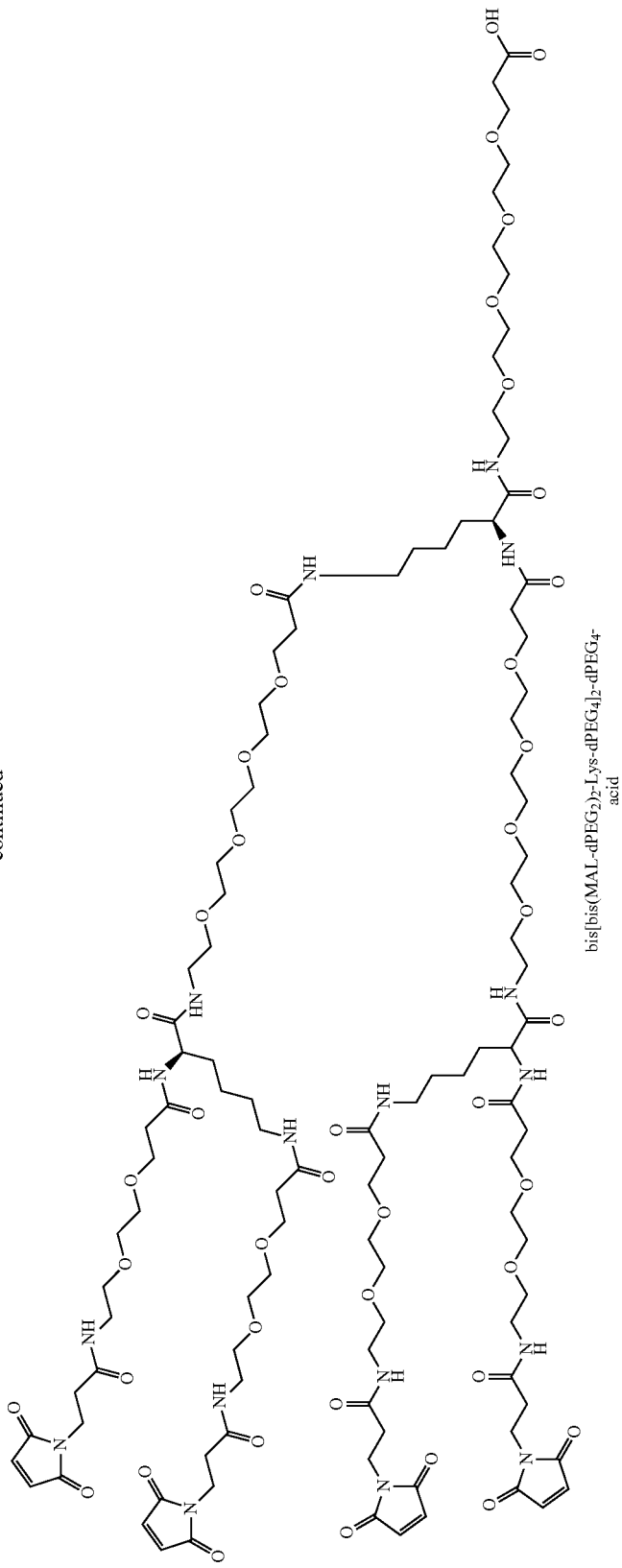
bis[bis(MAL-dPEG₂)-Lys-dPEG₄]₂-dPEG₄-acid

In the glove box under an atmosphere of dry nitrogen, to a 25 mL 3-necked reaction vessel containing an egg-shaped stir bar and septa stoppers was added bis-MAL-dPEG®$_2$-Lysine-dPEG®$_4$-TFP ester (5.49 g, 4.72 mmol) dissolved in Dichloromethane (7.5 ml). Separately, in a 7 mL scintillation vial was dissolved Lysine-dPEG®4-acid (0.885 g, 2.249 mmol), 2,6-Lutidine (0.80 ml, 6.87 mmol), and Dichloromethane (1.5 ml). The reaction vessel was transferred to the fume hood and placed in a water bath. The vessel was fitted with a 10 mL addition funnel connected by a gas inlet adapter to a bleed of dry nitrogen. The addition funnel was charged with the amines solution. With stirring the amines solution was added by drop to the bis-MAL solution. The reaction was allowed to continue for 1 hour and was then checked by RP-HPLC, at which time, the reaction was found to be complete. The reaction mixture was washed 2×2 mL with 10% HCl saturated with brine. The aqueous washes were then combined and extracted 3×2 mL with dichloromethane. The dichloromethane extractions were combined with the organic layer from the reaction, and solvent was removed by rotary evaporation under reduced pressure at 30° C. The residue was taken up in dry dichloromethane and preadsorbed onto silica gel. The product was then purified on a Biotage Isolera Four. An initial gradient of 0%-15% (4:1 Methanol:Formic Acid) in Dichloromethane over 37 column volumes failed to elute the product off the column. An extended gradient of 15%-45% (4:1 Methanol:Formic Acid) in Dichloromethane over 15 column volumes was required to elute the product off the column. Fractions containing pure product were combined; and solvent was removed by rotary evaporation at 40° C. under reduced pressure. The combined pure material was taken up in 20 mL dry-dichloromethane and was 3×5 mL with saturated brine to remove formic acid. The dichloromethane was then removed by rotary evaporation at 30° C. under reduced pressure. A yield of 2.67 grams (49.8%) was obtained. However, the NMR spectrum showed that not all of the formic acid had been removed. Therefore, the product was taken up in a minimum volume of dichloromethane (about 15 mL) and washed 5×2 mL with saturated brine. The dichloromethane was removed as before to give 1.2 grams (22.4%) with a purity of 99.5% by RP-HPLC using ELSD. TLC: 30% Methanol, 70% Dichloromethane plus 5 drops glacial acetic acid/mL solvent. Rf 0.12. HPLC: ACID3045FF using a Supelco Discovery HS C18 column, 25 cm×4.6 mm. Product elutes at 16.405 minutes. Minor impurities at 16.121 minutes and 17.952 minutes. NMR (400 MHz, CDCl$_3$, δ): 7.316 ppm (m, 7H?); 6.997 (br s, 3H); 6.847 (br s, 2H); 6.697 (s, 8H); 4.404 (broad, overlapping multiplets); 3.793 (t, 3H); 3.715 (t, 16H); 3.504 (t, 16H); 3.372 (m, 16H); 3.174 (q, 6H); 3.528 (overlapping triplets, 24H); 1.767 (m, 3H); 1.622 (m, 3H); 1.480 (m, 6H); 1.334 (m, 6H).

Bis[Bis(MAL-dPEG$_2$)$_2$-Lys-dPEG$_4$]$_2$-dPEG$_4$-Amido-dPEG$_{12}$-Tris(-dPEG$_{24}$-m)$_3$:

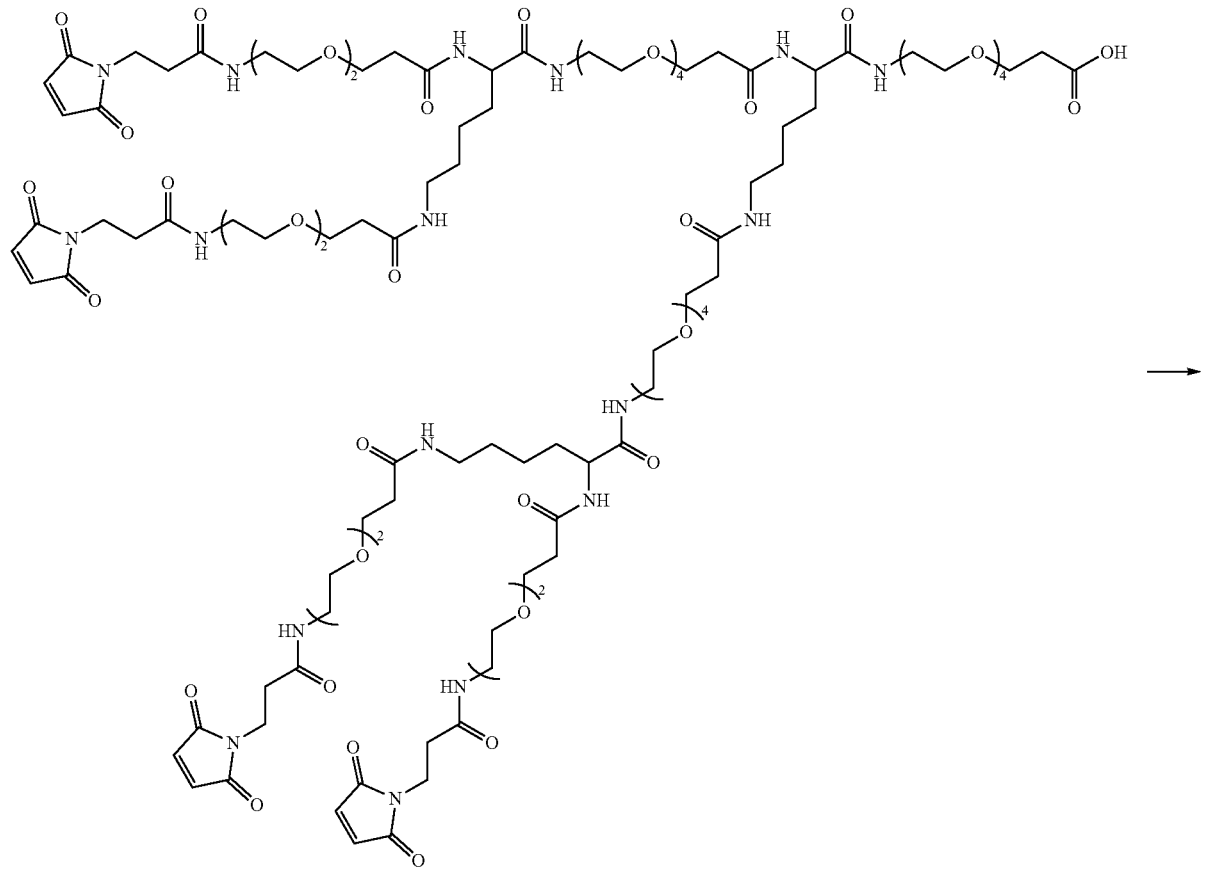

bis[bis(MAL-dPEG$_2$)$_2$-Lys-dPEG$_4$]$_2$-dPEG$_4$-acid

-continued

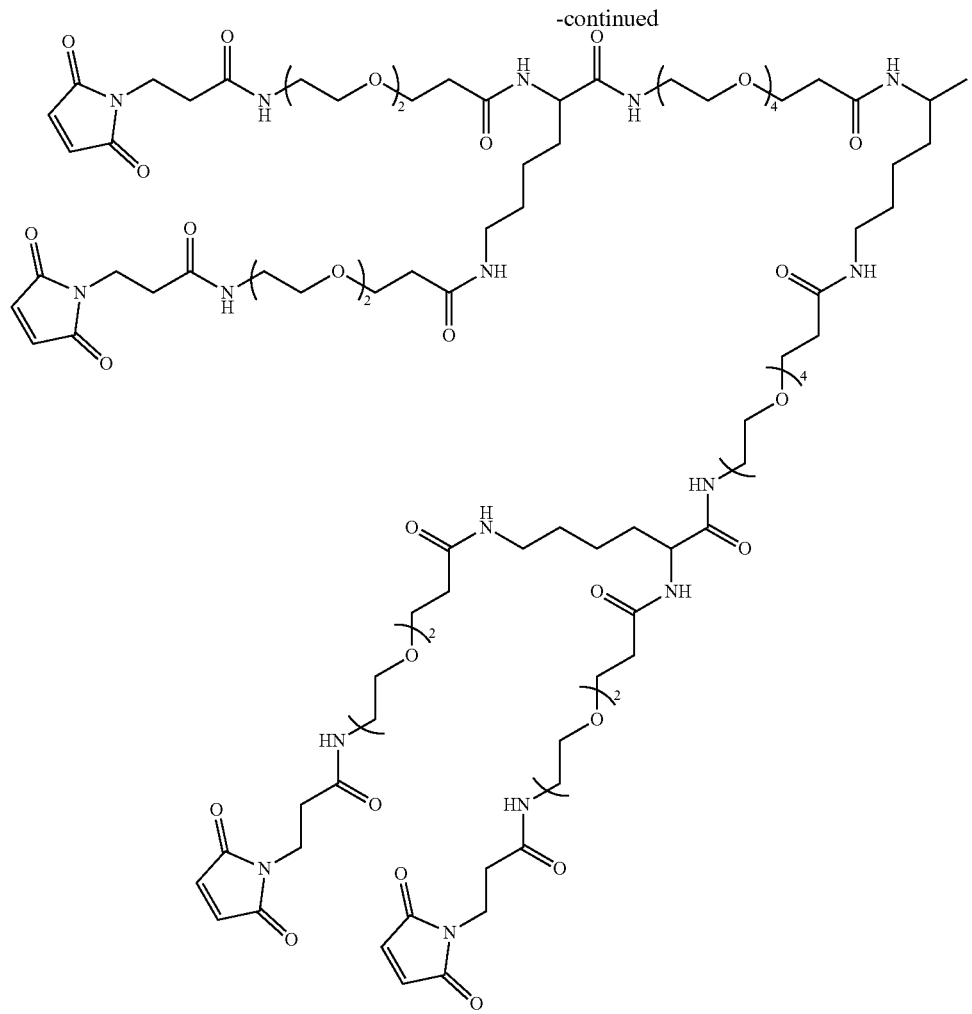

bis[bis(MAL-dPEG2)2-Lys-dPEG4]2-dPEG4-amino-dPEG12-Tris(-dPEG-24--m)3

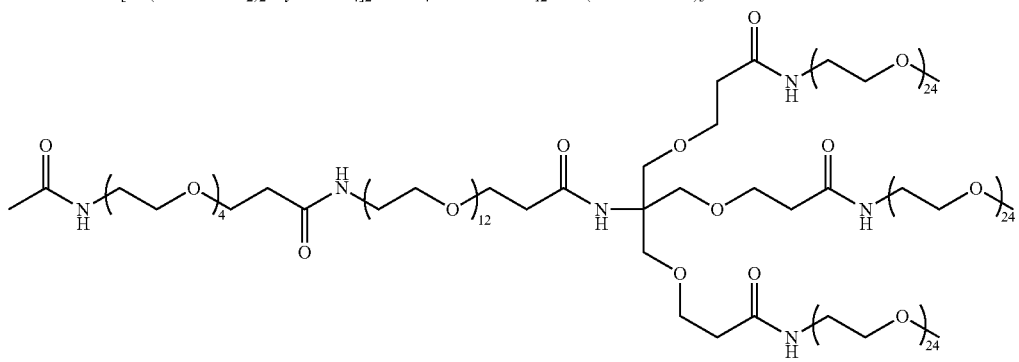

A 25 mL RBF fitted with nitrogen blanket was charged with the PS carbodimide (this lot had a loading of 1.29 mmol/g, so 327 mg were added). Bis[bis(mal-2)2Lys-4]2-Lys-4-acid (0.604 g, 0.253 mmol) was dissolved in DMF (4.22 ml) and added to the resin and the mixture was stirred for 15 minutes. H2N-12-tris(24-m)3 (0.7 g, 0.169 mmol) was added in a single portion and the reaction was stirred at room temp for 72 h. HPLC (Amines3045FF method) still indicated the starting amine and the tetra(mal). There were multiple products seen along with one major product. HPLC (Acids3045FFmethod) indicated one major product. The resin was filtered off over celite and rinsed with DCM. The solvent was removed under reduced pressure and 2 mL ACN was added to the DMF solution. 8 mL of $Et_2O$ was dripped in until cloudiness. 1 g of celite was added and 16 mL additional $Et_2O$ was dripped in. The celite was filtered off, finished with 5% ACN/$Et_2O$ (2×25 mL), and then washed off with DCM. The DCM was removed under reduced pressure and trituration provided 951 mg of a white powdery solid. Reverse phase TLC suggested a gradient of $H_2O$/MeOH would separate the mixture. The sample was dissolved in water and purified on an Isco Rf using a Biotage 60 g C18 column, H₂O (A), and MeOH (B). The column was primed with 10% B and the sample was liquid loaded. A gradient was run at loom) for 1CV then ramping to 60% B over 8CV and holding at 60% B until the first peak eluted. It was then ramped to 85% to elute the second peak and then flushed with 100% B. 16-22 were pooled and concentrated to give 113 mg (10%) of a pale yellow powdery solid. The NMR indicated the presence of a small amount ring-opened maleimic acid, but as this would not interfere with subsequent conjugation it was used without further purification.

HPLC (Acids3045FF method): RT 27.25 min, purity 94.2%. $^1$H NMR (400 MHz, CDCl$_3$, δ): 7.53-7.07 (overlapping m, 11H), 6.95. (m, 3H), 6.85-6.62 (overlapping m and maleimide s, 11H), 6.54 (br, 1H), 4.41 (m, 3H), 3.89-3.22 (overlapping m and MeO s, 459H), 3.17 (m, 8H), 2.60-2.32 (overlapping t, 30H), 1.77 (m, 3H); 0.1.64 (m, 3H), 1.48 (m, 6H), 1.31 (m, 6H).

Example 2

Preparation of Exendin Conjugates

Materials

Exendin 4-Cys (Exe-4) was synthesized by Ohio Peptide using solid phase peptide synthesis techniques and purified by reverse phase HPLC. Exe-C contains the 39 amino acids of native exendin 4, a Gila monster salivary protein, attached to a C-terminal cysteine.

Conjugation

The following conjugates were prepared:
1. Exe-4-S—N-Ethyl Malimide
2. Exe-4-S-MAL-m-dPEG-12
3. Exe-4-S-MAL-dPEG12-Tris(m-dPEG-24)₃
4. (Exe-4-S-MAL-dPEG-2)2-dPEG-Lysine-dPEG-4-amido-dPEG-12-Tris(m-dPEG-24)₃

The conjugation reactions for Compounds 2-4 (see above) contained 1.6 mL of 1.25 mg/mL Exe-4 in deionized water, 0.2 mL of a 1 M sodium phosphate buffer (pH 6.5) containing 10 mM EDTA, and 0.2 mL of a 20 mM solution of the maleimide compound dissolved in dimethylacetamide. After incubation for 1 hour at room temperature, 0.2 mL of a 100 mM solution of N-ethylemaleimide was added to each reaction. The reactions were allowed to proceed for an additional 15 minutes at room temperature and then concentrated to 1.5 mL via a centrifugal concentrator. The products were stored at 4° C. prior to purification.

The conjugation reaction for Compound 1 (see above) contained 1.6 mL of 1.25 mg/mL Exe-4, 0.2 mL of a 1 M sodium phosphate buffer (pH 6.5) containing 10 mM EDTA, and 0.2 mL of a 100 mM solution of N-ethylmaleimide (Compound 1) dissolved in dimethylacetamide. The reaction was allowed to proceed at room temperature for 1 hour, concentrated to 1.5 mL, and then stored at 4° C. prior to purification.

Purification

The Exe-4 conjugates were purified on a Superdex 75 column (Hi Load 16/600, GE Healthcare) equilibrated in a 0.05 M sodium phosphate buffer (pH 7.2) containing 0.15 M sodium chloride at a flow rate of 1.0 mL/minute.

Example 3

Attachment Core Ac and Template Related Examples

PhthN-dPEG₄-Tyr-OBn

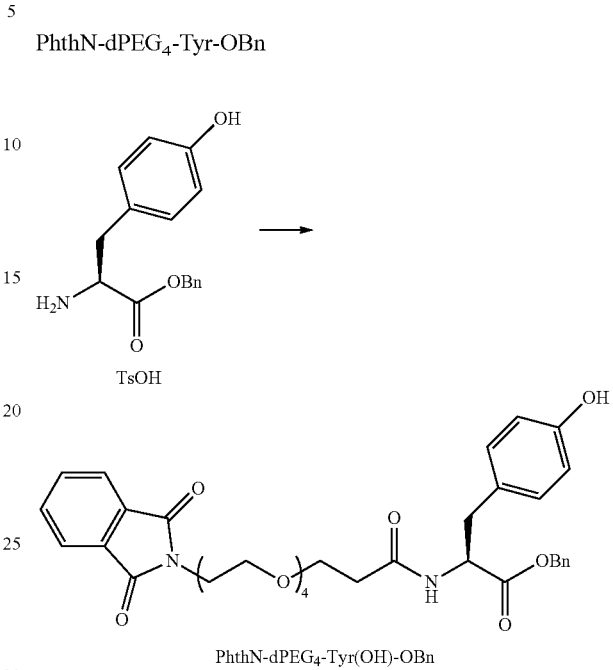

PhthN-dPEG₄-Tyr(OH)-OBn

A 1 L 3-neck RBF fitted with nitrogen blanket and cooling bath was set up for this reaction. PhthN-4-acid (17.6 g, 44.5 mmol) was dissolved in the flask followed by N-methyl morpholine (14.41 ml, 142 mmol) and H₂N-Tyr(OH)-OBn toluene sulfonate (21.72 g, 49.0 mmol). HOBt hydrate (1.128 g, 6-68 mmol) was added in a single portion and the mixture was stirred for 10 minutes and then cooled in an ice bath. EDC (12.80 g, 66.8 mmol) was added in a single portion and the reaction was slowly allowed to warm to room temp overnight. HPLC (Acid4020 method) indicated complete consumption of sm and formation of a less polar product. TLC (95:5 and 90:10 DCM:IPA) also indicated complete consumption of dPEG. The solvent was removed under reduced pressure and the residue was taken up in 300 mL H₂O and extracted with EtOAc (3×300 mL). TLC indicated the product had been extracted. They were washed with 10% HCl (3×75 mL), sat aq NaHCO₃ (3×75 mL), brine (50 mL), dried over Na₂SO₄, filtered over celite, and concentrated under reduced pressure to give 26.7 g of a viscous dark yellow oil. The oil was preabsorbed onto 50 g of SiO2 and purified on an Isco Rf using a 330 g column, DCM (A), and IPA (B). The column was primed with 15% B for 1CV and 0% B for 2CV. The SLSC was inserted and a gradient was run at 0% B for 1CV and ramping to 5% B over 4CV. The gradient was held at 5% B until the impurity eluted and was then ramped to 10% B over 4CV and held at 10% for 5CV. TLC analysis indicated fractions 14-42 were pure so they were pooled and concentrated to give 23.45 g (81%) of a cloudy viscous pale yellow oil. TLC analysis (90:10 DCM:IPA) confirmed the pure product was a single spot by TLC. HPLC (Acid4020 method): RT 15.42 min, purity 100%. $^1$H NMR (400 MHz, CDCl$_3$, δ): 7.83 (m, 2H), 7.71 (m, 2H), 7.38 (m, 5H), 7.14 (s, 1H), 7.00 (d, 1H), 6.83 (d, 2H), 6.69 (d, 2H), 5.15 (dd, 2H), 4.92 (m, 1H), 3.90 (t, 2H), 3.75-3.25 (m, 16H), 3.04 (d, 2H), 2.48 (m, 2H).

PthN-dPEG₁₂-Tyr-OBn

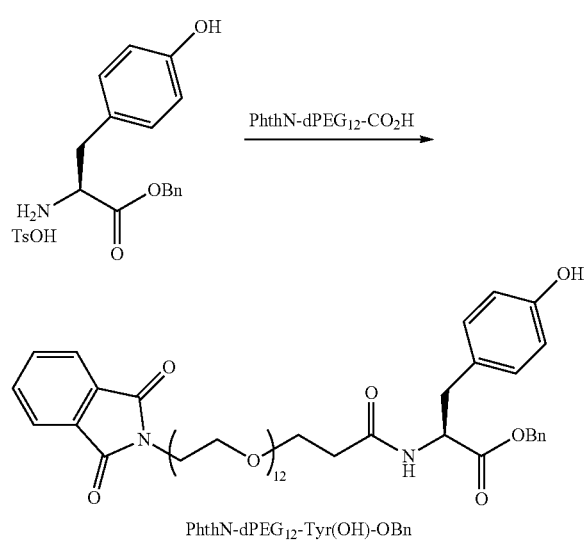

A 250 mL 3-neck RBF fitted with nitrogen blanket and cooling bath was set up for this reaction. PhthN-12-acid (10 g, 13.37 mmol) was dissolved followed by N-methyl morpholine (4.33 ml, 42.8 mmol) and H$_2$N-(Tyr-OH)-OBn toluene sulfonate (6.52 g, 14.71 mmol). HOBt hydrate (0.339 g, 2.006 mmol) was added in a single portion and the mixture was stirred for 10 minutes and then cooled in an ice bath. EDC (3.85 g, 20.06 mmol) was added in a single portion and the reaction was slowly allowed to warm to room temp overnight. HPLC (Acid60 method) indicated complete consumption of sm and formation of a less polar product. TLC (95:5 and 90:10 DCM:IPA) also indicated complete conversion. The solvent was removed under reduced pressure and the residue was taken up in 120 mL H2O and extracted with EtOAc (3×100 mL). TLC indicated the product had been extracted. They were washed with 10% HCl (3×25 mL), sat aq NaHCO$_3$ (3×25 mL), brine (50 mL), dried over Na$_2$SO$_4$, filtered over celite, and concentrated under reduced pressure to give 13.6 g of a viscous dark yellow oil. HPLC (Acids60 method) indicated a single product with 98% purity by ELSD and 100% by 254. There was a small amount of a more polar impurity. TLC (95:5 and 90:10 DCM:IPA) also indicated a single major spot with a small amount of a less polar impurity. The oil was preabsorbed onto 30 g of SiO$_2$ and purified on an Isco Rf using a 120 g column, DCM (A), and IPA (B). The column was primed with 15% B for 1CV and 0% B for 2CV. The SLSC was inserted and a gradient was run at 0% B for 1CV and ramping to 5% B over 5CV. The gradient was held at 5% B until the impurity eluted and was then ramped to 10% B over 4CV and held at 10% for 5CV. The gradient was then increased to 15% B to finish eluting product. TLC analysis indicated fractions 14-60 were pure product so they were pooled and concentrated to give 10.98 g of a cloudy viscous pale yellow oil. HPLC (Acid60 method): RT 10.80 min, purity 99%. $^1$H NMR (400 MHz, CDCl$_3$, δ): 7.84 (m, 2H), 7.49 (s, 1H), 7.72 (m, 2H), 7.35 (m, 5H), 7.01 (d, 1H), 6.85 (d, 2H), 6.73 (d, 2H), 5.15 (dd, 2H), 4.92 (m, 1H), 3.90 (t, 2H), 3.75-3.31 (m, 50H), 3.05 (d, 2H), 2.48 (m, 2H).

PhthN-dPEG$_{12}$-Tyr(-dPEG$_4$-TBE)-OBn:

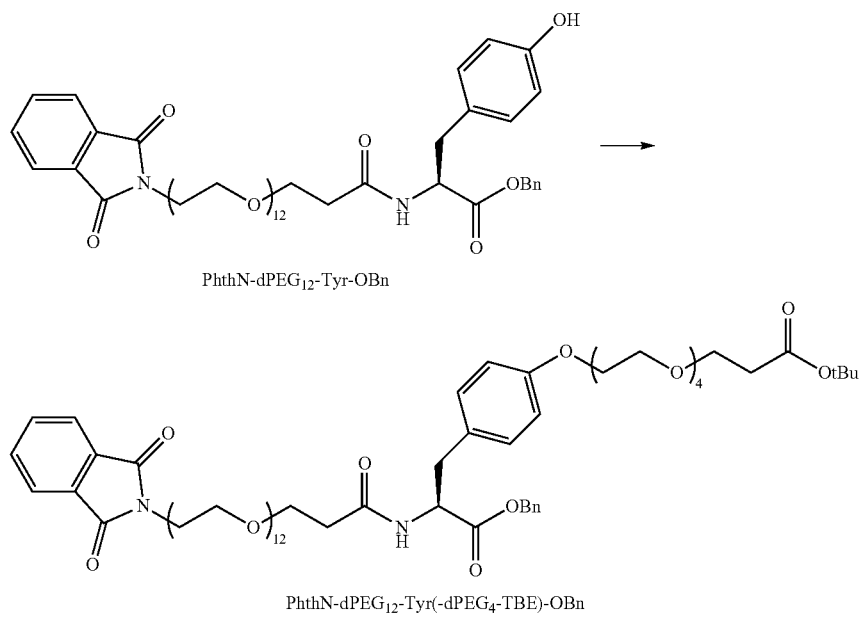

A 50 mL RBF fitted with addition funnel and cooling bath was charged with PhthN-12-Tyr(OH)-OBn (5 g, 4.99 mmol) and HO-4 TBE (1.932 g, 5.99 mmol). THF (15.98 ml) was added and after complete dissolution Triphenylphosphine (1.703 g, 6.49 mmol) was added and the mixture was cooled in an ice bath. Diisopropyl azodicarboxylate (1.262 ml, 6.49 mmol) was dissolved in THF (4.00 ml) and placed in the addition funnel and was added dropwise and the reaction was allowed to slowly warm to room temp overnight. HPLC (Acid60 method) indicated a trace of the starting phenol and the HO-4-TBE so additional Triphenylphosphine (0.262 g, 0.999 mmol) was added followed by additional Diisopropyl azodicarboxylate (0.194 ml, 0.999 mmol). TLC (2/1 DCM/hexanes and EtOH) indicated a single major product. The solvent was removed under reduced pressure and the residue was taken up in water (120 mL) and extracted with toluene (3×30 mL). TLC analysis indicated the product and the PPh₃O were extracted by the toluene. The extracts were combined, washed with brine, dried over Na₂SO₄, filtered over celite, and concentrated under reduced, pressure to give 10.224 g of a viscous yellow oil. The residue was pre-absorbed on to 15 g of SiO₂ and purified on an Isco Rf on a 120 g column using 2/1 DCM/hexanes (A) and EtOH (B). The column was primed with 10% B for 1CV and 0% B for 2CV. The SLSC was, inserted and a gradient was run at 0% B for 2CV and ramping to 5% B over 5CV. The gradient was held at 5% B for 1/2 CV and was then ramped to 10% B over 2CV and held at 10% for 5CV. TLC analysis indicated fractions 1.7-33 were pure so they were pooled and concentrated to give 4.479 g of a clear pale yellow viscous oil. Despite the good TLC and HPLC profiles, NMR indicated there was approximately 45 mol % of the isopropyl ether from coupling with residual IPA. This corresponded to a yield of 2.7 g (41.4%) of the desired product. Since this could be removed after the next step, no further purification was attempted. TLC (2/1 DCM/hexanes and EtOH) indicated a single spot. HPLC (Acids60 method): RT 15.36 min, purity 98.6%.

¹H NMR (400 MHz, CDCl₃, δ): 7.82 (m, 2H), 7.69 (m, 2H), 7.33 (m, 3H), 7.27 (m, 2H), 6.92 (dd, 2H), 6.78 (m, 1H), 6.72 (dd, 2H), 5.11 (m, 2H), 4.84 (m, 1H), 4.46 (q, 0.4H), 4.05 (br t, 2H), 3.91-3.48 (m, 61H), 3.02 (m, 2H), 2.50-2.41 (overlapping t, 4H), 1.41 (s, 5.3H), 1.29 (d, 2.6H). PhthN-dPEG₁₂-Tyr(-dPEG₄-acid)-OBn:

A 100 mL RBF was charged with the mixture of PhthN-12-Tyr(O-4-TBE)-OBn (2.45 g, 1.877 mmol) and PhthN-12-Tyr(O-iPr)-OBn (1.55 g, 1.486 mmol). Formic acid (3.60 ml, 94 mmol) was added and the reaction was heated at 30° C. for 48 h. The mixture was diluted in DCM, washed with water, washed, with brine, dried over Na₂SO₄, filtered over celite, and concentrated under reduced pressure to give 4.879 g of a viscous yellow oil. The residue was pre-absorbed on to 10 g of SiO₂ and purified on an Isco Rf using a 40 g column, 2/1 DCM (A), and EtOH (B). The column was primed with 10% B for 1CV and 0% B for 2CV. The SLSC was inserted and a gradient was run at 0% B for 1CV and ramping to 5% B over 5CV. The gradient was held at 5% B for 5 CV until the first peak had eluted and was then ramped to 20% B over 4CV and held at 20% for 5CV. It was finally increased to 30% B. TLC analysis indicated very poor separation and much of the product came out with the impurity. Fractions 4-6 were pooled and concentrated to give 1.896 g of a pale yellow oil. Fractions 7-40 were pooled and concentrated to give 1.248 g of a pale yellow oil. Fractions 4-6 were again subjected to chromatography on the same reconditioned column. The sample was liquid loaded with DCM and a gradient was run at 2% B for 2CV and ramping to 5% B over 5CV. The gradient was then ramped to 30% B over 4CV and held at 30% for 5CV. TLC analysis indicated better separation, however there were still a few mixed fractions. Fractions 10-19 were pooled and concentrated to give 0.695 g of a pale yellow oil that was mainly unconverted i-Pr ether by HPLC and NMR. Fractions 20-31 were

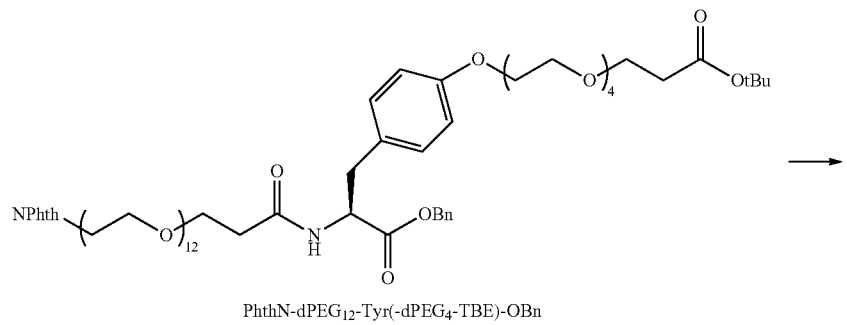

PhthN-dPEG₁₂-Tyr(-dPEG₄-TBE)-OBn

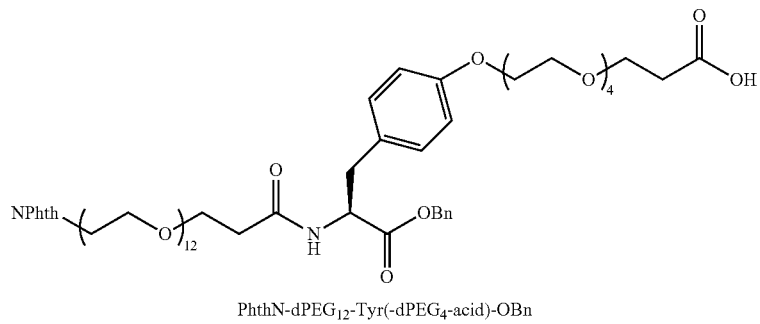

PhthN-dPEG₁₂-Tyr(-dPEG₄-acid)-OBn pooled, combined with the pure portion from the first run, and concentrated to 1.686 g (72%) of a pale yellow oil. TLC analysis indicated a single major spot. HPLC (Acids60 method): RT 11.43 min, purity 99.4%. $^1$H NMR (400 MHz, CDCl$_3$, δ): 7.85 (m, 2H), 7.72 (m, 2H), 7.35 (m, 3H), 7.28 (m, 2H), 6.94 (dd, 2H), 6.78 (m, 1H), 6.76 (dd, 2H), 5.11 (m, 2H), 4.84 (m, 1H), 4.09 (m, 2H), 3.93-3.82 (m, 4H), 3.79-3.43 (m, 63H), 3.03 (m, 2H), 2.56 (t, 2H), 2.48 (dt, 2H). PhthN-dPEG$_{12}$-Tyr(-Et-NH-boc)-OBn:

PhthN-dPEG$_{12}$-Tyr(-Et-NH-boc)-OH:

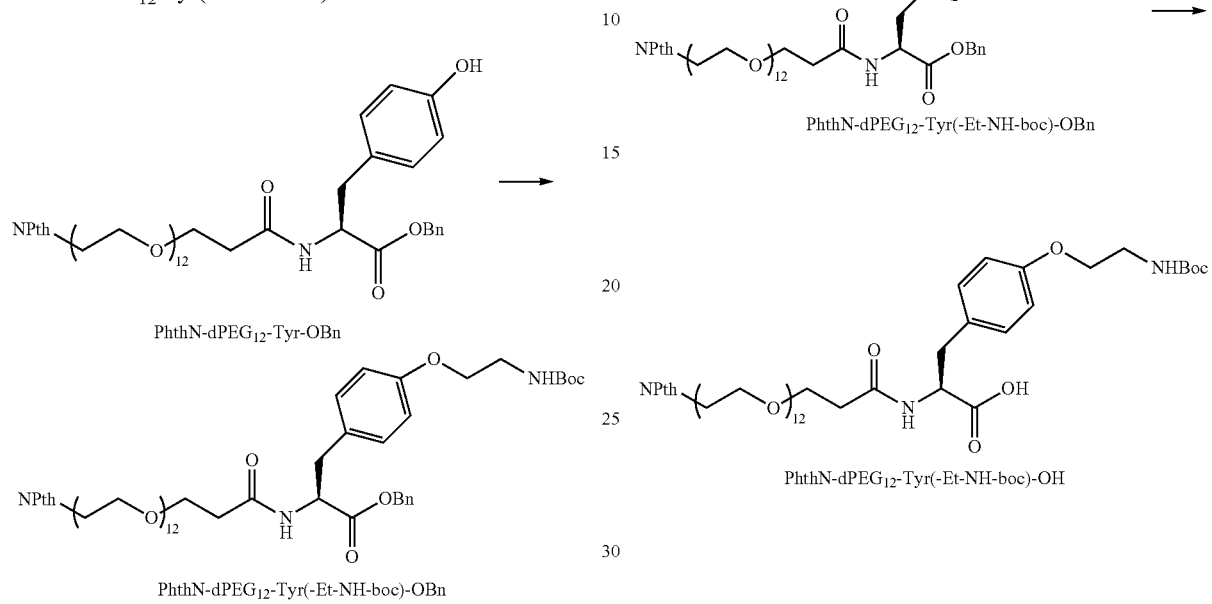

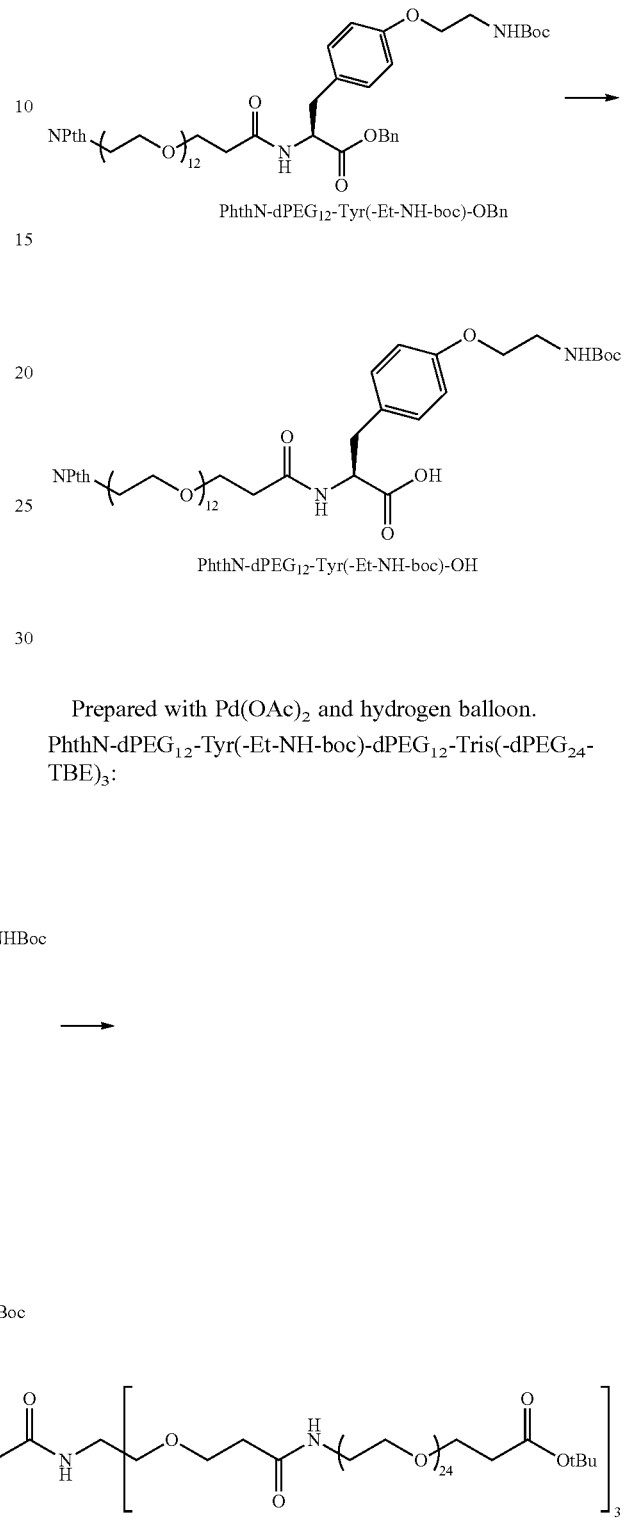

Prepared using PhthN-dPEG$_{12}$-Tyr-OBn (5 g, 4.99 mmol) and commercially available HO-Et-NHBoc.

Prepared with Pd(OAc)$_2$ and hydrogen balloon.

PhthN-dPEG$_{12}$-Tyr(-Et-NH-boc)-dPEG$_{12}$-Tris(-dPEG$_{24}$-TBE)$_3$:

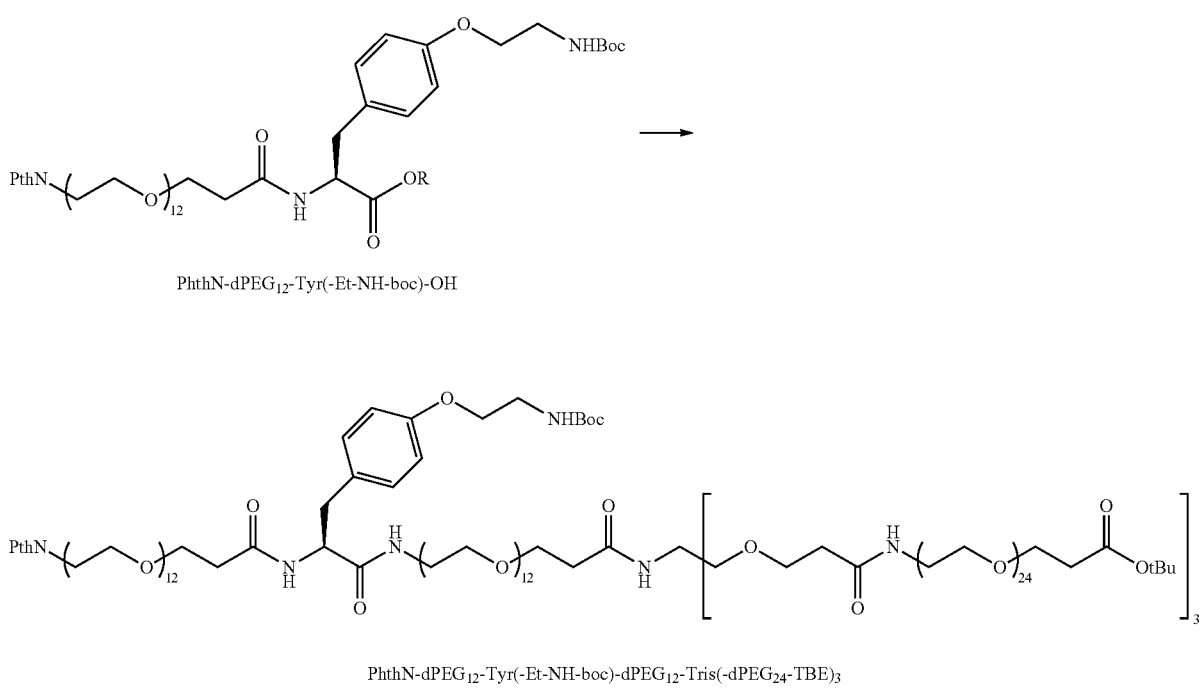

Prepared using PthN-dPEG12-Tyr(-Et-NHBoc)-OH and H$_2$N-dPEG$_{12}$-Tris(-dPEG$_{24}$-TBE)$_3$.

PhthN-dPEG$_{12}$-Tyr(-Et-NH$_2$)-dPEG$_{12}$-Tris(-dPEG$_{24}$-TBE)$_3$:

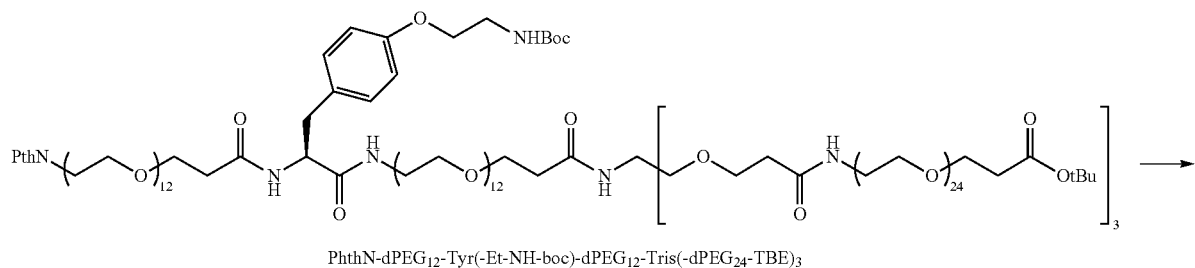

PhthN-dPEG$_{12}$-Tyr(-Et-NH-boc)-dPEG$_{12}$-Tris(-dPEG$_{24}$-TBE)$_3$

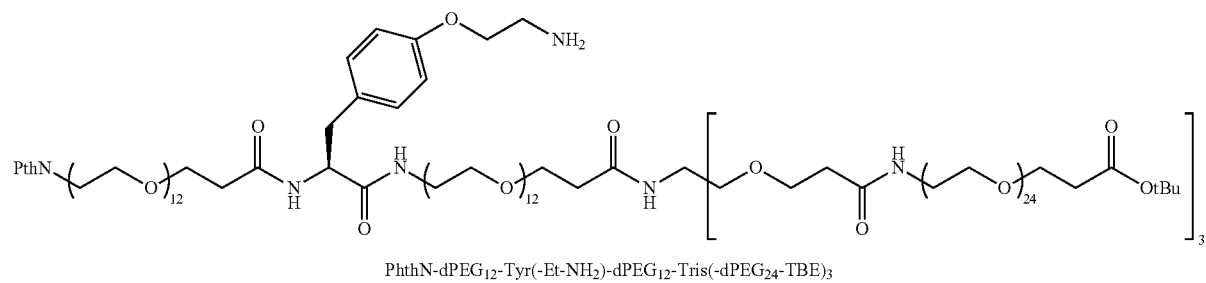

PhthN-dPEG$_{12}$-Tyr(-Et-NH$_2$)-dPEG$_{12}$-Tris(-dPEG$_{24}$-TBE)$_3$

Prepared using PhthN-dPEG$_{12}$-Tyr(-Et-NHBoc)-dPEG$_{12}$-Tris(-dPEG$_{24}$-TBE)$_3$ anhydrous HCl/dioxane at 0 C for 30 min.

PhthN-dPEG$_{12}$-Tyr(-Et-NH-dPEG$_{12}$-ICG)-dPEG$_{12}$-Tris(-dPEG$_{24}$-TBE)$_3$:

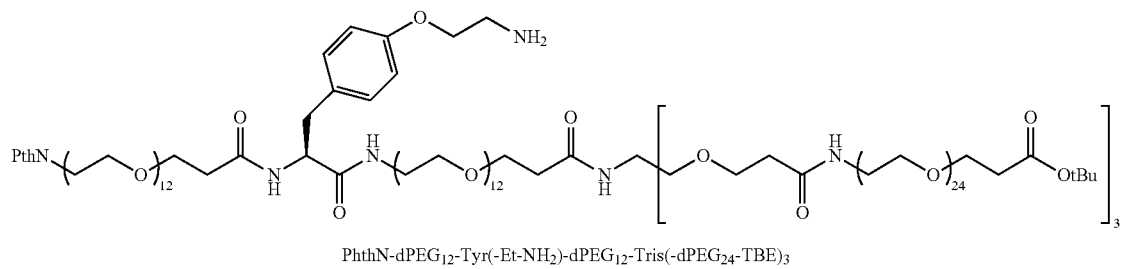

PhthN-dPEG$_{12}$-Tyr(-Et-NH$_2$)-dPEG$_{12}$-Tris(-dPEG$_{24}$-TBE)$_3$

-continued

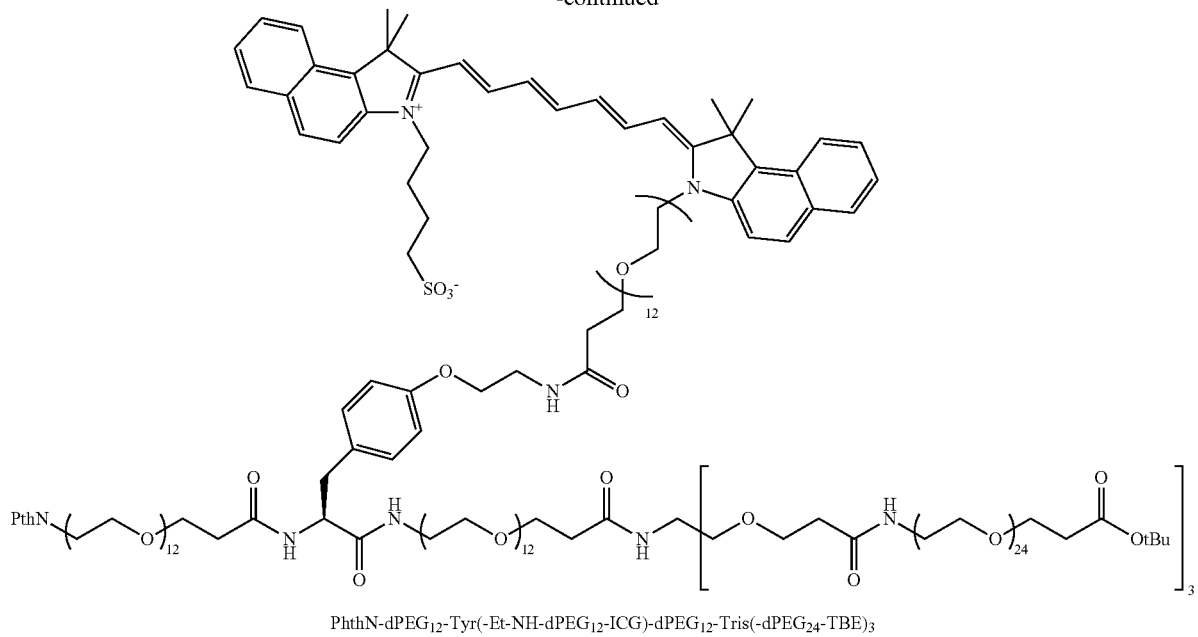

PhthN-dPEG$_{12}$-Tyr(-Et-NH-dPEG$_{12}$-ICG)-dPEG$_{12}$-Tris(-dPEG$_{24}$-TBE)$_3$ Prepared using PthN-12-Tyr(O-Et-NH$_2$)-12-tris(24-TBE)$_3$ and ICG-12-NHS.

PhthN-dPEG$_{12}$-Tyr(-dPEG$_{12}$-TBE)-OBn:

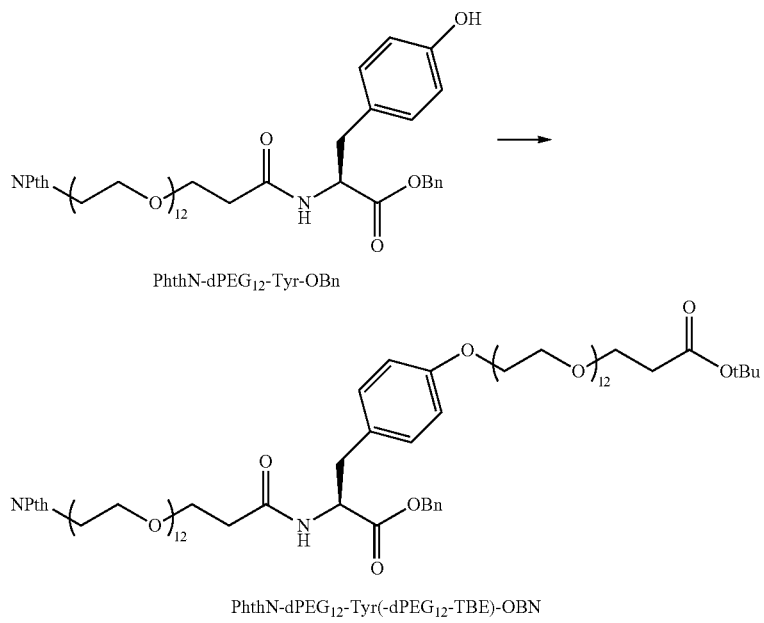

PhthN-dPEG$_{12}$-Tyr-OBn

PhthN-dPEG$_{12}$-Tyr(-dPEG$_{12}$-TBE)-OBN

A 50 mL RBF fitted with addition funnel and cooling bath was charged with PhthN-12-Tyr(OH)-OBn (2.5 g, 2.497 mmol) and HO-12-TBE (2.022 g, 3.00 mmol). THE (13.32 ml) was added and after complete dissolution Triphenylphosphine (0.851 g, 3.25 mmol) was added. The flask was cooled in an ice bath. Diisopropyl azodicarboxylate (0.631 ml, 3.25 mmol) was dissolved in THF (3.33 ml), placed in the addition funnel, added dropwise, and the reaction was allowed to slowly warm to room temp overnight. HPLC (Acid60method) indicated a major product, and several minor products as well as a trace of residual phenol. TLC (90:10 DCM:IPA and 80:20 2/1 DCM/EtOAc: IPA) indicated one major product and several minor spots.

The solvent was removed under reduced pressure and the residue was taken up in water (80 mL) and washed with 2/1 EtOAc/hexanes (3×15 mL). TLC analysis indicated PPh$_3$O and some of the less polar spots were extracted while the product mainly stayed in the water. It was washed once more with EtOAc/hexanes. The aq layer was salted and extracted with toluene (2×20 mL), the extracts were combined, washed with brine, dried over. Na$_2$SO$_4$, filtered over celite, and concentrated under reduced pressure to give 2.42 g of a viscous yellow oil. The residue was preabsorbed onto 4 g of SiO$_2$ and purified on the Rf on a 40 g column using 2/1 DCM/EtOAc (A) and IPA (B). The column was primed with 20% B for 1CV and 0% B for 2CV. The SLSC was inserted and a gradient was run at 5% B for 3CV and ramping to 20% B over 11CV and holding at 20% B until eluted. TLC analysis indicated fractions 1-20 contained, impurities while 21-24 were mixed with product: Pure product was in fractions 25-50 and these were pooled and concentrated to 1.096 g (27%.) of a clear pale yellow viscous oil. TLC (90:10 DCM:IPA and 80:20 2/1 DCM/EtOAc:IPA) indicated a single spot. HPLC (Acids60 method): RT 15.19 min, purity 100%.

$^1$H NMR (400 MHz, CDCl$_3$, δ): 7.83 (m, 2H), 7.72 (m, 2H), 7.34 (m, 3H), 7.28 (m, 2H), 6.94 (dd. 2H), 6.80 (br, 1H), 6.76 (dd, 2H), 5.12 (m, 2H), 4.86 (m, 1H), 4.07 (t, 2H), 3.89 (t, 2H), 3.87-3.67 (m, 96H), 3.03 (m, 2H), 2.54-2.38 (overlapping t, 4H), 1.44 (s, 9H).

PhthN-dPEG$_{12}$-Tyr(-dPEG$_{12}$-TBE)-OH:

reduced pressure to give 1.102 g of a viscous yellow oil. HPLC indicated 100% purity, however TLC (90:10 DCM: MeOH) indicated a trailing baseline impurity. The residue was preabsorbed onto 2 g of SiO$_2$ and purified on the Rf on a 12 g column using DCM (A) and MeOH (B). The column was primed with 20% B for 1CV and 0% B for 2CV. The SLSC was inserted and a gradient was run at 0% B for 2CV and ramping to 14% B over 18CV and holding at 18% B.

TLC analysis indicated fractions 16-38 were pure product so they were pooled and concentrated to give 806 mg (84%) of a clear pale yellow oil. HPLC (Acids60 method): RT 12.31 min, purity 100%. $^1$H NMR (400 MHz, CDCl$_3$, δ): 7.83 (m, 2H), 7.72 (m, 2H), 7.09 (dd. 2H), 6.99 (br d, 1H), 6.81 (dd, 2H), 4.76 (m, 1H), 4.08 (t, 2H), 3.89 (t, 2H), 3.87-3.67 (m, 96H), 3.09 (m, 2H), 2.54-2.38 (overlapping t, 4H), 1.44 (s, 9H).

PhthN-dPEG$_{12}$-Tyr(-dPEG$_{12}$-NHBoc)-OBn:

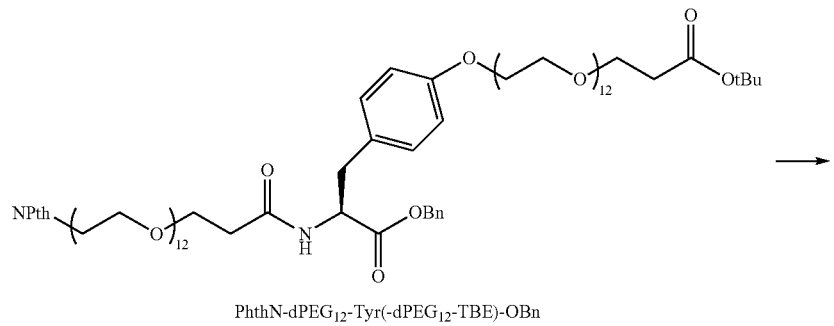

PhthN-dPEG$_{12}$-Tyr(-dPEG$_{12}$-TBE)-OBn

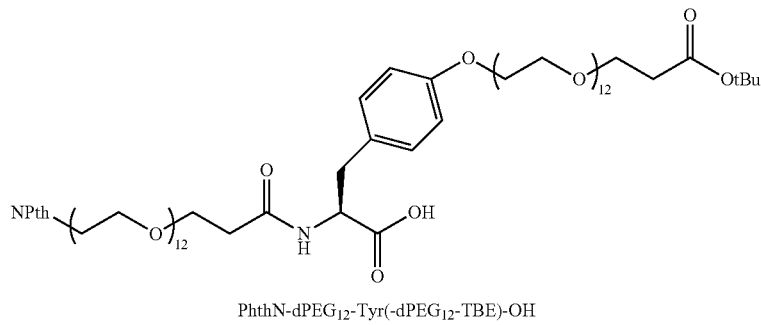

PhthN-dPEG$_{12}$-Tyr(-dPEG$_{12}$-TBE)-OH

A 50 mL RBF was charged with PthN-12-Tyr(O-12-TBE)-OBn (1.011 g, 0.610 mmol), THF (2.439 ml), and 2-Propanol (9.76 ml). Charcoal (10× weight of Pd(OAc)$_2$, 68 mg) was added followed by Palladium(II) acetate (6.85 mg, 0.030 mmol). The reaction was placed under a balloon of H2 and stirred vigorously for 3 hours. TLC (90:10 DCM:MeOH) indicated complete consumption of sm and formation of a single major spot. HPLC (Acid60 method) indicated complete consumption of sm and formation of a single major product. The reaction was diluted with DCM, filtered, rinsed with DCM, and concentrated under reduced pressure. The oil was taken up in DCM (50 mL), washed with 10% aq HCl (2×5 mL), brine (5 mL), dried over Na2SO4, filtered over celite, and concentrated under

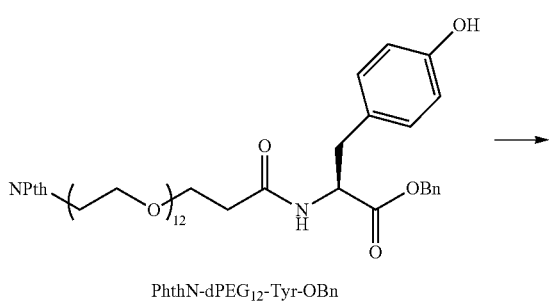

PhthN-dPEG$_{12}$-Tyr-OBn

-continued

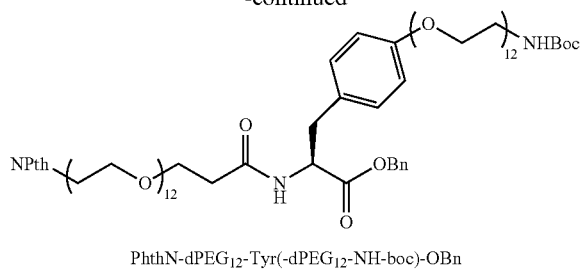

PhthN-dPEG$_{12}$-Tyr(-dPEG$_{12}$-NH-boc)-OBn

Prepared by reacting PthN-12-Tyr(OH)-OBn and HO-12-NHBoc.

H2N-dPEG$_{12}$-Tyr(-dPEG$_{12}$-NHBoc)-OBn:

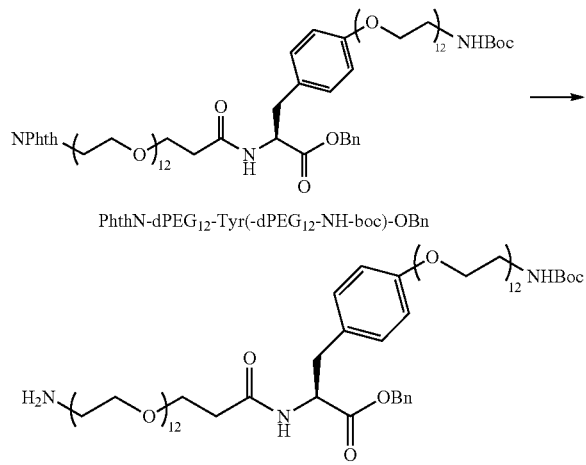

PhthN-dPEG$_{12}$-Tyr(-dPEG$_{12}$-NH-boc)-OBn

H$_2$N-dPEG$_{12}$-Tyr(-dPEG$_{12}$-NH-boc)-OBn

Prepared using PhthN-dPEG$_{12}$-Tyr(-dPEG$_{12}$-NHBoc)-OBn and hydrazine monohydrate.

PthN-dPEG$_{12}$-Tyr(-dPEG$_{12}$-Gn(Boc)$_2$)-OBn:

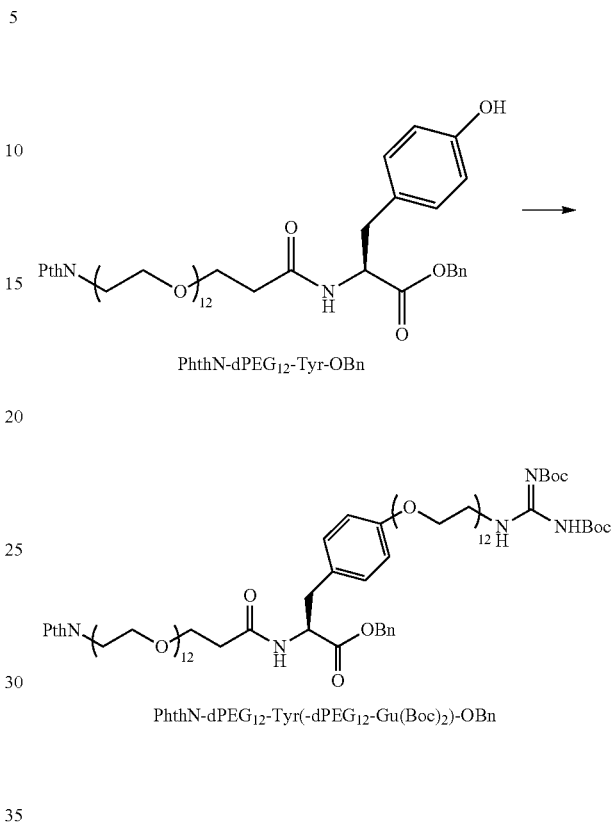

PhthN-dPEG$_{12}$-Tyr-OBn

PhthN-dPEG$_{12}$-Tyr(-dPEG$_{12}$-Gu(Boc)$_2$)-OBn

Prepared with PhthN-dPEG$_{12}$-Tyr-OBn and HO-dPEG$_{12}$-Gn(Boc)$_2$.

H$_2$N-dPEG$_{12}$-Tyr(-dPEG$_{12}$-Gn(Boc)$_2$)-OBn:

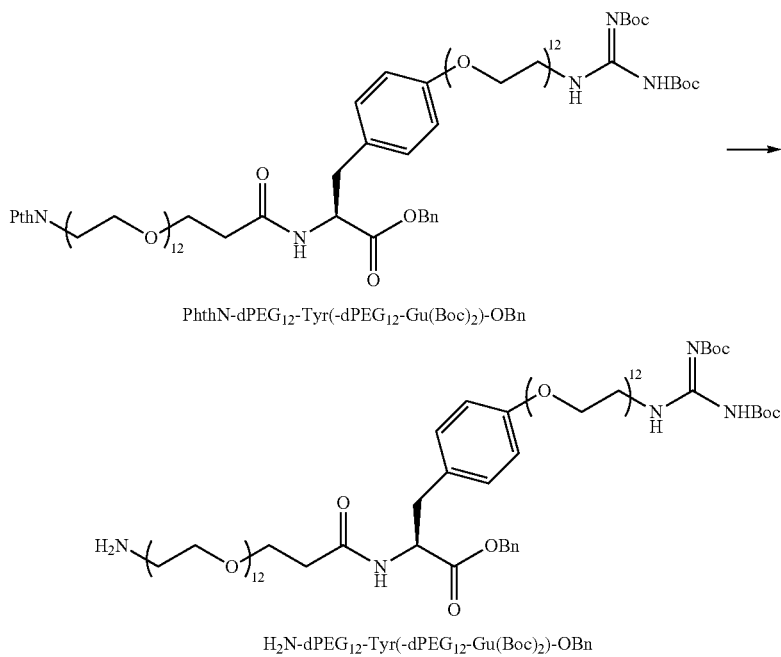

PhthN-dPEG$_{12}$-Tyr(-dPEG$_{12}$-Gu(Boc)$_2$)-OBn

H$_2$N-dPEG$_{12}$-Tyr(-dPEG$_{12}$-Gu(Boc)$_2$)-OBn

319

Prepared using PhthN-dPEG₁₂-Tyr(-dPEG₁₂-Gn(Boc)₂)-OBn and hydrazine monohydrate.

320

PhthN-dPEG₁₂-Tyr(-dPEG₁₂-TBE)-dPEG₄-Tyr(-dPEG₁₂-NHBoc)-OBn:

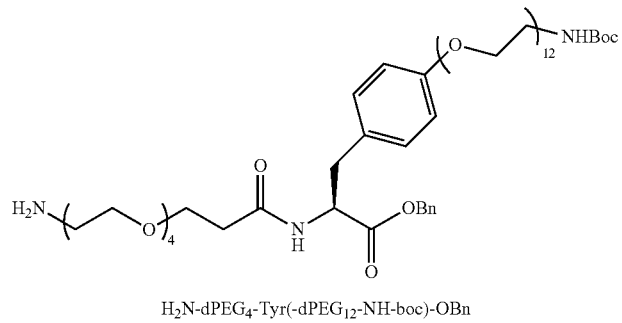

H₂N-dPEG₄-Tyr(-dPEG₁₂-NH-boc)-OBn

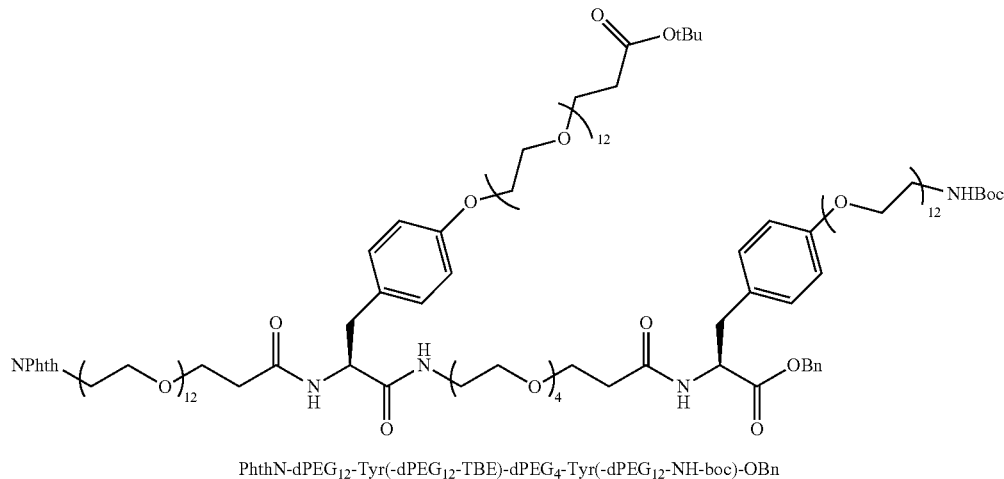

PhthN-dPEG₁₂-Tyr(-dPEG₁₂-TBE)-dPEG₄-Tyr(-dPEG₁₂-NH-boc)-OBn

Prepared using PhthN-dPEG₁₂-Tyr(-dPEG₁₂-TBE)-OH and H2N-dPEG₄-Tyr(-dPEG₁₂-NHBoc)-OBn.

PhthN-dPEG₁₂-Tyr(-dPEG₁₂-TBE)-dPEG₄-Tyr(-dPEG₁₂-NHBoc)-OH:

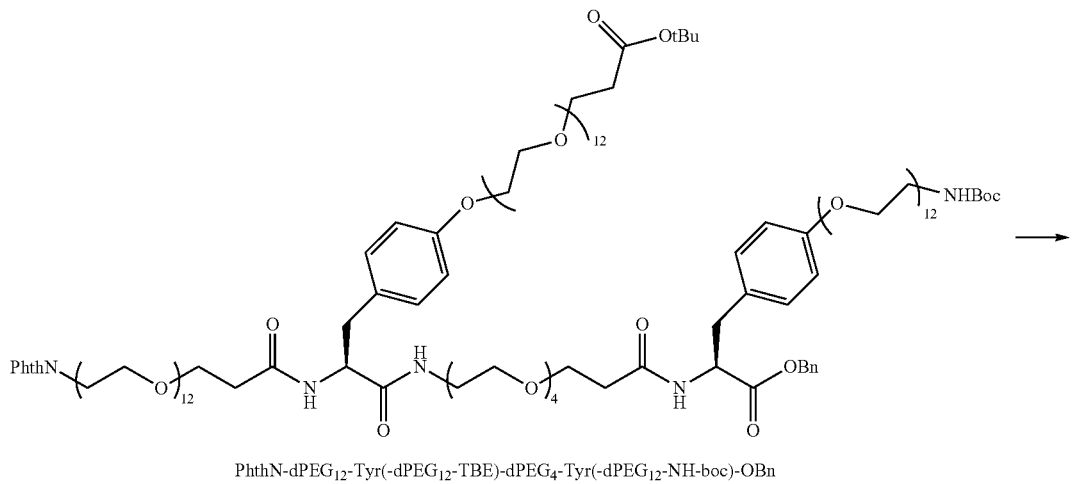

PhthN-dPEG₁₂-Tyr(-dPEG₁₂-TBE)-dPEG₄-Tyr(-dPEG₁₂-NH-boc)-OBn

-continued

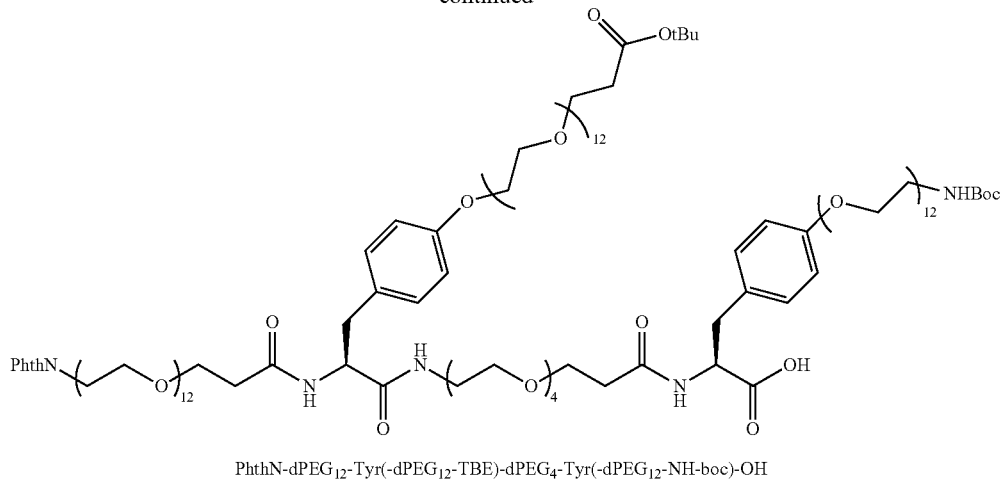

PhthN-dPEG₁₂-Tyr(-dPEG₁₂-TBE)-dPEG₄-Tyr(-dPEG₁₂-NH-boc)-OH

Prepared using PhthN-dPEG₁₂-Tyr(-dPEG₁₂-TBE)-dPEG₄-Tyr(-dPEG₁₂-NHBoc)-OBn and H2N-dPEG₄-Tyr(-dPEG₁₂-NHBoc)-OBn.

PhthN-dPEG₁₂-Tyr(-dPEG₁₂-TBE)-dPEG₄-Tyr(-dPEG₁₂-NHBoc)-dPEG₁₂-Tris(dPEG₂₄-m)₃:

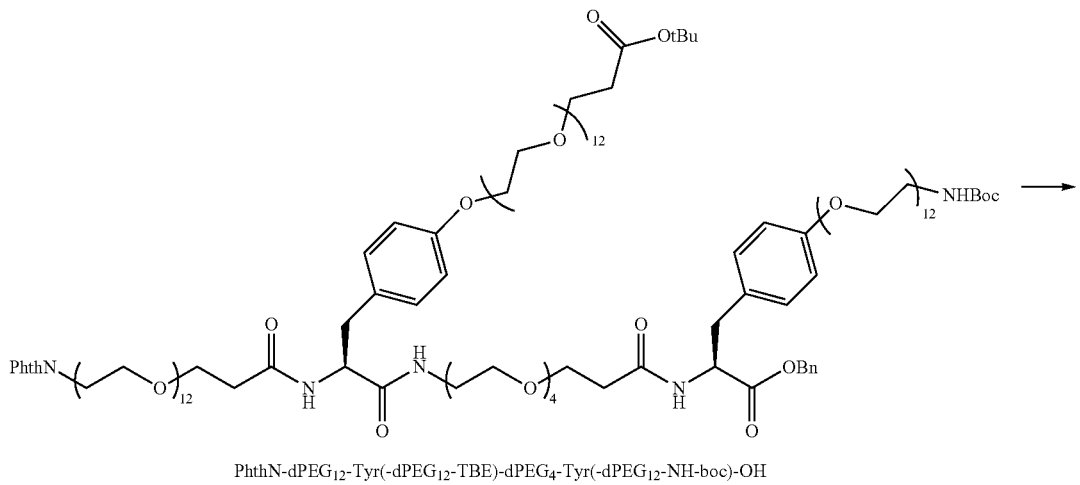

PhthN-dPEG₁₂-Tyr(-dPEG₁₂-TBE)-dPEG₄-Tyr(-dPEG₁₂-NH-boc)-OH

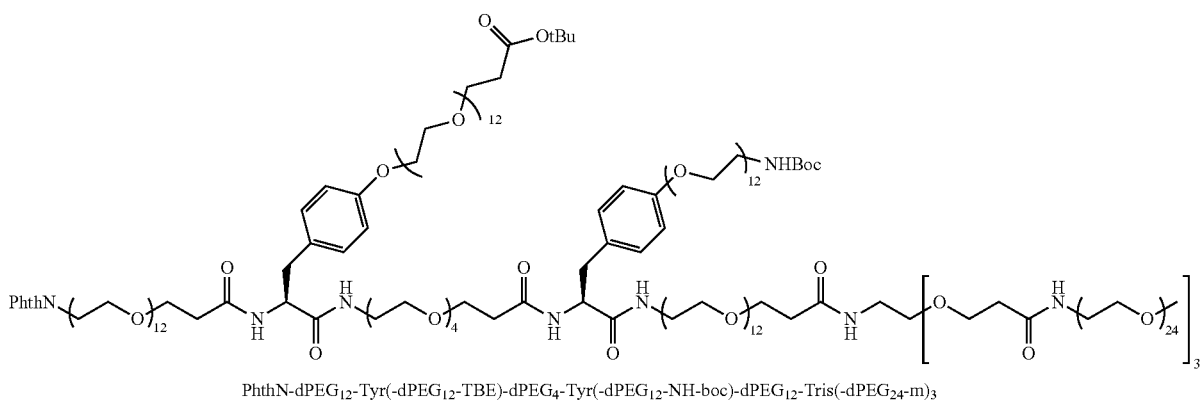

PhthN-dPEG₁₂-Tyr(-dPEG₁₂-TBE)-dPEG₄-Tyr(-dPEG₁₂-NH-boc)-dPEG₁₂-Tris(-dPEG₂₄-m)₃

Prepared using PhthN-dPEG$_{12}$-Tyr(-dPEG$_{12}$-TBE)-dPEG$_4$-Tyr(-dPEG$_{12}$-NHBoc)-OH and H2N-dPEG$_{12}$-Tris(-dPEG$_{24}$-m)$_3$.

Example 4

Preparation by SPPS

Templates containing 3 and 4 alternating lysine:dPEG$_4$ units were constructed using lysine protected on the α-amine by an Fmoc group and the ε-amine by a t-Boc group, and Fmoc-dPEG$_4$-acid by conventional solid phase peptide synthesis The ε-amines were de-protected during the final cleavage of the template from the support resin.

Example 5

Conjugate Preparation

Preparation of 107-1A4 and Its F(ab')$_2$ Fragment

The monoclonal antibody 107-1A4, an IgG$_1$ mAb, which is reactive with the prostate-specific membrane antigen found in prostate tissue and upregulated in prostate cancer, was obtained, and purified as previously described.28 The F(ab')$_2$ fragment was prepared from intact mAb by digestion using pepsin (5.2 µg/mL in 80 mM NaOAc, pH 3.9) at 37° C. for 24 h. The F(ab')$_2$ produced was purified on a Protein A column followed by a Fractogel TMAE column (EM Science, Gibbstown, N.J.). The purified F(ab')$_2$ was stored at refrigerator temperature. The 107-1A4 F(ab')$_2$ was converted to Fab'-SH just prior to conjugation as described in the Experimental Procedures below.

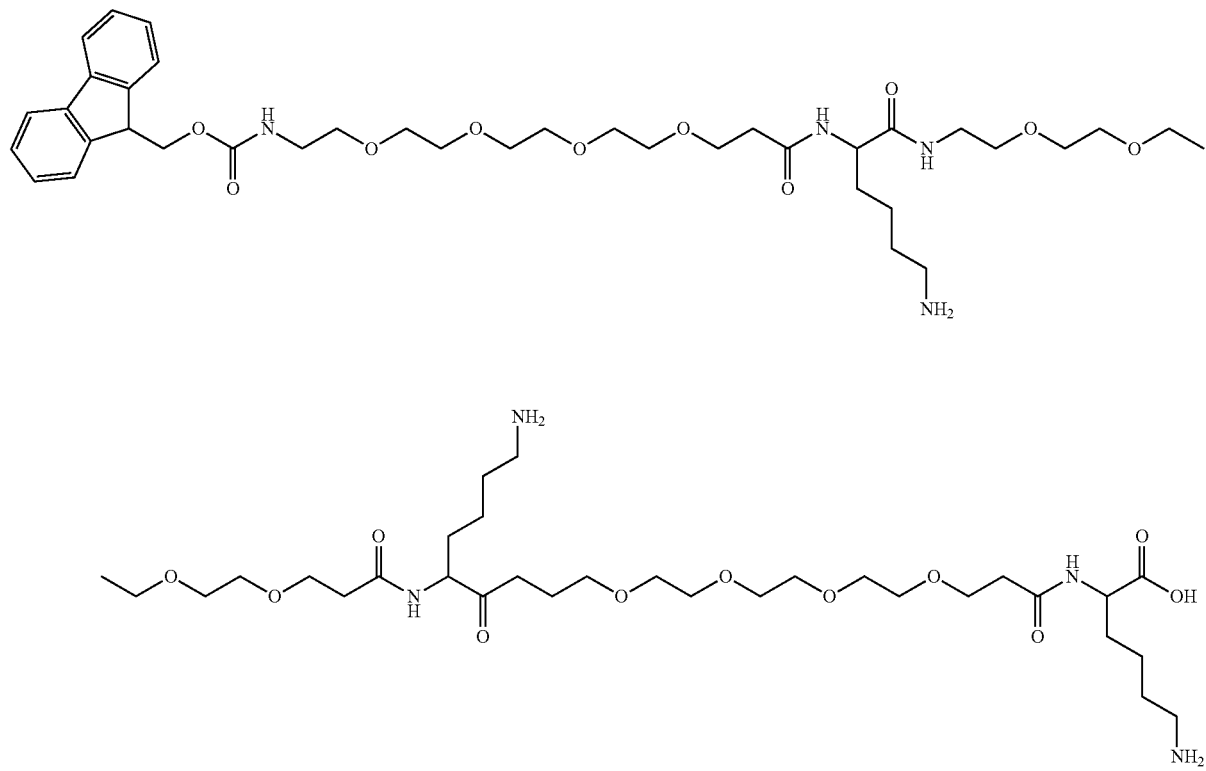

Fmoc-NH-dPEG$_4$-(Lys)-dPEG$_4$-(Lys)-dPEG$_4$-(Lys)-OH

MALDI-TOFF ANALYSIS
Theoretical MW=1365.65
Actual MW=1366.86

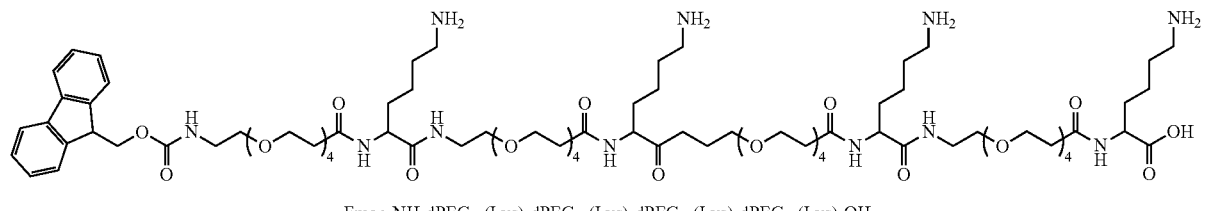

Fmoc-NH-dPEG$_4$-(Lys)-dPEG$_4$-(Lys)-dPEG$_4$-(Lys)-dPEG$_3$-(Lys)-OH

MALDI-TOFF ANALYSIS
Theoretical MW=1741.11
Actual MW=1743.04

Preparation of Fab'-SH Conjugate
To 1.7 mL of 2.9 mg/mL F(ab')$_2$ in PBS was added 68 µL of 100 mM DTT to make a final concentration of 4 mM DTT. This was gently mixed for 45 min at room temperature before passing through PD-10 column eluting with PBS pH 6.5 with 1 mM EDTA: Protein containing fractions were combined to give 4 mL. To this, 1:2 mg of sodium tetrathionate was added (0.3 mg/mL in final solution). This material was concentrated over 20 min to 0.5 mL and passed over another PD-10 column equilibrated in PBS pH6.5 with 1 mM EDTA. The protein containing fractions were combined to yield 2 mL of 2.0 mg/mL: To 0.410 mL of the above 'ab' (0.824 mg) was added 20 eq. of the desired maleimide in 100 µL PBS pH 6.5 with 1 mM' EDTA. This was allowed to react for 1 hr before placing on the HPLC. After 30 min at room temperature, a 10 µL aliquot of a 23.8 mg/mL N-ethylmaleimide (NEM) solution in DMF was added to react with the remaining sulfhydryl groups. After 10 min at room temperature, the mixture was run over a PD-10 column. The protein fractions were eluted in PBS and combined to yield a 64-80% protein recovery.

Conjugations to. Prepare Fab'-S-MAL-dPEG$_4$-Tris(-dPEG$_{12}$-m)$_3$; Fab'-S-MAL-dPEG$_4$-Tris(-dPEG$_{24}$-m)$_3$; Fab'-S-MAL-dPEG$_4$-Tris(-dPEG$_{24}$-m)$_3$; Fab'-S-MAL-dPEG$_4$-Tris(-dPEG$_4$-Tris(-dPEG$_{12}$-m)$_3$)$_3$ and Fab'-NEM.

Maleimide terminated branched-chain discrete PEG (dPEG®) compounds, MAL-dPEG$_4$-Tris(-dPEG$_{12}$-m)$_3$, MAL-dPEG$_4$-Tris(-dPEG$_{24}$-m)$_3$, MAL-dPEG$_4$-Tris(-dPEG$_{24}$-acid)$_3$ and MAL-dPEG$_4$-Tris(-dPEG$_4$-Tris(-dPEG$_{12}$-m)$_3$)$_3$ were conjugated with two different MAb Fab' fragments. As a control, N-ethyl maleimide (NEM) was also conjugated under the same reaction conditions. The sulfhydryl conjugations were conducted with freshly prepared Fab' at pH 6.5 for 1 h at room temperature using 20 equiv. of the respective branched dPEG amine or NEM. Conjugation reactions were followed by size-exclusion (SE)-HPLC. Fab' conjugates were characterized by IEF, SDS-PAGE and MS analyses.

Radioiodination.

These Fab' conjugates were radiolabeled using chloramine-T and Na[$^{125}$I]I. To 25 µl of 500 mM sodium phosphate, pH 6:8 was Combined With 29=37 µL. (0.1 mg @ 2.7-3.5 mg/mL). To this, 0.5 µL of I-125 (168-265 µCi) was added followed by 10 µL of 1 mg/mL Chloramine-T in water. After 0.5 min at RT, the reaction was quenched by adding 10 µL of 10 mg/mL sodium metabisulfite in water. Each reaction was then run over a NAP-10 (G-25) column and collected in PBS. Radiochemical yields were 56-75% with 60-70% protein recovery.

Biodistribution Study.

A biodistribution study was conducted under a protocol approved by the Institutional Animal Care and Use Committee (IACUC) at the University of Washington. Male nude mice were purchased and housed for 1 week in the isolator facility prior to beginning the study. A solution of each conjugate (excluding the Fab'-S-MAL-dPEG$_4$-Tris(m-dPEG$_{12}$)$_3$) was diluted with phosphate buffered saline (PBS) to prepare a solution for injection of ~100 mL/mouse. This quantity was injected into each of 10 athymic mice via the lateral tail vein. The actual amount of injectate each animal received was determined by weighing the administering syringe before and after injection. Groups of 5 mice were sacrificed at 1 and 4 h post injection. The tissues were excised, blotted free of blood, weighed, and counted. Blood weight was estimated to be 6% of the total body weight. Calculation of the percent injected dose (% ID) and percent injected dose per gram (% ID/g) in the tissues was accomplished using internal standards for $^{125}$I or $^{131}$I counts.

Example 6

Imaging Examples

Preparation of CC49 Fab'-Branched dPEG Antibody Conjugates

An Unexpected Difference in the Reactivities of F(Ab')$_2$ Produced by Ficin and Pepsin Proteolysis CC49, a full length mouse IgG, was reacted with the Ficin, a cysteine endopeptidase from figs, to produce the F(ab')$_2$ fragment. When this F(ab')$_2$ fragment was reduced, selectively reoxidized, and reacted with maleimide activated branched dPEGS, as described in the preparation of CC49 F(ab')-dPEGX, the predominant product was the. Fab' fragment bound to a single dPEG.

F(ab')$_2$ fragments are more commonly prepared by reaction of antibodies with bovine pepsin, a digestive proteinase. When the F(ab')$_2$ fragment prepared using pepsin was reacted as described above, similar amounts of the mono-dPEGX conjugate and higher molecular weight conjugates were formed. The higher molecular weight conjugates were tentatively identified as CC49 Fab'-(dPEGX)$_2$ and CC49-Fab'-(dPEG)$_3$.

Preparation of CC49 F(ab')$_2$

Ficin Purification. Ficin (0.1 mL of a 19.2 mg/mL slurry; Sigma) is diluted to 4 mg/mL in a 0.01 M Tris Buffer (pH 8.5) and desalted on a size exclusion column (PD10, GE Healthcare) equilibrated in the same buffer. The excluded protein (1.5 mL) is then applied to a 0.5 mL Q-Sepharose gravity flow column that is also equilibrated in the 0.01 M Tris Buffer, pH 8.5. The concentration of ficin, which does not bind to the column, is determined by the A(280) of the column flow through, using 2.1 as the A(280) absorbance of a 1 mg/mL ficin solution.

Reaction of Ficin with CC49. CC49 (1.5 mL of a 2 mg/mL solution in PBS) is combined with an equal volume of a 0.2 M Hepes Buffer containing 2 mM. EDTA (pH 7). Purified ficin (0.1 mg) and freshly prepared cysteine (0.03 mL of a 1.33 mM solution in DI water) then are added and the reaction is allowed to proceed overnight at 37° C. to produce CC49 F(ab')$_2$.

Purification of CC49 F(ab')$_2$. The reaction product is concentrated to 0.5 mL on a centrifugal molecular concentrator (Millipore, 10,000 MW cutoff) and then desalted on a PD10 column that is equilibrated in a 0.01 M Tris Buffer, pH 8.5. The excluded protein is then applied to a 1 mL Q-Sepharose (GE Healthcare) gravity flow column that is equilibrated in the same buffer. The column is washed with 9 mL of the equilibration buffer and the product F(ab')$_2$ is eluted with the same buffer containing 0.1 M sodium chloride. The product containing fractions are adjusted to pH 7.4 by the addition of a 1 M solution of monopotassium phosphate. The concentration of the F(ab')$_2$ is determined by its absorbance at 0.280 nm (1 mg/mL has an absorbance of 1.4).

Analysis of CC49 F(ab')$_2$. The CC49 F(ab')$_2$ was analyzed by SDS-PAGE on a 4-20% gradient gel under non-reducing conditions. The product contained a single major band that migrated, compared with standards, at ~120 kDa (theoretical MW 100 kDa) while the starting CC49 antibody migrated at ~180 kDa (theoretical MW 150 kDa). Proteins that contain disulfide bridges, such as CC49 and CC49 F(ab')$_2$, do not bind their expected amount of SDS when they are not reduced and, hence, show less mobility on the gel and a higher apparent molecular weight.

Preparation of Conjugates

The first two Fab' conjugates CC49 Fab'-dPEG12-Tris (dPEG24 acid)3 and CC49 Fab'-dPEG12-Tris(dPEG12 acid) were prepared by reducing the F(ab')$_2$ fragments and then using an air oxidation step to reform the disulfide bonds between the heavy and light chains and to form a disulfide bond between two of the three cysteines in the heavy chain hinge region. This method leaves a single unpaired cysteine thiol in the hinge region that is free for conjugation to the MAL-dPEGs.

The air oxidation method proved to be highly variable and was replaced by re-oxidation of the disulfides using sodium tetrathionate. The single unpaired cysteine in the hinge region is protected by this method, most likely as a sulfenylthiosulfate. This protected cysteine is converted to a free thiol by treatment with a low concentration of mercaptoethylamine. This second method, which is highly reproducible, was used for the preparation of CC49 Fab'-NEM, CC49 Fab'-dPEG$_{12}$-Tris(m-dPEG$_{24}$)$_3$, and CC49 Fab'-dPEG$_{12}$-Tris(dPEG$_{12}$-Tris(m-dPEG$_{11}$)$_3$)$_3$. This second method is described in the write up below.

Reduction of CC49 F(ab)$_2$ to Fab'

A solution of 1 mg CC49 monoclonal antibody (or just CC49, as used below) F(ab)$_2$ in 0.5 mL of a pH 7.4 buffer is adjusted to 4 mM dithiothreitol (DTT; Fluka) by the addition of 0.02 mL of a freshly prepared solution of 0.1 M DTT in water. The reaction is incubated at RT for 45 minutes and then desalted on a PD10 column equilibrated in an 0.1 M sodium phosphate buffer, pH 6.5 containing 1 mM EDTA (pH 6.5 Buffer). The product (1.5 mL) is collected in the column's exclusion volume.

Reoxidation

The reduced product (1.5 mL) is combined with 0.167 mL of a freshly prepared solution of 3 mg/mL sodium tetrathionate in DI water (Sigma) and the reaction is incubated at RT for 15 minutes. The reaction is then applied to three PD10 columns (0.5 mL/column) equilibrated in pH 6.5 buffer and the excluded protein containing fractions (4.5 mL) are combined and concentrated to 0.5 mL via a centrifugal concentrator (Millipore).

Deprotection

The reoxidized product (0.5 mL) is combined with 0.056 mL of a freshly prepared 11 mM mercaptoethylamine (MEA; TCI) solution in DI water (final MEA conc.=1.1 mM). The reaction is incubated for 4 hours at RT and then conjugated with Mal-dPEGX.

Conjugation

The deprotected product (1.5 mL) is combined with 0.167 mL of a 10 mM solution of MAL-dPEGX in dimethylacetamide (DMAC). The reaction is allowed to proceed for 4 hours at RT and then quenched by the addition 100 mM N-ethylmaleimide in DMAC (0.075 mL).

Purification

Size Exclusion Chromatography. The conjugate product (1.5 mL) is applied to a Superdex 200 column (Hi Load 16/600, GE Healthcare) equilibrated in a 0.05 M sodium phosphate buffer (pH 7.2) containing 0.15 M Sodium Chloride at a flow rate of 0.5 mL/minutes. The fractions are analyzed by their absorbance at 280 nm and aliquots of the product fractions are concentrated and analyzed by SDS-PAGE. Fractions that contain purified product are combined and concentrated to ~0.5 mL via a centrifugal concentrator. From gel analysis, it is estimated that the purities of CC49 Fab'-dPEG$_{12}$-Tris(dPEG$_{24}$ acid)$_3$, CC49 Fab'-dPEG$_{12}$-Tris (dPEG$_{12}$ acid)$_3$, CC49 Fab'-dPEG$_{12}$-Tris(m-dPEG$_{24}$)$_3$, and Fab'-NEM are ~97%.

In the case of CC49 Fab'-dPEG$_{12}$-Tris(dPEG$_{12}$-Tris(m-dPEG$_{11}$)$_3$)$_3$, the product co-elutes with F(ab')$_2$ on the Superdex 200 column. This result, which did not occur with the other conjugates, is, not predicted from the molecular weights of the conjugate and the F(ab')$_2$ fragment, which are ~56 kDa and ~100 kDa respectively. However, it is has been reported in the literature that dPEGs have hydrodynamic volumes that are significantly greater than those predicted from their molecular weights.

Anion Exchange Chromatography. The Superdex 200 product of CC49 Fab'-dPEG$_{12}$-Tris(dPEG$_{12}$-Tris(m-dPEG$_{11}$)$_3$)$_3$ was buffer exchanged on a PD10 column equilibrated in 0.01 M Tris Buffer, pH 8.75. The protein then was applied to a 0.5 mL Q-Sepharose column (gravity flow) that was equilibrated in the same buffer. The column was washed with 3 mL of the pH 8.75 buffer and the product was then eluted with the same buffer containing 0.03 M sodium chloride. The product containing fractions were combined and concentrated to 0.25 mL on a centrifugal concentrator. The product was then combined with 3.75 mL of 0.05 M sodium phosphate buffer containing 0.15 M sodium chloride and concentrated a second time to 0.4 mL.

Example 7

SDS-PAGE Gels

Conjugate: CC49
Fab'-dPEG12-Tris(dPEG12-Tris(m-dPEG11)3)3

Gel Conditions: 4-20%, Non-Reducing

Gel 1: Reaction Intermediates, Conjugate, and Superdex 200 Fractions are displayed in FIG. 2. The major impurities in the conjugation product (lane 6) are the reoxidized Fab' and F(ab)$_2$ fragments. The gels of the Superdex 200 product fractions (lanes 7-10) indicate that this column effectively removes the Fab' fragments from CC49 Fab'-dPEG12-Tris (dPEG12-Tris(m-dPEG11)3)3. The F(ab)$_2$ fragment, in contrast, co-migrates with the conjugate. This result, which did not occur with the other smaller conjugates, is not predicted from the molecular weights of the conjugate and the F(ab')$_2$ fragment, which are ~56 kDa and, ~100 kDa respectively. However, it is has been reported in the literature that dPEGs have hydrodynamic volumes that are significantly greater than those predicted from their molecular weights.

Figure 3:
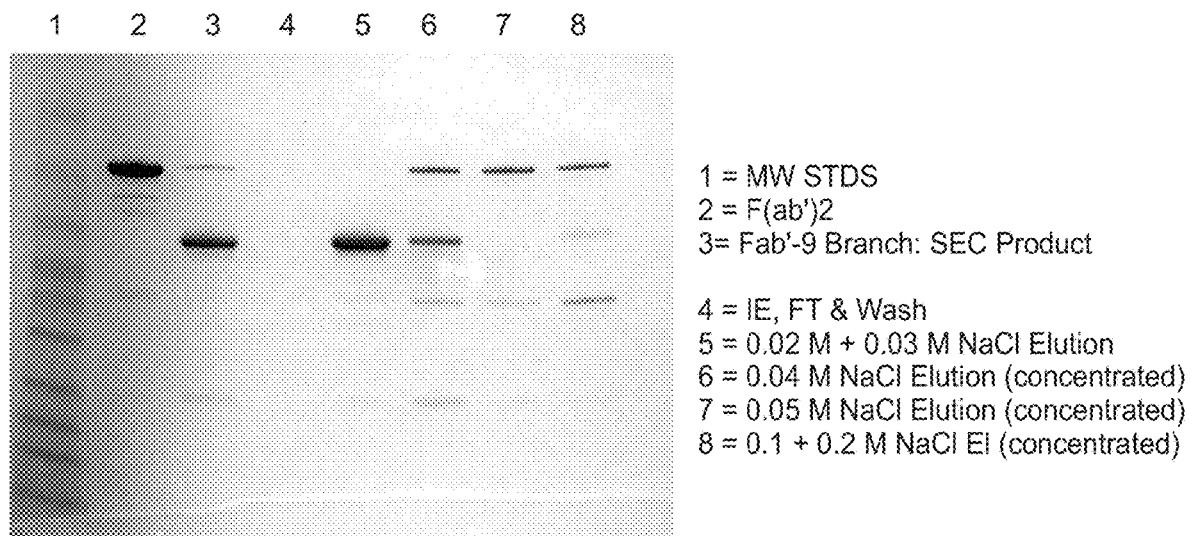

GEL 2: Ion Exchange Purification Fractions are displayed in FIG. 3. Proteins with disulfide linkages, when run on SDS-PAGE gels under non-reducing conditions, don't bind their full complement of SDS and hence don't migrate as far as they would under reducing conditions. This leads to apparent molecular weights that are higher than the actual molecular weights. The CC49 Fab'-dPEG12-Tris(dPEG12-Tris(m-dPEG11)3)3 conjugate and the F(ab')2 impurity both bound to the Q-Sepharose anion exchange column. The conjugate (lane 5) eluted at 0.02-0.03 M NaCl while the F(ab')$_2$ fragment didn't elute until 0.04 M NaCl.

Mass Spectroscopy Data

Maldi-TOFF Analysis

MS(A): CC49 Fab'-dPEG$_{12}$-Tris(dPEG$_{24}$ acid)$_3$
Concentration=0.4 mg/mL
Buffer=0.05 M sodium phosphate, pH 7.2, 0.15 M NaCl
Theoretical MW=52,622 (calculation from Fab'-NEM)
Actual MW=52, 630
MS(B): CC49 Fab'-dPEG$_{12}$-Tris(dPEG$_{12}$ acid)$_3$
Concentration=0.26 mg/mL
Buffer=0.05 M sodium phosphate, pH 7.2, 0.15 M NaCl
Theoretical MW=51,036 (calculation from Fab'-NEM)

Figure 4:
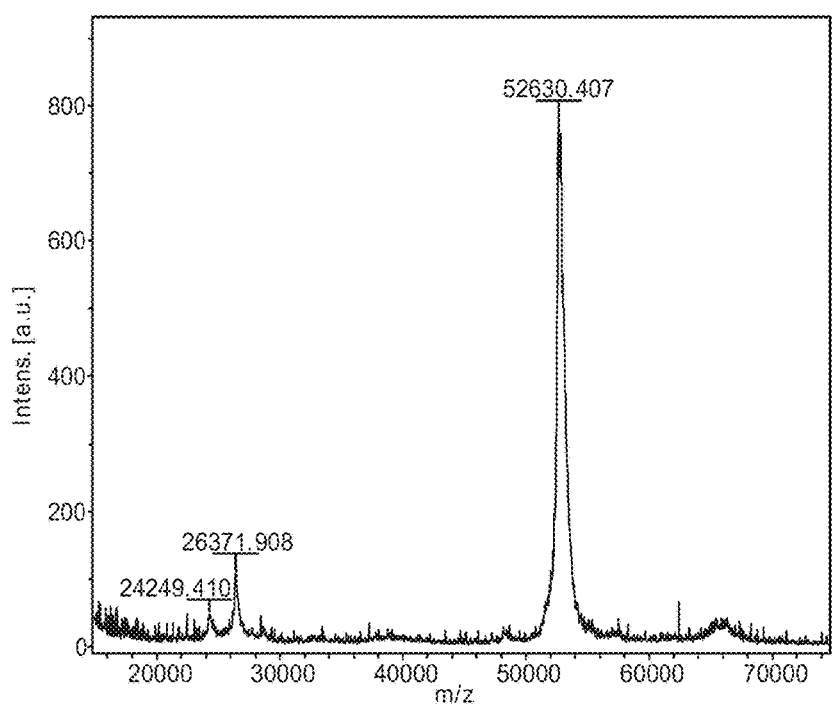
FIGS. 4, 5, and 6 display the mass spectroscopy results for the antibody conjugates of FIGS. 2 and 3.
Figure 5:
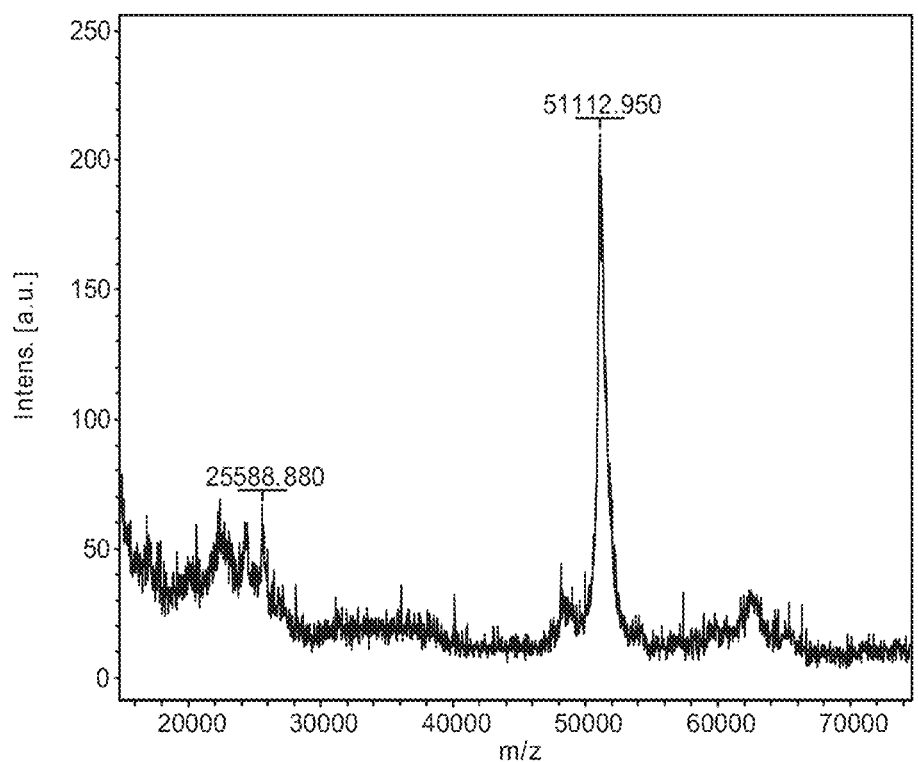
Figure 6:
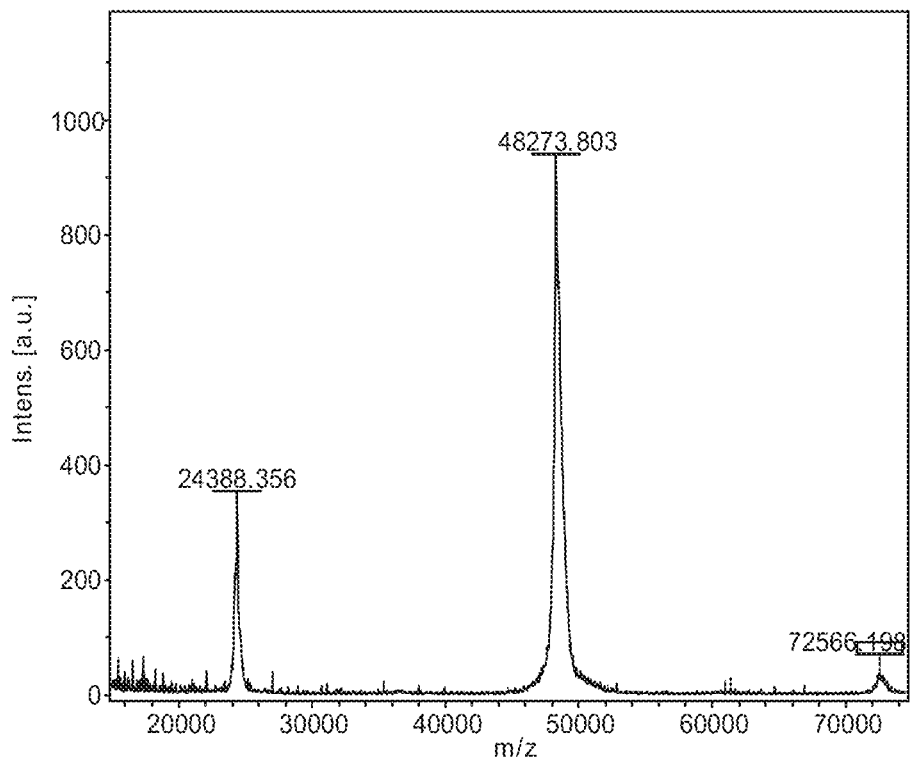
Figure 7:
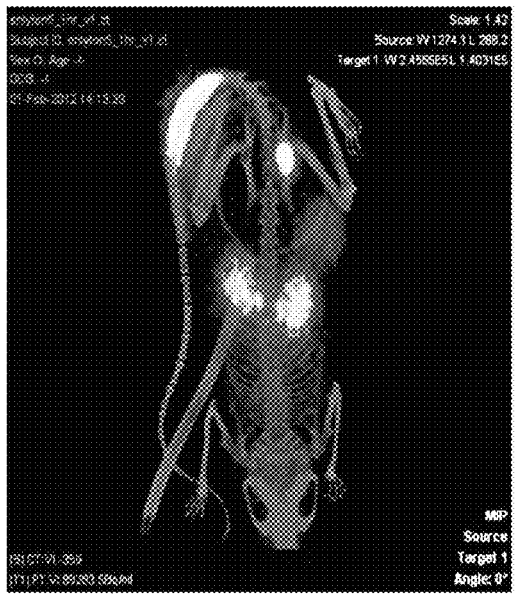
FIGS. 7-40 display fused CT/PET images for several different modified antibodies, as reported in the Examples.
Figure 8:
Figure 9:
Figure 10:
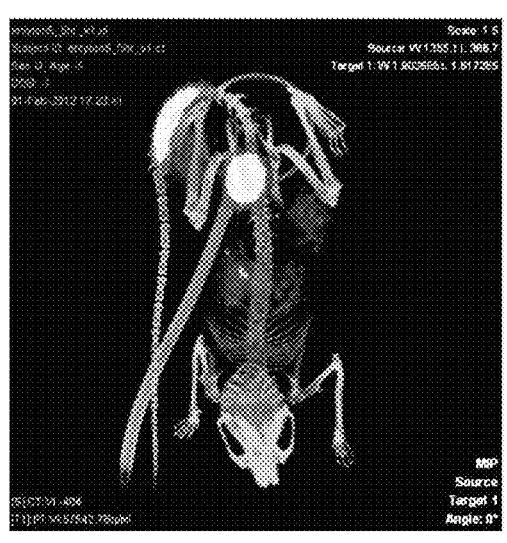
Figure 11:
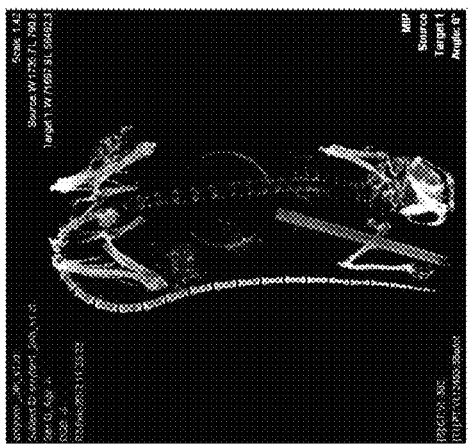
Figure 12:
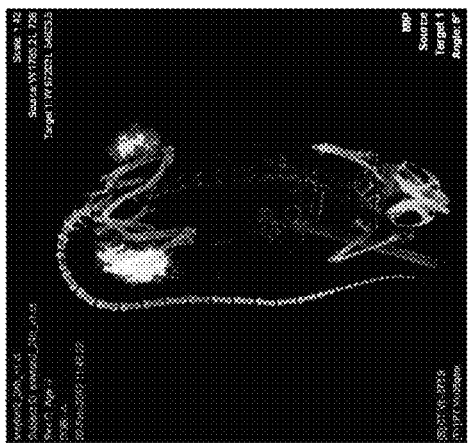
Figure 13:
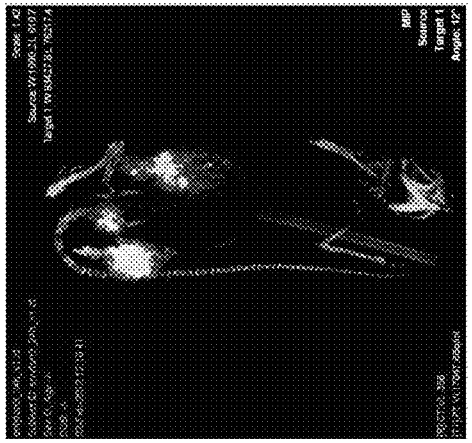

Actual MW=51, 113
MS(NEM): 0.57 mg/mL
Buffer=0.05 M sodium phosphate, pH 7.2, 0.15 M NaCl
Actual MW=48, 274 (since the exact position of the ficin cleavage is unknown, the theoretical MW cannot be calculated).
No di or tri-pegylated molecules visible.
FIGS. 4, 5, and 6 display the mass spectroscopy results for the antibody conjugates described above.

mCC49 Competition ELISA

We used a competition assay to determine the relative binding constants for the following mCC49 fragments: F(ab')$_2$, Fab'-NEM, Fab'-dPEG$_{12}$-Tris(dPEG$_{24}$ acid)$_3$.

A fixed concentration of mCC49 (0.033 ug/mL) was added to the wells of an ELISA plate coated with BSM Each fragment was added to a series of wells at concentrations series from 24 ug/mL to 0.01 ug/mL The amount of mCC49 that bound to each well was determined by an HRP labeled Goat Anti Mouse antibody that is specific for the Fc region of mCC49

The fragment concentration that inhibited the binding of mCC49 by 50% ($I_{1/2}$) was the same for Fab'-NEM and Fab'-dPEG$_{12}$-Tris(dPEG$_{24}$ acid)$_3$ The I½ for the Fab' fragments was ~40× higher than that for the F(ab')$_2$ fragment We previously found that mCC49 and its F(ab')$_2$ fragment had very similar normal ELISA curves. The mCC49 competition ELISA results are seen graphically in FIG. 44.

Example 8

Mouse Imaging Study

Radiolabeling Procedure (Iodo-Gen™ Method)
I. Equipment and Reagents Required
1. sterilized, de-pyrogenated glass reaction vessel coated with IODO-GEN™ (SOP 310.0) (5-10 ml serum vials or 13 mm×100 mm test tubes)
2. sterile, pyrogen-free phosphate buffer, 0.1 M. pH 7.2
3. sterile, pyrogen-free phosphate buffered saline
4. 1 Sephadex G-25M (PD-10 disposable) column with tip
5. Iodine-124 medium concentration, high activity, sodium iodide for protein iodination in pH=9.5, concentration—100 mCi/ml (IBA Molecular, Dulles VA)
6. protein to be radiolabeled
7. 10 sterilized, de-pyrogenated glass test tubes—12×75 mm
8. 1 sterile Millex-GV 0.22 micron, 13 mm low protein binding filter unit (Millipore—cat. no: SLGV0130S)
9. microliter pipettes (Eppendorf)
10. sterilized plastic tips for microliter pipette
11. parafilm—2 cm.×2 cm.
12. close calibrator
13. fume hood
14. dry and wet radioactive waste containers
15. disposable gloves
16. lead shielding and lead containers for reaction vessel and test tubes
17. 2-5 ml. sterile, pyrogen-free syringes with needles
18. 1-3.5 in. spinal needle.

Procedure
(Note: the specific activity desired will determine the quantities of protein and Iodine-124 used below.)
I. Place the desired amount of protein into the IODO-GEN™ reaction vessel.
2. Add the desired amount of iodine-124 into the IODO-GEN™ reaction vessel.
3. Add 50 µl of 0.1M, 7.2 pH phosphate buffer solution to reaction vessel.
4. Cover the reaction vessel with parafilm.
5. Incubate reaction vessel for 20 minutes with occasional swirling.
6. Place reaction vessel into dose calibrator to determine radioactivity added.
7. Stop reaction by removing reaction mixture from reaction vessel and placing mixture onto gel bed of Sephadex G-25M column (this separates unbound Iodine-124).
8. Allow mixture to elute through column. (Note: the iodinated protein is collected from the column after the void volume has been eluted—approximately 2 ml).
9. Place 1 ml phosphate buffered saline onto gel bed of Sephadex G-25M column and allow to elute through column.
10. Place 4 ml phosphate buffered saline onto gel bed of Sephadex G-25M column and allow to elute through column. (Note: begin to collect Iodinated protein if you have not done so already).
11. Collect fractions of 10 drops of eluted iodinated protein—total of 10 fractions.
12. Assay the 10 fractions using the dose calibrator.
13. Collect the fractions, which have the highest radioactivity and pool them together in a sterile, pyrogen-free syringe.
14. Assay syringe of the collected iodinated fractions.
15. Filter radiolabeled protein using Millex-GV 0.22 micron low protein binding filter unit into a sterile pyrogen-free syringe.
16. Assay syringe of the filtered radiolabeled protein.
17. Remove a sample for quality assurance procedures.

Description of Animals
a. Female nude mice background, 4-5 weeks in age, were used in this project. For every 7 animals injected with tumors, 4 will actually show tumors in the useful size range.
b. The nude mice will receive 6×10$^6$ cells subcutaneously in 0.1 mL volumes in order to initiate tumors.
c. Nude mice are received on a routine basis from commercial sources. The mouse colony is routinely surveyed for adventitious agents by serological and histopathological procedures. Upon arrival, the mice are conditioned for up to one week and then moved into an experimental protocol.
d. The anesthetized mice are injected subcutaneously or intradermally into the flank area. For this injection, the mouse is held by a fold in the skin at the back and a 25G needle inserted through the skin. The animal(s) is observed on a routine basis for tumor development and signs of distress.

Imaging Example
Mouse Images

The mouse image figures correspond to use of the following radiolabelled antibodies with the indicated branched dPEG reagents:

TABLE 4

| Modified Antibody Used | Time Post Injection (hrs) | Figure Number |
|---|---|---|
| Fab'-dPEG$_{12}$-Tris(dPEG$_{24}$ acid)$_3$ | 1 | 8 |

TABLE 4-continued

| Modified Antibody Used | Time Post Injection (hrs) | Figure Number |
|---|---|---|
| Fab'-dPEG$_{12}$-Tris(dPEG$_{24}$ acid)$_3$ | 5 | 8-10 (8 is control) |
| Fab'-dPEG$_{12}$-Tris(dPEG$_{24}$ acid)$_3$ | 24 | 11-16 |
| Fab'-dPEG$_{12}$-Tris(dPEG$_{24}$ acid)$_3$ | 48 | 17-22 (22 is control) |
| Fab'-dPEG$_{12}$-Tris(dPEG$_{24}$ acid)$_3$ | 72 | 23-28 |
| CC49 Fab'-dPEG$_{12}$-Tris(m-dPEG$_{24}$)$_3$ | 24 | 29, 30 |
| CC49 Fab'-dPEG$_{12}$-Tris(m-dPEG$_{24}$)$_3$ | 72 | 31, 32 |
| CC49Fab-NEM | 5 | 33-36 |
| CC49Fab-NEM | 24 | 37-40 |

The external imaging, as shown in the fused CT/PET images in FIGS. 8-40 reveal remarkable and unexpected results, in particular, the CC49 Fab'-dPEG$_{12}$-Tris(dPEG$_{24}$ acid)$_3$. At 5 hours there was good imaging of the tumors with some background evident. At 24 hours post injection, again, the tumors were well imaged with continuing diminution of background. At 48 and 72 hours post injection, virtually no background is evident in the fused. CT/PET images.

The methoxy derivative, CC49 Fab'-dPEG$_{12}$-Tris(m-dPEG$_{24}$)$_3$ at both 24 and 72 hours post injection also reveals little background, with the CC49 Fab'-dPEG$_{12}$-Tris(dPEG$_{24}$ acid)$_3$ derivative being superior in reducing background. The control, of CC49 Fab'-NEM, at 5 and 24 hours post injection still did not reduce background to an acceptable level. It, indeed, is surprising that the small branched dPEG acid construct derivatives performed as well as they did in diminishing background and retaining excellent BD and PK, as will be revealed below.

Biodistribution Data

Confirmatory to the images described above and shown in the drawings is the biodistribution (BD) data collected for the mice in the imaging study.

TABLE 5

Comparison of Biodistribution (% ID/g) of 124-I-m CC49 Fab'-dPEG12-Tris(dPEG24 acid)3 and 124-I-mCC49Fab-NEM in nude mice at 72 h (n = 5)

| Organ | $^{124}$I-mCC49Fab-dPEG24-acid | $^{124}$I-mCC49Fab-NEM |
|---|---|---|
| blood | 0.10 ± 0.05 | 0.13 ± 0.15 |
| lungs | 0.13 ± 0.04 | 0.12 ± 0.05 |
| heart | 0.10 ± 0.04 | 0.08 ± 0.04 |
| liver | 0.75 ± 0.41 | 0.23 ± 0.18 |
| spleen | 0.25 ± 0.09 | 0.18 ± 0.09 |
| pancreas | 0.08 ± 0.05 | 0.08 ± 0.05 |
| GI | 0.10 ± 0.05 | 0.12 ± 0.10 |
| Kidneys | 0.37 ± 0.20 | 0.14 ± 0.06 |
| muscle | 0.14 ± 0.08 | 0.07 ± 0.04 |
| skin | 0.15 ± 0.07 | 0.15 ± 0.04 |
| tumor | 5.09 ± 0.83 | 3.83 ± 1.50 |

TABLE 6

Comparison of Tumor to Organ (% ID/g) of 124-I-m CC49 Fab'-dPEG12-Tris(dPEG24 acid)3 and 124-I-mCC49Fab-NEM in nude mice at 72 h (n = 5)

| Organ | $^{124}$I-mCC49Fab-dPEG24-acid | $^{124}$I-mCC49Fab-NEM |
|---|---|---|
| blood | 74.46 ± 69.64 | 46.02 ± 23.55 |
| lungs | 42.23 ± 17.69 | 33.18 ± 10.02 |
| heart | 63.45 ± 36.80 | 55.87 ± 22.55 |
| liver | 8.78 ± 5.22 | 25.96 ± 19.56 |
| spleen | 22.69 ± 8.49 | 22.79 ± 4.94 |
| pancreas | 93.20 ± 52.26 | 80.18 ± 50.15 |
| GI | 59.05 ± 22.32 | 46.44 ± 38.73 |
| Kidneys | 16.84 ± 6.81 | 30.02 ± 15.39 |
| muscle | 50.19 ± 35.42 | 61.00 ± 12.28 |
| skin | 42.61 ± 23.08 | 25.75 ± 12.28 |
| Tumor Carcass | 41.34 ± 19.14 | 46.85 ± 23.90 |

Figure 44:
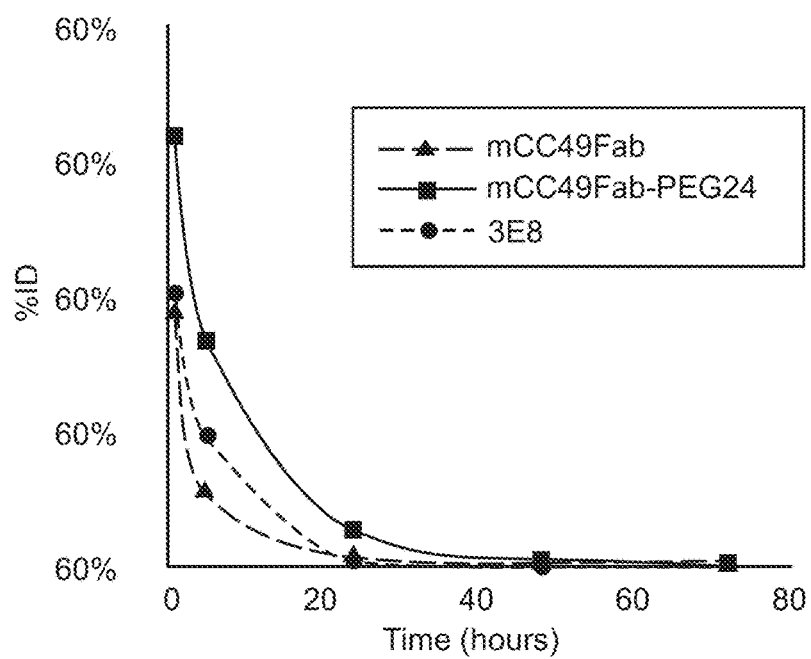
FIG. 44 graphically portrays the $^{124}$I activity change in blood post injection of $^{124}$I-mCC49Fab-NEM, $^{124}$I-m CC49 Fab'-dPEG$_{12}$-Tris(dPEG$_{24}$ acid)$_3$, and $^{124}$I-3E8ΔCH2, an antibody with a MW of 120,000.

FIG. 44 graphically portrays the $^{124}$I activity change in blood post injection of $^{124}$ i-mCC49Fab-NEM, $-^{124}$I-m CC49 Fab'-dPEG$_{12}$-Tris(dPEG$_{24}$ acid)$_3$, and $^{124}$I-3E8ΔCH2, an antibody with a MW of 120,000. Blood was collected at 1, 5, 24, 48, and 72 hrs after injection. Data was converted to % ID of whole blood pool and presented as average±SD (n=5).

TABLE 7

Comparison of Biodistribution (% ID/g) of $^{124}$I-m CC49 Fab'-dPEG$_{12}$-Tris(dPEG$_{24}$ acid)$_3$ (n = 5), $^{124}$I-mCC49Fab-NEM(n = 5), and $^{124}$I-m CC49 Fab'-dPEG$_{12}$-Tris(m-dPEG$_{24}$)$_3$ (n = 2) in nude mice at 72 hr

| Organ | $^{124}$I-mCC49Fab'-dPEG$_{12}$-Tris(dPEG$_{24}$acid)$_3$ | $^{124}$I-mCC49Fab-NEM | $^{124}$I-mCC49Fab'-dPEG$_{12}$-Tris(m-dPEG$_{24}$)$_3$ |
|---|---|---|---|
| blood | 0.10 ± 0.05 | 0.13 ± 0.15 | 0.03 ± 0.00 |
| lungs | 0.13 ± 0.04 | 0.12 ± 0.05 | 0.20 ± 0.20 |
| heart | 0.10 ± 0.04 | 0.08 ± 0.04 | 0.04 ± 0.00 |
| liver | 0.75 ± 0.41 | 0.23 ± 0.18 | 0.19 ± 0.06 |
| spleen | 0.25 ± 0.09 | 0.18 ± 0.09 | 0.39 ± 0.09 |
| pancreas | 0.08 ± 0.05 | 0.08 ± 0.05 | 0.02 ± 0.00 |
| GI | 0.10 ± 0.05 | 0.12 ± 0.10 | 0.03 ± 0.00 |
| Kidneys | 0.37 ± 0.20 | 0.14 ± 0.06 | 0.10 ± 0.04 |
| muscle | 0.14 ± 0.08 | 0.07 ± 0.04 | 0.02 ± 0.00 |
| skin | 0.15 ± 0.07 | 0.15 ± 0.04 | 0.05 ± 0.01 |
| Tumor | 5.09 ± 0.83 | 3.83 ± 1.50 | 2.91 ± 0.91 |
| Carcass | 0.18 ± 0.16 | 0.09 ± 0.04 | 0.07 ± 0.03 |
| MW | ~52.6 kDa | ~48.3 kDa | ~56.6 kDa |

Example 9

PK data was taken with additional normal female athymic mice as follows:

TABLE 9

Fab-dPEG-A: m CC49 Fab'-dPEG$_{12}$-Tris(dPEG$_{24}$ acid)$_3$

| Time after Injection (hrs) | Mouse 1 | Mouse 2 | Mouse 3 |
|---|---|---|---|
| 0 | 54.7 | 31.49 | 36.4 |
| 0.5 | 24.95 | 26.11 | 21.84 |
| 1 | 13.02 | 14.91 | 12.25 |
| 2 | 9.33 | 17.8 | 12.43 |
| 3 | 8.59 | 10.35 | 10.64 |
| 6 | 7.87 | 8.46 | 7.71 |
| 22 | 0.85 | 0.61 | 1.57 |

TABLE 9-continued

Fab-dPEG-A: m CC49 Fab'-dPEG$_{12}$-Tris(dPEG$_{24}$ acid)$_3$

| Time after Injection (hrs) | Mouse 1 | Mouse 2 | Mouse 3 |
|---|---|---|---|
| 28 | 0.58 | 0.58 | 0.78 |
| 48 | 0.25 | 0.22 | 0.16 |

TABLE 10

Fab-dPEG-B: mCC49 CC49 Fab'-dPEG$_{12}$-Tris(dPEG$_{12}$ acid)$_3$

| Time after Injection (hrs) | Mouse 1 | Mouse 2 | Mouse 3 |
|---|---|---|---|
| 0 | 51.89 | 40.62 | 44.93 |
| 0.5 | 15.07 | 22.84 | 26.7 |
| 1 | 18.97 | 20.6 | 28.59 |
| 2 | 8.81 | 6.49 | 20.67 |
| 3 | 7.03 | 4.67 | 6.74 |
| 6 | 7.61 | 4.96 | 5.66 |
| 22 | 0.5 | 0.64 | 0.8 |
| 28 | 0.39 | 0.35 | 0.39 |
| 48 | 0.15 | 0.19 | 0.13 |

TABLE 11

Fab-dPEG-C: m CC49 Fab'-dPEG$_{12}$-Tris(m-dPEG$_{24}$)$_3$

| Time after Injection (hrs) | Mouse 1 | Mouse 2 | Mouse 3 |
|---|---|---|---|
| 0 | 18.28 | 41.69 | 26.12 |
| 0.5 | 17.36 | 22.73 | 17.88 |
| 1 | 11.01 | 14.68 | 18.72 |
| 2 | 7.48 | 14.09 | 9.15 |
| 3 | 9.78 | 11.44 | 4.93 |
| 6 | 4.4 | 7.75 | 4.14 |
| 22 | 0.48 | 0.62 | 0.69 |
| 28 | 0.27 | 0.53 | 0.29 |
| 48 | 0.11 | 0.13 | 0.13 |

TABLE 12

Fab-dPEG-D: m CC49 Fab'-dPEG$_{12}$-Tris(dPEG$_{12}$-Tris(m-dPEG$_{11}$)$_3$)$_3$

| Time after Injection (hrs) | Mouse 1 | Mouse 2 | Mouse 3 |
|---|---|---|---|
| 0 | 10.31 | 35.52 | 41.93 |
| 0.5 | 31.52 | 23.32 | 24.44 |
| 1 | 25.84 | 18.86 | 19.78 |
| 2 | 20.3 | 15.32 | 16.64 |
| 3 | 16.57 | 11.01 | 11.61 |
| 6 | 34.68 | 15.93 | 9.24 |
| 22 | 2.77 | 2.47 | 2.67 |
| 28 | 1.87 | 1.43 | 1.59 |
| 48 | 0.61 | 0.67 | 0.51 |

TABLE 13

Fab-NEM: mCC49 Fab'-NEM

| Time after Injection (hrs) | Mouse 1 | Mouse 2 | Mouse 3 |
|---|---|---|---|
| 0 | 29.58 | 30.89 | 41.48 |
| 0.5 | 13.61 | 0.95 | 17.79 |
| 1 | 5.83 | 5.36 | 8.27 |
| 2 | 5.01 | 4.65 | 5.18 |

TABLE 13-continued

Fab-NEM: mCC49 Fab'-NEM

| Time after Injection (hrs) | Mouse 1 | Mouse 2 | Mouse 3 |
|---|---|---|---|
| 3 | 4.39 | 2.72 | 3.21 |
| 6 | 2.68 | 1.93 | 9.25 |
| 22 | 0.23 | 0.18 | 0.2 |
| 28 | 0.48 | 0.29 | 0.14 |
| 48 | 0.1 | 0.09 | 0.13 |

Figure 42:
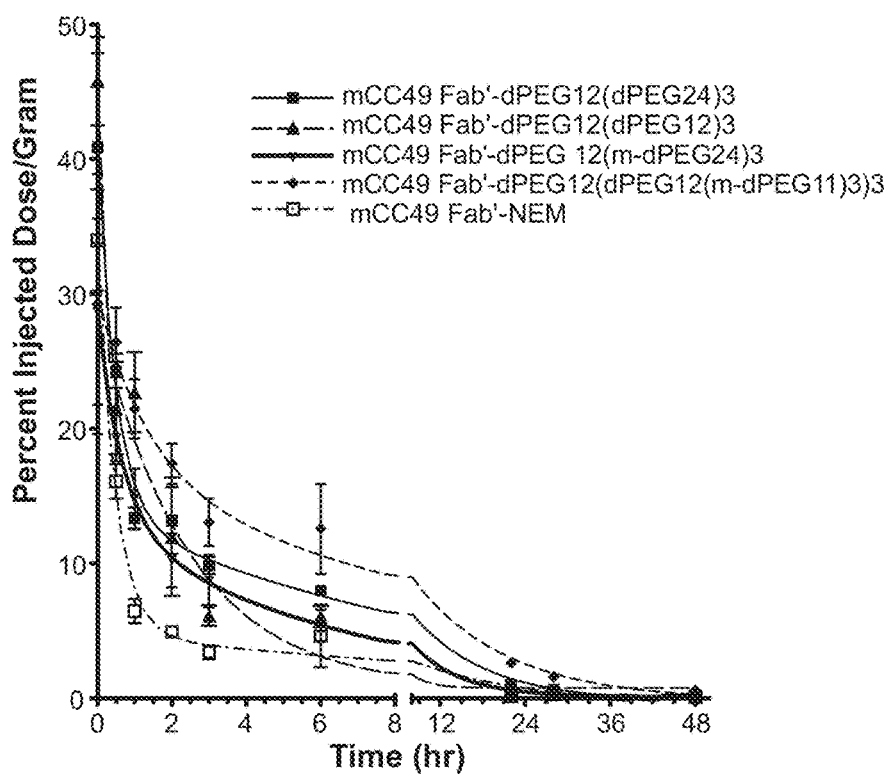
FIG. 42 graphically plots pharmacokinetic data taken with additional normal female athymic mice reported in Example 9.
Figure 43:
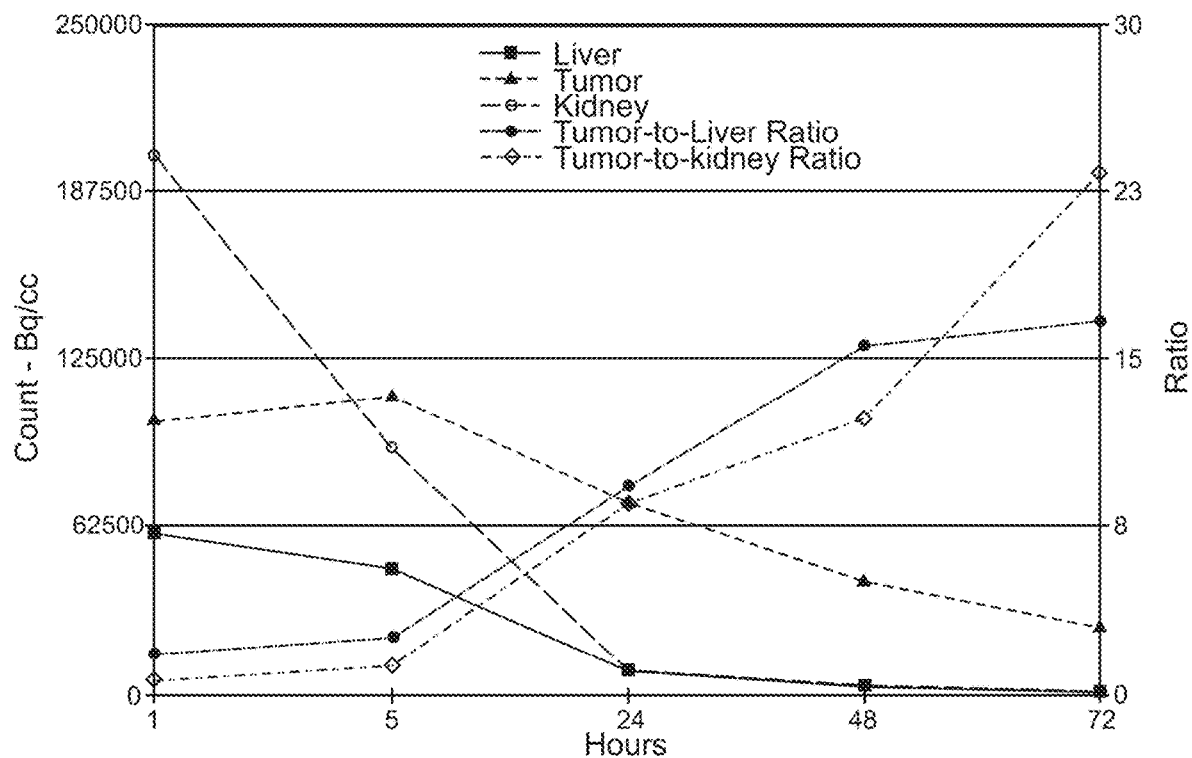
FIG. 43 provides biodistribution data as reported in Example 8 by graphically plotting the organ counts and organ:tumor ratio recorded.

These data are plotted in FIG. 42. The Fab-dPEG-D: mCC49 Fab'-dPEG$_{12}$-Tris(dPEG$_{12}$-Tris(m-dPEG$_{11}$)$_3$)$_3$ showed the least rapid clearance. The mCC49 Fab'-dPEG$_{12}$-Tris(dPEG$_{24}$ acid)$_3$ and the mCC49 Fab'-dPEG$_{12}$-Tris(m-dPEG$_{24}$)$_3$ were very similar in their clearance over time. The mCC49 Fab'-dPEG$_{12}$-Tris(dPEG$_{12}$ acid)$_3$ had early higher percent injected dose that dropped off rapidly to about 4 hours.

Nevertheless, these data again demonstrate the ability of the disclosed branched dPEG constructs to control and improve PK compared to constructs without the branched dPEG modification.

Example 10

Affinity Assay

A competition assay was run with a series of CC49-Fab'-branched dPEGs. In this run, single aliquots of each compound were assayed. The affinity constant of Fab'-NEM is defined as 1.0, and the binding constants of the branched dPEG conjugates are as follows:

TABLE 14

| Conjugate | Relative Affinity Constant (Ka) |
|---|---|
| CC49 Fab'-NEM | 1.0 |
| CC49 Fab'-dPEG$_{12}$-Tris(dPEG$_{24}$ acid)$_3$ (A) | 1.0 |
| CC49 Fab'-dPEG$_{12}$-Tris(dPEG$_{12}$ acid)$_3$ (B) | 0.3 |
| CC49 Fab'-dPEG$_{12}$-Tris(m-dPEG$_{24}$)$_3$ (C) | 0.3 |
| CC49 Fab'-dPEG$_{12}$-Tris(dPEG$_{12}$-Tris(m-dPEG$_{11}$)$_3$)$_3$ (D) | 0.4 |

From this data, it is clear that the Relative Affinity Constant, which is a measure of how well the Fab' binds to its molecular target, is minimally impacted by conjugation to branched dPEG products.

Example 11

Immunogenicity of dPEG Products

Polyethylene glycol is a widely used polymer in drug delivery systems. Several antibodies that recognize all forms of PEG; large, small and branched have been developed by the immunization of animals with PEG's conjugated to KLH and are commercially available (Maine Biotechnology Services, Life Technologies, Enzo Life Sciences).

A Sandwich ELISA using 5 ug/mL monoclonal mouse anti-PEG antibody was coated by passive absorption on a microtiter plate and incubating with a series of dPEG-peptide conjugates at a range of concentrations from 1,000 ng/mL to 15,000 ng/mL. dPEG-peptide conjugate was detected with 0.0.5 ug/mL rabbit anti-PEG antibody, followed by biotinylated-goat-anti-rabbit secondary antibody incubated with streptavidin-horseradish peroxidase conjugate. The plate was washed to remove excess HRP conjugate and visualized with TMB. No binding was observed for any of the dPEG-peptide conjugates. Molecular weights of the dPEG products were: linear dPEG 1,239, linear dPEG 2,296 and branched dPEG 3,946 respectively.

A competitive ELISA assay was also developed, using polyclonal rabbit anti-PEG, PEG-biotin and dPEG peptide conjugates in the range of 5 ng/mL to 10,000 n/mL, molecular weights as above. After incubation with Streptavidin-horseradish peroxidase conjugate, washing and visualization with TMB, no competitive binding was observed.

A Western blot was run comparing a dPEG-peptide, molecular weight 1,239 conjugate versus a polydisperse-peptide conjugate, molecular weight 20,000. The PEG was detected by a rabbit PEG-antibody in PBST with 1% BSA and incubated over night at room temperature. Goat-anti-rabbit-horseradish peroxidase conjugate in PBST with 1% BSA was added for 1 hour at room temperature. The gel was visualized using an ECL kit from GE Healthcare. While the 20,000 MW polydisperse-peptide conjugate was clearly visible, no image was observed with the dPEG®-peptide conjugate.

These results indicate that antibodies elicited to polydisperse PEG in animal models and which can be used to detect various sizes and concentrations of polydisperse PEG's and PEG-conjugates, do not recognize dPEG products.

Example 12

Exendin Conjugates Evaluation

Cell Culture Methods.

RIN-m5F is a stable cell line, derived from a transplantable rat islet tumor (Gazdar A F, Chick W L, Oie H K, Sims H L, King D L, Weir G C, Lauds V: Continuous, clonal, insulin- and somatostatin-secreting cell lines established from a transplantable rat islet cell tumor. *Proc Natl Acad Sci USA* 1980, 77:3519-3523). These insulin-secreting cells express large numbers of the glucagon-like peptide receptor, on their surface and bind the agonist, Exendin-4 (Göke R, Fehmann H, Linn T, Schmidt H, Krause M, Eng J, Göke B: Exendin-4 is a high potency agonist and truncated exendin-(9-39)-amide an antagonist at the glucagon-like peptide 1-(7-36)-amide receptor of insulin-secreting, beta-cells. *The Journal of Biological Chemistry* 1993, 268:19650-19655). Cells were purchased from The American Type Culture Collection (ATCC, Manassas, Va.) and cultured in RPMI-1640 media containing 10% fetal bovine serum (Atlanta Biologicals, Atlanta Ga.). Cells were maintained at 370 C in a humidified CO2 incubator (5% CO2) and sub-cultured weekly at, a ratio, of 1:5. RIN-m5F cells grew as patchy cells with an epithelial morphology.

For ligand binding or insulin secretion studies, cells were trypsinized as described by the supplier and cell numbers were determined on a hemocytometer. The cells were plated into 48 or 96-well plates at a density greater than 1-5×104 cells per well. In some experiments, the plates were pre-treated with collagen or poly-Lysine before cell plating. Cells were grown for at least 48 hours prior to beginning cell studies.

While the compositions and methods have been described with reference to various embodiments, those skilled in the art will understand that various changes may be made and equivalents may be substituted for elements thereof without departing from the scope and essence of the disclosure. In addition, many modifications may be made to adapt a particular situation or material to the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

We claim:

1. A single molecule construct that modulates the in vivo pharmacokinetics of a biologically active molecule and has a polydispersity index of 1 represented by:

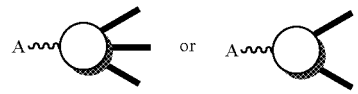

where,
(a) A is a biologically active group or a chemically reactive or reactable moiety;
(b) the wavy line, ～～～, is a linear discrete polyethylene glycol chain containing between about 4 and 48 discrete ethylene oxide residues optionally substituted with N, S, Si, Se, P, aryl groups, or alkyl groups; and having chemically reactive or reactable end groups that are independently reactable; and optionally having branching side chains which can contain diagnostic or therapeutic groups and being cleavable;
(c) BC is a branching core containing a carbon core with 3 or 4 reactable sites, one of said carbon reactable sites being unique, for attachment of ～～～ and the other 2 or 3 carbon reactable sites being independently reactive or reactable moieties, for attachment of ■■■ respectively; and
(d)

are part of

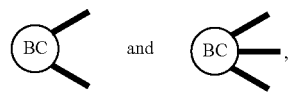

where the solid lines, ■■■ are discrete polyethylene glycol containing chains that have between about 8 and 72 ethylene oxide residues and have a terminal moiety, wherein the terminal moiety is a methyl group, a methoxy group, or a charged group wherein each charged group independently is an amine group, a carboxylate group, a phosphate group, a sulfonate group, or a zwitterionic group.

2. The single molecule construct of claim 1, wherein A comprises a preferential locator that binds with a biological moiety, said preferential locator being one or more of a cell surface and matrix antigen, transport protein, or receptor protein.

3. The single molecule construct of claim 2, wherein said preferential locator A is one or more of an antibody, antibody fragment, engineered antibody, engineered fragment, peptide substrate, peptomimetic substrate, cytokine, aptamer, siRNA, vitamin, or steroid.

4. The single molecule construct of claim 1, wherein A is a nanoparticle, microparticle, engineered molecular scaffold that contains multiple functionalities, or an engineered chemically reactable group.

5. The single molecule construct of claim 1, wherein A is a chemically reactable moiety being one or more of an alkyl or aryl functionalized 1° or 2° amine, hydroxyl, aldehyde, ketone, carboxylate, active carboxylate ester, thiol, maleimide, haloacetyl, vinyl sulfone, oxyamine, hydrazide, acylhydrazide, azide, alkyne, or alkene, where the chemically reactive moiety can be in the form of a chemically reactable moiety.

6. The single molecule construct of claim 1, wherein the solid lines in

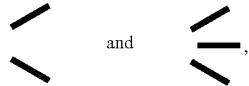

as part of

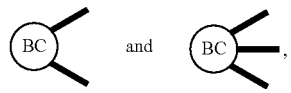

respectively are terminated by a charged group that is either negative, positive or zwitterionic.

7. The single molecule construct of claim 6, wherein said charged group is a carboxylate group.

8. The single molecule construct of claim 6, wherein said charged group contains one or more nitrogen atoms.

9. The single molecule construct of claim 6, wherein said zwitterionic moiety contains both a nitrogen atom and a carboxylate group.

10. The single molecule construct of claim 1, wherein each wavy line, ∿∿∿∿∿ , contains between 8 and 24 ethylene oxide groups.

11. The single molecule construct of claim 1, wherein each solid line, ▬▬▬▬ , independently, contains between 8 and 64 ethylene oxide groups.

12. The single molecule construct of claim 11, wherein each wavy line, ∿∿∿∿∿ , attached to BC contains, independently, between 8 and 64 ethylene oxide groups.

* * * * *

UNITED STATES PATENT AND TRADEMARK OFFICE
CERTIFICATE OF CORRECTION

PATENT NO. : 11,505,525 B2
APPLICATION NO. : 15/630986
DATED : November 22, 2022
INVENTOR(S) : Paul D. Davis et al.

Page 1 of 1

It is certified that error appears in the above-identified patent and that said Letters Patent is hereby corrected as shown below:

In the Claims

At Claim 1, Column 336, about Lines 19-21, replace:

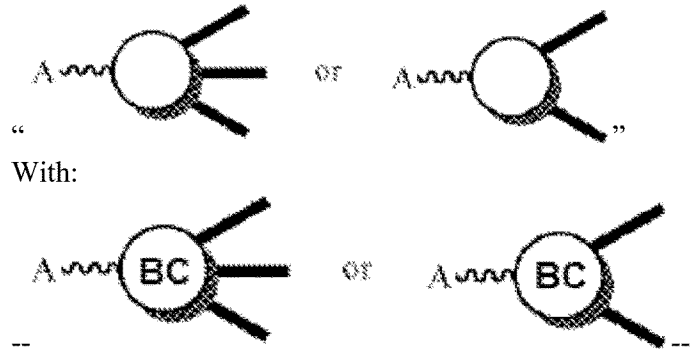

With:

"" and ""

Signed and Sealed this
Twenty-third Day of May, 2023

Katherine Kelly Vidal
*Director of the United States Patent and Trademark Office*